United States Patent
Bath et al.

(10) Patent No.: US 11,058,845 B2
(45) Date of Patent: *Jul. 13, 2021

(54) RESPIRATORY PRESSURE TREATMENT SYSTEM

(71) Applicant: ResMed Pty Ltd, Bella Vista (AU)

(72) Inventors: Andrew Roderick Bath, Sydney (AU); Mark Bertinetti, Sydney (AU); Paul Frederick Birchall, Sydney (AU); Tommy Chung Yeung Chui, Sydney (AU); Dawn Rosemary Churchill, Sydney (AU); Clementine Le Loc'h, Sydney (AU); Justin John Formica, Sydney (AU); Matthew Rolf Harrington, Sydney (AU); Ronald James Huby, Sydney (AU); Jeegarkumar Kapadia, Sydney (AU); Barton John Kenyon, Sydney (AU); Dimitri Marco Maurer, Gosford (AU); Saad Nasr, Sydney (AU); Joseph Samuel Ormrod, Sydney (AU); Jose Ignacio Romagnoli, Sydney (AU); Nathan John Row, Sydney (AU); Ian Malcolm Smith, Sydney (AU); Robert John Sparrow, Sydney (AU); Luke Andrew Stanislas, Sydney (AU); Zhuo Ran Tang, Sydney (AU); Ernie Wei-Chih Tsai, Sydney (AU); Hargopal Verma, Sydney (AU); Chengwei Zhu, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

This patent is subject to a terminal disclaimer.

(21) Appl. No.: 17/007,798

(22) Filed: Aug. 31, 2020

(65) Prior Publication Data

US 2020/0398016 A1 Dec. 24, 2020

Related U.S. Application Data

(63) Continuation of application No. 16/907,452, filed on Jun. 22, 2020, which is a continuation of application
(Continued)

(30) Foreign Application Priority Data

Dec. 17, 2013 (AU) ............................... 2013904923
May 27, 2014 (AU) ............................... 2014901997
(Continued)

(51) Int. Cl.
*A61M 16/00* (2006.01)
*A61M 16/10* (2006.01)
(Continued)

(52) U.S. Cl.
CPC ...... *A61M 16/109* (2014.02); *A61M 16/0066* (2013.01); *A61M 16/024* (2017.08);
(Continued)

(58) Field of Classification Search
CPC .............. A61M 16/109; A61M 16/024; A61M 16/0066; A61M 16/0683; A61M 16/0875;
(Continued)

(56) References Cited

U.S. PATENT DOCUMENTS

| 3,936,026 A | 2/1976 | Hampel et al. |
|---|---|---|
| 4,351,327 A | 9/1982 | Rinne |

(Continued)

FOREIGN PATENT DOCUMENTS

| CN | 2327396 | 7/1999 |
|---|---|---|
| CN | 1691437 | 11/2005 |

(Continued)

OTHER PUBLICATIONS

Notification of the First Office Action dated Jul. 3, 2020 issued in Chinese Application No. 2018108462971 with English translation (19 pages).
(Continued)

*Primary Examiner* — Steven O Douglas
(74) *Attorney, Agent, or Firm* — Nixon Vanderhye P C.

(57) ABSTRACT

A respiratory pressure therapy (RPT) device is disclosed for treatment of respiratory-related disorders. The RPT device includes a pressure generator, a pneumatic block, a chassis and a device outlet for delivering a supply of flow of gas to a patient interface. The RPT device also comprises a humidifier including a water reservoir.

30 Claims, 120 Drawing Sheets

Related U.S. Application Data

No. 16/853,812, filed on Apr. 21, 2020, which is a continuation of application No. 15/104,789, filed as application No. PCT/AU2014/050426 on Dec. 17, 2014, now abandoned.

(60) Provisional application No. 61/987,245, filed on May 1, 2014.

(30) Foreign Application Priority Data

| May 27, 2014 | (AU) | ................................ | 2014901998 |
| May 27, 2014 | (AU) | ................................ | 2014901999 |
| May 30, 2014 | (AU) | ................................ | 2014902071 |

(51) Int. Cl.
*A61M 16/16* (2006.01)
*A61M 16/06* (2006.01)
*A61M 16/08* (2006.01)
*H01Q 1/48* (2006.01)
*H01Q 1/38* (2006.01)

(52) U.S. Cl.
CPC .... *A61M 16/0683* (2013.01); *A61M 16/0875* (2013.01); *A61M 16/16* (2013.01); *A61M 16/0063* (2014.02); *A61M 16/107* (2014.02); *A61M 16/1055* (2013.01); *A61M 2205/14* (2013.01); *A61M 2205/3584* (2013.01); *A61M 2205/3592* (2013.01); *A61M 2205/42* (2013.01); *A61M 2205/50* (2013.01); *A61M 2205/505* (2013.01); *A61M 2205/7518* (2013.01); *A61M 2209/08* (2013.01); *H01Q 1/38* (2013.01); *H01Q 1/48* (2013.01)

(58) Field of Classification Search
CPC .............. A61M 16/16; A61M 16/0063; A61M 16/107; A61M 16/1055; A61M 2205/14; A61M 2205/3584; A61M 2205/3592; A61M 2205/42; A61M 2205/50; A61M 2205/505; A61M 2205/7518; A61M 2209/08; H01Q 1/38; H01Q 1/48
See application file for complete search history.

(56) References Cited

U.S. PATENT DOCUMENTS

| 4,782,832 | A | 11/1988 | Trimble et al. |
| 4,944,310 | A | 7/1990 | Sullivan |
| 5,558,084 | A | 9/1996 | Daniell |
| 5,564,415 | A | 10/1996 | Dobson |
| 5,607,316 | A | 3/1997 | Ishikawa |
| 5,916,493 | A | 6/1999 | Miller |
| 5,943,473 | A | 8/1999 | Levine |
| 6,135,432 | A | 10/2000 | Hebblewhite |
| 6,397,841 | B1 | 6/2002 | Kenyon |
| 6,398,197 | B1 | 6/2002 | Dickinson |
| 6,532,959 | B1 | 3/2003 | Berthon-Jones |
| 6,554,260 | B1 | 4/2003 | Lipscombe |
| 6,581,594 | B1 | 6/2003 | Drew et al. |
| 6,690,924 | B1 | 2/2004 | Jan et al. |
| 6,935,337 | B2 | 8/2005 | Virr |
| 7,096,864 | B1 | 8/2006 | Mayer |
| 7,111,624 | B2 | 9/2006 | Thudor et al. |
| 7,137,388 | B2 | 11/2006 | Virr |
| 7,157,035 | B2 | 1/2007 | Edirisuriya et al. |
| 7,393,222 | B2 | 7/2008 | Asakura |
| 7,413,173 | B2 | 8/2008 | DiMatteo et al. |
| 7,439,929 | B2 | 10/2008 | Ozkar |
| 7,478,635 | B2 | 1/2009 | Wixey et al. |
| 7,677,246 | B2 | 3/2010 | Kepler et al. |
| 7,866,944 | B2 | 1/2011 | Kenyon et al. |
| 7,942,824 | B1 | 5/2011 | Kayyali et al. |
| 8,544,465 | B2 | 10/2013 | Smith et al. |
| 8,545,416 | B1 | 10/2013 | Kayyali et al. |
| 8,636,002 | B2 | 1/2014 | McAuley et al. |
| 8,636,479 | B2 | 1/2014 | Kenyon et al. |
| 8,638,014 | B2 | 1/2014 | Sears et al. |
| 8,677,993 | B2 | 3/2014 | Cortez, Jr. et al. |
| 8,985,105 | B2 | 3/2015 | Burton et al. |
| 2002/0014240 | A1 | 2/2002 | Truschel |
| 2004/0017318 | A1 | 1/2004 | Annabi et al. |
| 2005/0166921 | A1 | 8/2005 | Devries et al. |
| 2006/0144405 | A1 | 7/2006 | Gunaratnam et al. |
| 2006/0266365 | A1 | 11/2006 | Stallard |
| 2007/0132117 | A1 | 6/2007 | Pujol et al. |
| 2007/0193583 | A1 | 8/2007 | Reed |
| 2007/0277827 | A1 | 12/2007 | Bordewick et al. |
| 2008/0072900 | A1 | 3/2008 | Lithgow et al. |
| 2008/0105257 | A1 | 5/2008 | Klasek |
| 2008/0276939 | A1 | 11/2008 | Tiedje |
| 2008/0316118 | A1 | 12/2008 | Baliarda et al. |
| 2009/0044808 | A1 | 2/2009 | Guney et al. |
| 2009/0050156 | A1 | 2/2009 | Ng et al. |
| 2009/0110378 | A1 | 4/2009 | Bradley et al. |
| 2009/0120434 | A1 | 5/2009 | Smith et al. |
| 2009/0152445 | A1 | 6/2009 | Gardner |
| 2009/0156952 | A1 | 6/2009 | Hunter et al. |
| 2010/0000534 | A1 | 1/2010 | Kooij et al. |
| 2010/0154796 | A1 | 6/2010 | Smith et al. |
| 2011/0023874 | A1 | 2/2011 | Bath et al. |
| 2011/0155132 | A1 | 6/2011 | Virr et al. |
| 2011/0180068 | A1 | 7/2011 | Kenyon et al. |
| 2011/0271956 | A2 | 11/2011 | Smith et al. |
| 2011/0309992 | A1 | 12/2011 | Ali |
| 2012/0012109 | A1 | 1/2012 | Chalvignac |
| 2012/0240932 | A1 | 9/2012 | Gusky et al. |
| 2013/0206140 | A1 | 8/2013 | Kepler et al. |
| 2013/0269700 | A1 | 10/2013 | Lapoint et al. |
| 2013/0310713 | A1 | 11/2013 | Weber et al. |
| 2014/0264975 | A1 | 9/2014 | Bath et al. |
| 2016/0022954 | A1 | 1/2016 | Bath et al. |
| 2016/0310691 | A1 | 10/2016 | Bath et al. |
| 2020/0306490 | A1 | 10/2020 | Bath et al. |
| 2020/0316332 | A1 | 10/2020 | Bath et al. |

FOREIGN PATENT DOCUMENTS

| CN | 1829549 A | 9/2006 |
| CN | 101024105 A | 8/2007 |
| CN | 101052985 A | 10/2007 |
| CN | 201042552 Y | 4/2008 |
| CN | 101541367 A | 9/2009 |
| CN | 201775525 U | 3/2011 |
| CN | 201823138 | 5/2011 |
| CN | 102170932 A | 8/2011 |
| CN | 102686282 A | 9/2012 |
| CN | 102725015 A | 10/2012 |
| CN | 103055400 A | 4/2013 |
| CN | 103124575 A | 5/2013 |
| CN | 203183455 | 9/2013 |
| EP | 1 127 583 A2 | 8/2001 |
| EP | 1 369 141 A1 | 12/2003 |
| EP | 1 898 337 A1 | 3/2008 |
| EP | 1 900 387 A1 | 3/2008 |
| EP | 2 245 985 A1 | 11/2010 |
| EP | 2 471 568 A2 | 7/2012 |
| FR | 2579896 A1 | 10/1986 |
| GB | 1364127 A | 8/1974 |
| JP | H03213293 | 9/1991 |
| JP | 2001-274719 | 10/2001 |
| JP | 2005-27217 | 1/2005 |
| JP | 2006-109534 A | 4/2006 |
| JP | 2009-508647 | 3/2009 |
| JP | 2009-511218 | 3/2009 |
| JP | 2010-501315 | 1/2010 |
| JP | 2011-005240 | 1/2011 |
| JP | 2011-525833 | 9/2011 |
| JP | 2013-018017 A | 1/2013 |
| TW | 432746 | 5/2001 |
| TW | 200711671 A | 4/2007 |

(56) References Cited

FOREIGN PATENT DOCUMENTS

| WO | WO 1998004310 | 2/1998 |
|---|---|---|
| WO | WO 1998034665 | 8/1998 |
| WO | WO 2000078381 | 12/2000 |
| WO | WO 02/078775 A2 | 10/2002 |
| WO | 03/043560 A2 | 5/2003 |
| WO | WO 2004073778 | 9/2004 |
| WO | 2005/063323 A1 | 7/2005 |
| WO | WO 2005063328 | 7/2005 |
| WO | WO 2006074513 | 7/2006 |
| WO | WO 2006/138331 A1 | 12/2006 |
| WO | WO 2006130903 | 12/2006 |
| WO | 2007/038152 | 4/2007 |
| WO | WO 2007/038152 A2 | 4/2007 |
| WO | WO 2007/051230 A1 | 5/2007 |
| WO | WO 2009052560 | 4/2009 |
| WO | 2009/156921 | 12/2009 |
| WO | WO 2010/031126 A1 | 3/2010 |
| WO | WO 2010135785 | 12/2010 |
| WO | WO 2011056080 | 5/2011 |
| WO | WO 2011/122964 A1 | 10/2011 |
| WO | WO 2011/149362 A1 | 12/2011 |
| WO | 2012/095764 A1 | 7/2012 |
| WO | WO 2012/154064 A2 | 11/2012 |
| WO | WO 2012160477 | 11/2012 |
| WO | WO 2012171072 | 12/2012 |
| WO | 2013/002650 | 1/2013 |
| WO | WO 2013020167 | 2/2013 |
| WO | 2013/135318 A1 | 9/2013 |
| WO | 2013/151447 A1 | 10/2013 |
| WO | 2013/163687 A1 | 11/2013 |
| WO | 2014/007655 A2 | 1/2014 |
| WO | WO 2014/025266 | 2/2014 |
| WO | WO 2014/053010 A1 | 4/2014 |
| WO | WO 2014/138804 A1 | 9/2014 |
| WO | 2014/205513 A1 | 12/2014 |

OTHER PUBLICATIONS

First Examination Report dated Aug. 27, 2020 issued in New Zealand Application No. 766847 (3 pages).
First Examination Report dated Sep. 21, 2020 issued in New Zealand Application No. 760188 (7 pages).
First Examination Report dated Sep. 21, 2020 issued in New Zealand Application No. 760191 (3 pages).
First Examination Report dated Sep. 18, 2020 issued in New Zealand Application No. 760194 (4 pages).
First Examination Report dated Sep. 18, 2020 issued in New Zealand Application No. 760195 (4 pages).
First Examination Report dated Sep. 18, 2020 issued in New Zealand Application No. 760196 (4 pages).
First Examination Report dated Sep. 25, 2020 issued in New Zealand Application No. 760189 (4 pages).
First Examination Report dated Sep. 25, 2020 issued in New Zealand Application No. 760192 (4 pages).
First Examination Report dated Sep. 25, 2020 issued in New Zealand Application No. 760193 (4 pages).
Extended European Search Report dated Aug. 6, 2019 issued in European Application No. 19157258.5 (25 pages).
First Office Action issued in translation (13 pages) related Japanese Application No. 2016-540619, dated Oct. 29, 2018, with English translation (13 pages).
First Office Action issued in related Taiwanese Application No. 1031440004 dated Nov. 8, 2018, with English translation, (11 pages).
First Examination Report issued in New Zealand Application No. 749247 dated Jan. 18, 2019 (2 pages).
Notice of Opposition to Grant of Patent (Section 21) filed Jun. 27, 2016 by Fisher & Paykel Healthcare Limited in New Zealand Application No. 630762 (2 pages).
Statement of Case dated Aug. 26, 2016 filed by Fisher & Paykel Healthcare Limited in New Zealand Application No. 630762 (9 pages).

Amended Notice of Opposition to Grant of Patent (Section 21), with no markups, dated Aug. 26, 2016, filed by Fisher & Paykel Healthcare Limited in New Zealand Application No. 630762 (2 pages).
Amended Notice of Opposition to Grant of Patent (Section 21), with markups, dated Aug. 26, 2016, filed by Fisher & Paykel Healthcare Limited in New Zealand Application No. 630762 (2 pages).
Dolan, Brian, "Philips Respironics offers SleepMapper app to motivate, inform sleep apnea patients", Mobihealthnews, Apr. 25, 2013, (1 page).
HomeCare Magazine, "Connectivity Drives Compliance", Apr. 28, 2016, http://www.homecaremag.com/hmeproducts/connectivitydrivescompliance (8 pages).
Second Amended Notice of Opposition to Grant of Patent (Section 21), with no markups, dated Nov. 22, 2016, filed by Fisher & Paykel Healthcare Limited in New Zealand Application No. 630762 (2 pages).
Second Amended Notice of Opposition to Grant of Patent (Section 21), with markups, dated Nov. 22, 2016, filed by Fisher & Paykel Healthcare Limited in New Zealand Application No. 630762 (2 pages).
Amended Statement of Case, with no markups, dated Nov. 21, 2016 filed by Fisher & Paykel Healthcare Limited in New Zealand Application No. 630762 (10 pages).
Amended Statement of Case, with markups, dated Nov. 21, 2016 filed by Fisher & Paykel Healthcare Limited in New Zealand Application No. 630762 (11 pages).
Second Amended Statement of Case, with no markups, dated Jan. 25, 2017 filed by Fisher & Paykel Healthcare Limited in New Zealand Application No. 630762 (11 pages).
Second Amended Statement of Case, with markups, dated Jan. 25, 2017 filed by Fisher & Paykel Healthcare Limited in New Zealand Application No. 630762 (10 pages).
Third Amended Notice of Opposition to Grant of Patent (Section 21), with no markups, filed Feb. 7, 2018 by Fisher & Paykel Healthcare Limited in New Zealand Application No. 630762 (2 pages).
Third Amended Notice of Opposition to Grant of Patent (Section 21). with markups, filed Feb. 7, 2018 by Fisher & Paykel Healthcare Limited in New Zealand Application No. 630762 (2 pages).
Third Amended Statement of Case, with no markups, dated Feb. 7, 2018 filed by Fisher & Paykel Healthcare Limited in New Zealand Application No. 630762 (13 pages).
Third Amended Statement of Case, with markups, dated Feb. 7, 2018 filed by Fisher & Paykel Healthcare Limited in New Zealand Application No. 630762 (13 pages).
Xu, Lie Jie, and Guo, Yong-Xin, "Dual-Band Implantable Antenna with Open-End Slots on Ground", IEEE Antennas and Wireless Propagation Letters, vol. 11, 2012, pp. 1564-1567 (4 pages).
First Office Action issued in Taiwanese Application No. 103121801 dated Jun. 20, 2018 with English translation (7 pages).
Extended European Search Report issued in European Application No. 18 16 7630.5 dated Jun. 20, 2018, (10 pages).
First Office Action issued in related Japanese Application No. 2016-522136 dated May 14, 2018, with English translation, 8 pages.
First Office Action issued in Chinese Application No. 201480075670.8 dated Mar. 19, 2018, with English translation, 11 pages.
European Search Report issued in related European Application No. 14871575.8-1664, dated Sep. 20, 2017, (16 pages).
Kin-Lu Wong, "*Compact and Broadband Microstrip Antennas*", (2002) (340 pages).
First Office Action issued in related Chinese Application No. 201480046956.3 with English translation, dated Mar. 28, 2017, 15 pages.
Extended Search Report issued in related European Application No. 14818607.5, dated Nov. 15, 2016, 8 pages.
International Preliminary Report on Patentability for PCT/AU2014/050426 dated Jun. 16, 2016, 8 pages.
International Search Report for PCT/AU2014/050089, dated Oct. 1, 2014, 12 pages.
Written Opinion of the ISA for PCT/AU2014/050089, dated May 28, 2015, 6 pages.

(56) References Cited

OTHER PUBLICATIONS

Written Opinion of the ISA for PCT/AU2014/050089, dated Oct. 1, 2014, 7 pages.
International Preliminary Report on Patentability for PCT/AU2014/050089, dated Jun. 15, 2015, 50 pages.
West, "Respiratory Physiology", Lippincott Williams & Wilkins, 9th edition published 2011, 8 pages.
"BalContact Springs Current Carrying Contact Elements DM-7, BalContact Advantages", Bal Seal Canted Coil Spring Catalog, Report No. 621-9, 2003, Bal Seal Engineering Company, Inc., 27 pages.
Patent Examination Report No. 1 issued in related Australian Application No. 2014301955, dated Feb. 16, 2016, 2 pages.
First Examination Report issued in related New Zealand Application No. 631008, dated Feb. 18, 2016, 2 pages.
Written Opinion for PCT/AU2014/050426 dated Mar. 16, 2015, 7 pages.
International Search Report for PCT/AU2014/050426 dated Mar. 16, 2015, 8 pages.
Notice of Reasons for Rejection dated Jan. 20, 2020 issued in Japanese Application No. 2019-010135 with English translation (16 pages).
Office Action dated Nov. 30, 2020 issued in Japanese Application No. 2019-010135 with English translation (10 pages).
First Examination Report dated Oct. 14, 2020 issued in New Zealand Application No. 760190 (5 pages).
Second Examination Report dated Dec. 24, 2020 issued in New Zealand Application No. 760194 (4 pages).
Second Examination Report dated Dec. 23, 2020 issued in New Zealand Application No. 760195 (4 pages).
Second Examination Report dated Dec. 23, 2020 issued in New Zealand Application No. 760196 (4 pages).
Second Examination Report dated Jan. 22, 2021 issued in New Zealand Application No. 760189 (3 pages).
Office Action dated Feb. 22, 2021 issued in Chinese Application No. 201810846297.1 with English translation (11 pages).
Second Examination Report dated Feb. 24, 2021 issued in New Zealand Application No. 751047 (3 pages).
John Crane Type 6 Elastomer Bellows Seal, https://web.archive.org/web/20091229113803/http:/www.allsealsinc.com/johncrane/type6johncrane.pdf, captured Dec. 29, 2009, (4 pages).

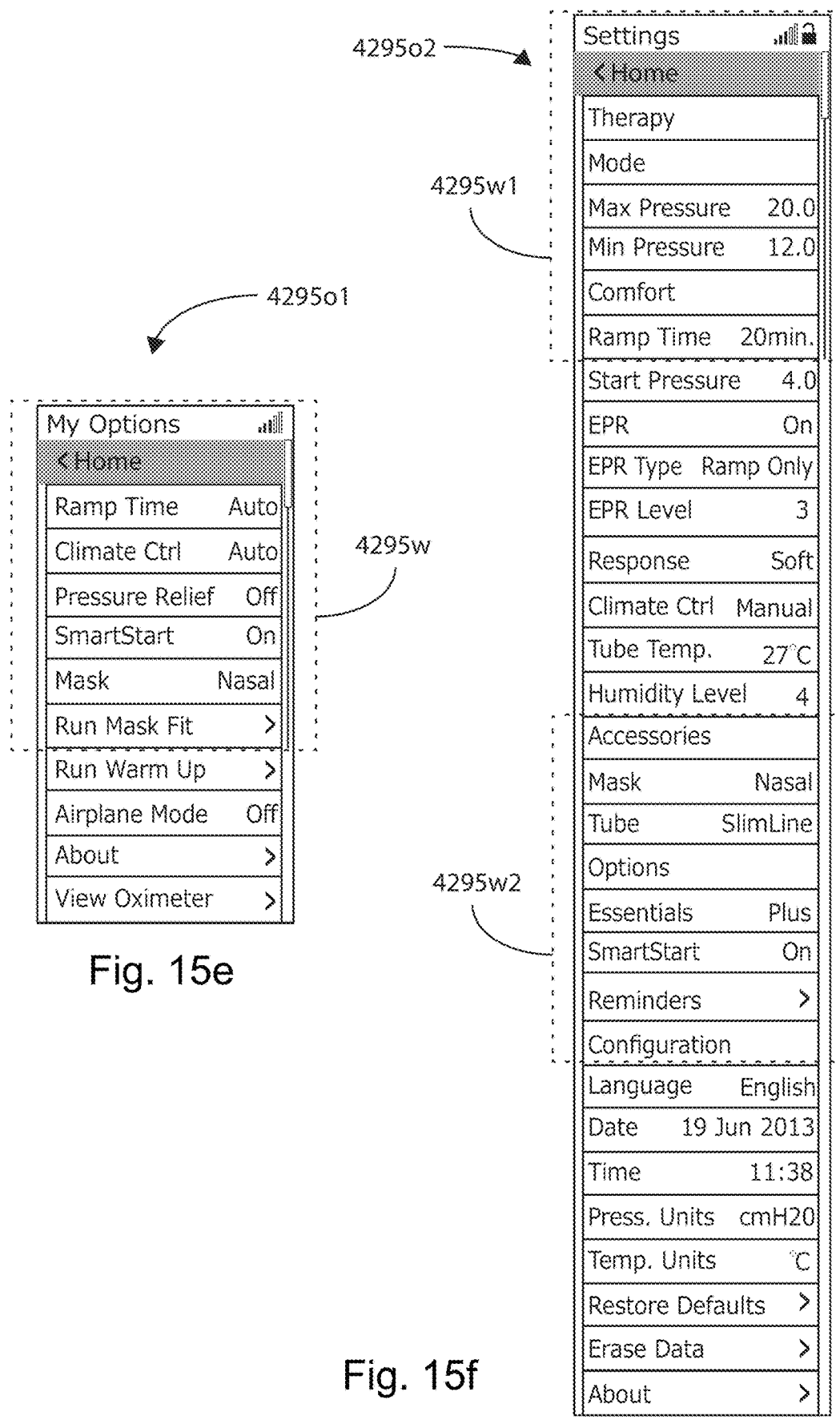

4295a1

4295a2

4295a3

4295a4

4295a5

4295a6

4295a7

4295a8

4295b1

4295b2

4295b3

4295b4

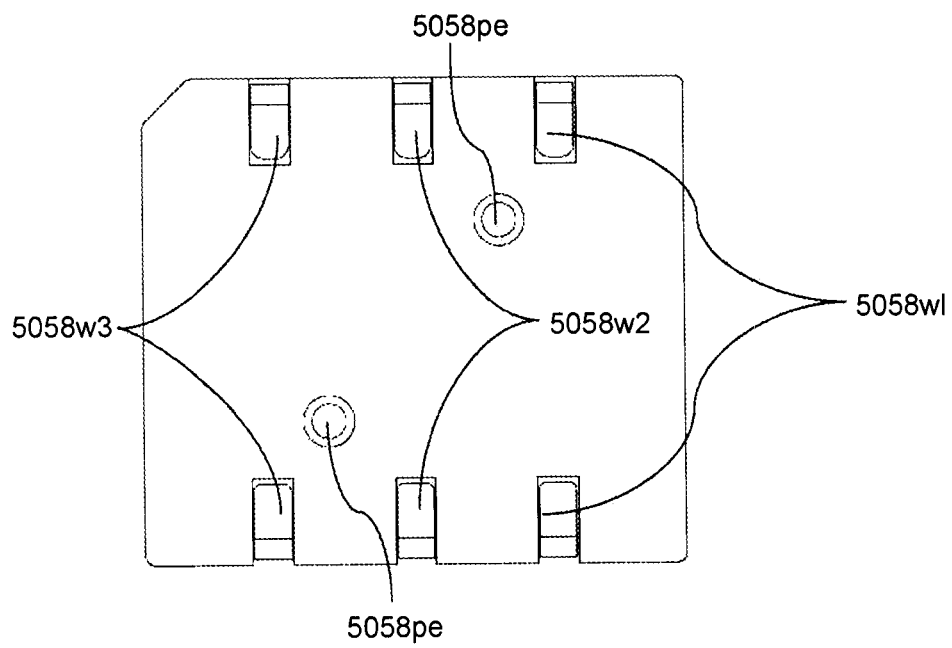
Fig. 18z1
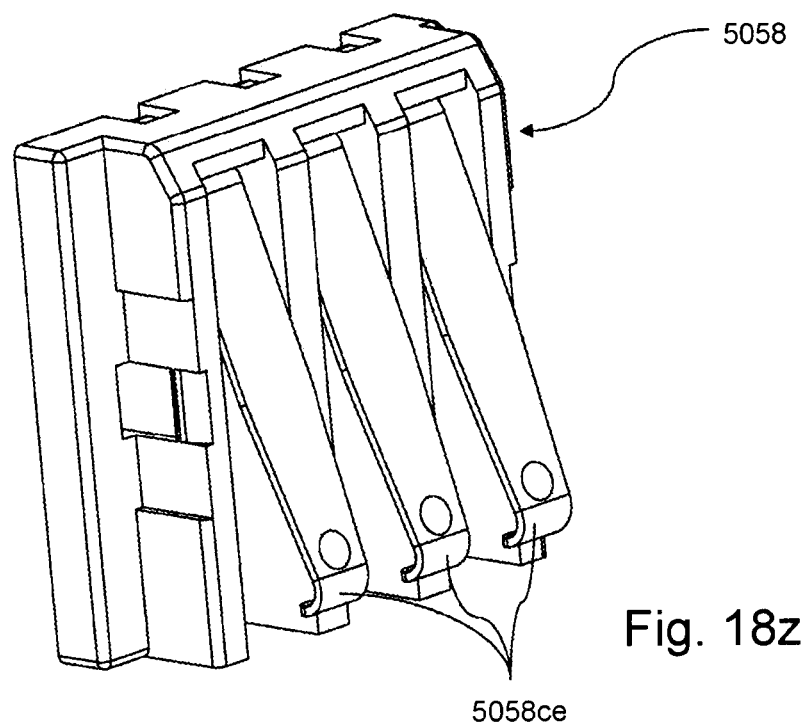
Fig. 18z2

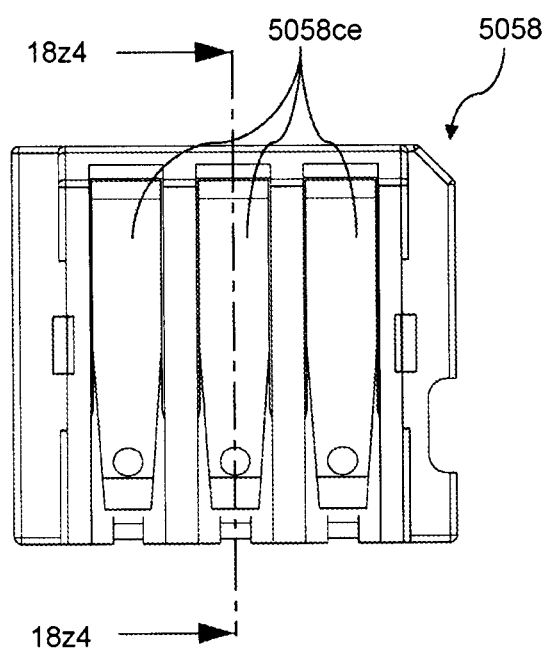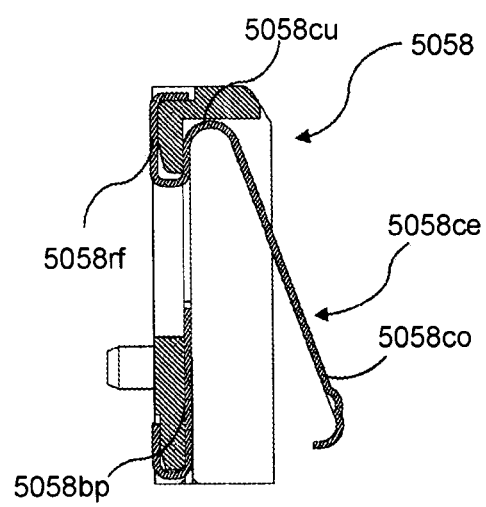
Fig. 18z3
Fig. 18z4

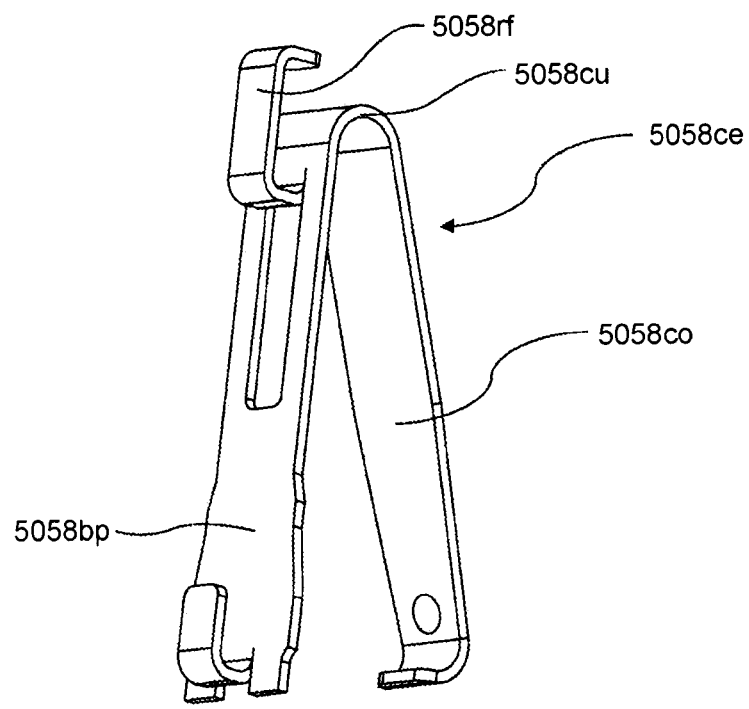
Fig. 18z5
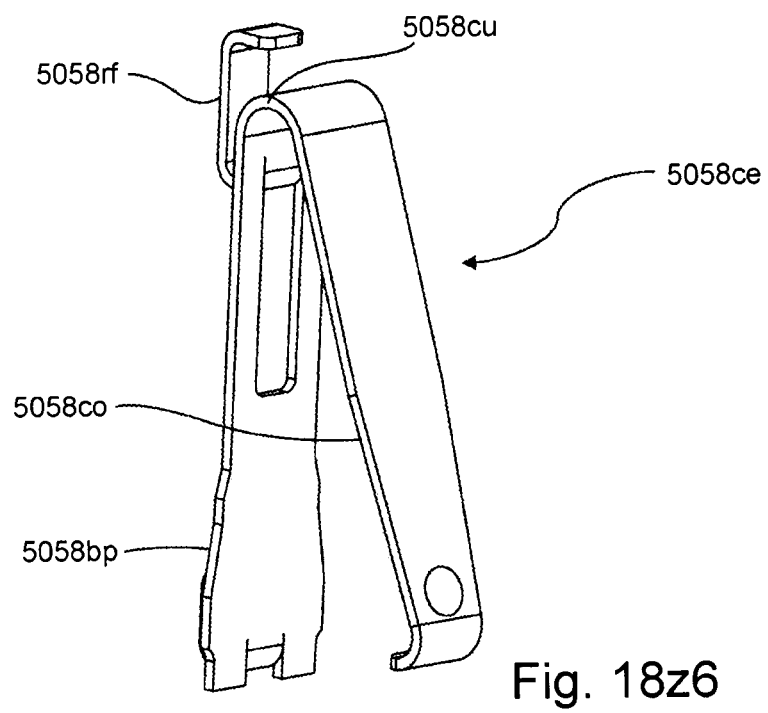
Fig. 18z6

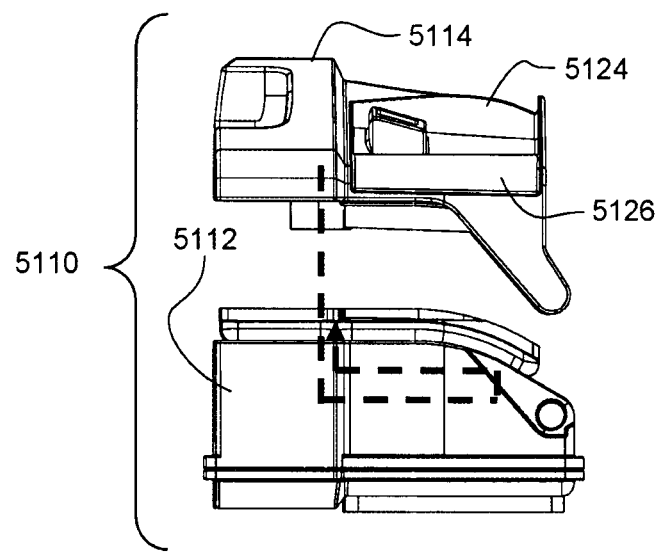
Fig. 29b
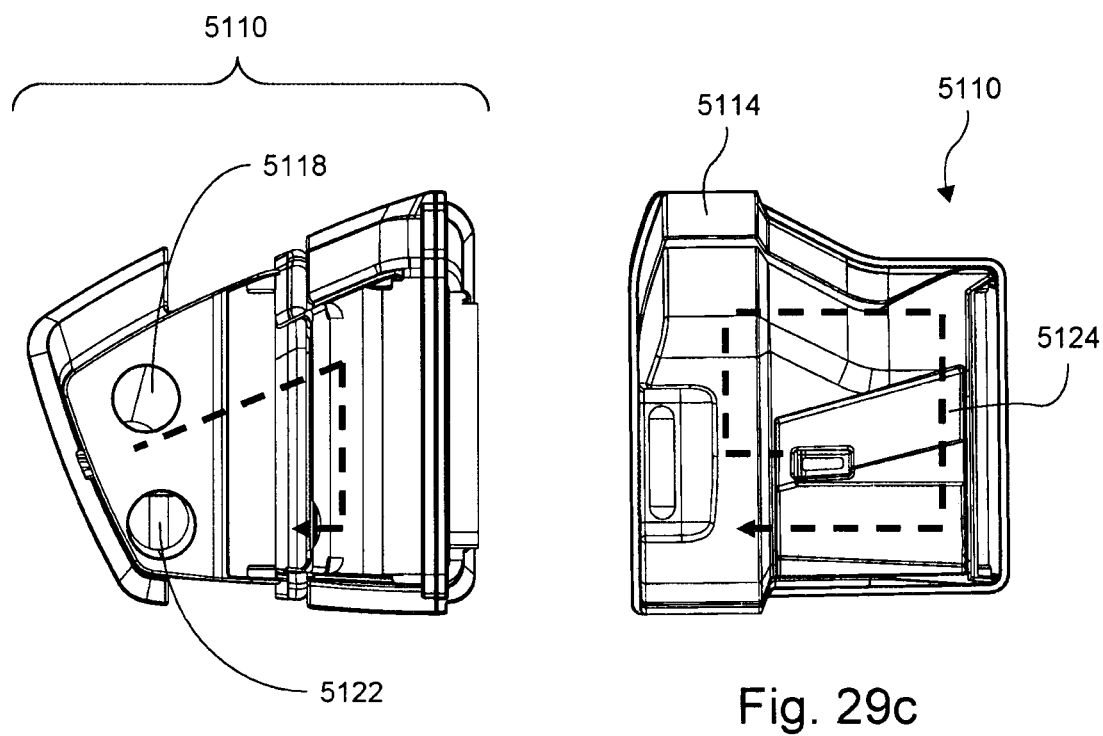
Fig. 29a
Fig. 29c

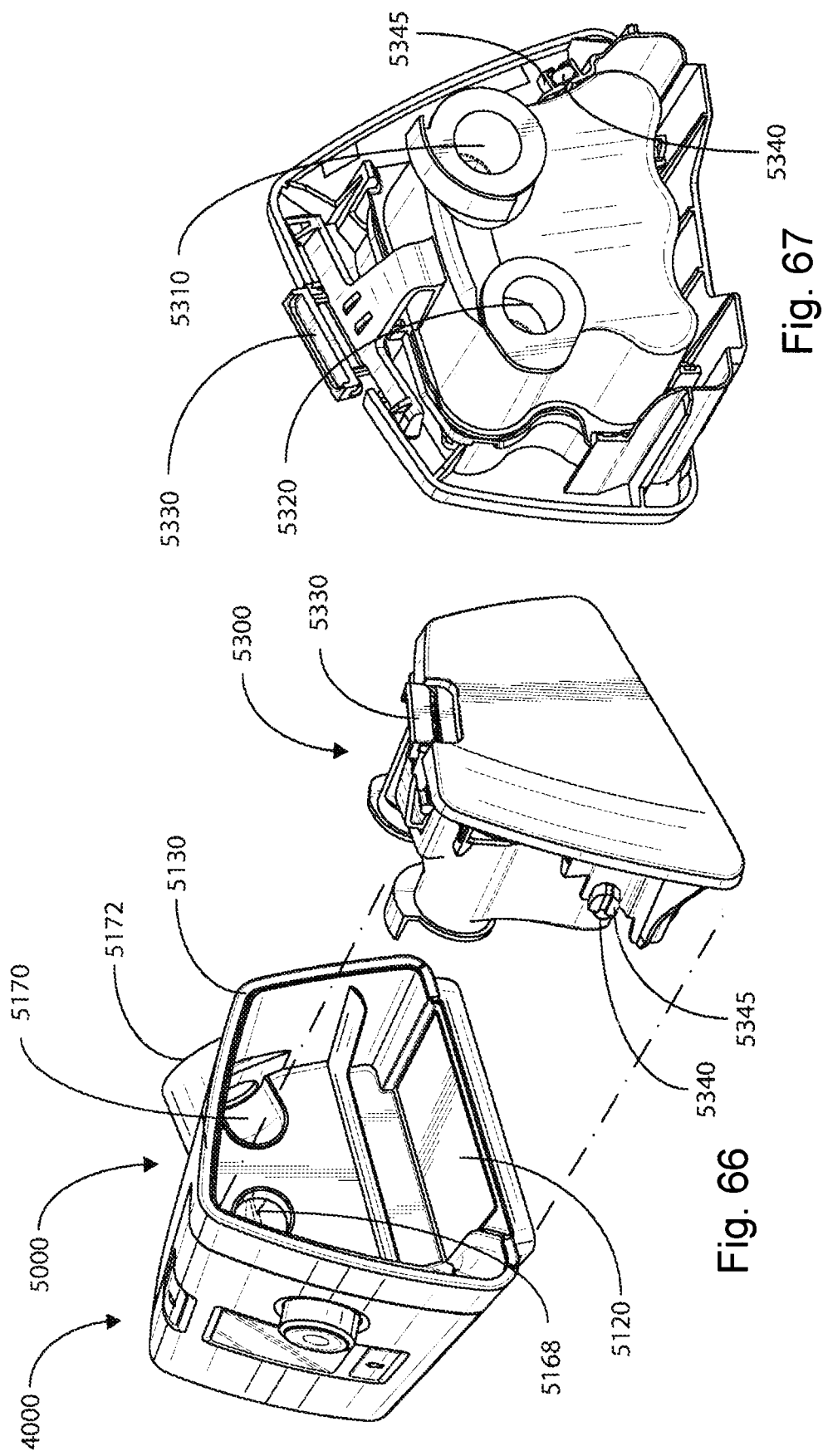

RESPIRATORY PRESSURE TREATMENT SYSTEM

1 CROSS-REFERENCE TO RELATED APPLICATIONS

This application is a continuation of U.S. application Ser. No. 16/907,452, filed Jun. 22, 2020, now U.S. Pat. No. 10,864,343, which is a continuation of U.S. application Ser. No. 16/853,812, now, filed Apr. 21, 2020, which is a continuation of U.S. application Ser. No. 15/104,789, now abandoned, filed Jun. 15, 2016, which is the U.S. national phase of International Application No. PCT/AU2014/050426, filed Dec. 17, 2014, and claims priority to Australian Provisional Patent Application Nos. AU 2013904923, filed Dec. 17, 2013, AU 2014901998, filed May 27, 2014, AU 2014901999, filed May 27, 2014, AU 2014901997, filed May, 27 2014, and AU 2014902071, filed May, 30 2014, and U.S. Provisional Patent Application U.S. 61/987,245, filed May 1, 2014, the entire contents of each of which are incorporated herein by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and assist to maintain adequate oxygen levels in the body by doing some or all of the work of breathing. The ventilatory support is provided via a patient interface. NIV has been used to treat CSR, OHS, COPD, MD and Chest Wall disorders.

Invasive ventilation (IV) provides ventilatory support to patients that are no longer able to effectively breathe themselves and may be provided using a tracheostomy tube.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its user, for example by providing a flow of air. The flow of air may be provided via a mask to the nose, the mouth or the nose and the mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

An example of the special requirements of certain RPT devices is acoustic noise.

| RPT Device name | A-weighted sound power level dB(A) | Year (approx.) |
|---|---|---|
| Table of noise output levels of prior RPT devices (one specimen only, measured using test method specified in ISO3744 in CPAP mode at 10 cmH₂O). | | |
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elise™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity, temperature (or both) of the flow of air in relation to ambient air when required, typically where the patient may be asleep or resting (e.g. at a hospital). As a result, a medical humidifier is preferably small for bedside placement, and it is preferably configured to only humidify, heat or humidify and heat the flow of air delivered to the patient without humidifying, heating or humidifying and heating the patient's surroundings. Room-based systems (e.g. a sauna, an air conditioner, an evaporative cooler), for example, may also humidify air that is breathed in by the patient, however they would also humidify, heat or humidify and heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to an apparatus for use in treating a respiratory disorder comprising a housing, a pressure generator within the housing and configured to supply a flow of air, a device outlet fluidly coupled to the pressure generator and configured to be coupled to an air circuit to deliver the flow of air to a patient interface for treating a respiratory disorder, and a wireless data communication interface integrated with the housing, the wireless data communication interface configured to connect to another device or a network.

A further aspect of the present technology relates to an apparatus wherein the wireless data communication interface is configured to connect to one or more of the Internet and a cellular telephone network.

A further aspect of the present technology relates to an apparatus wherein the wireless data communication interface uses one or more of CDMA, GSM, LTE, Wi-Fi, Bluetooth, and a consumer infrared protocol.

According to a further aspect of the present technology, the wireless data communication interface comprises an antenna within the housing.

According to a further aspect of the present technology, the wireless data communication interface further comprises an antenna ground plane.

A further aspect of the present technology relates to an apparatus wherein the antenna ground plane is vertically oriented.

A further aspect of the present technology relates to an apparatus wherein the antenna ground plane comprises one or more notches.

A further aspect of the present technology relates to an apparatus wherein the notches increase an effective total length of the ground plane.

A further aspect of the present technology relates to an apparatus wherein the notches increase the effective total length by more than approximately 25%.

One aspect of the present technology relates to an apparatus for humidifying a flow of breathable gas, comprising a heater plate, a chamber in fluid communication with the flow of breathable gas and a reservoir comprising a conductive portion in thermal engagement with the heater plate, the apparatus configured so that varying a first pressure of the flow of breathable gas in the chamber varies a level of thermal engagement between the conductive portion and the heater plate.

In one form, the reservoir further comprises an inlet and an outlet.

In one form, the thermal engagement is in a first direction that is substantially normal to a surface of the conductive portion.

In one form, the apparatus is further configured to vary a magnitude of a force between the conductive portion and the heater plate in the first direction as the first pressure is varied.

In one form, the chamber is part of the reservoir.

In one form, the chamber further comprises a variable portion.

In one form, the apparatus further comprises a dock configured to receive the reservoir, and the dock comprises the heater plate.

In one form, the dock further comprises a cavity having a top portion and a bottom portion, the bottom portion having the heater plate located thereon, the cavity configured to retain at least a portion of the reservoir therein.

In one form, the variable portion is compressed to enable insertion of the reservoir into the cavity of the dock.

In one form, the top portion of the cavity is moveable between an open and closed configuration to facilitate insertion of the reservoir into the cavity.

In one form, the variable portion is configured to adjust in size as the first pressure is varied to vary the level of thermal engagement between the heater plate and the conductive portion.

In one form, the reservoir further includes a base and a lid, the base structured to hold a volume of liquid and including the conducting portion.

In one form, the base and lid are pivotably coupled together.

In one form, the variable portion forms a seal between the base and lid.

In one form, the reservoir further includes a latch to secure the base and lid together.

In one form, the reservoir further comprises at least one handle to facilitate coupling of the reservoir to the dock.

In one form, the reservoir further includes a retaining clip adapted to engage with a recess on the dock to retain the reservoir in the cavity of the dock.

In one form, the reservoir is structured to prevent refilling of the reservoir when the reservoir is coupled to the dock.

In one form, at least a portion of the reservoir is prevented from being opened when the reservoir is coupled to the dock.

In one form, the reservoir includes a re-filling cap.

In one form, the apparatus further comprises an overfill protection element configured to prevent filling the reservoir above a predetermined maximum volume of water.

In one form, the overfill protection element comprises at least one orifice formed in a wall of the reservoir, the at least one orifice defines an egress path of water when the predetermined maximum volume of water is exceeded.

In one form, the overfill protection element comprises a sloped profile in the side profile of a wall of the reservoir, the sloped profile defines an egress path of water when the predetermined maximum volume of water is exceeded.

One aspect of the present technology relates to a method for varying thermal contact between a heater plate and a reservoir in a humidification system for humidifying a flow of breathable gas, the method comprising varying a pressure of the flow of breathable gas in the reservoir that is in fluid communication with the flow of breathable gas to vary a force between the heater plate and the reservoir.

Another aspect of the present technology relates to an apparatus for humidifying a flow of breathable gas, comprising a heater plate and a reservoir comprising an inlet to receive the flow of breathable gas, an outlet and a conductive portion in thermal contact with the heater plate, and wherein the apparatus is configured so that varying a pressure of the flow of breathable gas in the reservoir varies a force between the heater plate and the conductive portion in a direction of thermal contact.

In one form, the apparatus further comprises a dock connectable with the reservoir.

In one form, the dock is configured to constrain the reservoir from opening in the direction of thermal contact.

Another aspect of the present technology relates to a reservoir configured to contain a volume of liquid for humidifying a pressurised flow of breathable air, comprising a base portion comprising a conductive portion, a lid portion comprising an inlet and an outlet and a seal portion wherein the base portion and the lid portion are pivotably engaged and configurable in an open configuration and a closed configuration while pivotably engaged, and the seal sealingly engages the base portion and the lid portion when the reservoir is in the closed configuration.

In one form, the seal portion comprises an outlet tube, and a baffle, the baffle being configured to connect to the inlet tube.

Another aspect of the present technology relates to an apparatus for humidifying a flow of breathable gas, comprising a heater plate and a reservoir comprising an inlet, an outlet, a variable portion and a conductive portion in thermal contact with the heater plate, wherein the apparatus is configured so that varying a height of the variable portion varies a level of thermal engagement between the conductive portion and the heater plate.

In one form, the apparatus is configured so that the thermal engagement is in a first direction that is substantially normal to a surface of the conductive portion.

Another aspect of the present technology relates to a method of varying a level of thermal engagement in a humidifier apparatus, the method comprising (i) thermally engaging a heater plate with a conductive portion of a reservoir and (ii) varying a height of a variable portion of the reservoir to vary a level of thermal engagement between the conductive portion and the heater plate.

A reservoir to hold a predetermined maximum volume of water, comprising a base portion including an overfill protection element, wherein the reservoir is configured to be convertible between an open configuration and a closed configuration and the overfill protection element prevents filling the reservoir above the maximum volume of water when the reservoir is in the open configuration.

In one form, the seal portion is configured to sealingly engage the lid portion and the base portion when the reservoir is in the closed configuration.

In one form, the overfill protection element is configured so that excess water above the maximum volume of water will spill out via the overfill protection element when a maximum water capacity is exceeded and the base portion is in its normal, working orientation.

In one form, the overfill protection element is at least one orifice that defines an egress path of water when the maximum water capacity of the base portion is exceeded when the humidifier reservoir is in an open configuration.

In one form, the overfill protection element is a sloped profile in the side profile of the base portion that defines an egress path of water when the maximum water capacity of the base portion is exceeded when the humidifier reservoir is in an open configuration.

Another aspect of the present technology relates a method of preventing overfilling in a humidifier reservoir, the method comprising (i) incorporating an overfill protection element in a base portion of the humidifier reservoir and (ii) configuring the overfill protection element so that excess water above a predetermined maximum volume of water will spill out via the overfill protection element when a maximum water capacity is exceeded and the base portion is in its normal, working orientation.

In one form, the overfill protection element includes at least one orifice.

In one form, the overfill protection element includes a sloped profile.

Another aspect of the present technology relates to a reservoir configured to hold a predetermined maximum volume of water, comprising a plurality of walls forming a cavity structured to hold the predetermined maximum volume of water, an inlet tube configured to deliver a supply of breathable gas into the cavity, the inlet tube having an inlet interior end and an inlet exterior end and an outlet tube configured to deliver a humidified supply of breathable gas from the cavity, the outlet tube having an outlet interior end and an outlet exterior end, wherein the inlet interior end and the outlet interior end are located within the cavity and the inlet exterior end and the outlet exterior end are located in one of the plurality of walls of the cavity, a first axis defined by the inlet interior end and the inlet exterior end and a second axis defined by the outlet interior end and the outlet exterior end, wherein when the reservoir is tilted approximately 90 to normal working orientation the first axis is on a first angle such that the inlet interior end and the inlet exterior end are positioned at different heights, such that the predetermined maximum volume of water is below at least one of the inlet interior end or the inlet exterior end to prevent spillback of water through the inlet tube.

In one form, the reservoir is further configured so that when the reservoir is tilted approximately 90° to normal working orientation the second axis is on a second angle such that the outlet interior end and the outlet exterior end are positioned at different heights, such that the predetermined maximum volume of water is below at least one of the outlet interior end or the outlet exterior end to prevent spillback of water through the outlet tube.

Of course, portions of the aspects may form sub-aspects of the present technology. Also, various ones of the sub-aspects, aspects or both may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system including a patient 1000 wearing a patient interface 3000, in the form of a nasal pillows, receives a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 2A:
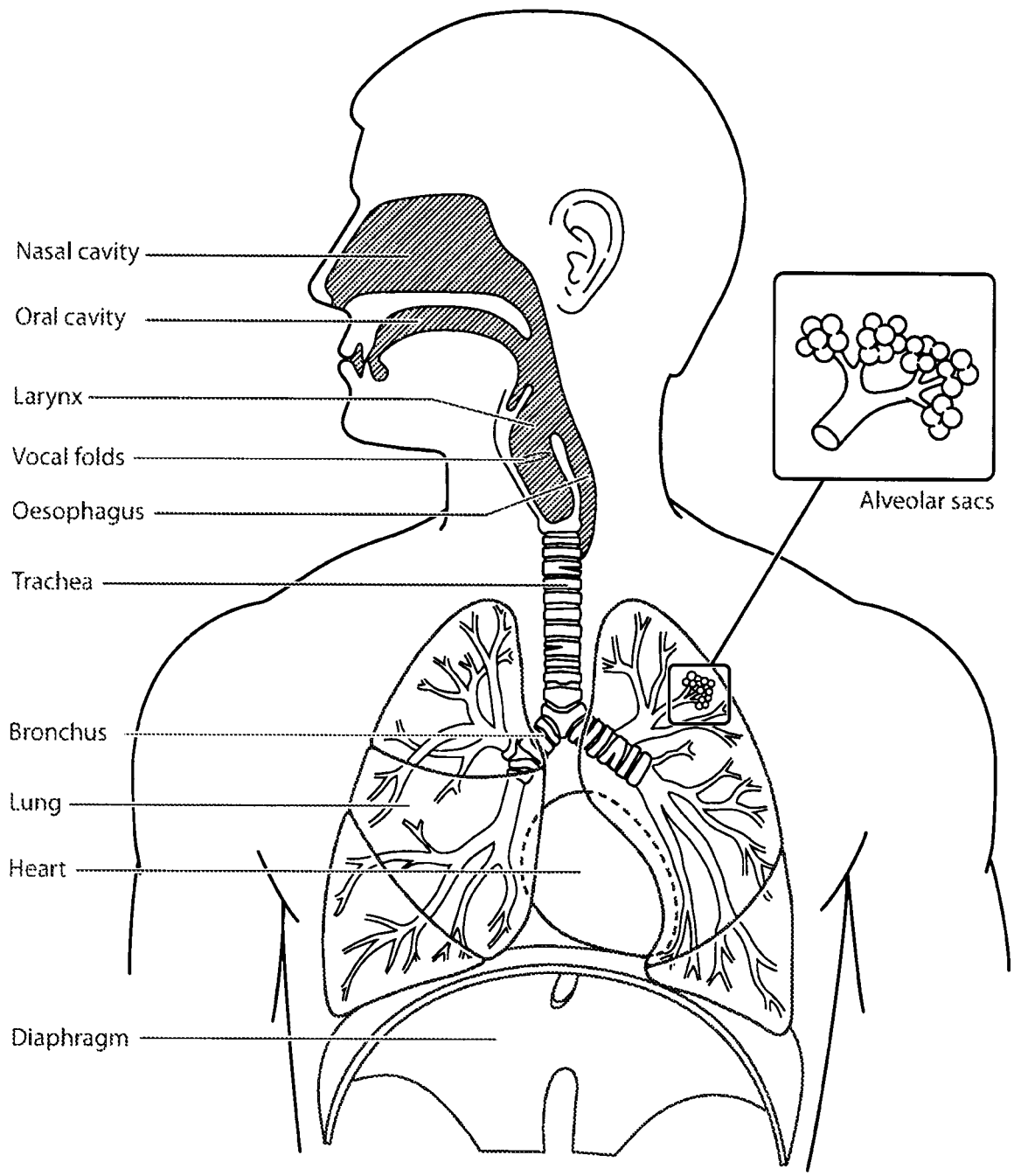

FIG. 2a shows an overview of a human respiratory system including the nasal and oral cavities, the larynx, vocal folds, oesophagus, trachea, bronchus, lung, alveolar sacs, heart and diaphragm.

4.3 Patient Interface

Figure 3A:
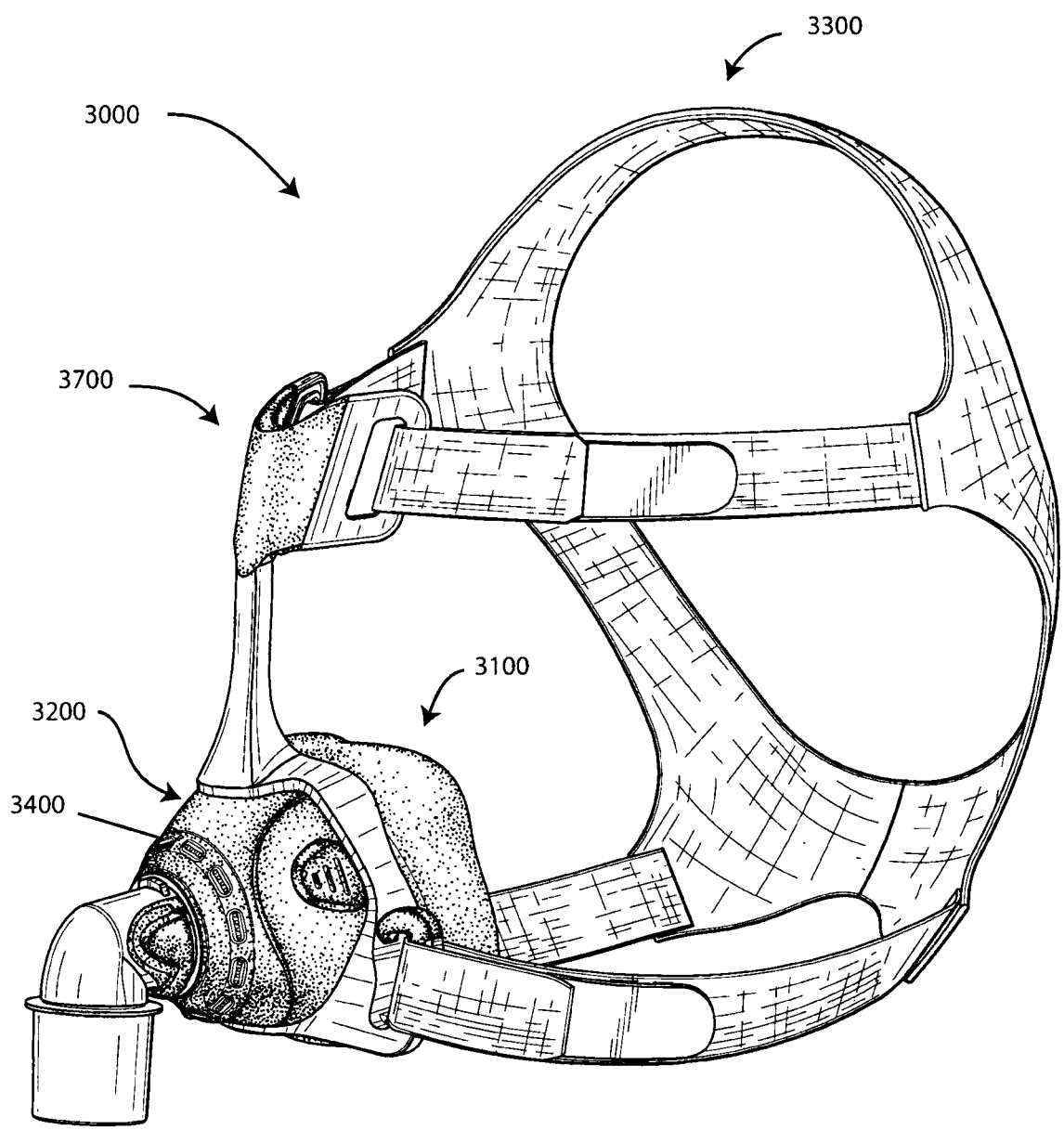

FIG. 3a shows a patient interface in the form of a nasal mask in accordance with one form of the present technology.

4.4 Breathing Waveforms

Figure 4:
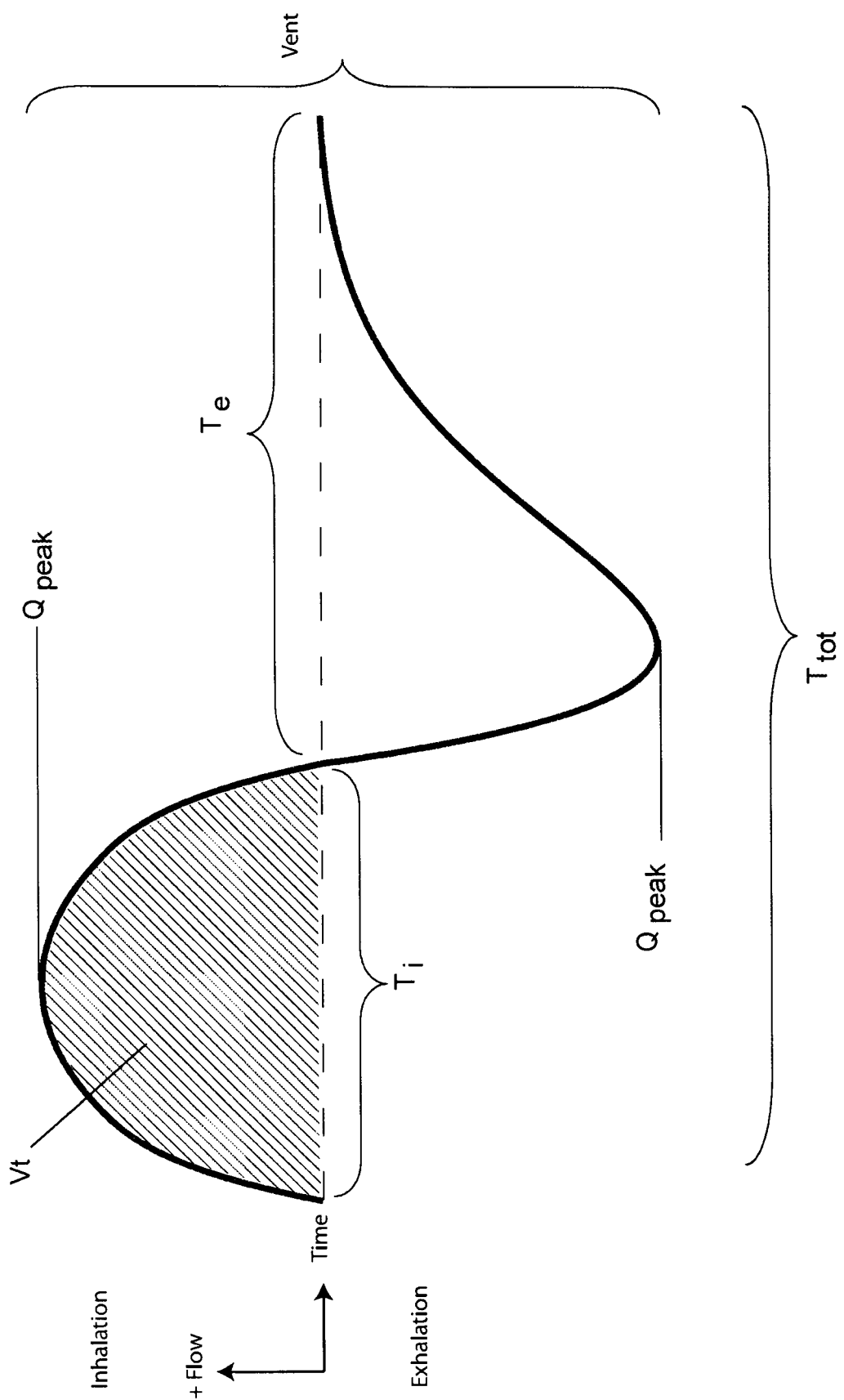

FIG. 4 shows a model typical breath waveform of a person while sleeping.

4.5 RPT Device and Humidifier

Figure 5A:
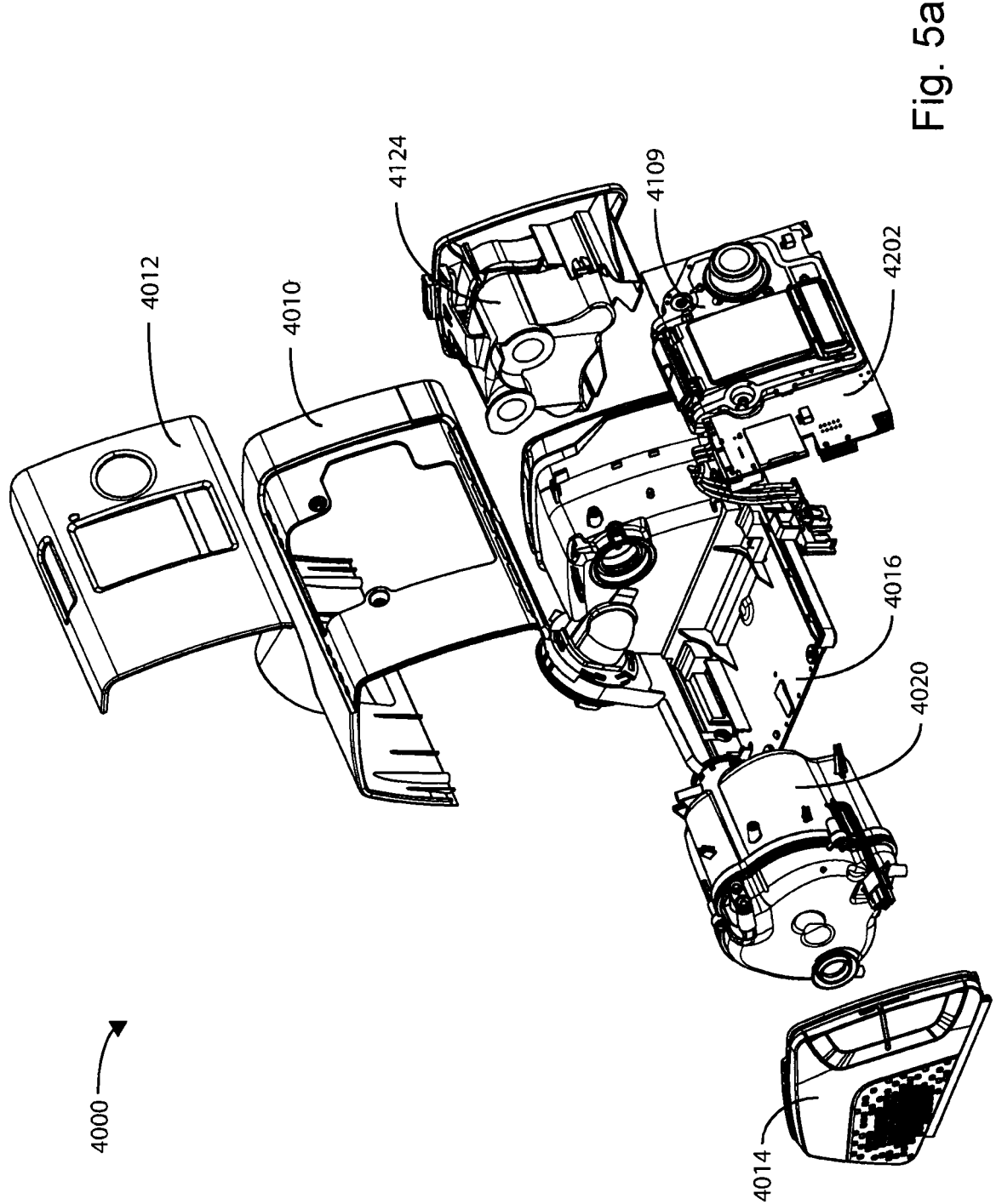

FIG. 5a shows an exploded perspective view of an RPT device 4000 in accordance with one form of the present technology.

Figure 5B:
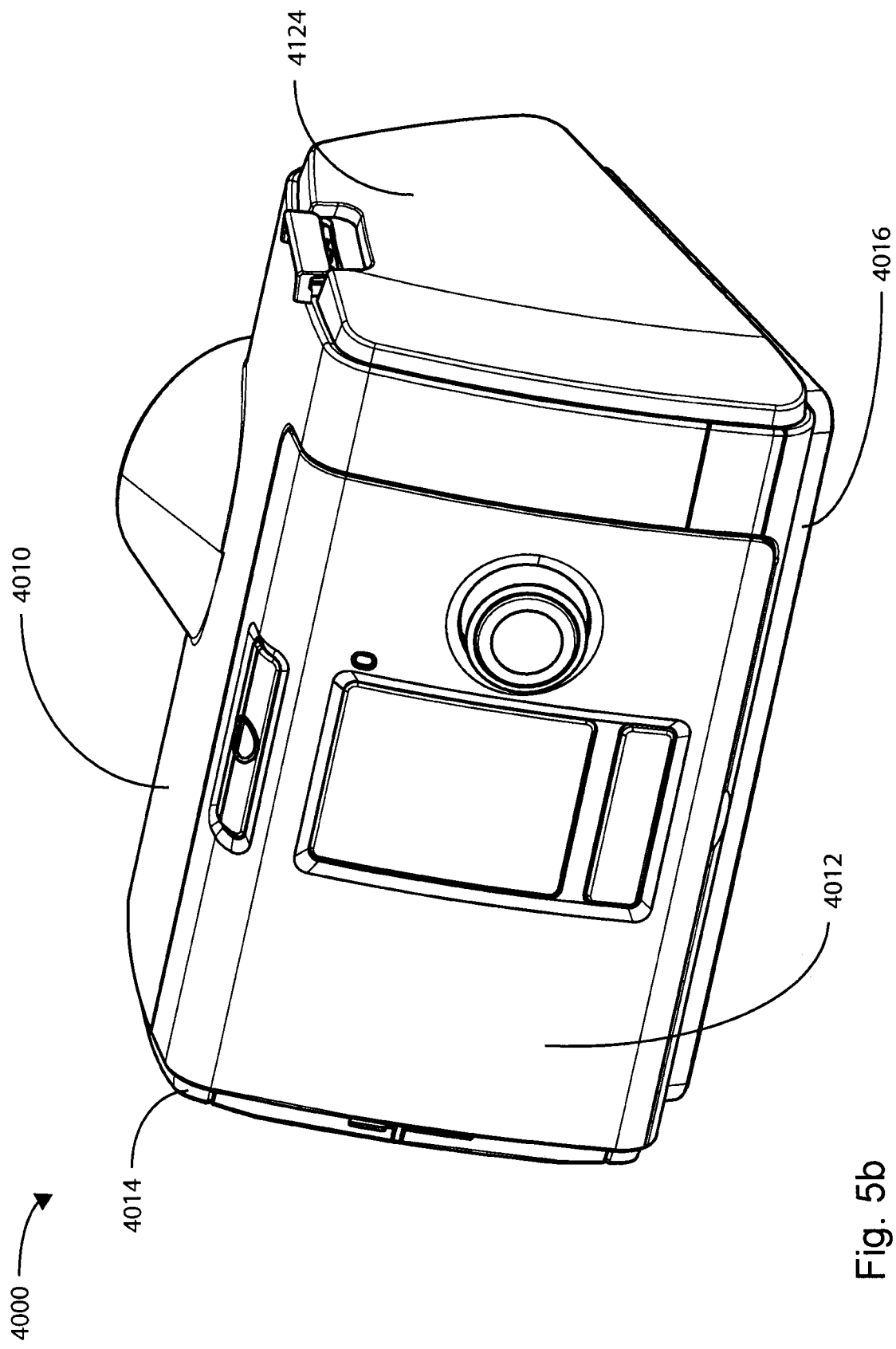

FIG. 5b shows a perspective view of an RPT device 4000 comprising an outlet muffler 4124 in accordance with one form of the present technology.

Figure 5C:
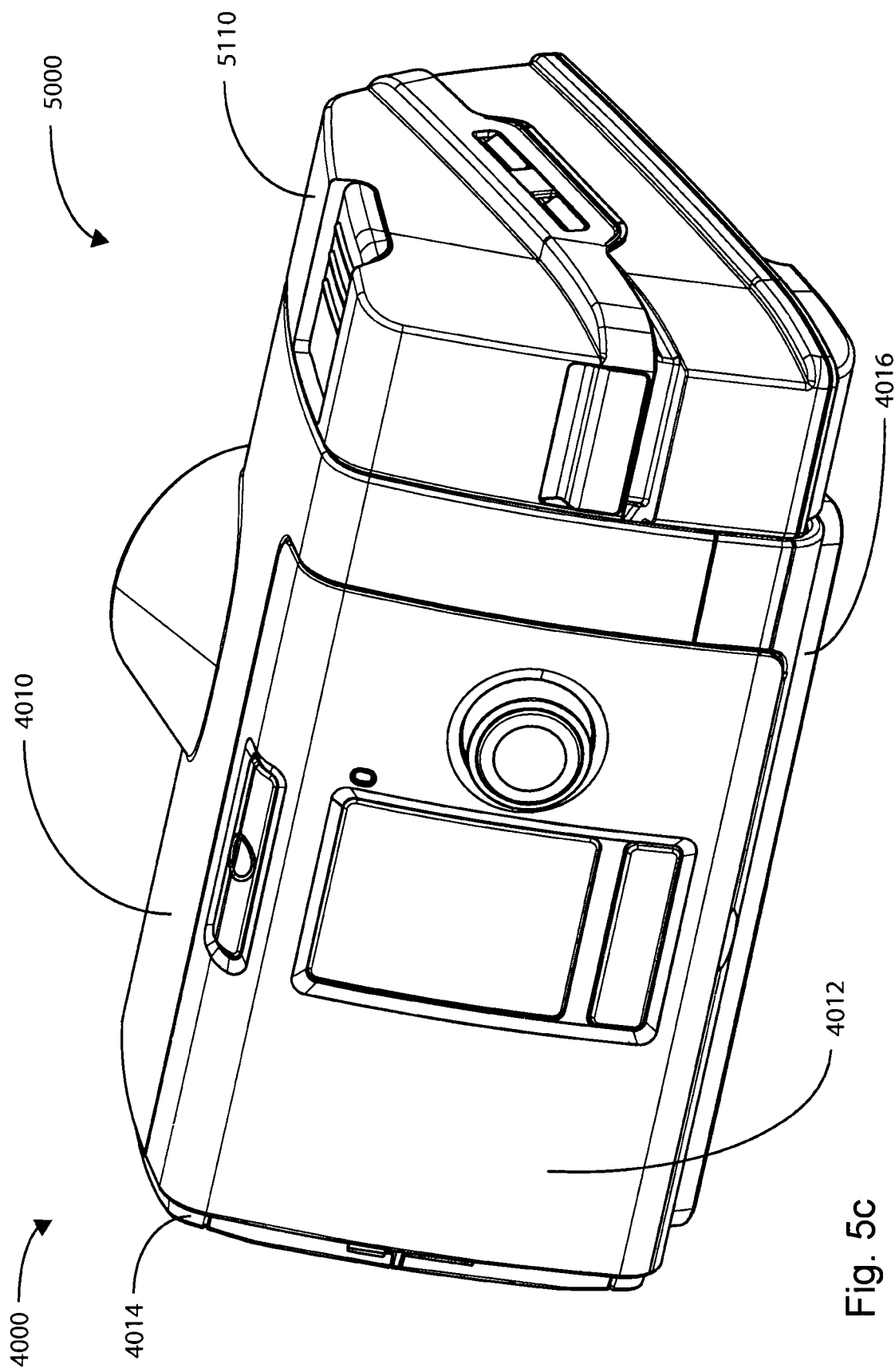

FIG. 5c shows a perspective view of an RPT device 4000 with an integrated humidifier 5000 comprising a water reservoir 5110 in accordance with one form of the present technology.

Figure 5D:
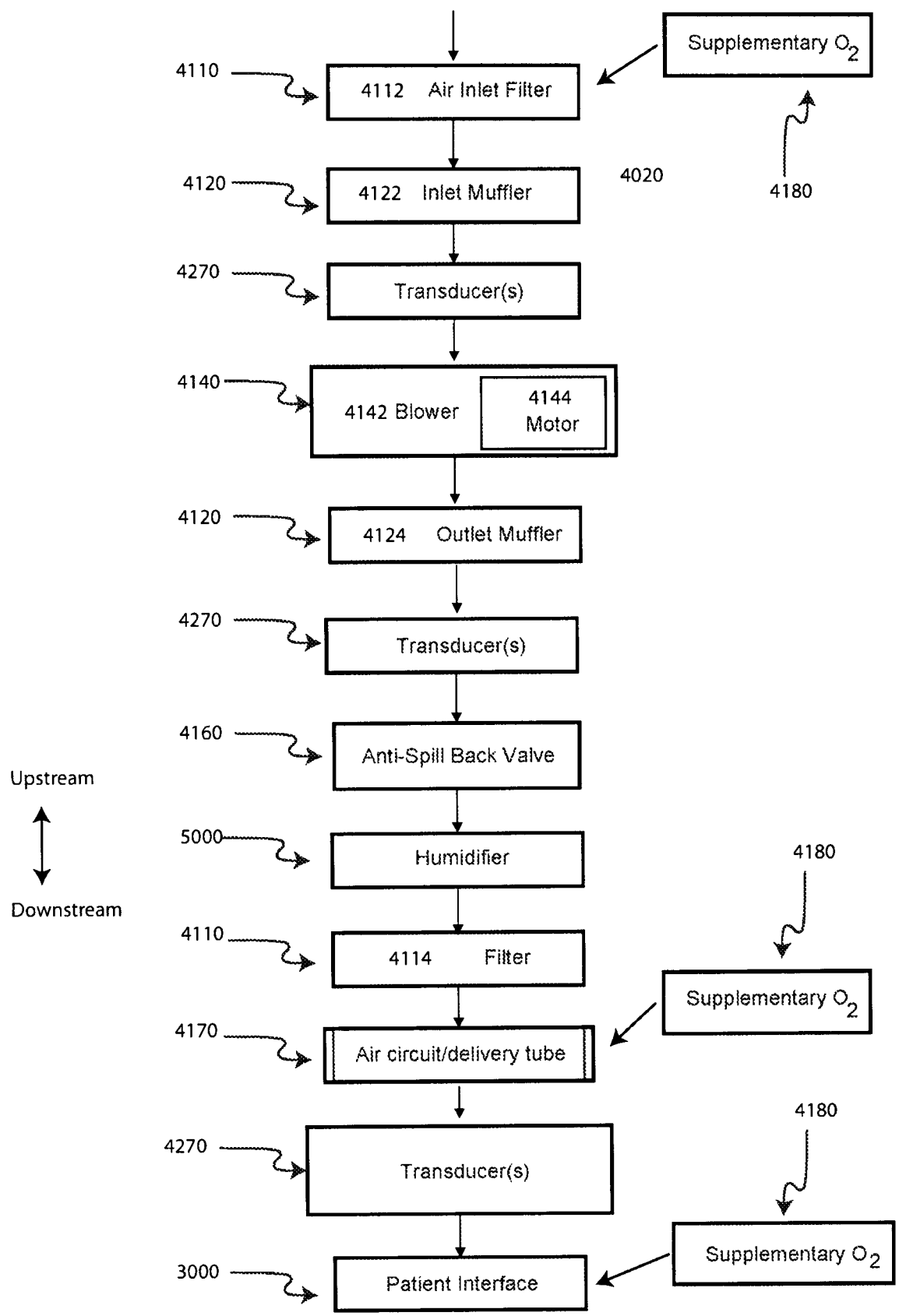

FIG. 5d shows a schematic diagram of the pneumatic path of an RPT device in accordance with one form of the present technology. The directions of upstream and downstream are indicated.

Figure 5E:
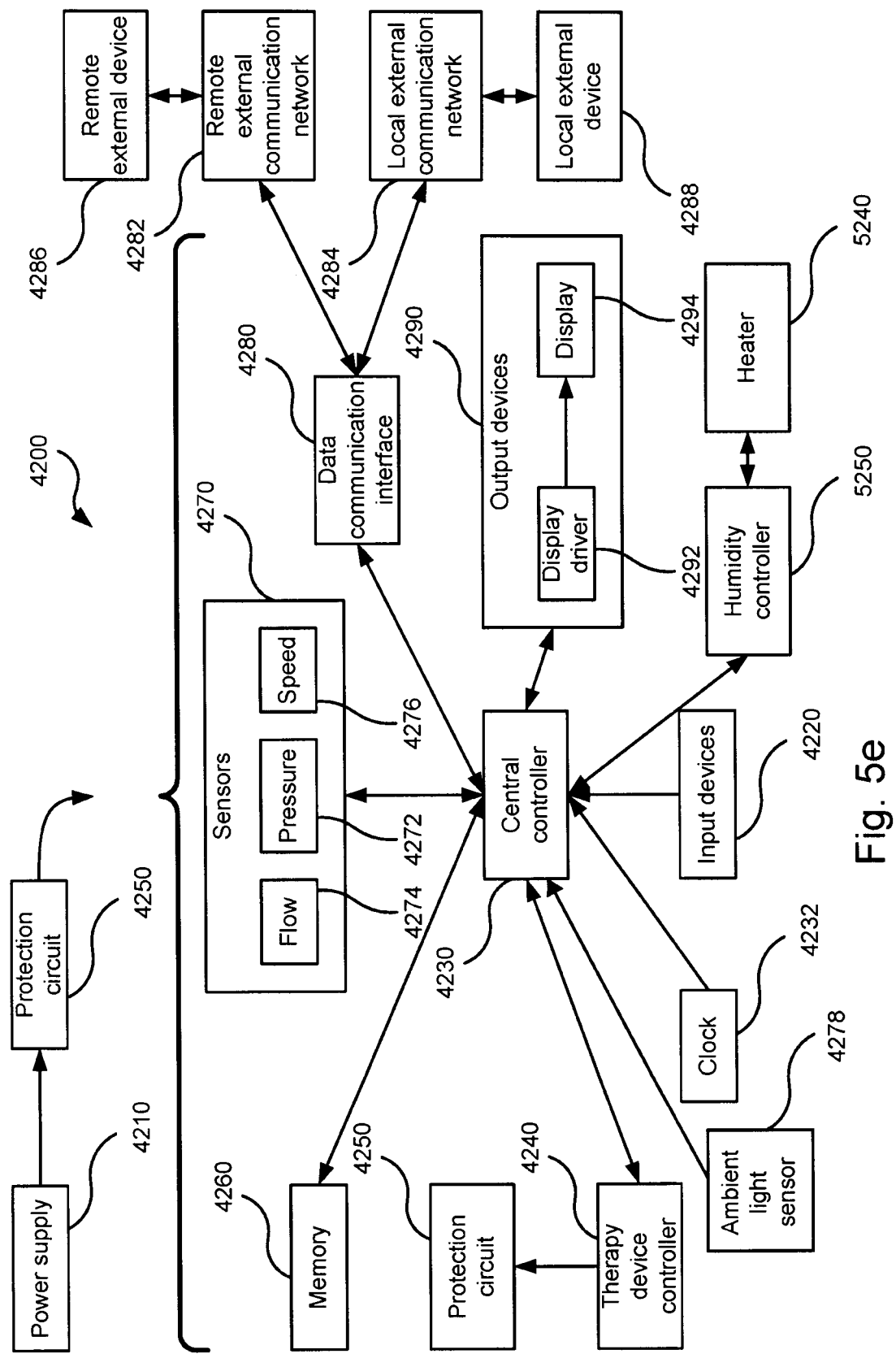

FIG. 5e shows a schematic diagram of the electrical components of an RPT device in accordance with one aspect of the present technology.

Figure 5F:
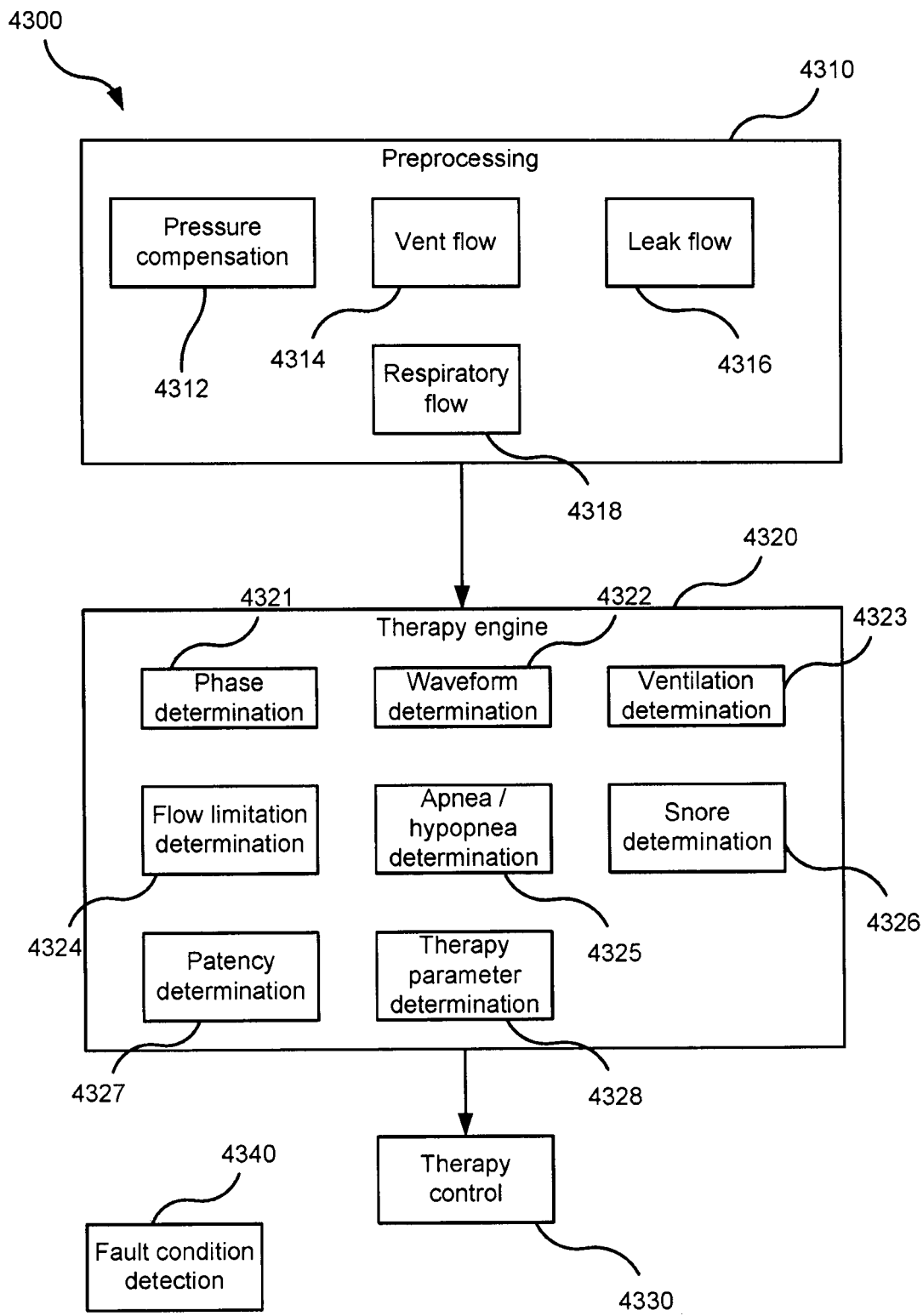

FIG. 5f shows a schematic diagram of the algorithms implemented in a PAP device in accordance with an aspect of the present technology. In this figure, arrows with solid lines indicate an actual flow of information, for example via an electronic signal.

Figure 5G:
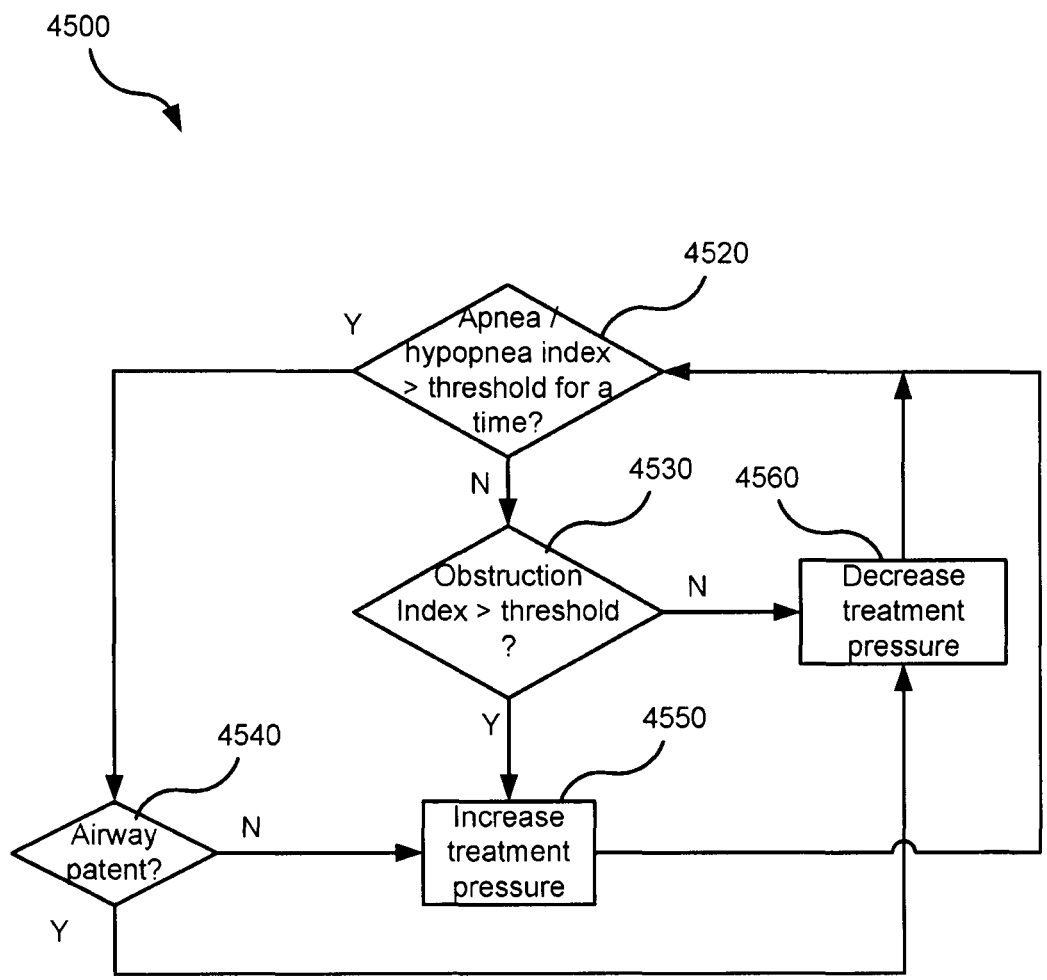

FIG. 5g is a flow chart illustrating a method carried out by the therapy engine of FIG. 5f in accordance with one aspect of the present technology.

Figure 5H:
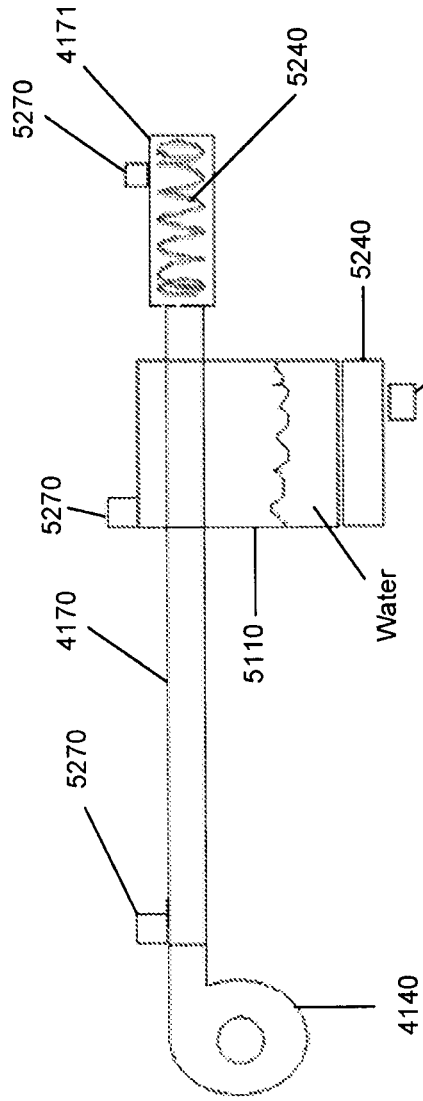

FIG. 5h shows a simplified representation of a humidifier connected to a blower and a patient conduit.

Figure 5I:
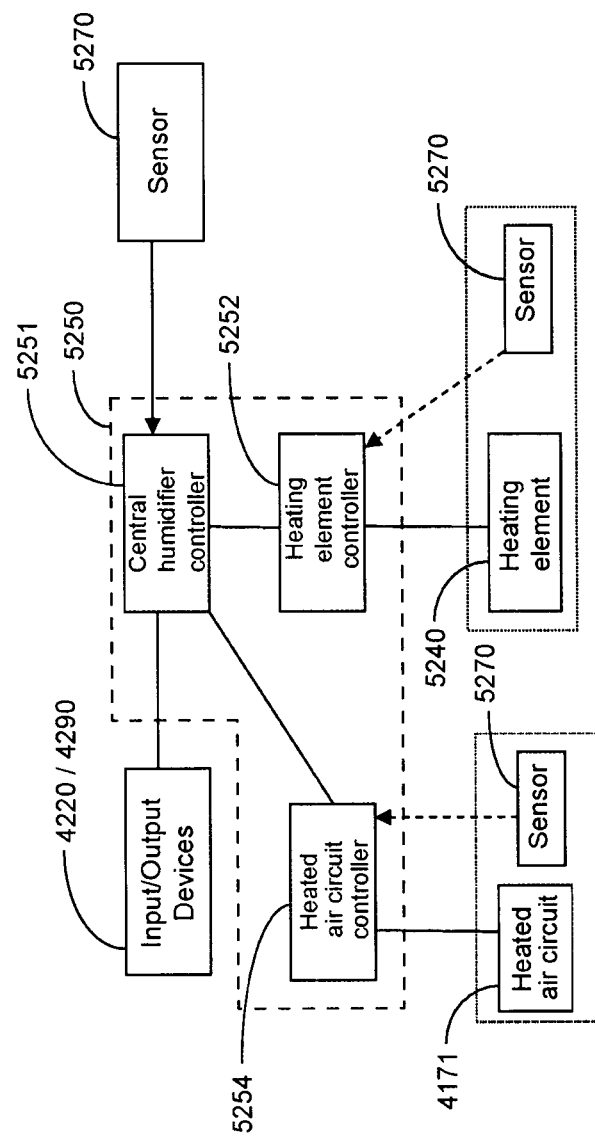

FIG. 5i shows a schematic of a humidifier.

Figure 6A:
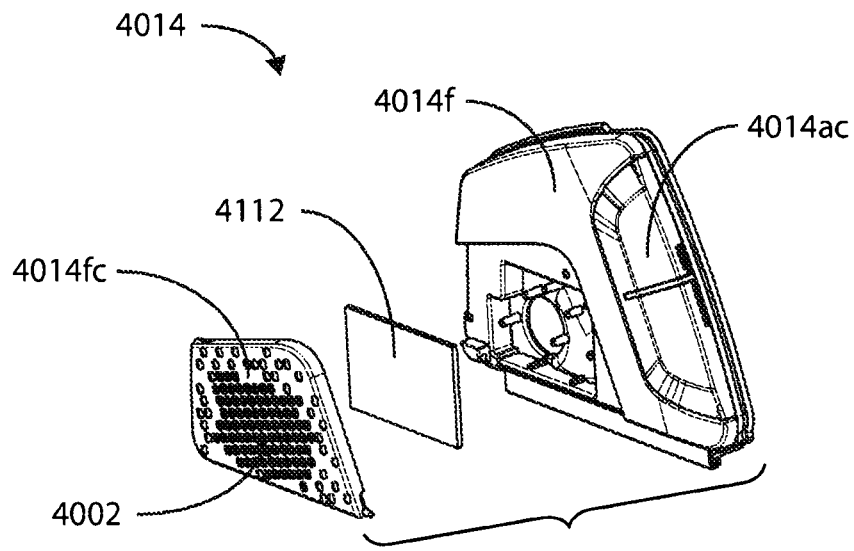

FIG. 6a shows a perspective view of a side panel 4014, showing the inlet air filter cover 4014fc and the inlet air filter 4112 in exploded view in accordance with one form of the present technology.

Figure 6B:
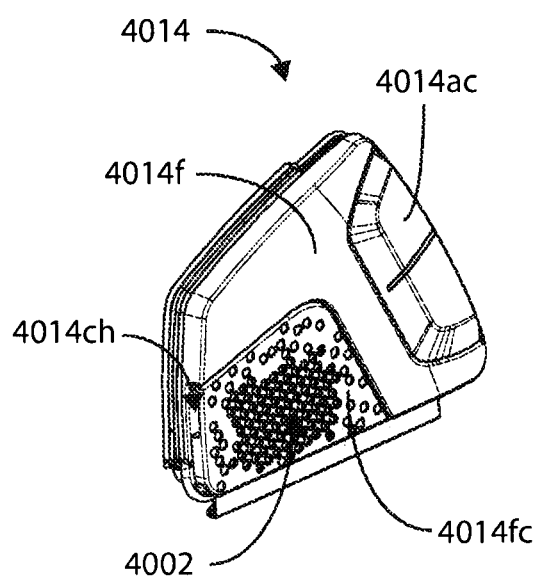

FIG. 6b shows a perspective view of a side panel 4014 including the RPT device inlet 4002 in accordance with one form of the present technology.

Figure 6C:
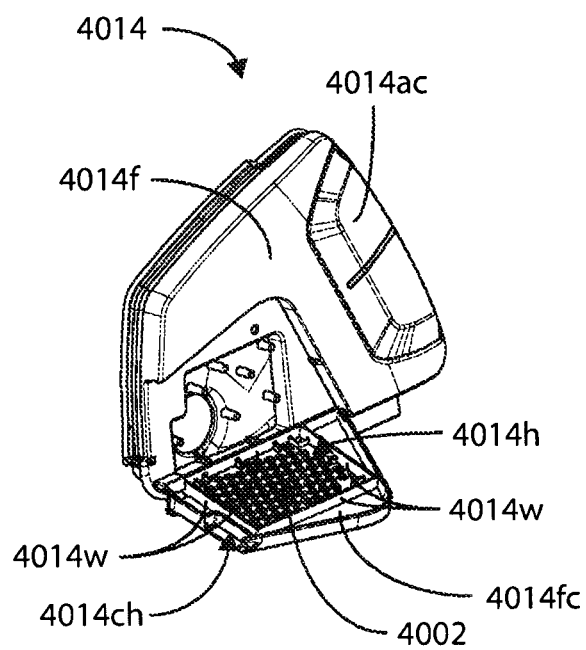

FIG. 6c shows a perspective view of a side panel 4014 showing the inlet air filter cover 4014fc in an open position in accordance with one form of the present technology.

Figure 6D:
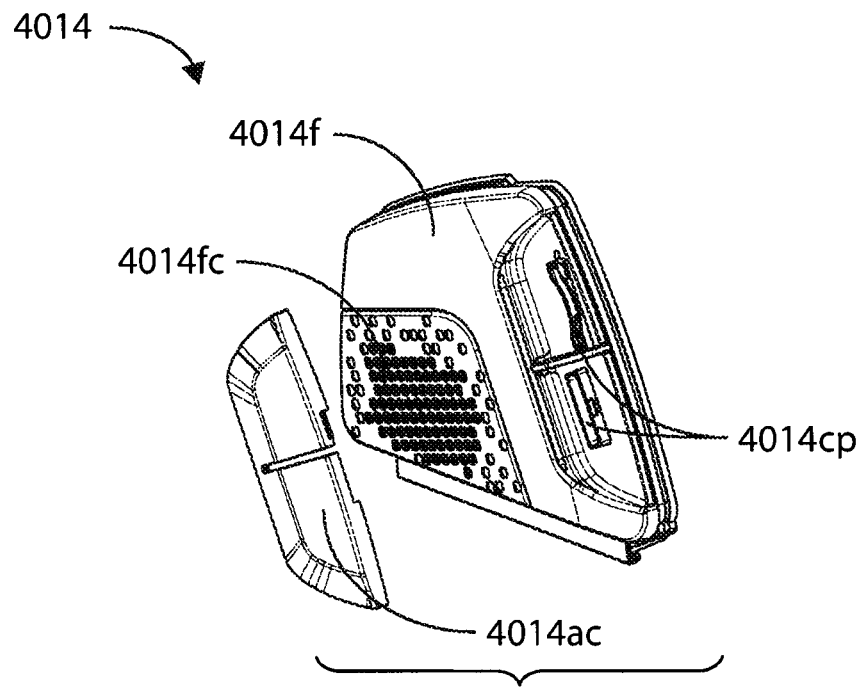

FIG. 6d shows a perspective view of a side panel 4014, showing the access covers 4014ac in exploded view in accordance with one form of the present technology.

Figure 6E:
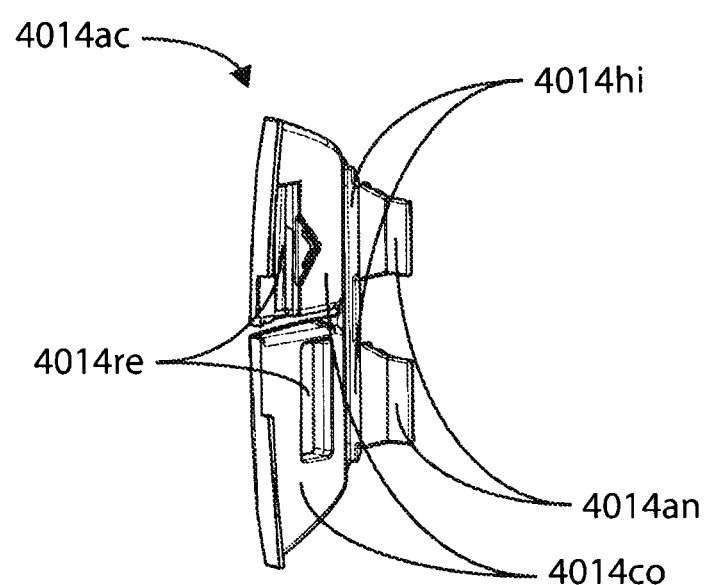

FIG. 6e shows a perspective view of the access covers 4014ac in accordance with one form of the present technology.

Figure 7A:
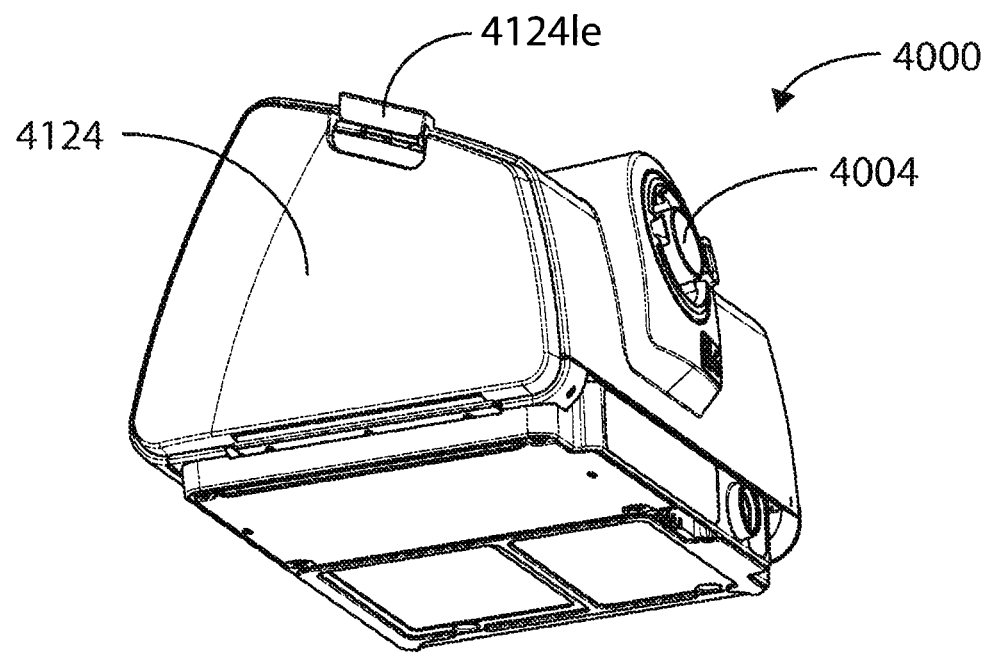

FIG. 7a shows a side perspective view of an RPT device 4000 comprising an outlet muffler 4124 in accordance with one form of the present technology.

Figure 7B:
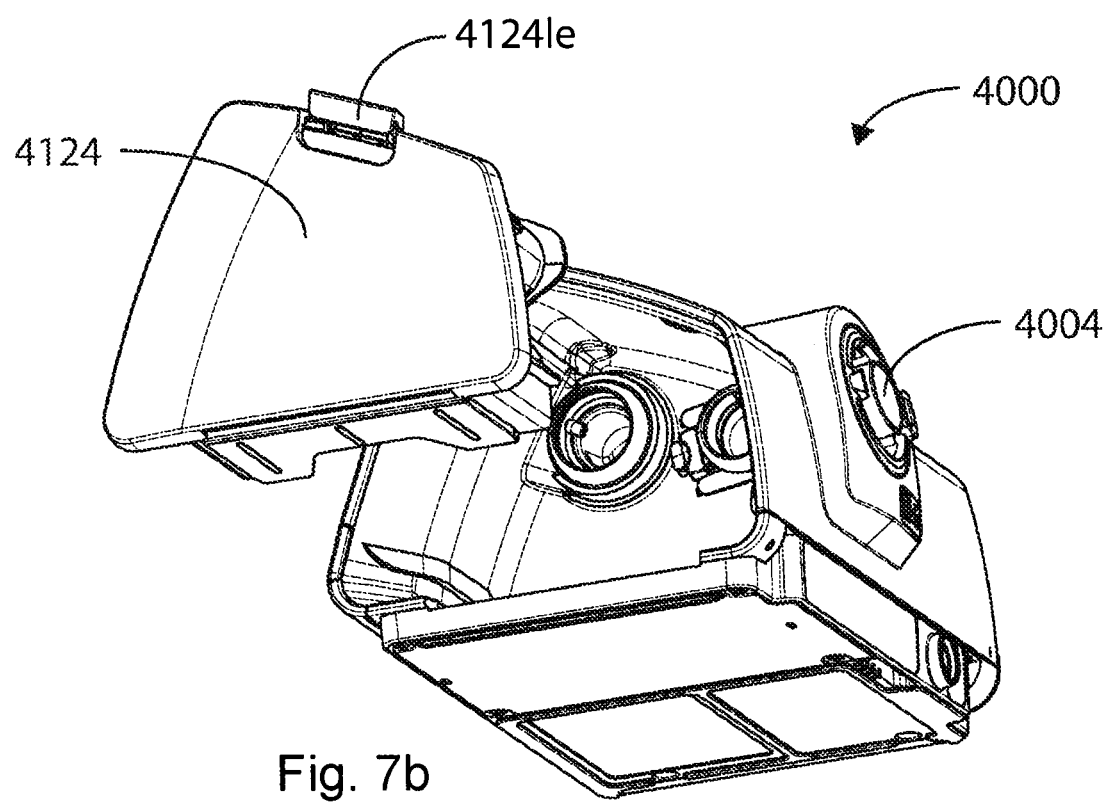

FIG. 7b shows a side perspective view of an RPT device 4000 showing an outlet muffler 4124 in exploded view in accordance with one form of the present technology.

Figure 7C:
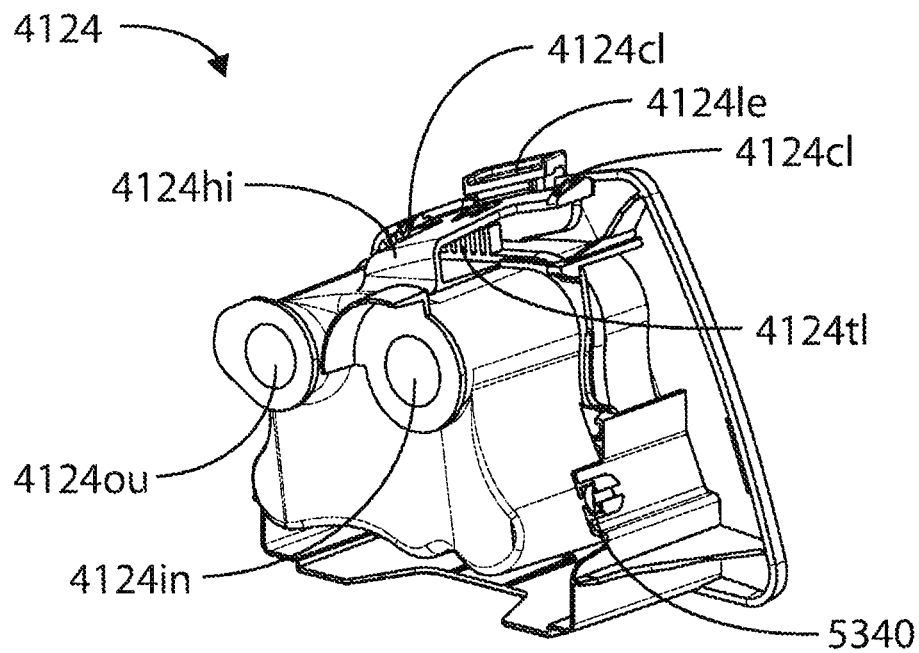

FIG. 7c shows a perspective view of an outlet muffler 4124 in accordance with one form of the present technology.

Figure 7D:
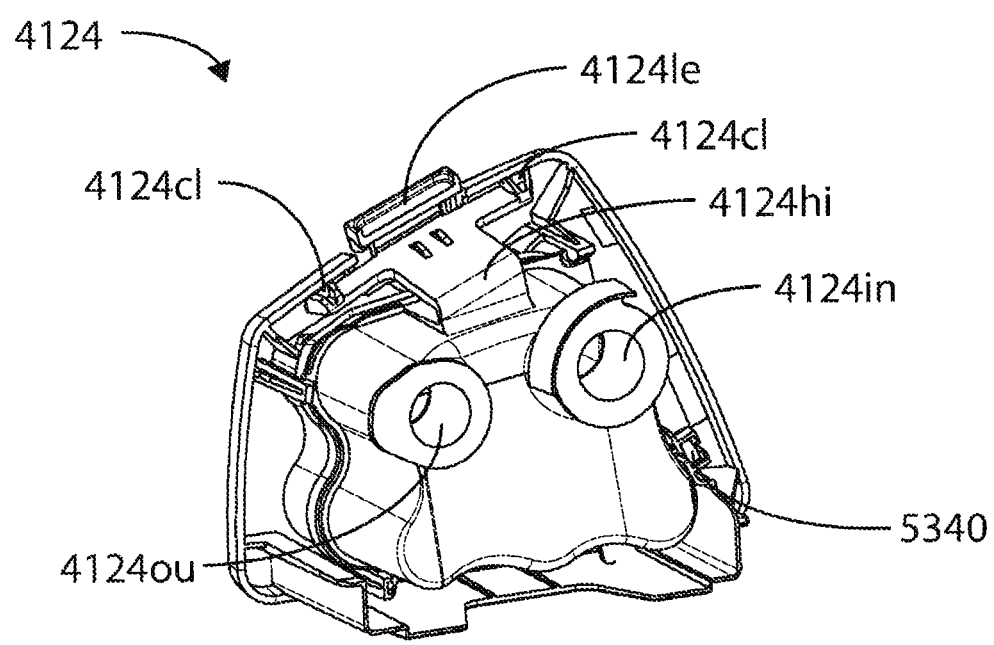

FIG. 7d shows another perspective view of an outlet muffler 4124 in accordance with one form of the present technology.

Figure 7E:
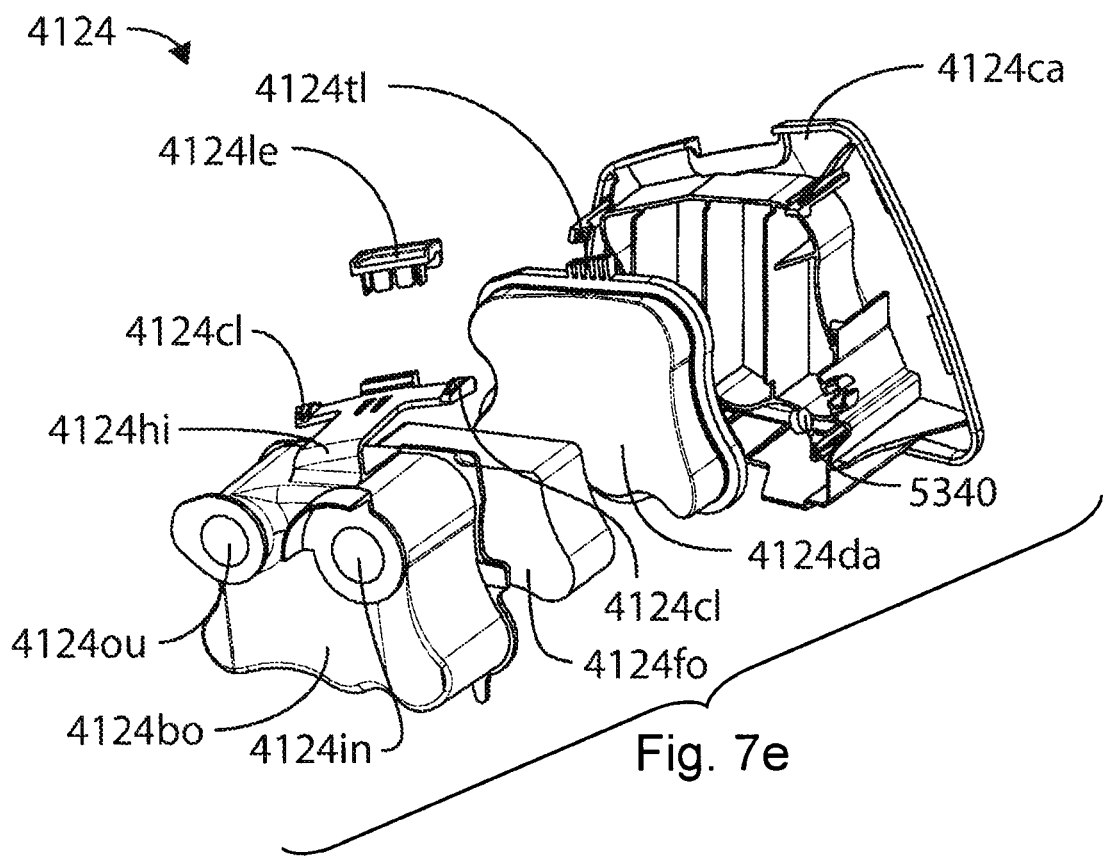

FIG. 7e shows an exploded perspective view of an outlet muffler 4124 in accordance with one form of the present technology.

Figure 7F:
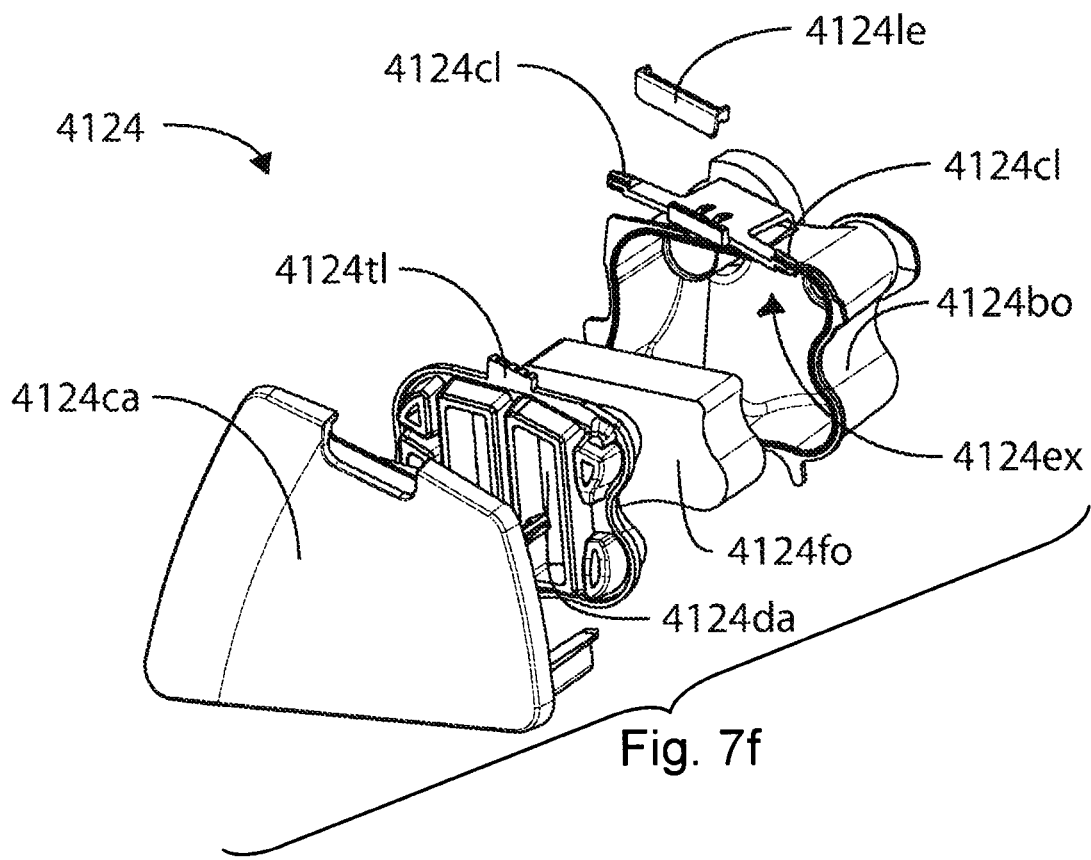

FIG. 7f shows another exploded perspective view of an outlet muffler 4124 in accordance with one form of the present technology.

Figure 8A:
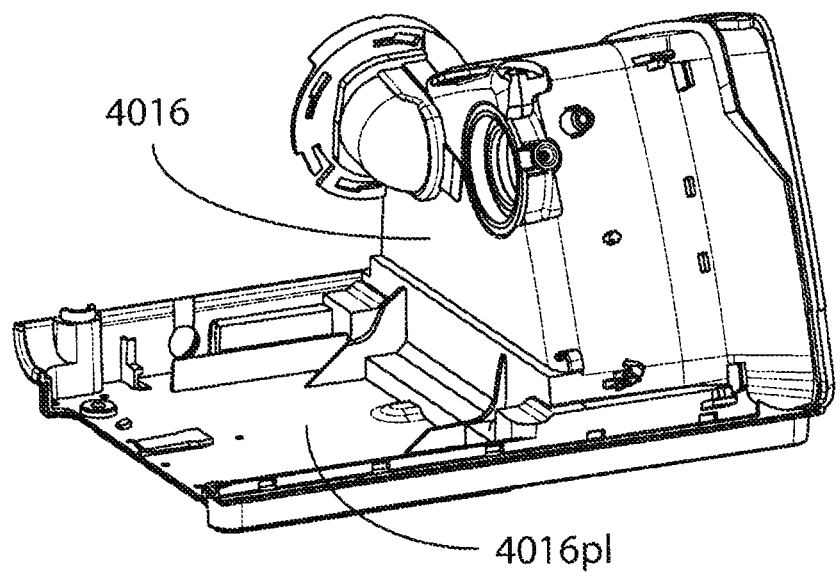

FIG. 8a shows a perspective view of a chassis 4016 in accordance with one form of the present technology.

Figure 8B:
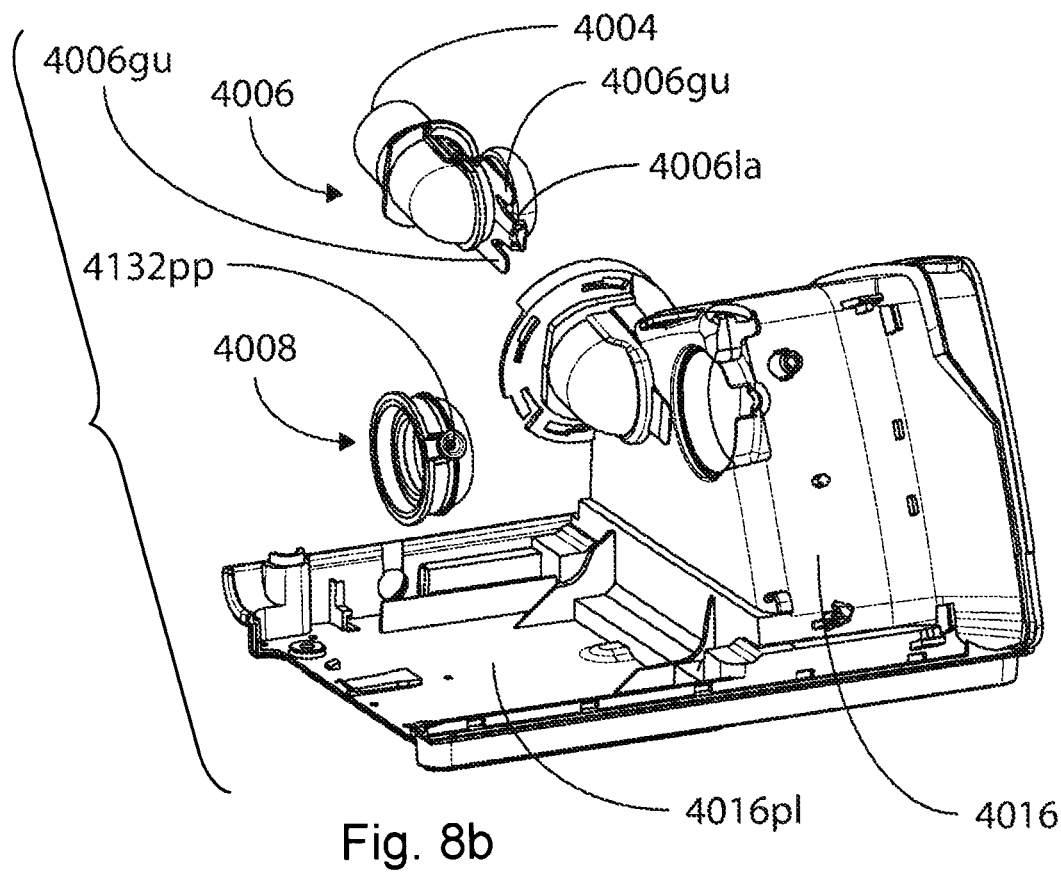

FIG. 8b shows a perspective view of a chassis 4016 showing an outlet tube 4006 and an intermediate tube 4008 in exploded view in accordance with one form of the present technology.

Figure 8C:
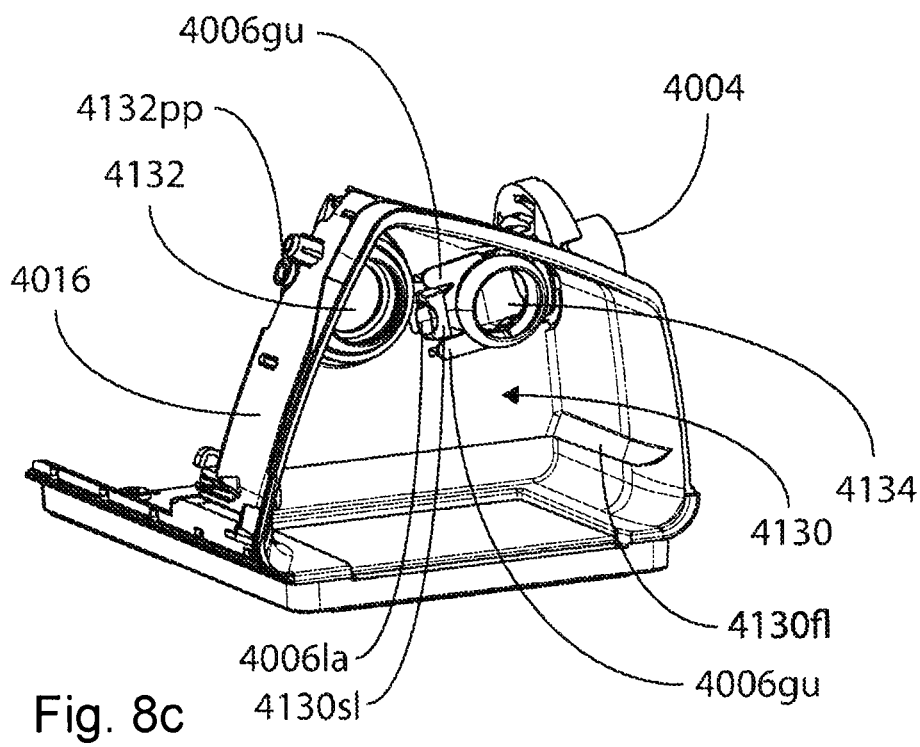

FIG. 8c shows a side perspective view of a chassis 4016 in accordance with one form of the present technology.

Figure 8D:
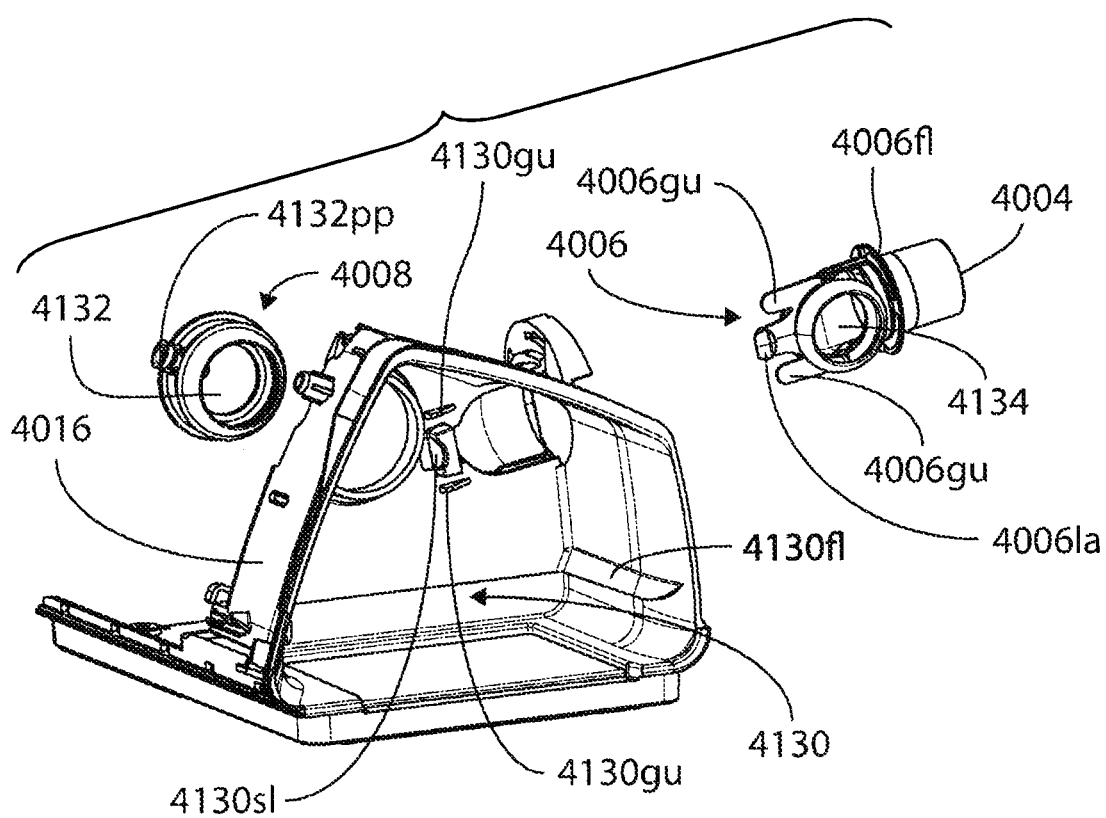

FIG. 8d shows a side perspective view of a chassis 4016 showing an outlet tube 4006 and an intermediate tube 4008 in exploded view in accordance with one form of the present technology.

Figure 8E:
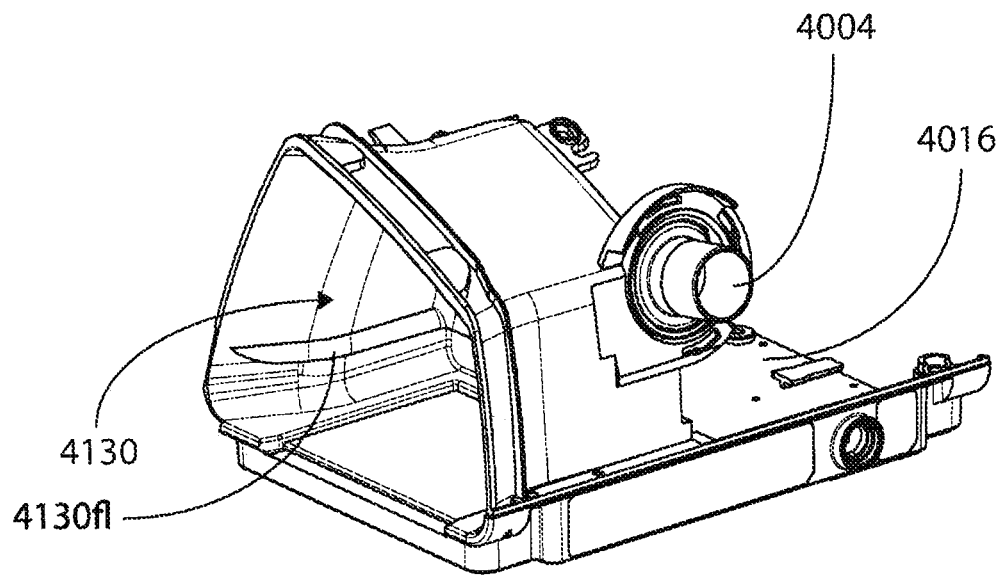

FIG. 8e shows a rear perspective view of a chassis 4016 in accordance with one form of the present technology.

Figure 8F:
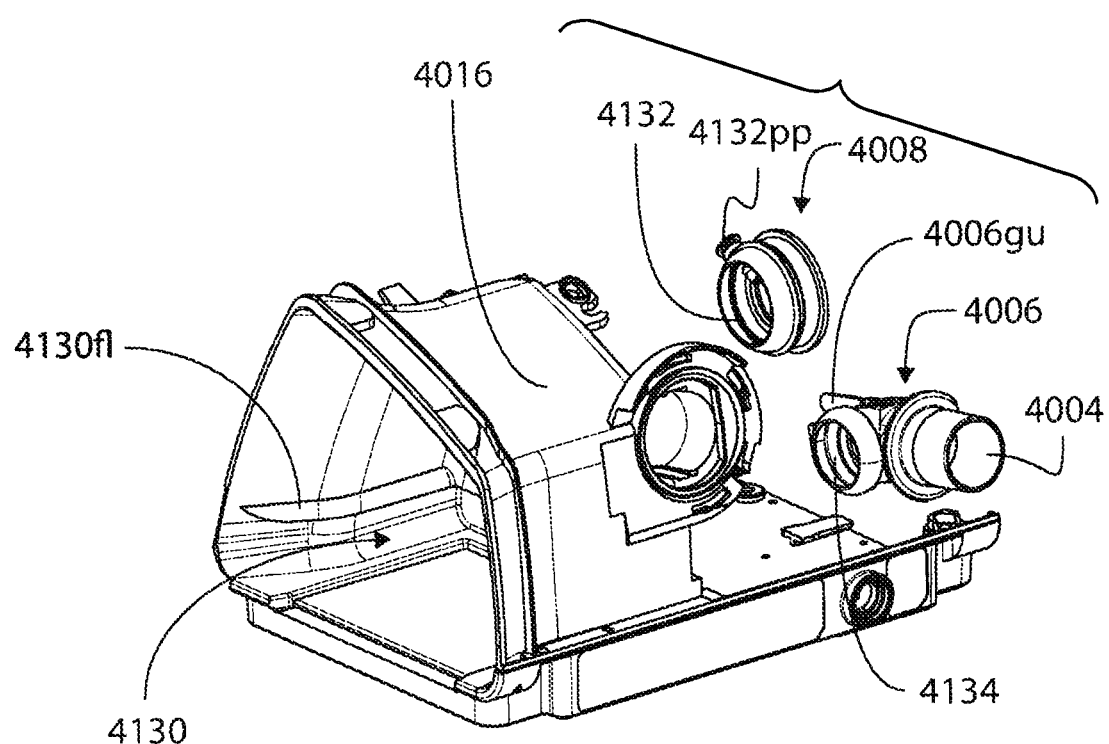

FIG. 8f shows a rear perspective view of a chassis 4016 showing an outlet tube 4006 and an intermediate tube 4008 in exploded view in accordance with one form of the present technology.

Figure 8G:
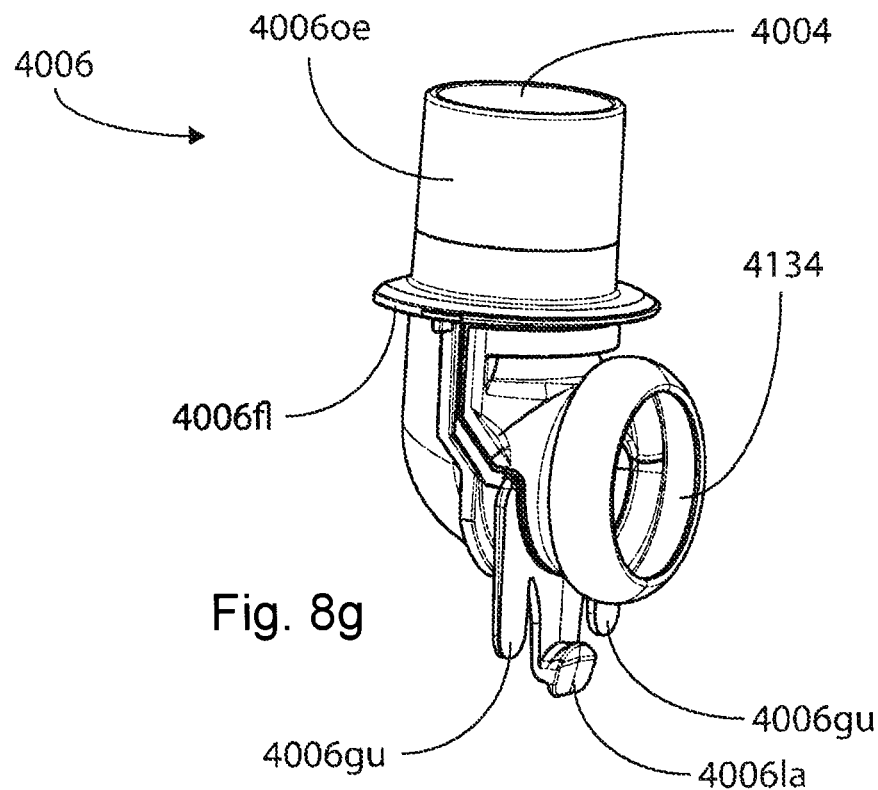

FIG. 8g shows a perspective view of the outlet tube 4006 in accordance with one form of the present technology.

Figure 8H:
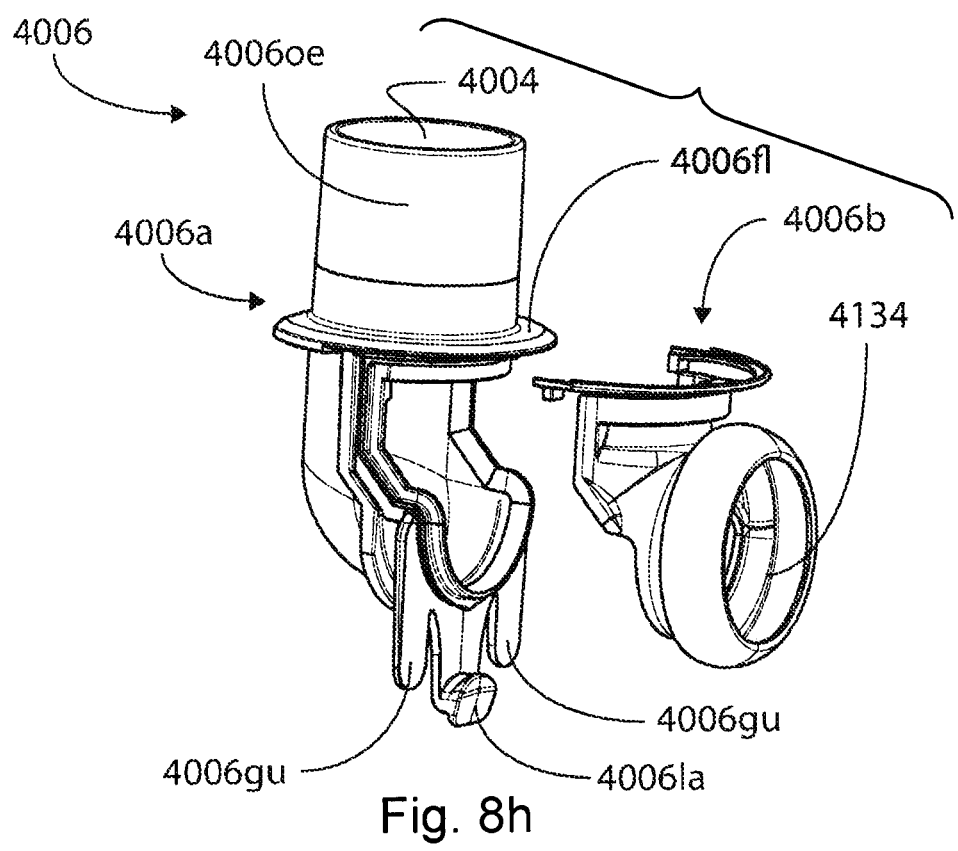

FIG. 8h shows an exploded perspective view of the outlet tube 4006 in accordance with one form of the present technology.

Figure 9A:
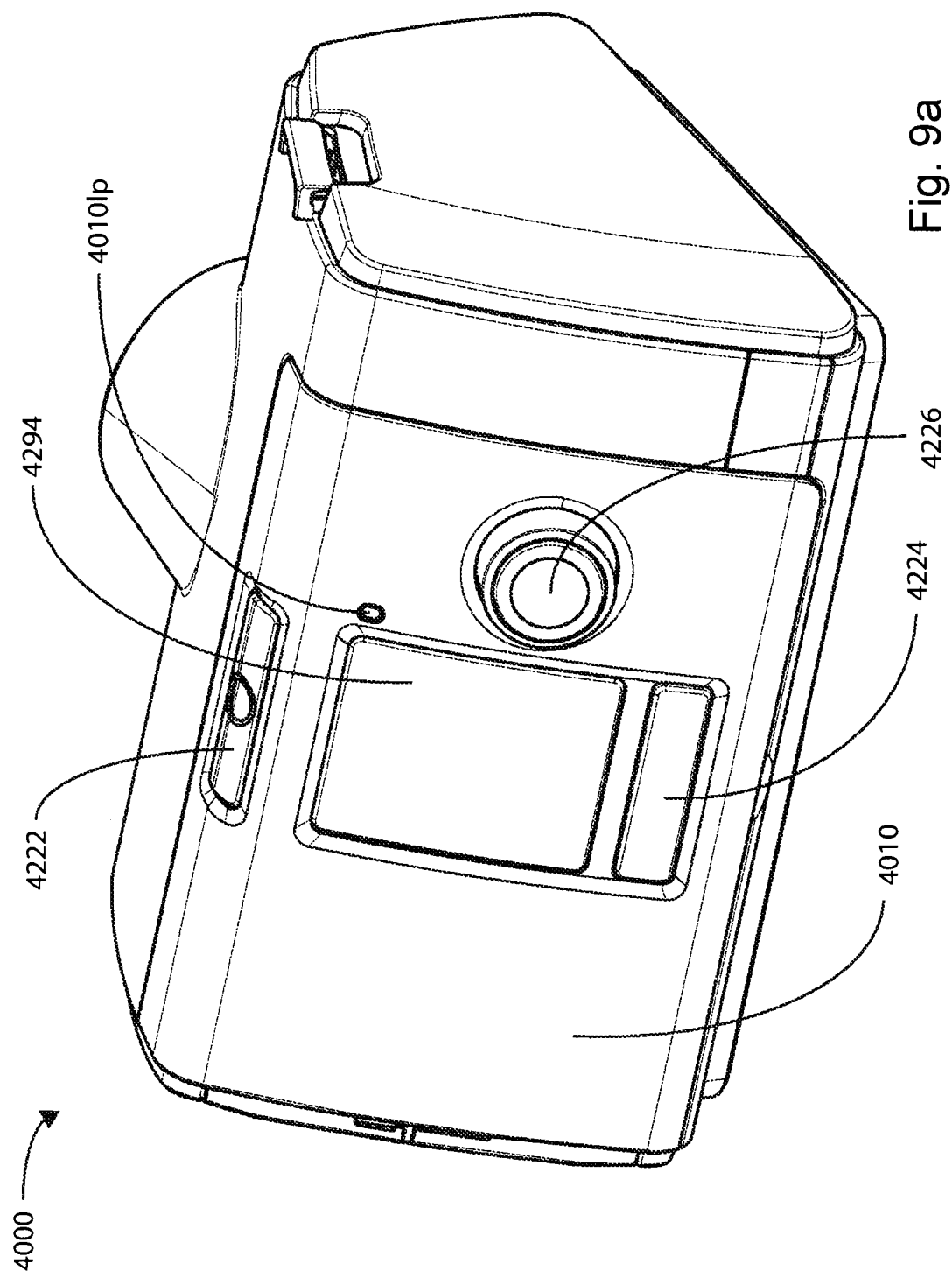

FIG. 9a shows a front perspective view of an RPT device 4000 in accordance with one form of the present technology.

Figure 10A:
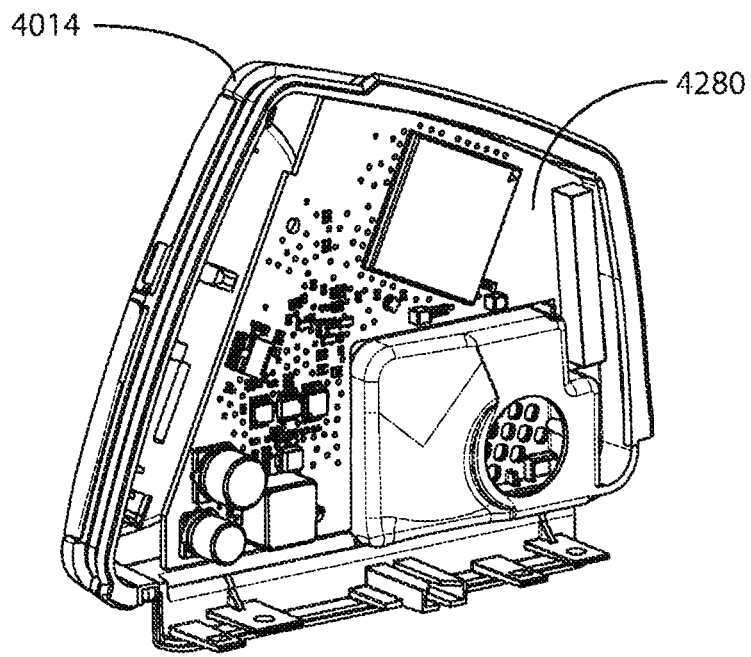

FIG. 10a shows a perspective view of a side panel 4014 including a data communication interface 4280 in accordance with one form of the present technology.

Figure 10B:
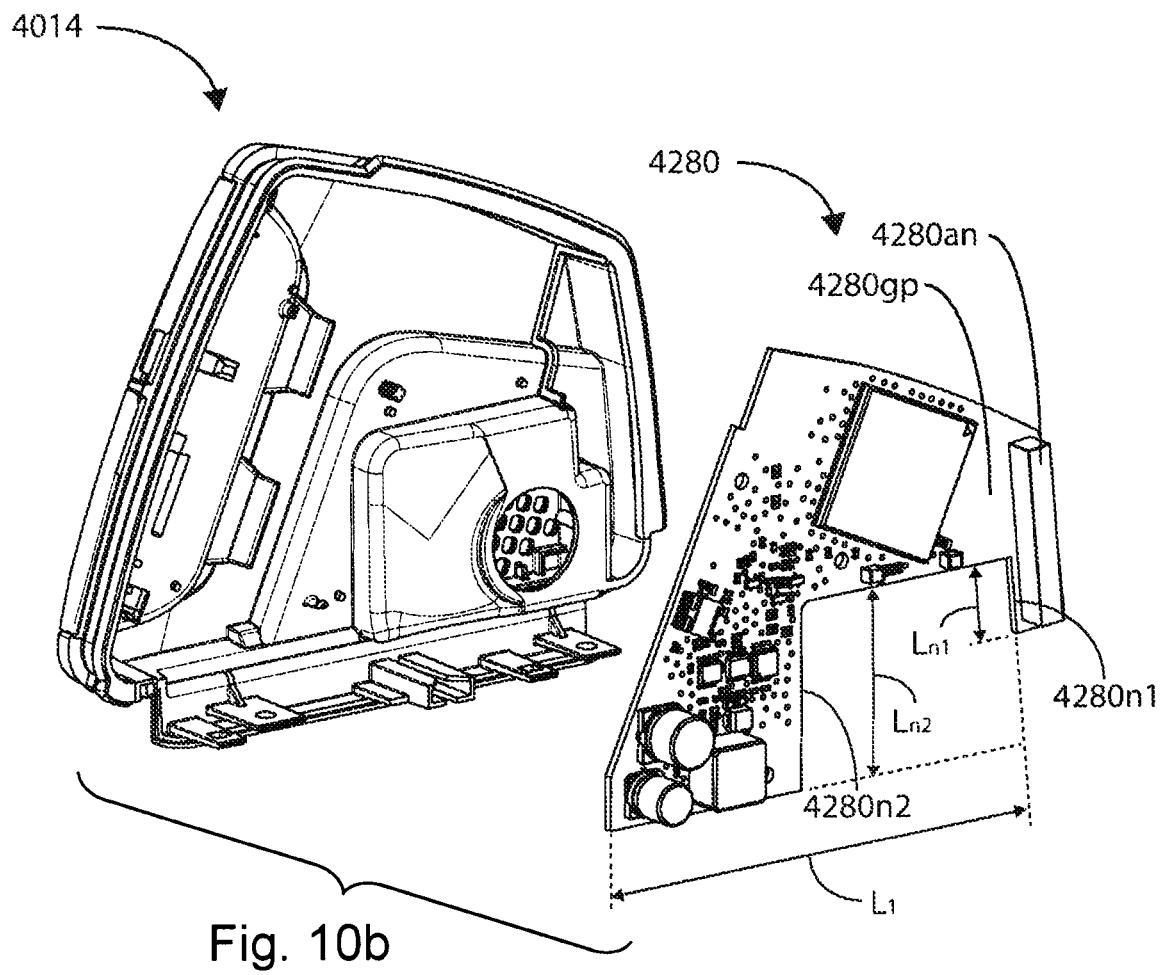

FIG. 10b shows an exploded perspective view of a side panel 4014 including a data communication interface 4280 in accordance with one form of the present technology.

Figure 11A:
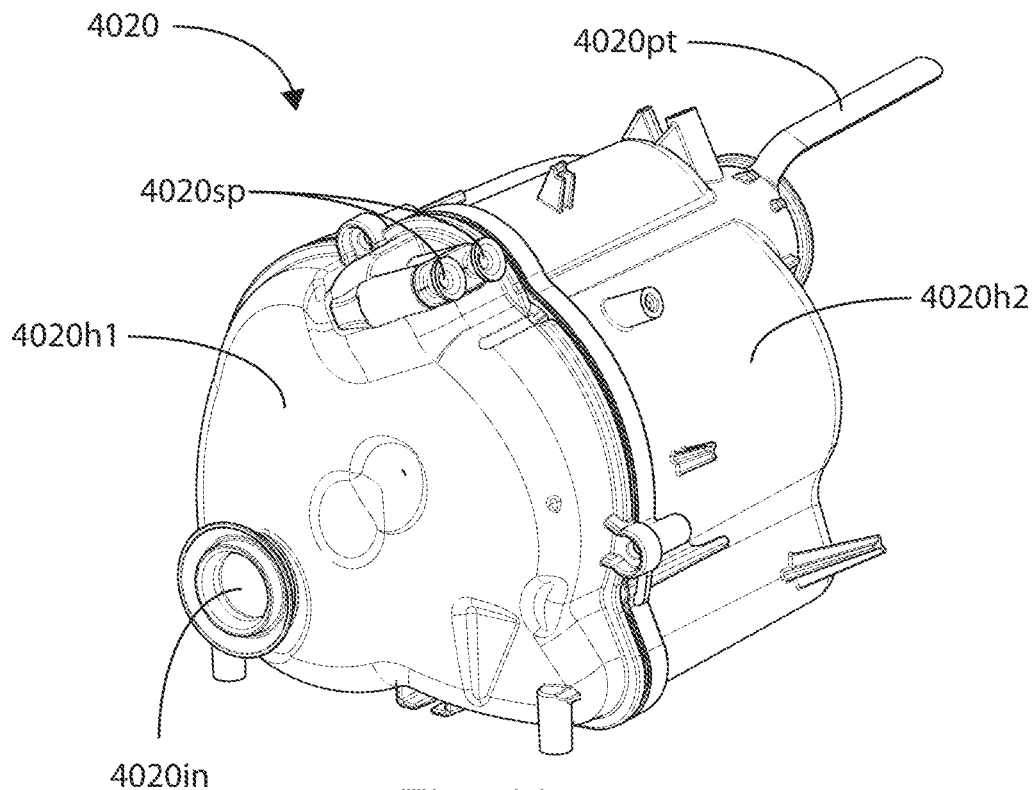

FIG. 11a shows a perspective view of a pneumatic block 4020 in accordance with one form of the present technology.

Figure 11B:
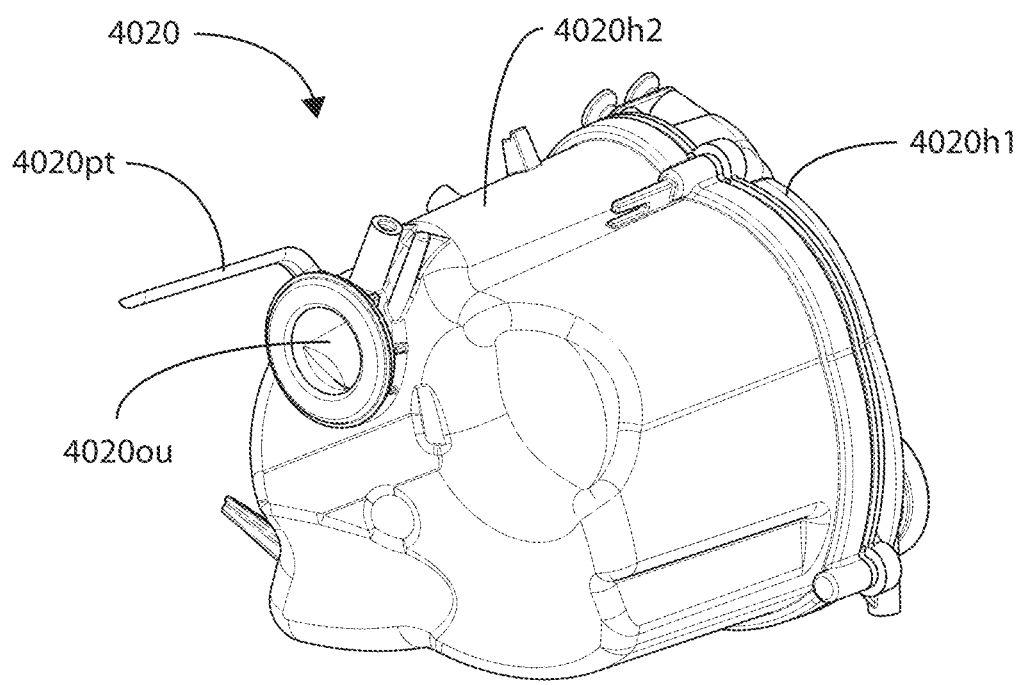

FIG. 11b shows another perspective view of a pneumatic block 4020 in accordance with one form of the present technology.

Figure 11C:
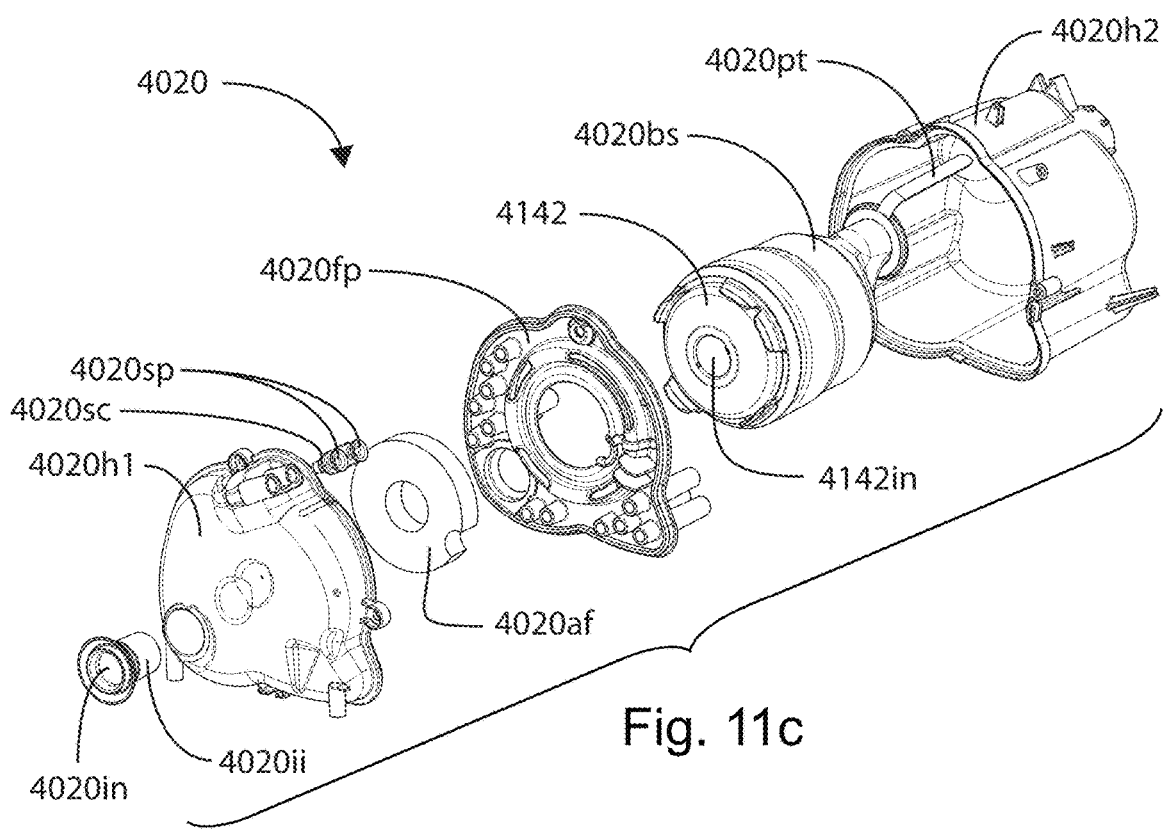

FIG. 11c shows an exploded perspective view of a pneumatic block 4020 in accordance with one form of the present technology.

Figure 11D:
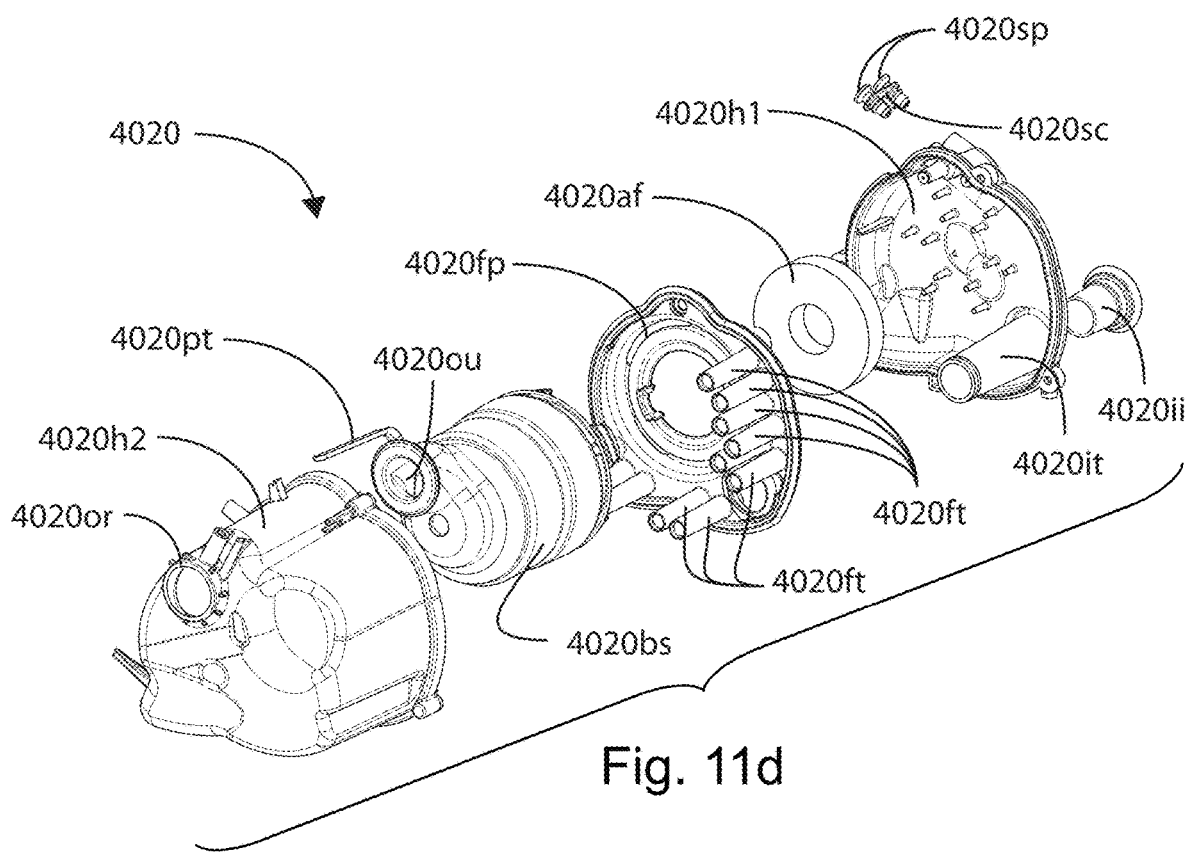

FIG. 11d shows another exploded perspective view of a pneumatic block 4020 in accordance with one form of the present technology.

Figure 11E:
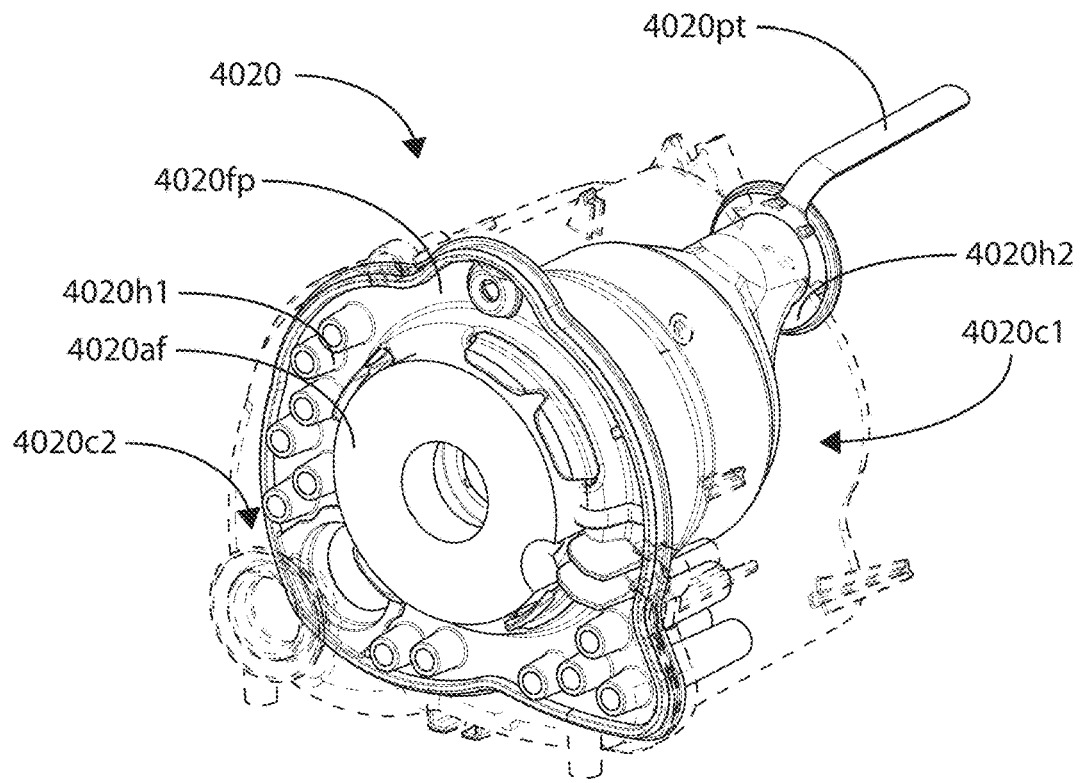

FIG. 11e shows a perspective view of a pneumatic block 4020 in accordance with one form of the present technology, showing the first PB housing 4020h1 and the second PB housing 4020h2 in phantom.

Figure 11F:
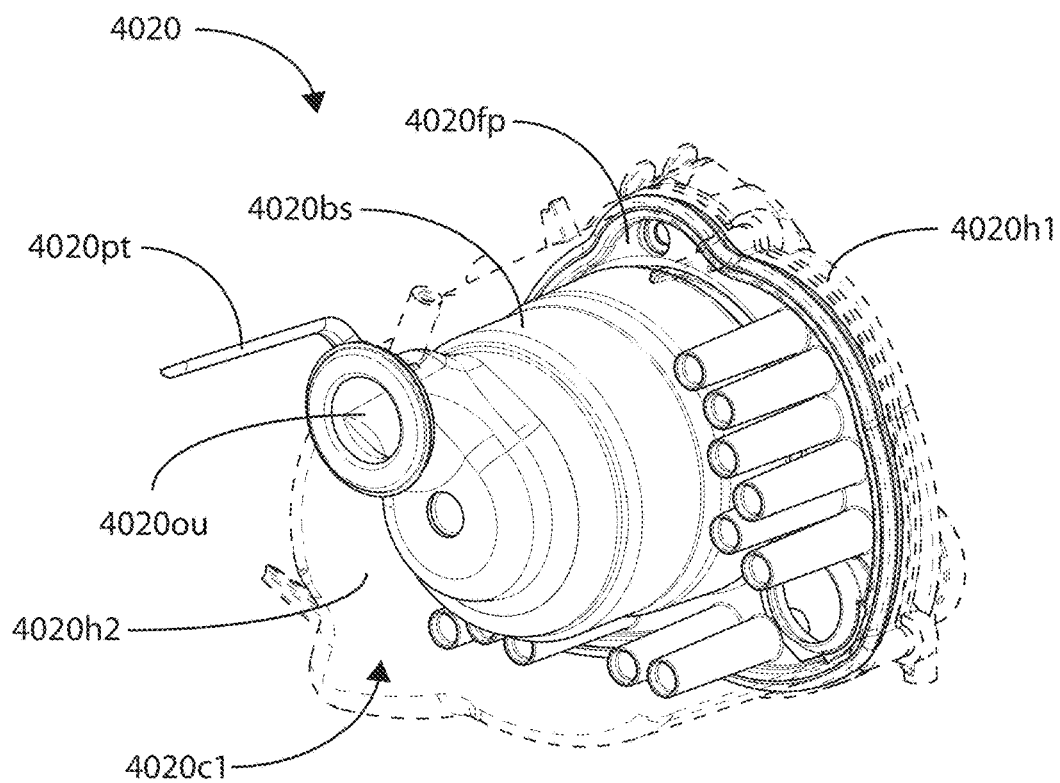

FIG. 11f shows another perspective view of a pneumatic block 4020 in accordance with one form of the present technology, showing the first PB housing 4020h1 and the second PB housing 4020h2 in phantom.

Figure 11G:
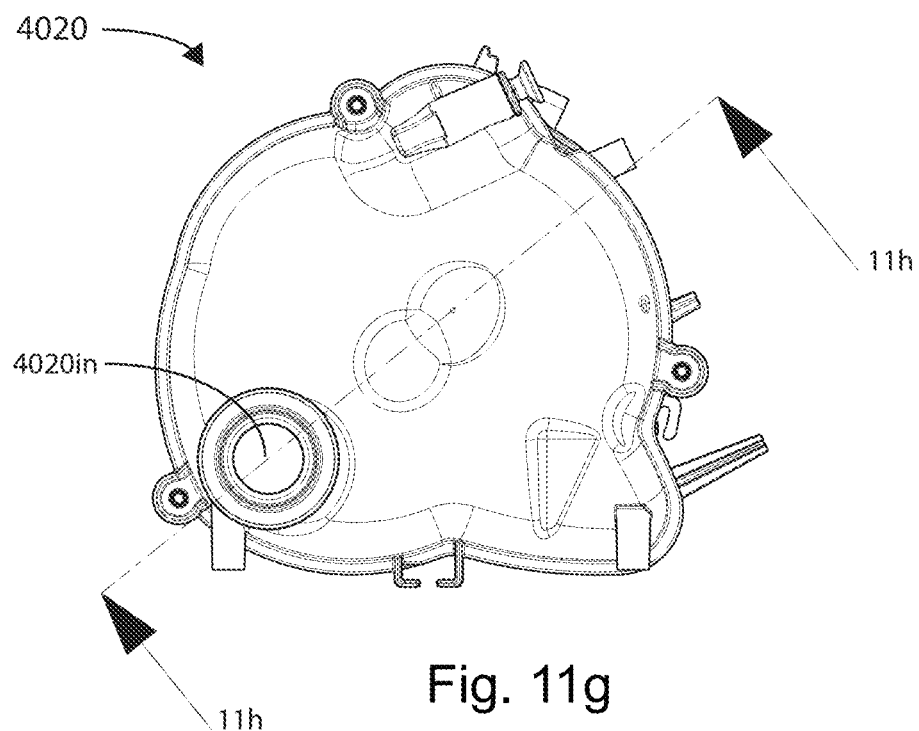
Figure 11H:
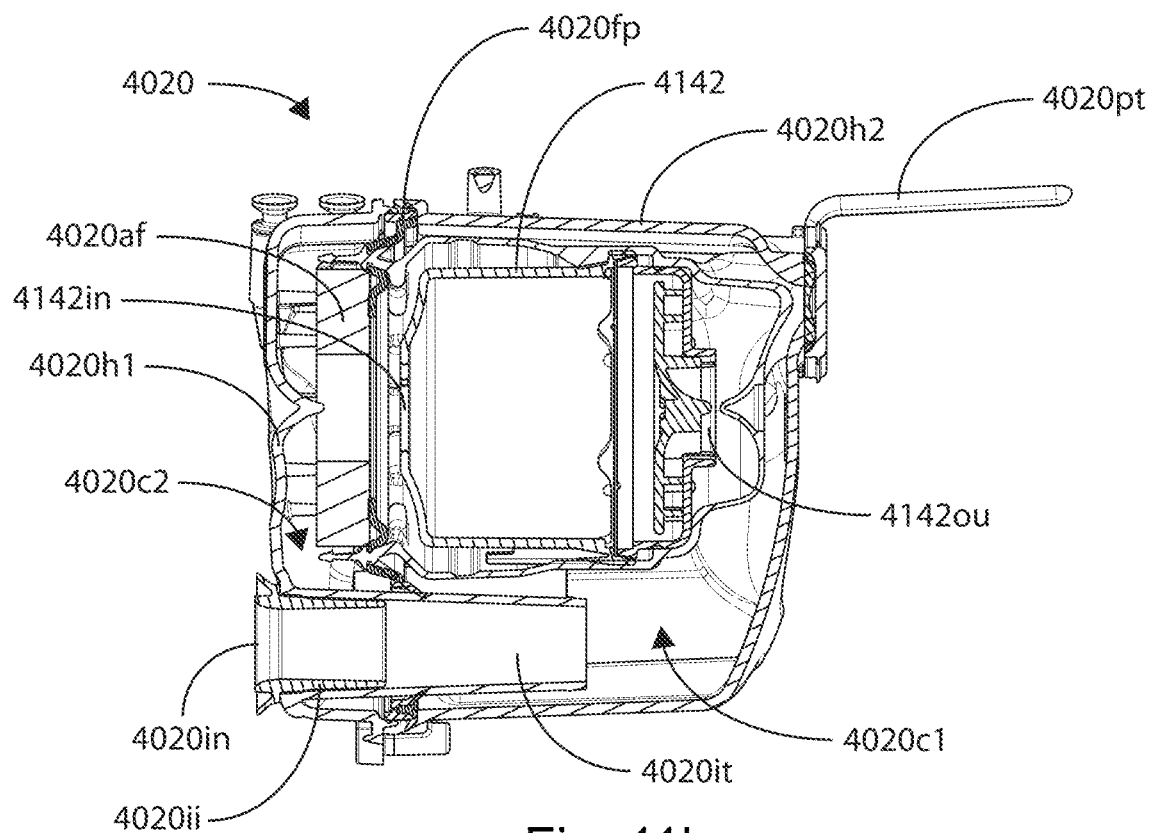

FIG. 11g shows an elevation view of a pneumatic block 4020 in accordance with one form of the present technology, showing the cross-section taken in FIG. 11h.

FIG. 11h shows a cross-section view of a pneumatic block 4020 in accordance with one form of the present technology as indicated on FIG. 11g.

Figure 11I:
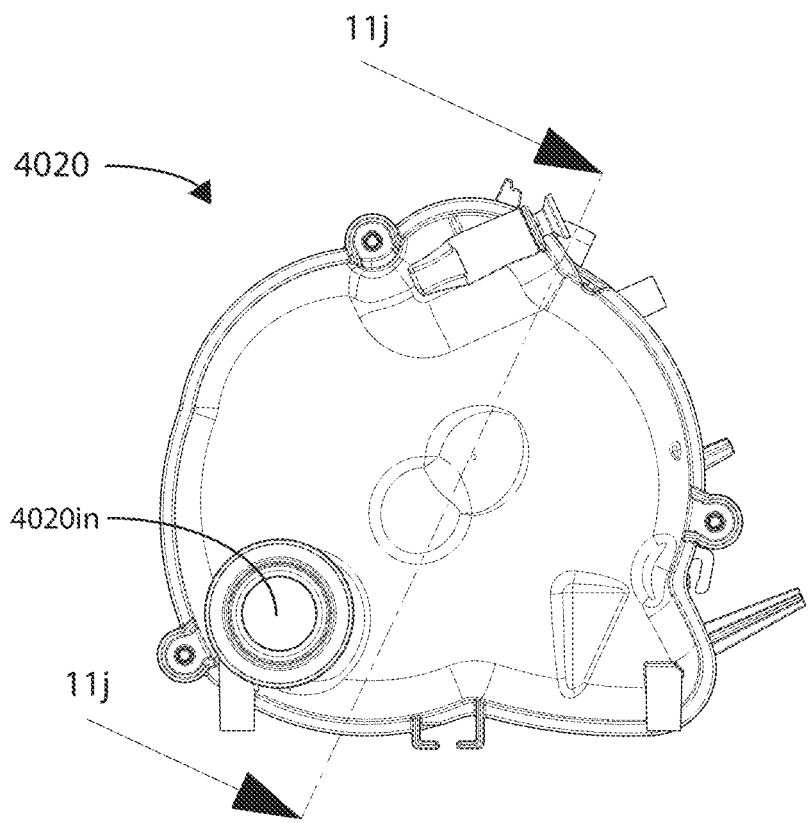
Figure 11J:
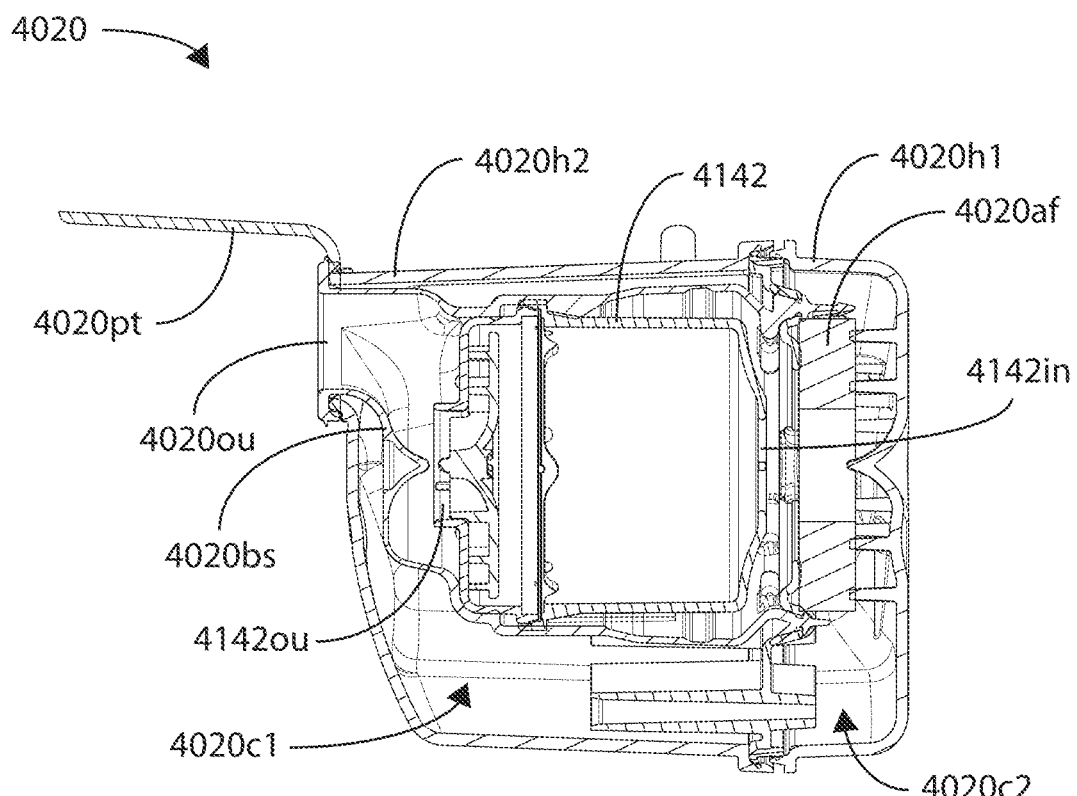

FIG. 11i shows an elevation view of a pneumatic block 4020 in accordance with one form of the present technology, showing the cross-section taken in FIG. 11j.

FIG. 11j shows a cross-section view of a pneumatic block 4020 in accordance with one form of the present technology as indicated on FIG. 11i.

Figure 11K:
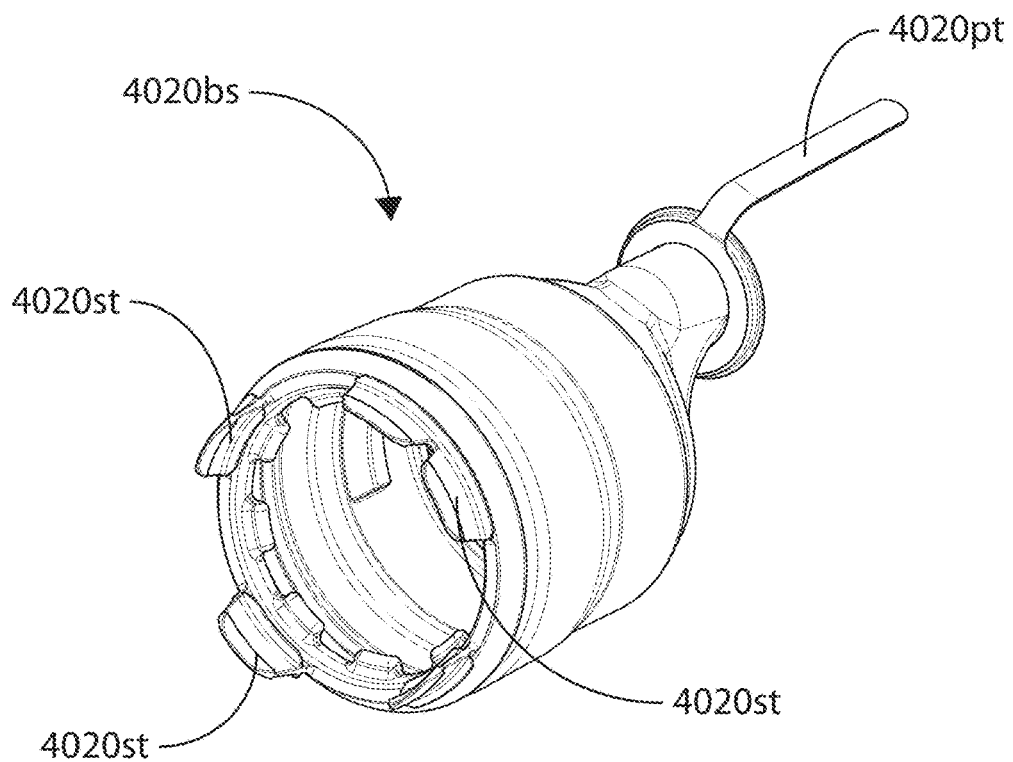

FIG. 11k shows a perspective view of a blower sleeve 4020bs in accordance with one form of the present technology.

Figure 11L:
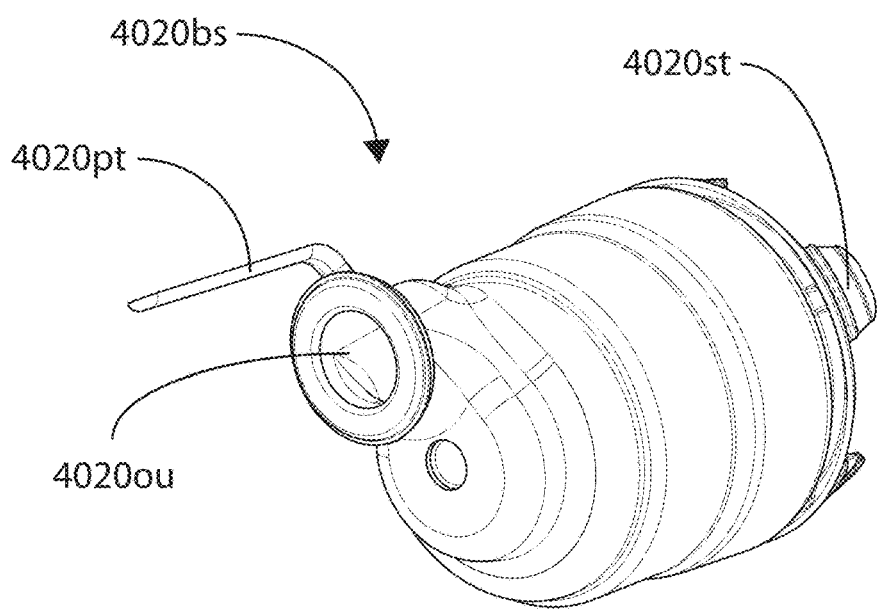

FIG. 11l shows another perspective view of a blower sleeve 4020bs in accordance with one form of the present technology.

Figure 11M:
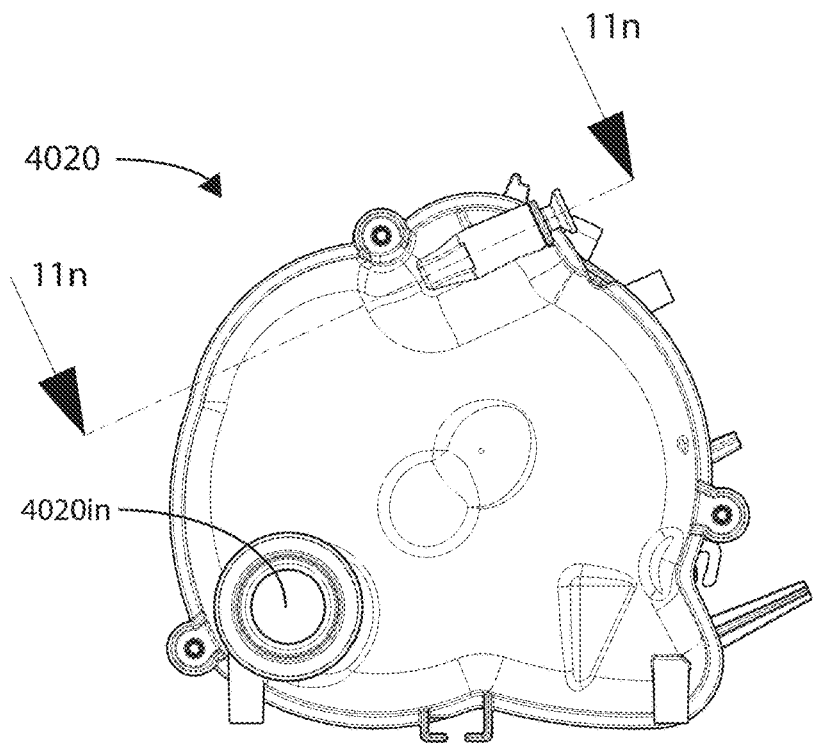
Figure 11N:
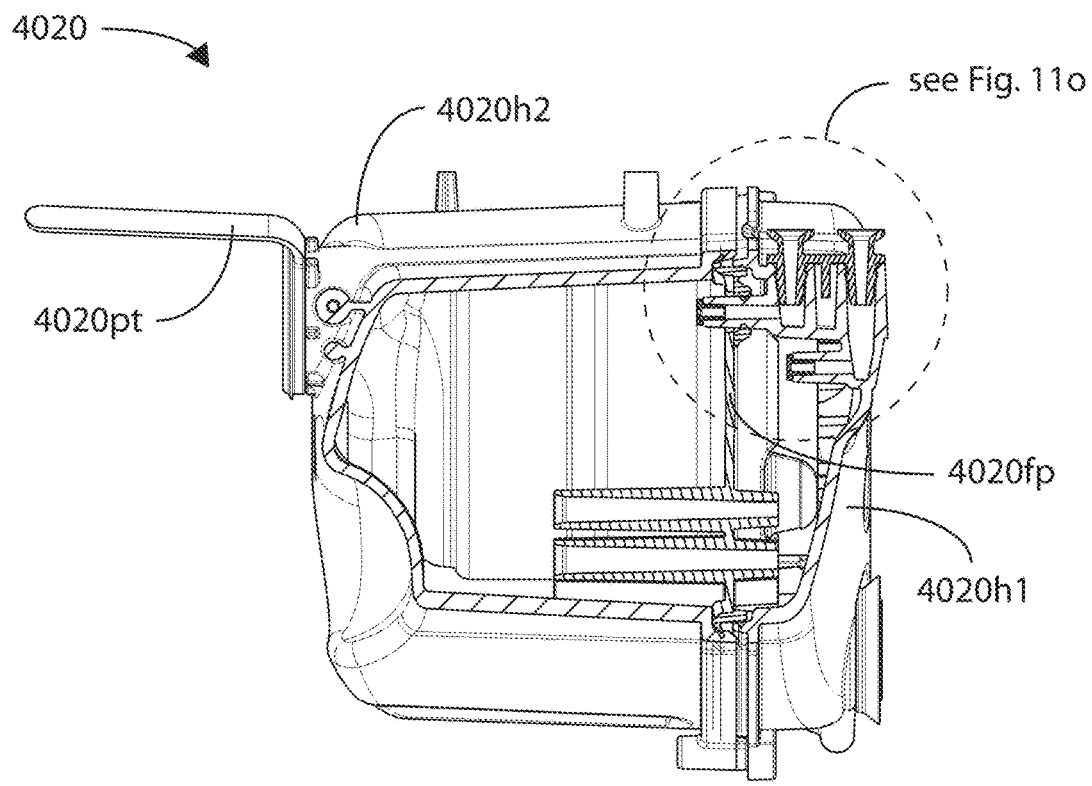

FIG. 11m shows a yet another elevation view of a pneumatic block 4020 in accordance with one form of the present technology, showing the cross-section taken in FIG. 11n.

FIG. 11n shows a cross-section view of a pneumatic block 4020 in accordance with one form of the present technology as indicated on FIG. 11m.

Figure 11O:
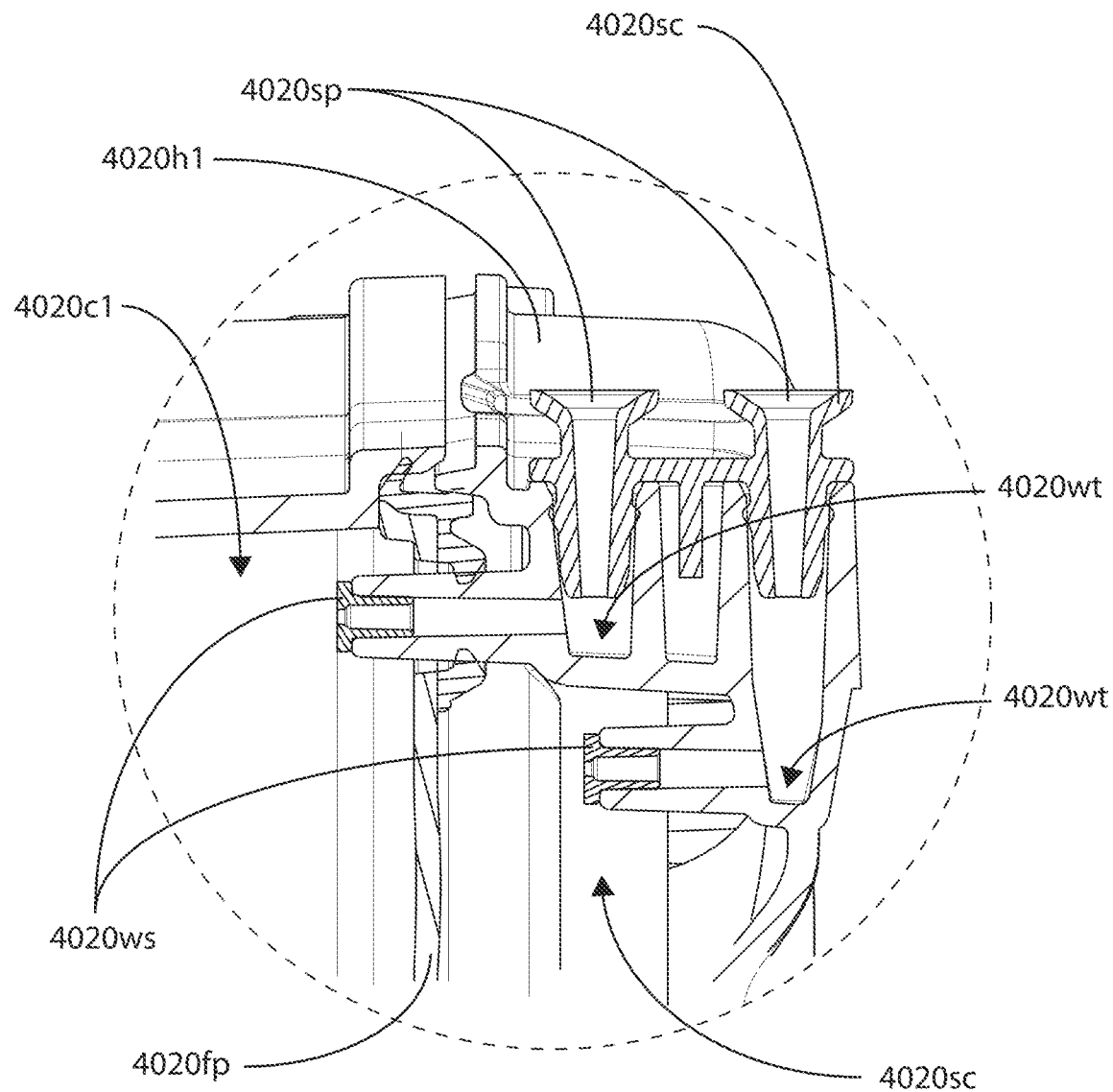

FIG. 11o shows a detailed cross-section view of a pneumatic block 4020 in accordance with one form of the present technology as indicated on FIG. 11n.

Figure 12A:
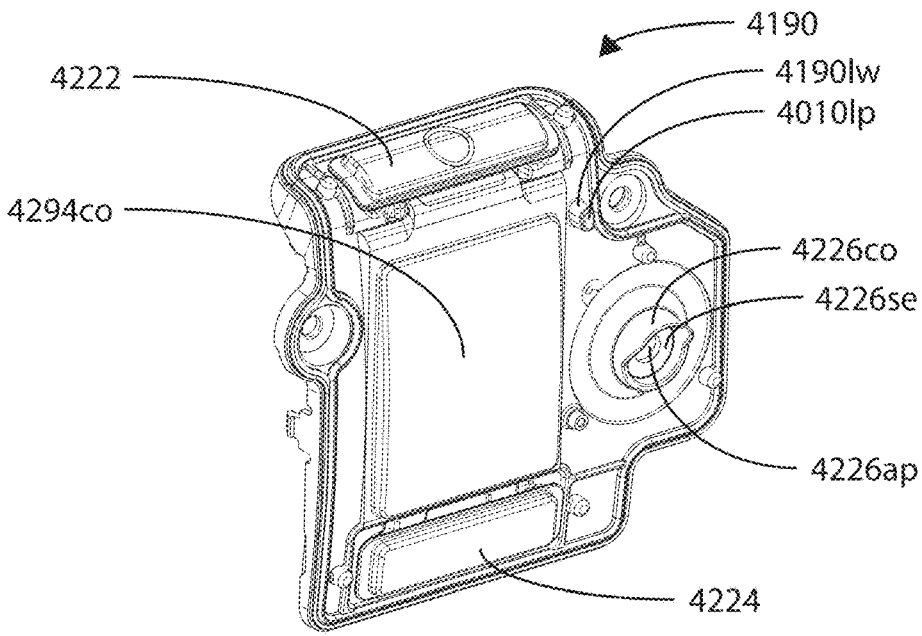

FIG. 12a shows a front perspective view of a user interface panel 4190 in accordance with one form of the present technology.

Figure 12B:
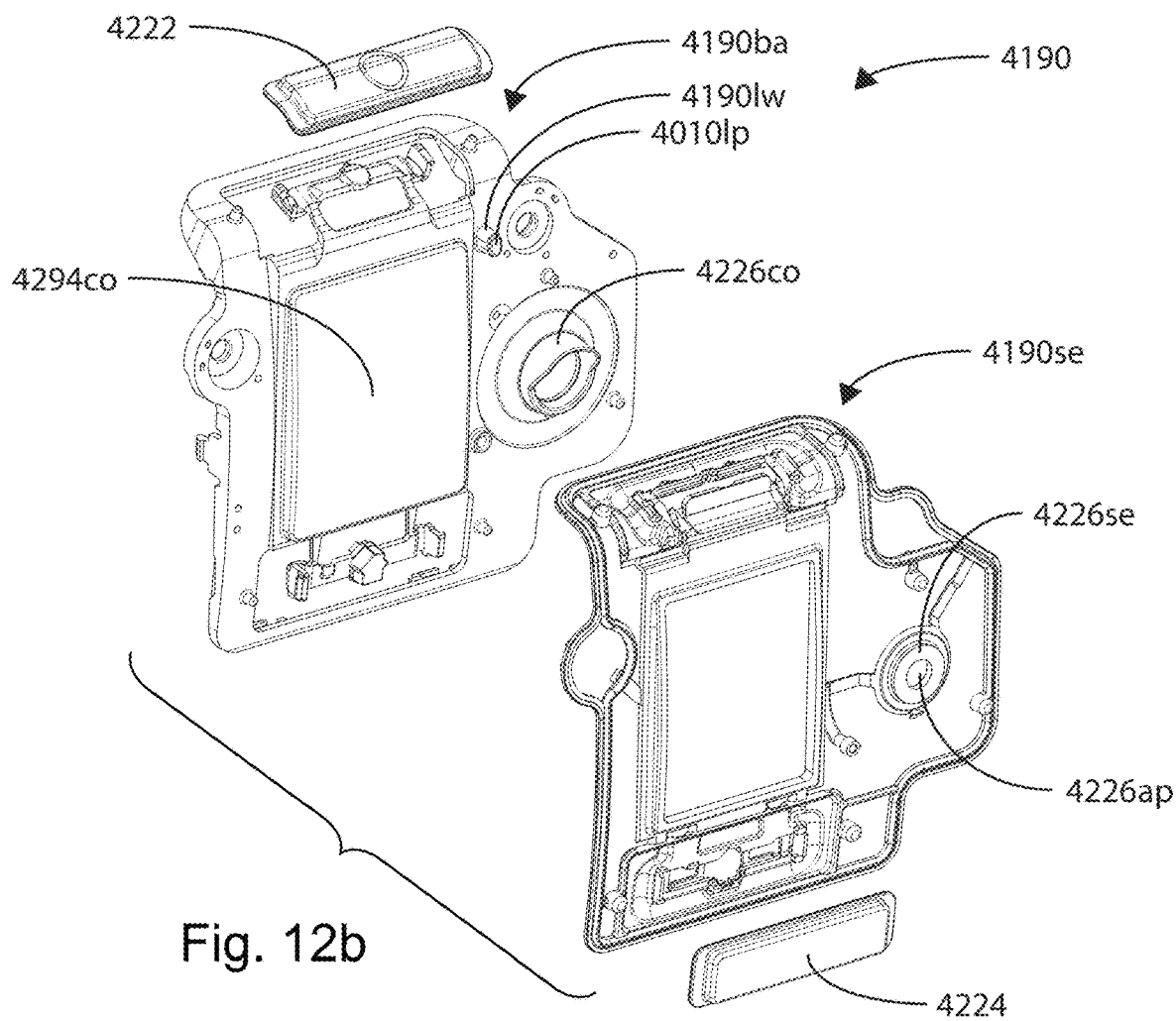

FIG. 12b shows an exploded front perspective view of a user interface panel 4190 in accordance with one form of the present technology.

Figure 12C:
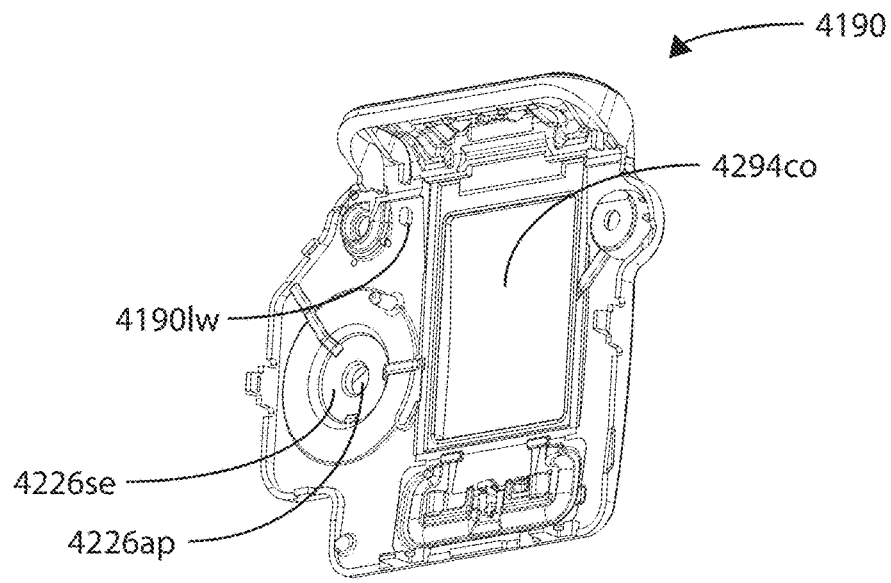

FIG. 12c shows a rear perspective view of a user interface panel 4190 in accordance with one form of the present technology.

Figure 12D:
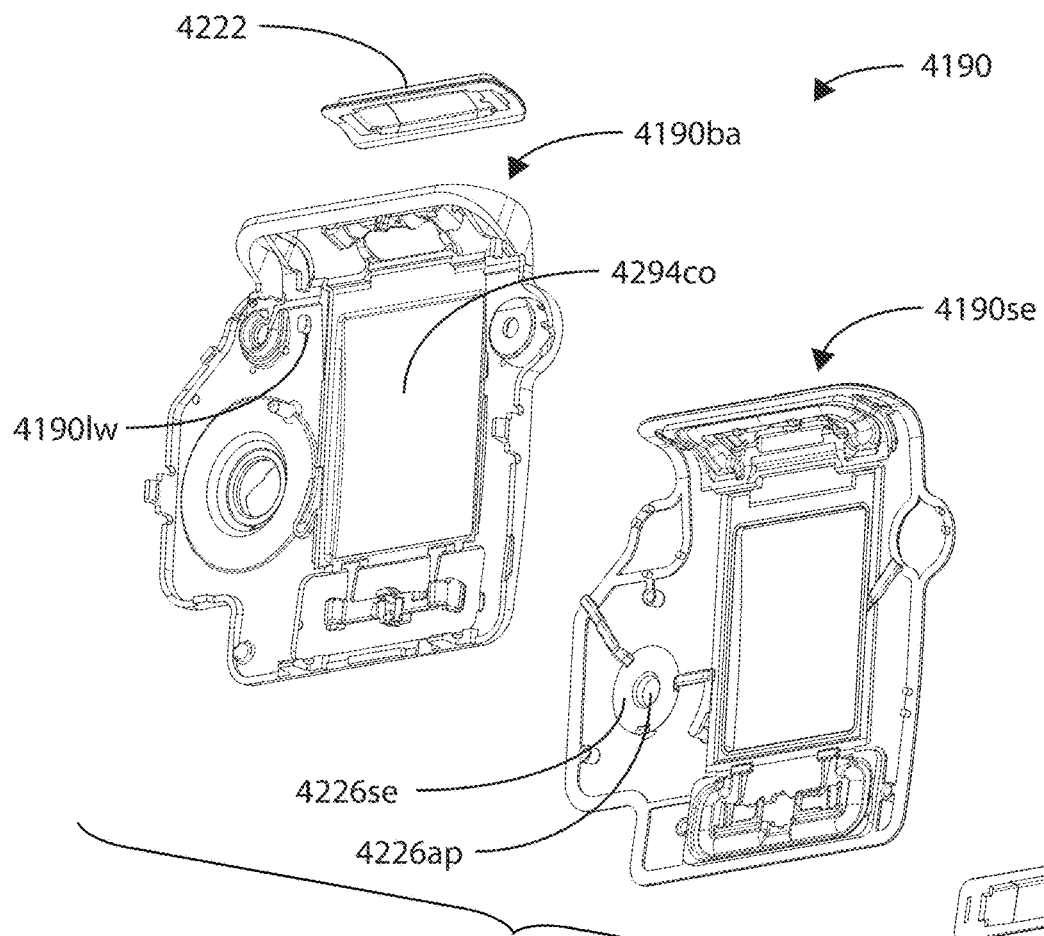

FIG. 12d shows an exploded rear perspective view of a user interface panel 4190 in accordance with one form of the present technology.

Figure 13A:
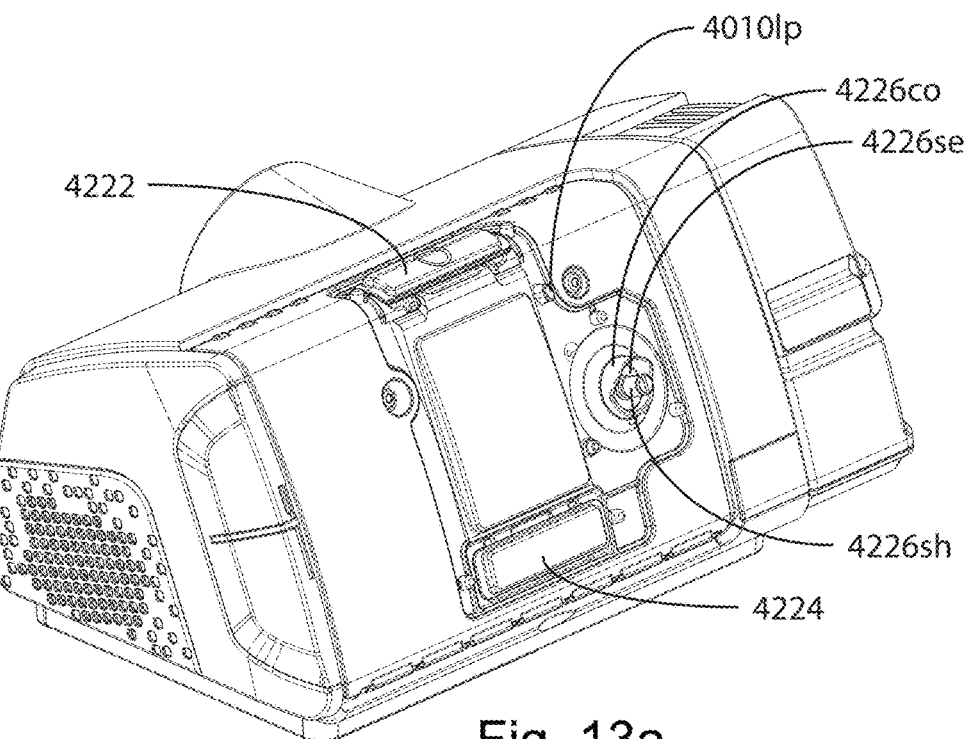

FIG. 13a shows a perspective view of an RPT device 4000 with the front panel 4012 hidden in accordance with one form of the present technology.

Figure 13B:
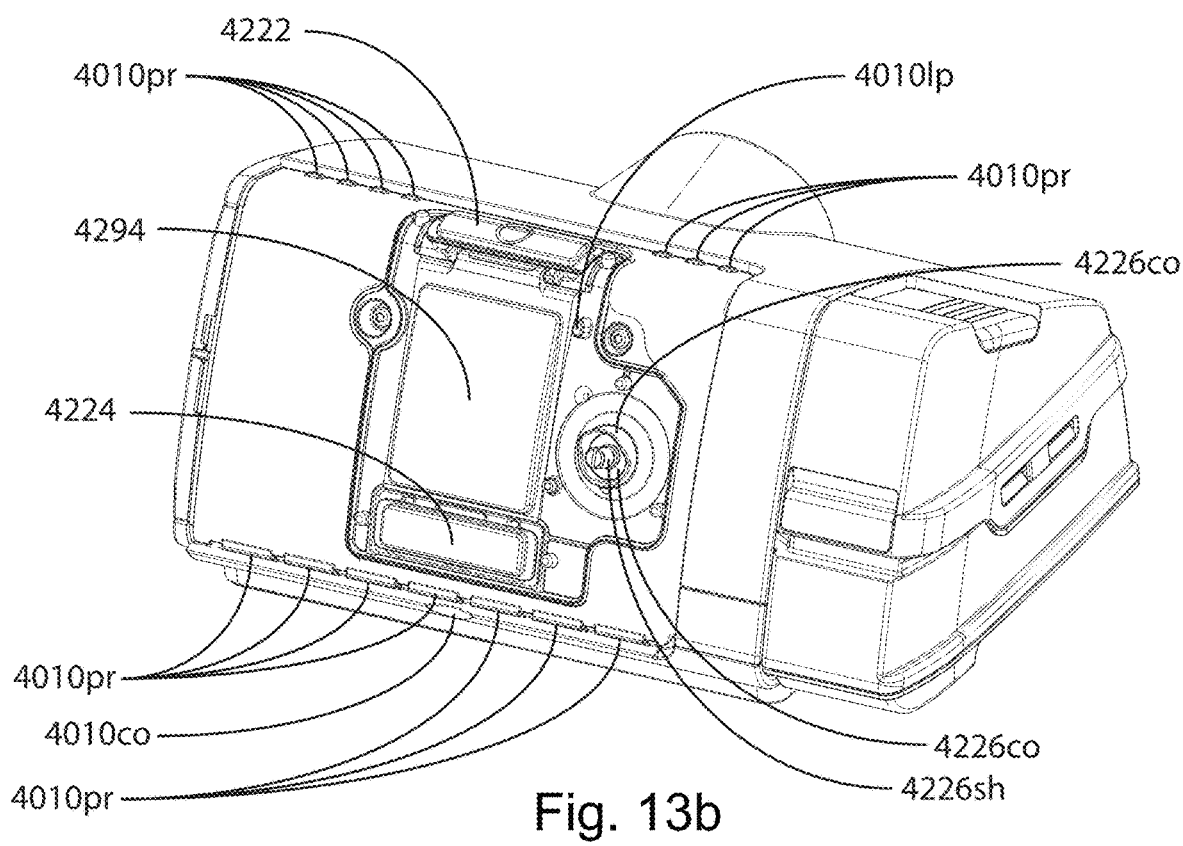

FIG. 13b shows another perspective view of an RPT device 4000 with the front panel 4012 hidden in accordance with one form of the present technology.

Figure 14A:
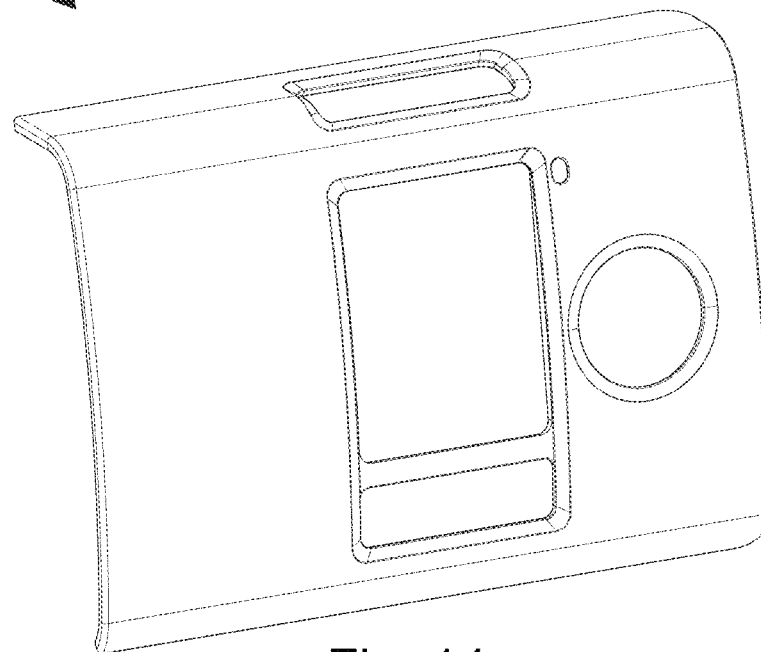

FIG. 14a shows a front perspective view of a front panel 4012 in accordance with one form of the present technology.

Figure 14B:
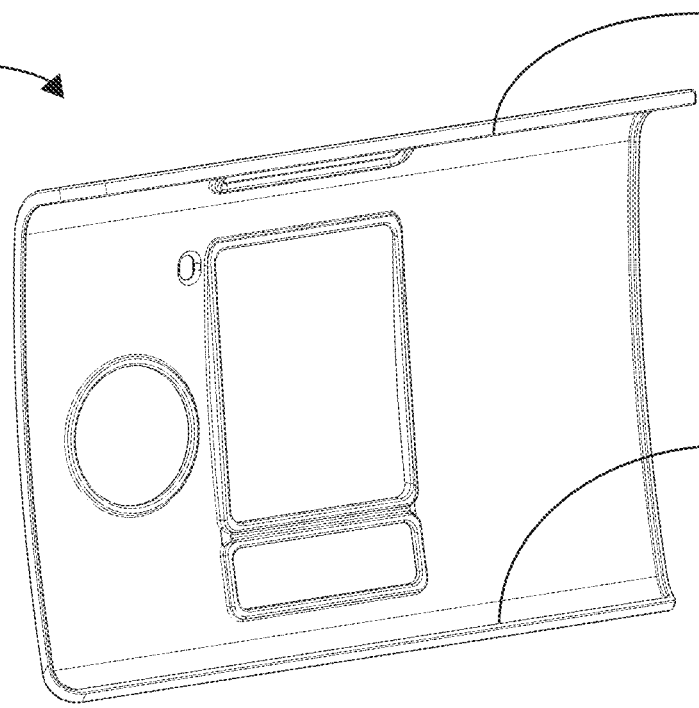

FIG. 14b shows a rear perspective view of a front panel 4012 in accordance with one form of the present technology.

Figures 15A, 15B:
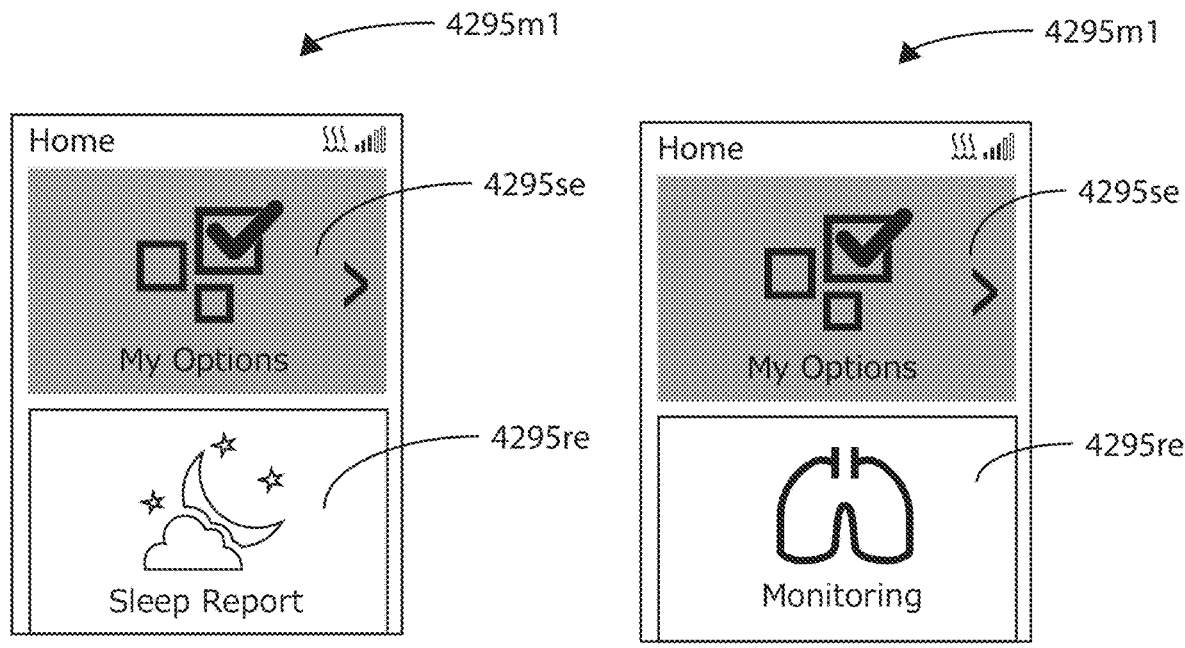

FIG. 15a shows a first menu screen 4295m1 in accordance with one form of the present technology.

FIG. 15b shows another first menu screen 4295m1 in accordance with one form of the present technology.

Figures 15C, 15D:
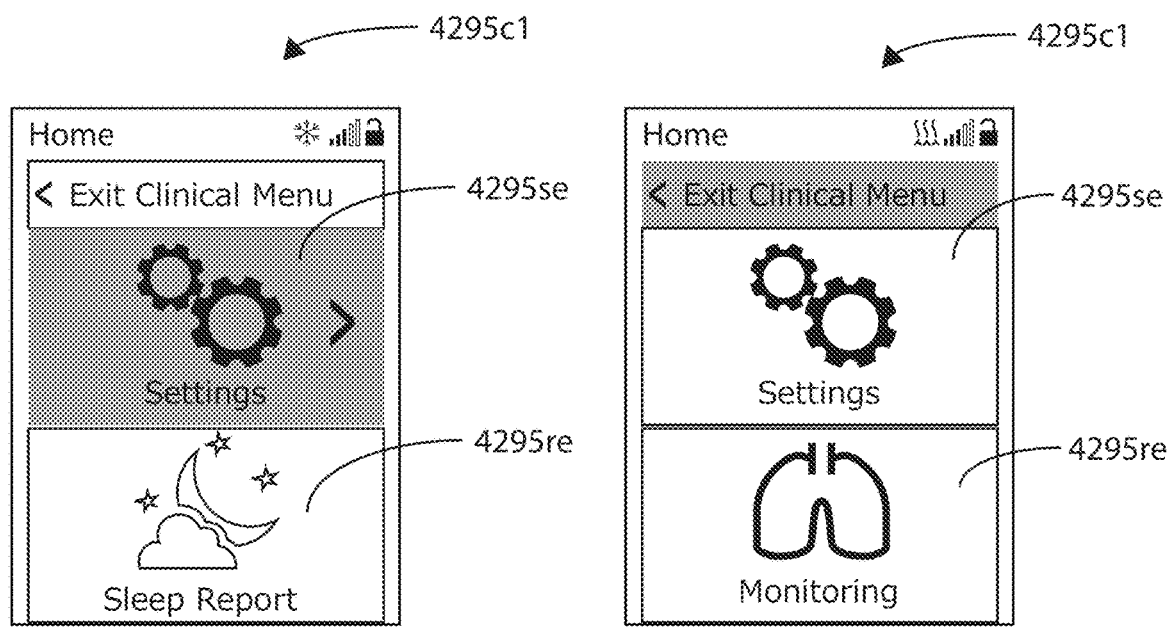

FIG. 15c shows a first clinical menu screen 4295m2 in accordance with one form of the present technology.

FIG. 15d shows another first clinical menu screen 4295m2 in accordance with one form of the present technology.

FIG. 15e shows a selectable sub-menu list 4295o1 in accordance with one form of the present technology.

FIG. 15f shows a selectable sub-menu list 4295o2 in accordance with one form of the present technology.

Figure 15G:
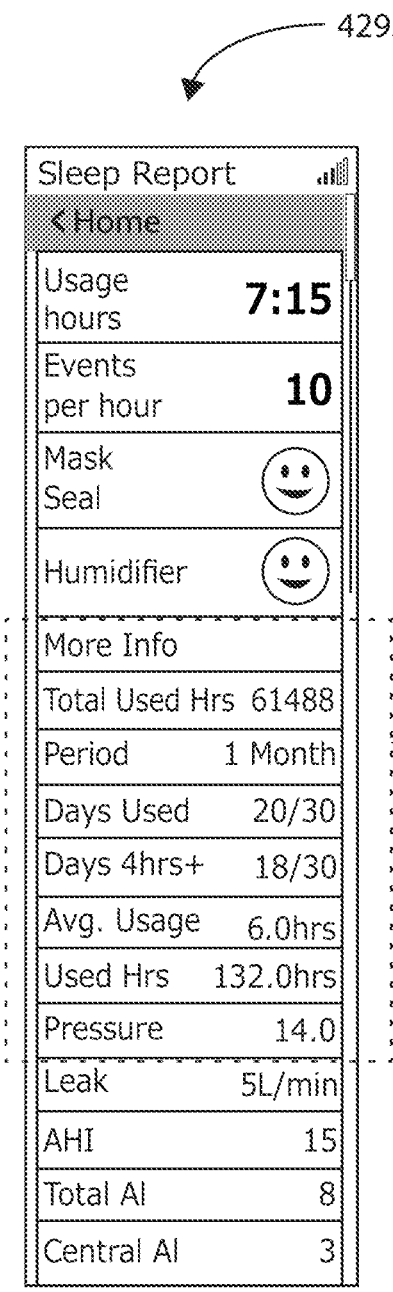

FIG. 15g shows a report sub-menu list 4295r1 in accordance with one form of the present technology.

Figure 15H:
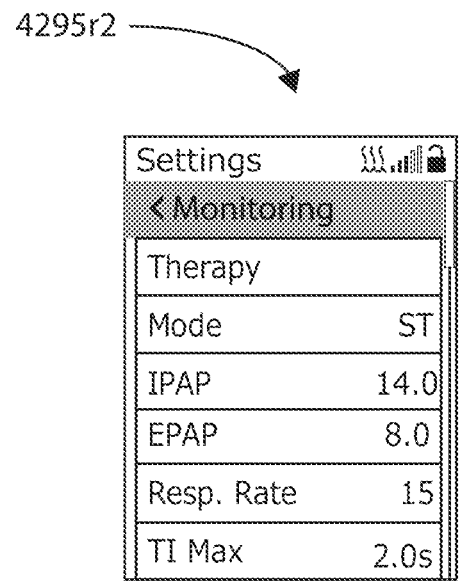

FIG. 15h shows a report sub-menu 4295r2 in accordance with one form of the present technology.

Figure 15I:
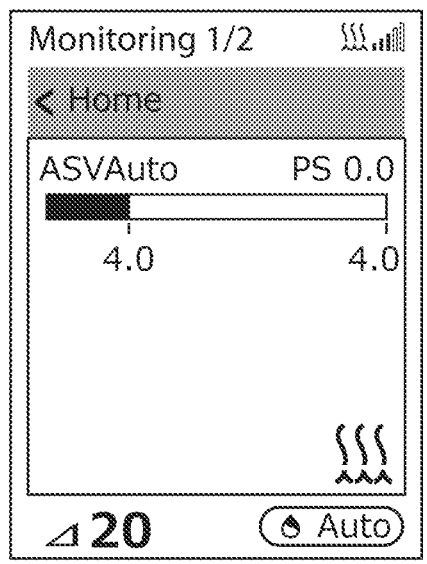

FIG. 15i shows a report sub-menu 4295r3 in accordance with one form of the present technology.

Figure 15J:
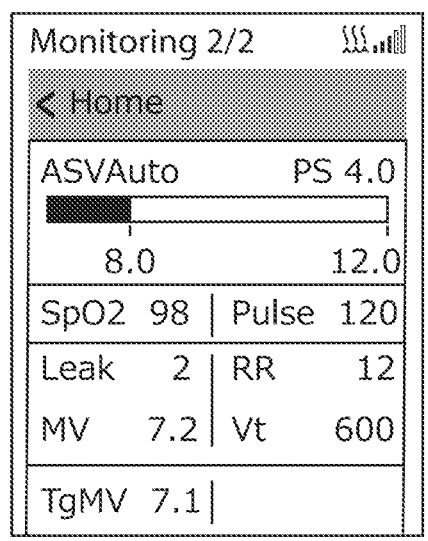

FIG. 15j shows a report sub-menu 4295r4 in accordance with one form of the present technology.

Figure 15K:
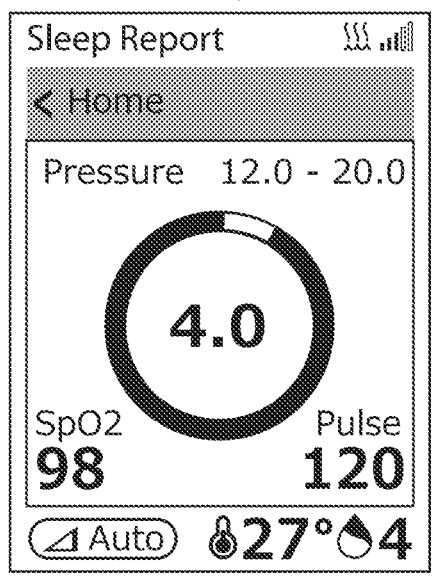

FIG. 15k shows a report sub-menu 4295a1 in accordance with one form of the present technology.

Figure 15L:
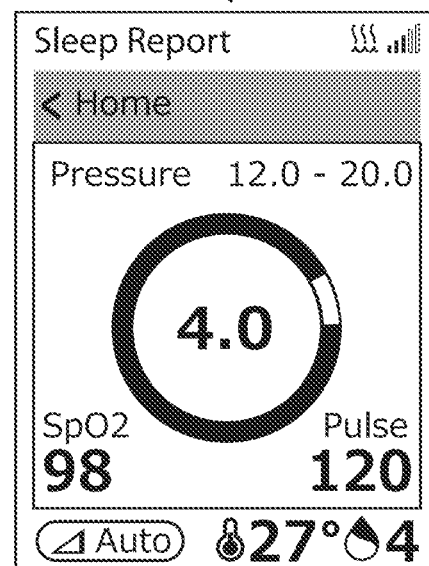

FIG. 15l shows a report sub-menu 4295a2 in accordance with one form of the present technology.

Figure 15M:
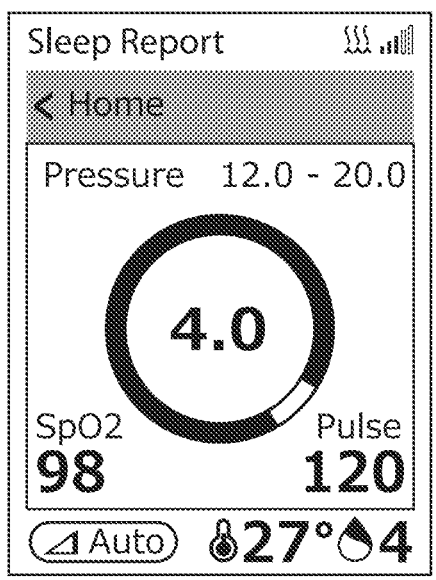

FIG. 15m shows a report sub-menu 4295a3 in accordance with one form of the present technology.

Figure 15N:
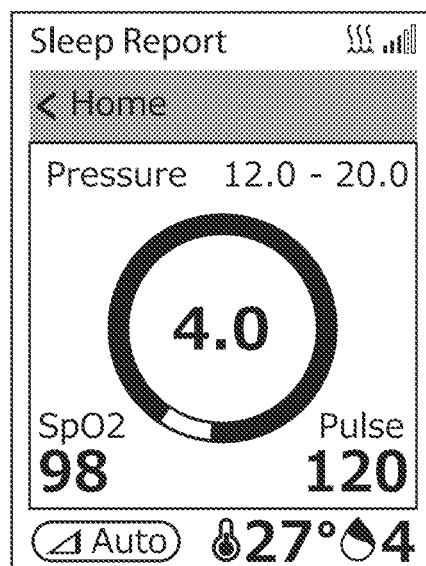

FIG. 15n shows a report sub-menu 4295a4 in accordance with one form of the present technology.

Figure 15O:
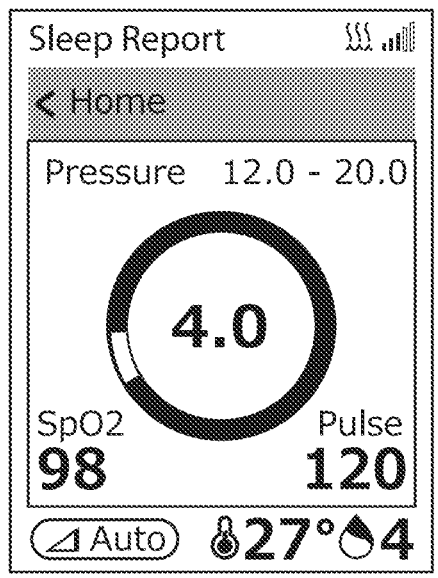
Figure 15P:
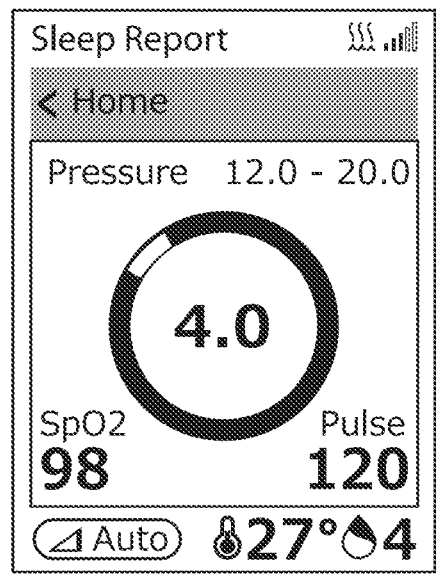

FIG. 15o shows a report sub-menu 4295a5 in accordance with one form of the present technology FIG. 15p shows a report sub-menu 4295a6 in accordance with one form of the present technology.

Figure 15Q:
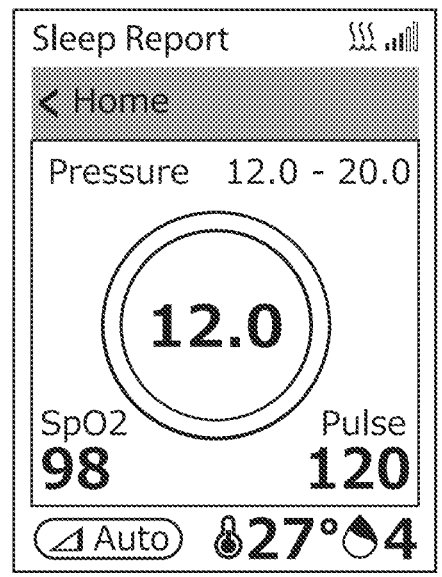

FIG. 15q shows a report sub-menu 4295a7 in accordance with one form of the present technology.

Figure 15R:
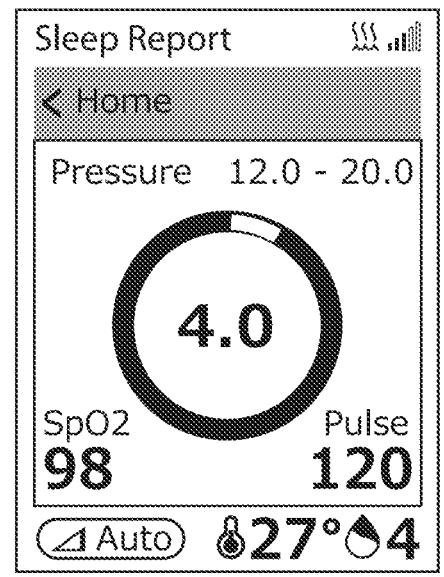

FIG. 15r shows a report sub-menu 4295a8 in accordance with one form of the present technology.

Figure 15S:
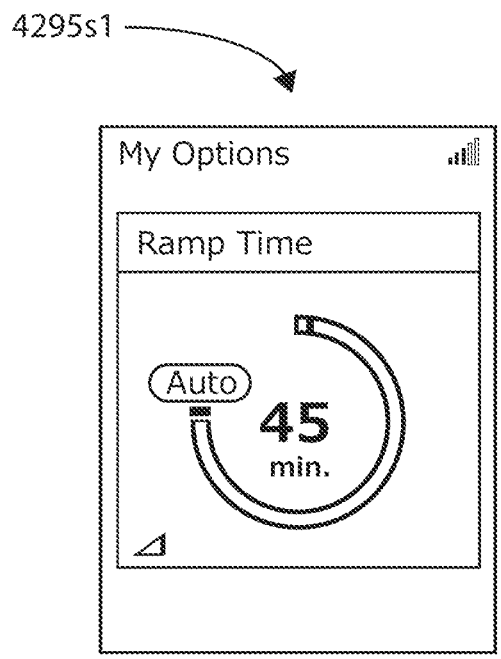

FIG. 15s shows a selectable sub-menu 4295s1 in accordance with one form of the present technology.

Figure 15T:
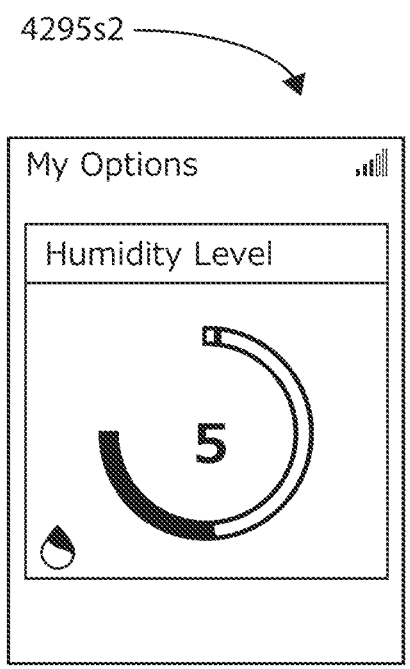

FIG. 15t shows a selectable sub-menu 4295s2 in accordance with one form of the present technology.

Figure 15U:
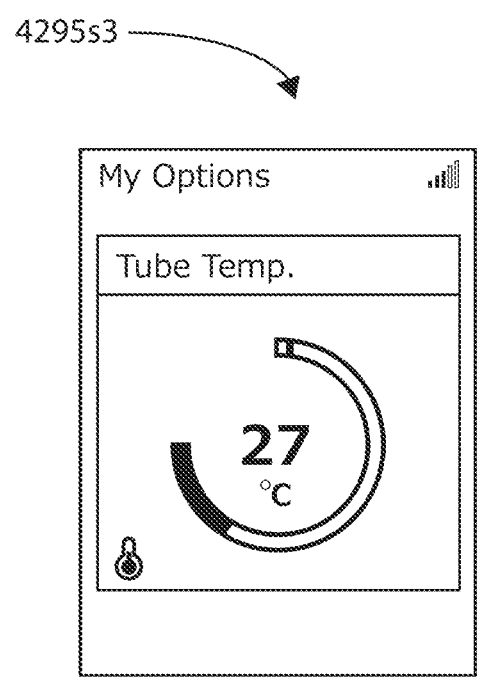

FIG. 15u shows a selectable sub-menu 4295s3 in accordance with one form of the present technology.

Figure 15V:
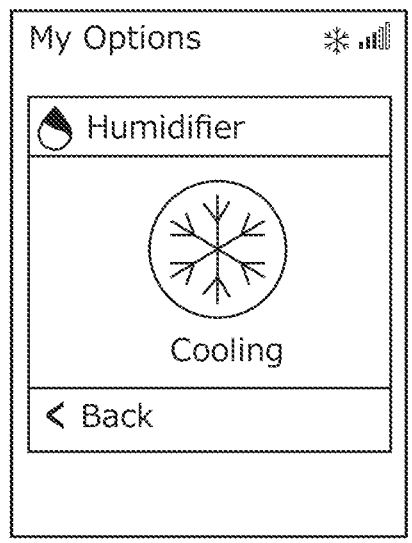

FIG. 15v shows a report sub-menu 4295b1 in accordance with one form of the present technology.

Figure 15W:
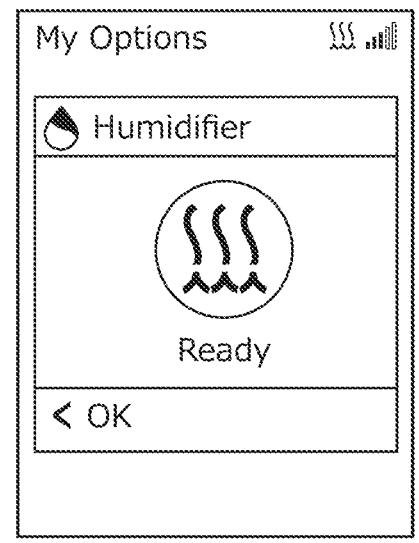

FIG. 15w shows a report sub-menu 4295b2 in accordance with one form of the present technology.

Figure 15X:
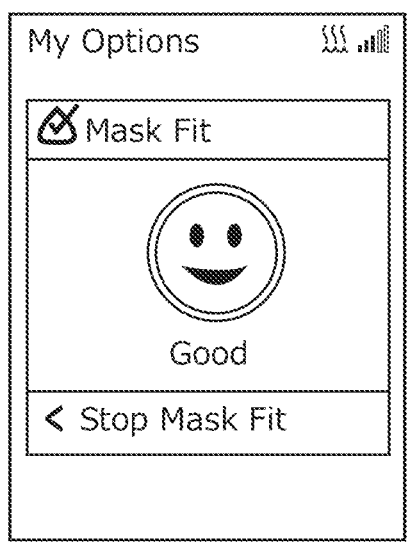

FIG. 15x shows a report sub-menu 4295b3 in accordance with one form of the present technology.

Figure 15Y:
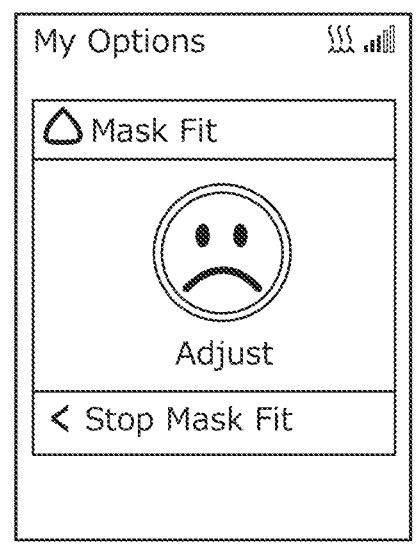

FIG. 15y shows a report sub-menu 4295b4 in accordance with one form of the present technology.

Figure 16A:
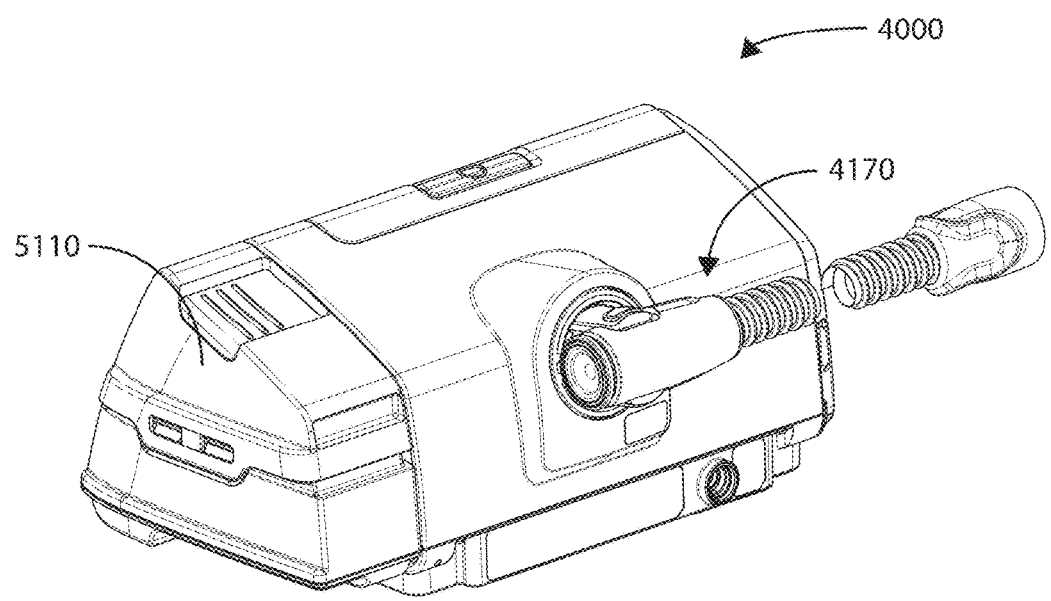

FIG. 16a shows a rear perspective view of an RPT device 4000 in accordance with one form of the present technology, showing an air circuit 4170 engaged with the RPT device 4000.

Figure 16B:
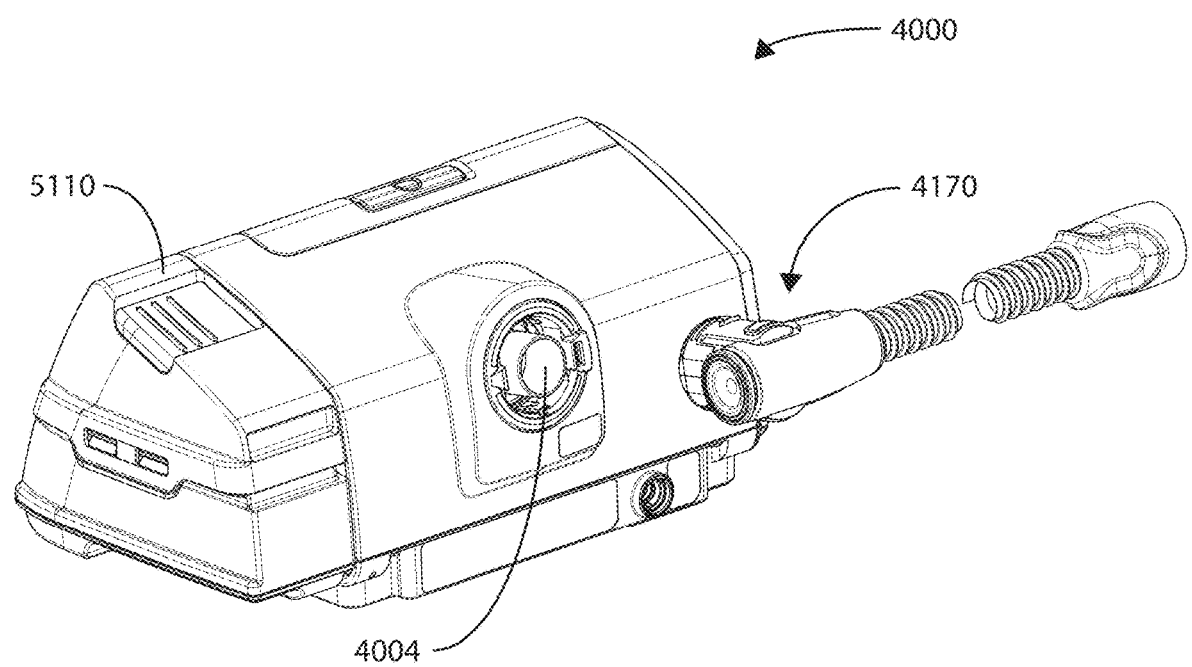

FIG. 16b shows a rear perspective view of an RPT device 4000 in accordance with one form of the present technology, showing an air circuit 4170 in exploded view.

Figure 16C:
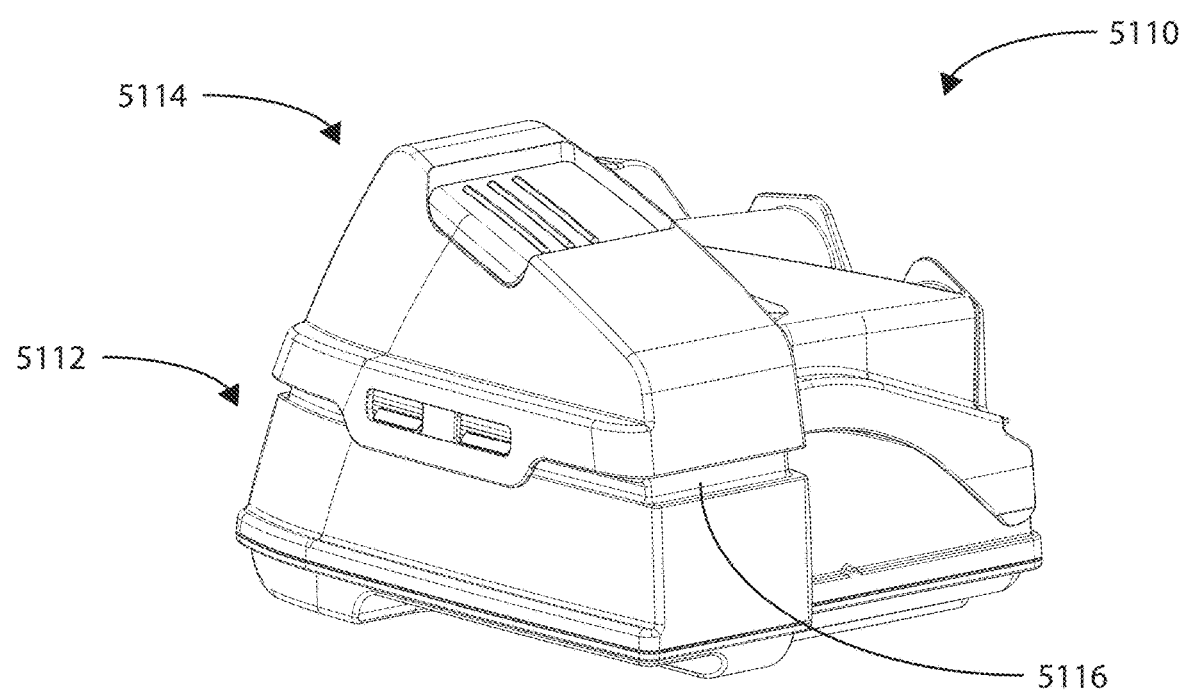

FIG. 16c shows a perspective view of a water reservoir 5110 in accordance with one form of the present technology.

Figure 16D:
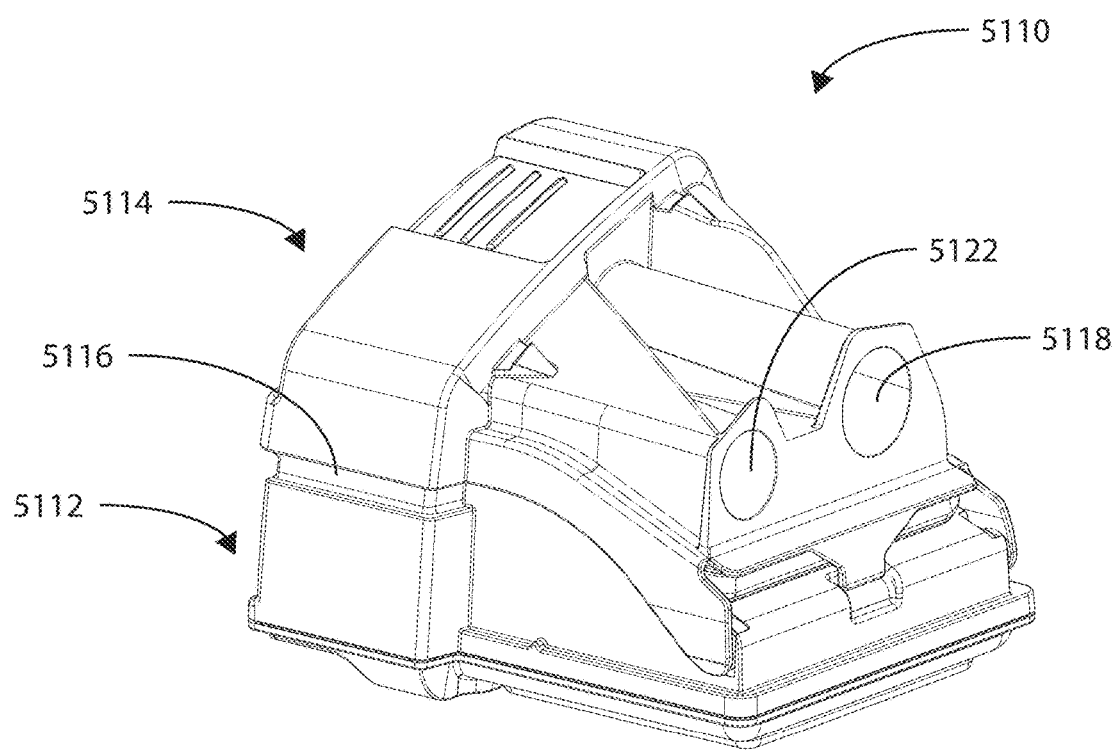

FIG. 16d shows another perspective view of a water reservoir 5110 in accordance with one form of the present technology.

Figure 16E:
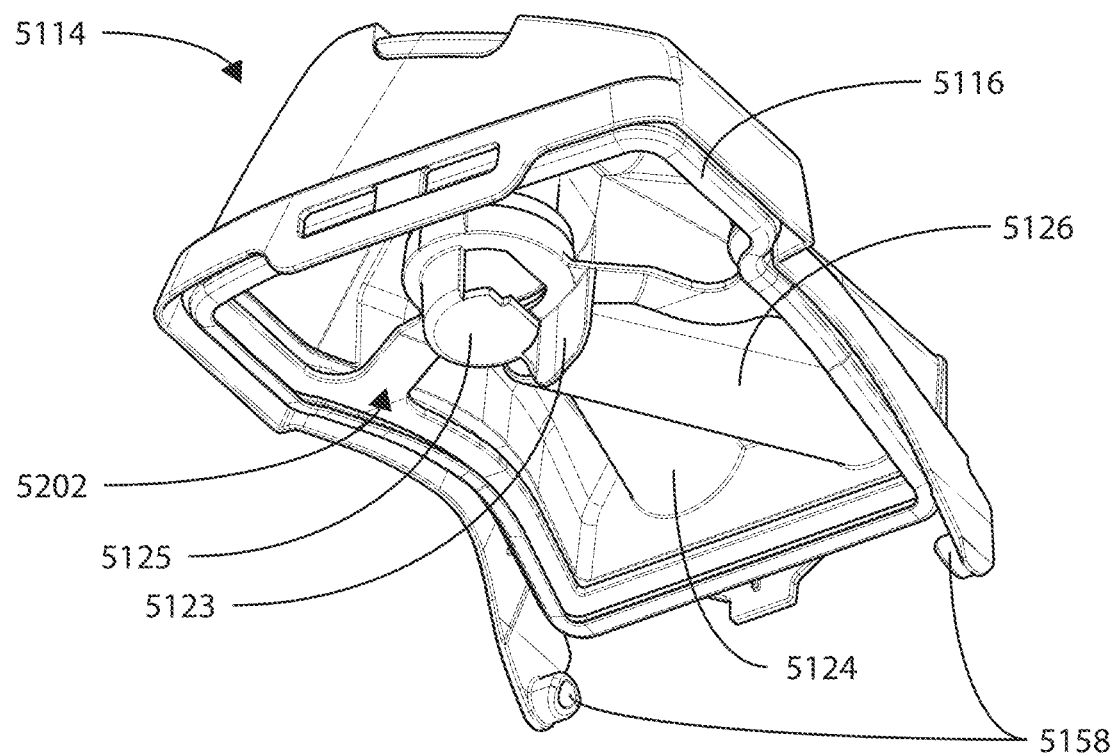

FIG. 16e shows a perspective view of a water reservoir lid 5114 and an intermediate portion 5202 in accordance with one form of the present technology.

Figure 16F:
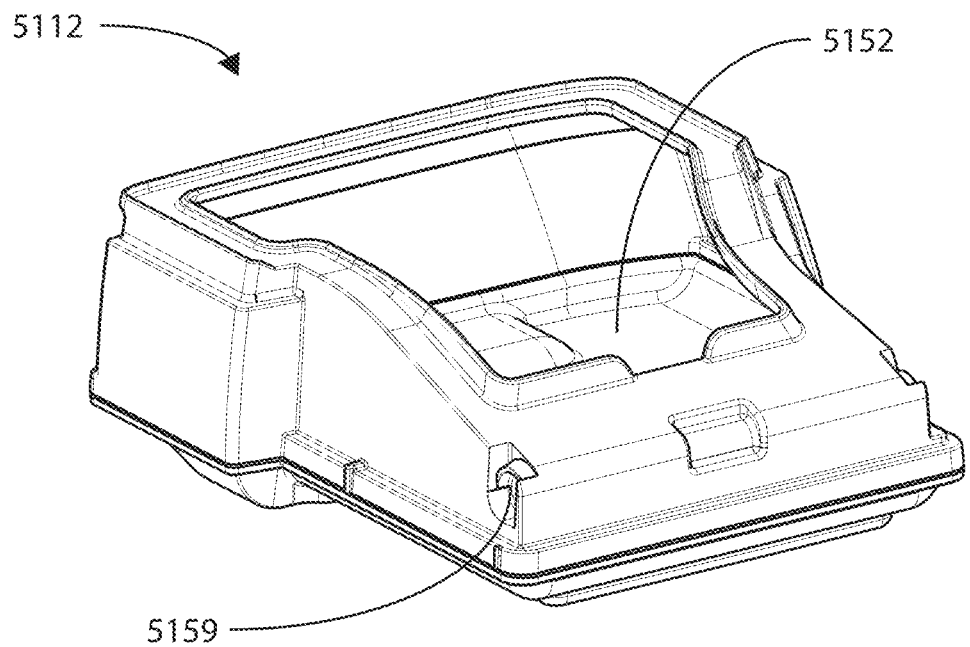

FIG. 16f shows a perspective view of a water reservoir base 5112 in accordance with one form of the present technology.

Figure 16G:
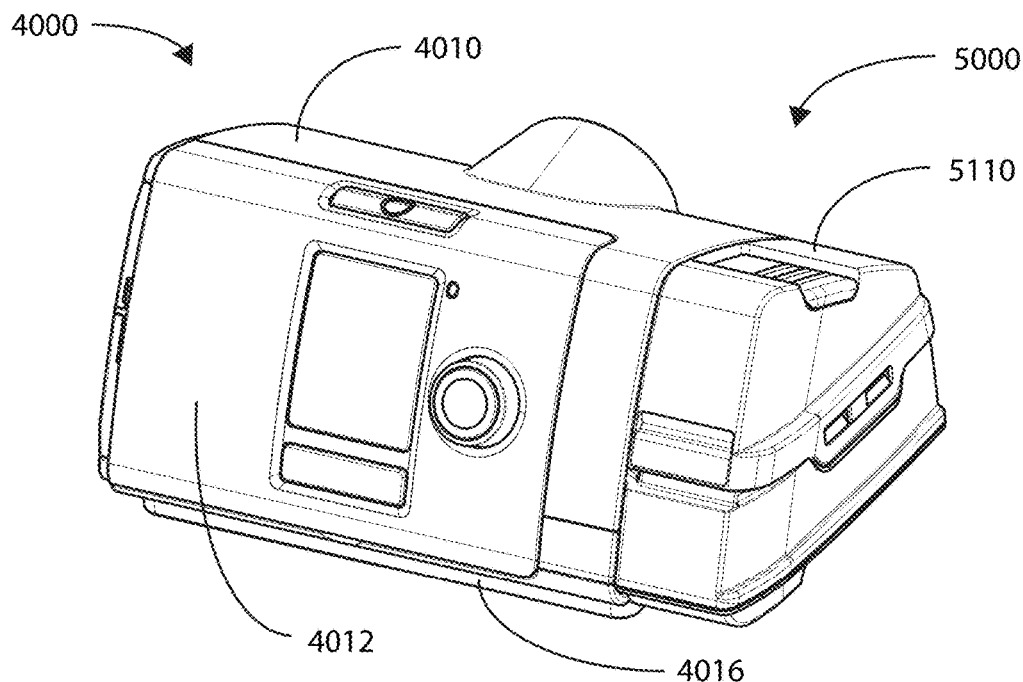

FIG. 16g shows a perspective view of an RPT device 4000 comprising an integrated humidifier 5000 and a water reservoir 5110 in accordance with one form of the present technology.

Figure 16H:
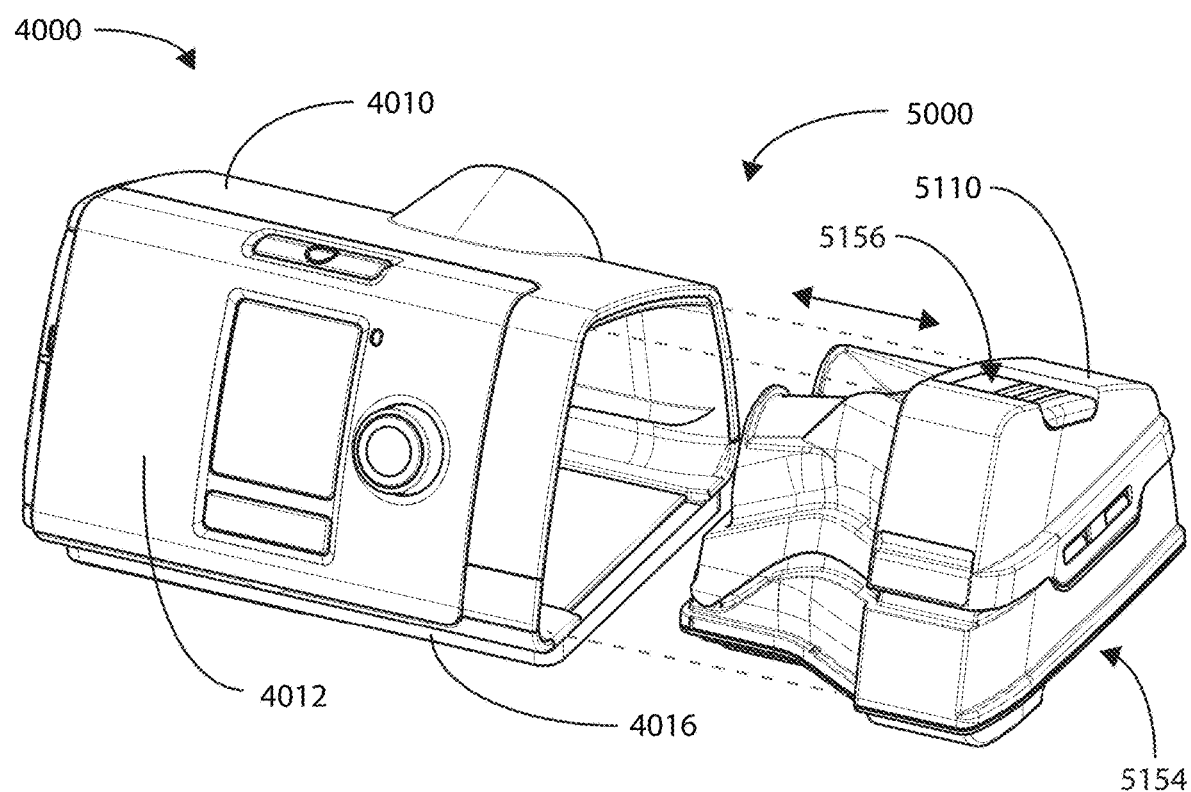

FIG. 16h shows a perspective view of an RPT device 4000 comprising an integrated humidifier 5000 in accordance with one form of the present technology, showing the water reservoir 5110 in exploded view.

Figure 16I:
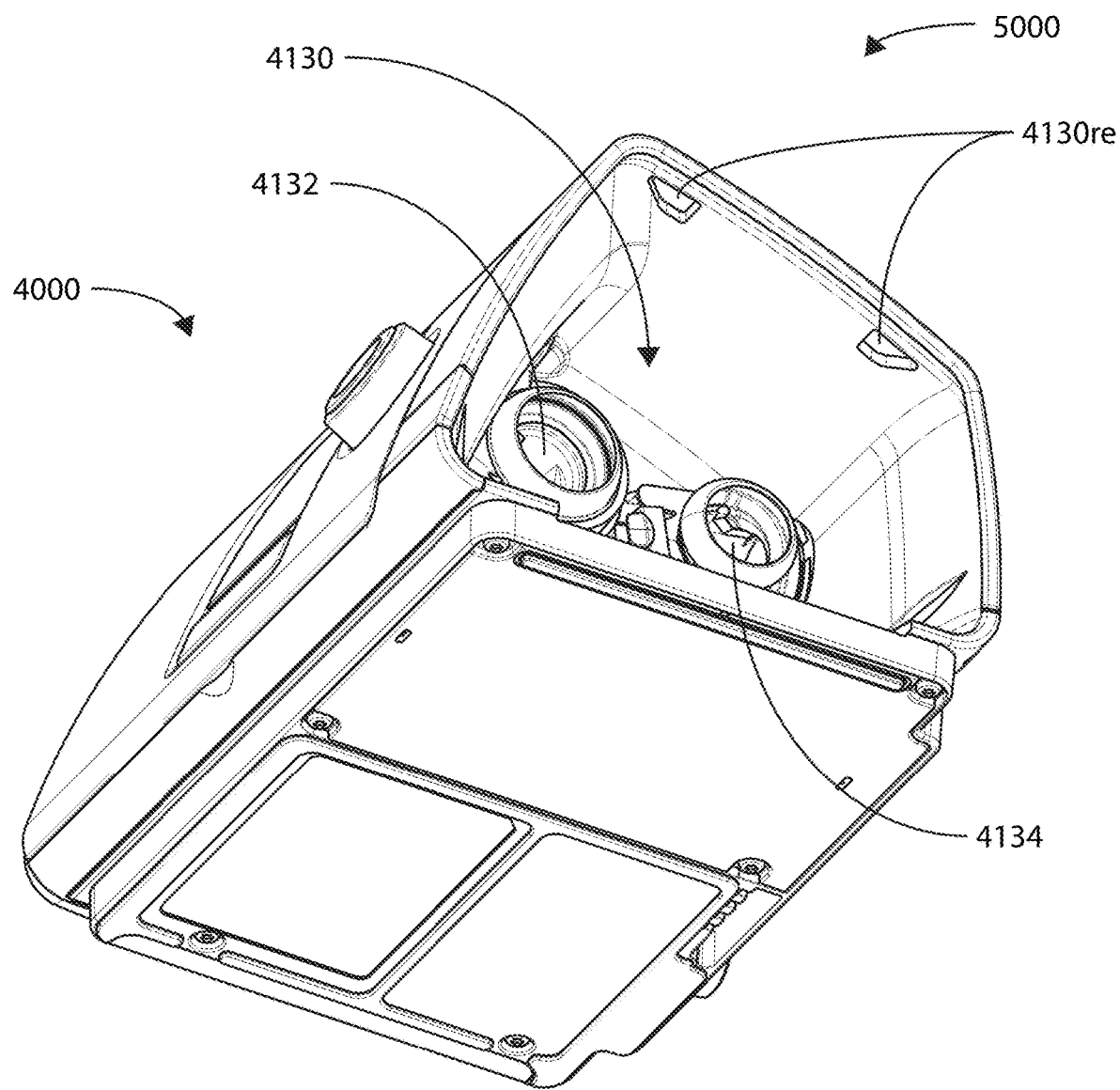

FIG. 16i shows a perspective view of an RPT device 4000 comprising an integrated humidifier 5000 in accordance with one form of the present technology, not showing the water reservoir 5110.

Figure 16J:
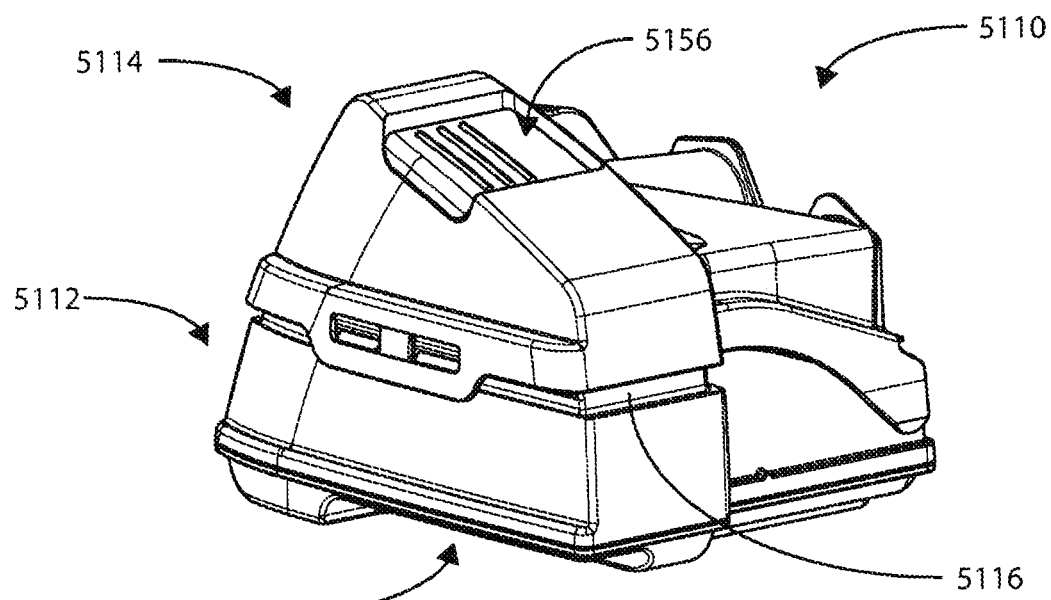

FIG. 16j shows a perspective view of a water reservoir 5110 in accordance with one form of the present technology, showing the water reservoir 5110 in a closed configuration.

Figure 16K:
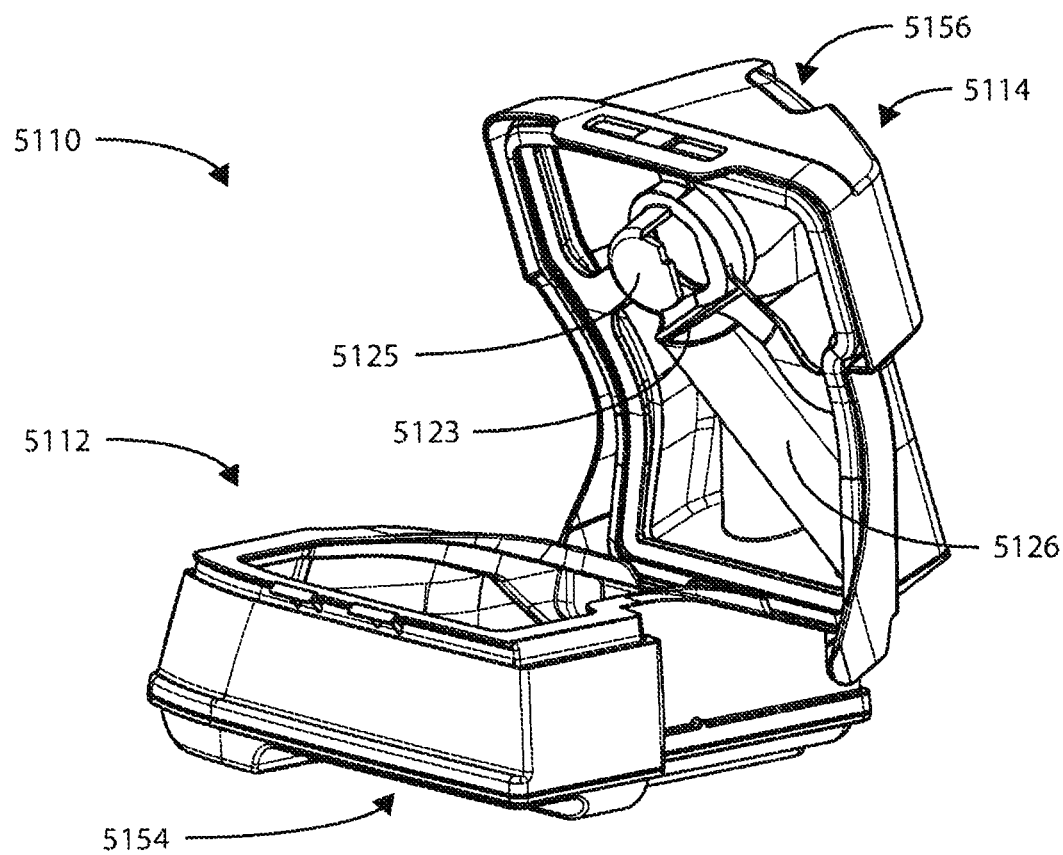

FIG. 16k shows a perspective view of a water reservoir 5110 in accordance with one form of the present technology, showing the water reservoir 5110 in an open configuration.

Figure 16L:
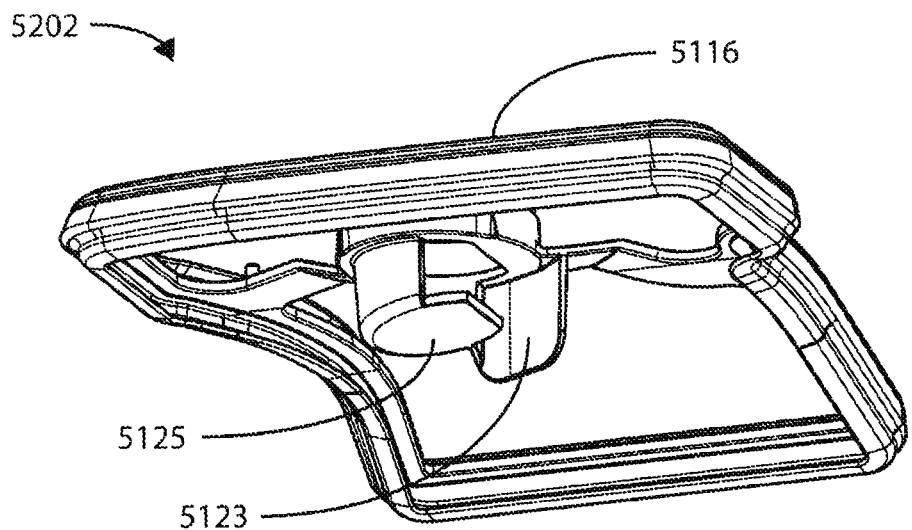

FIG. 16l shows a perspective view of an intermediate portion 5202 in accordance with one form of the present technology.

Figure 16M:
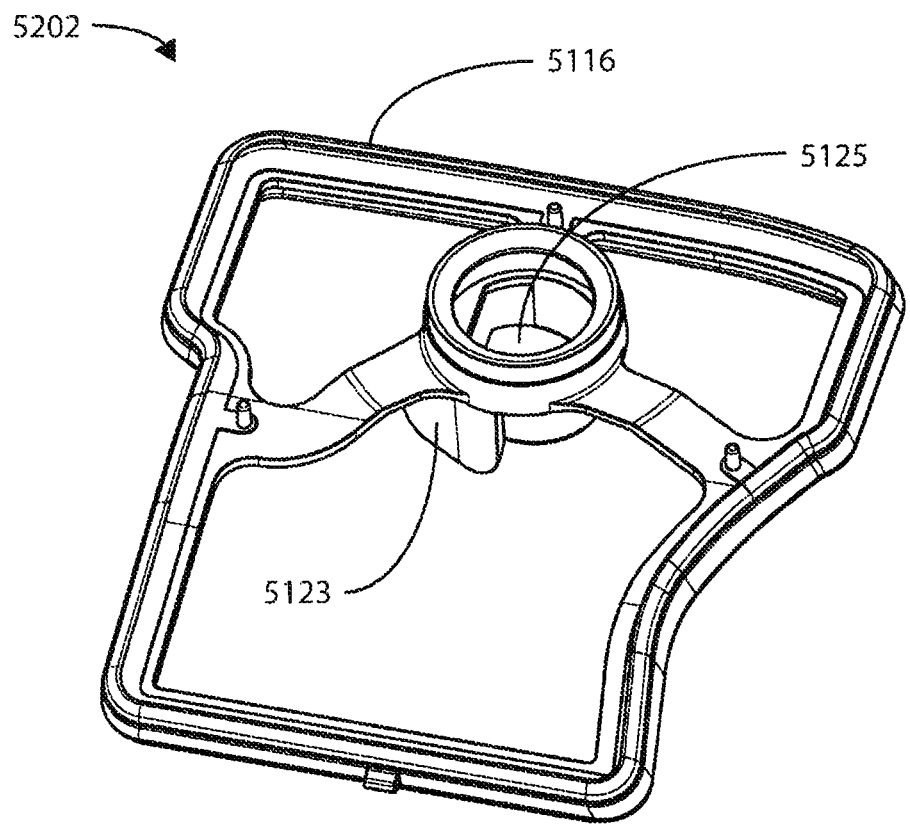

FIG. 16m shows a perspective view of an intermediate portion 5202 in accordance with one form of the present technology.

Figure 17A:
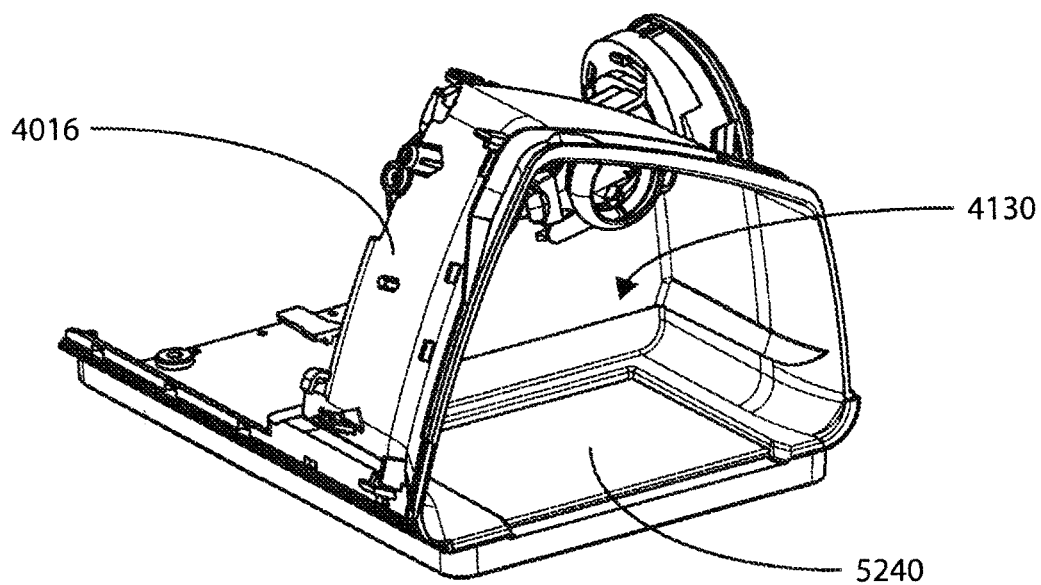

FIG. 17a shows a perspective view of a chassis 4016 in accordance with one form of the present technology.

Figure 17B:
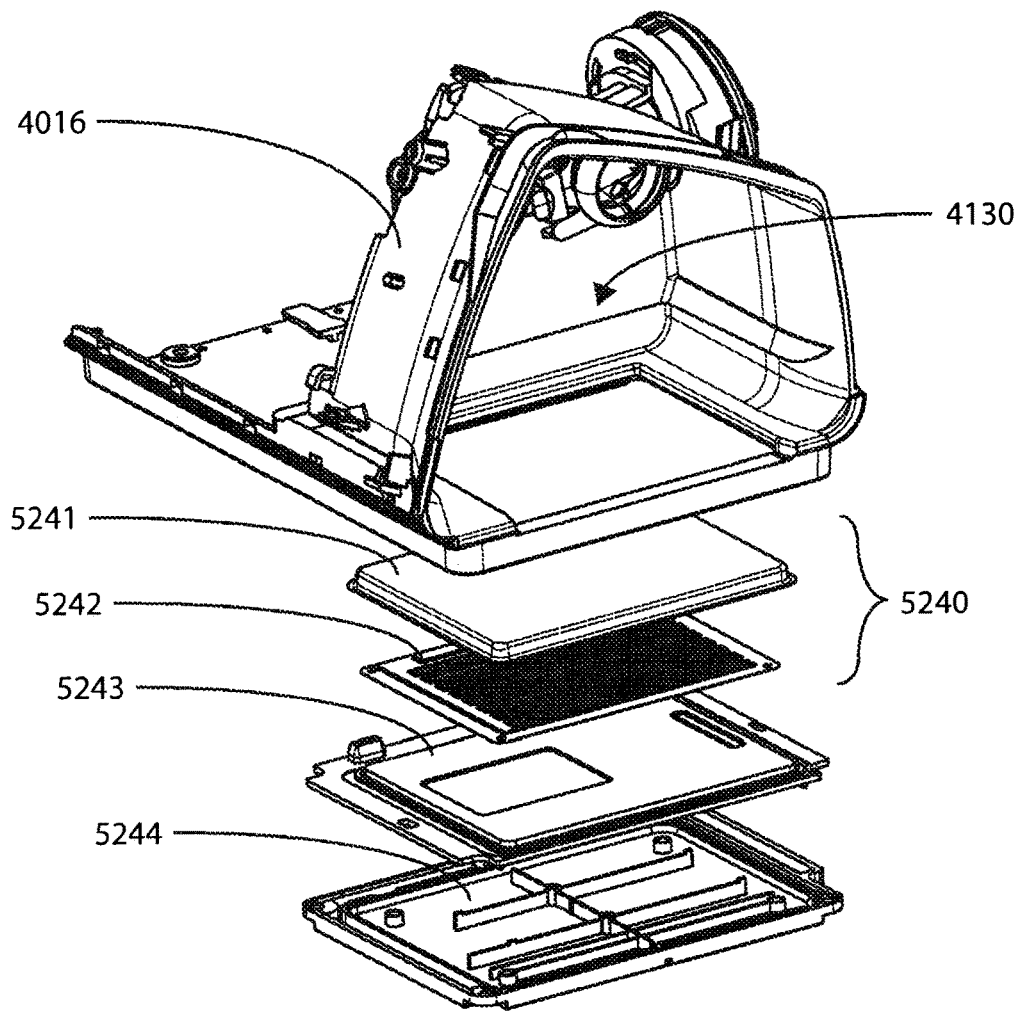

FIG. 17b shows a perspective view of a chassis 4016 in accordance with one form of the present technology, showing the heating element 5240 in exploded view.

Figure 17C:
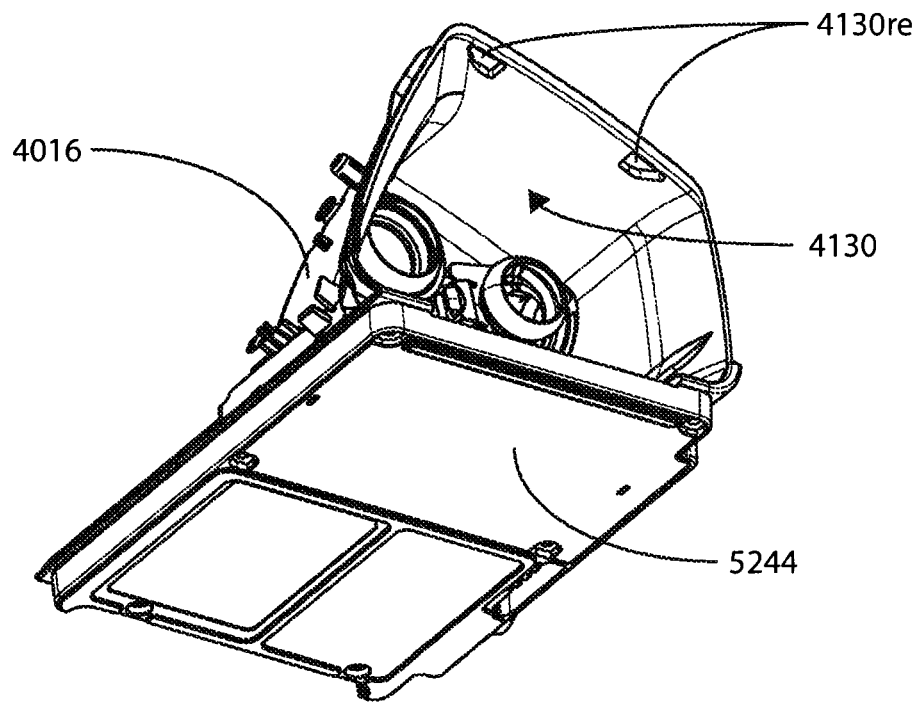

FIG. 17c shows a bottom perspective view of a chassis 4016 in accordance with one form of the present technology.

Figure 17D:
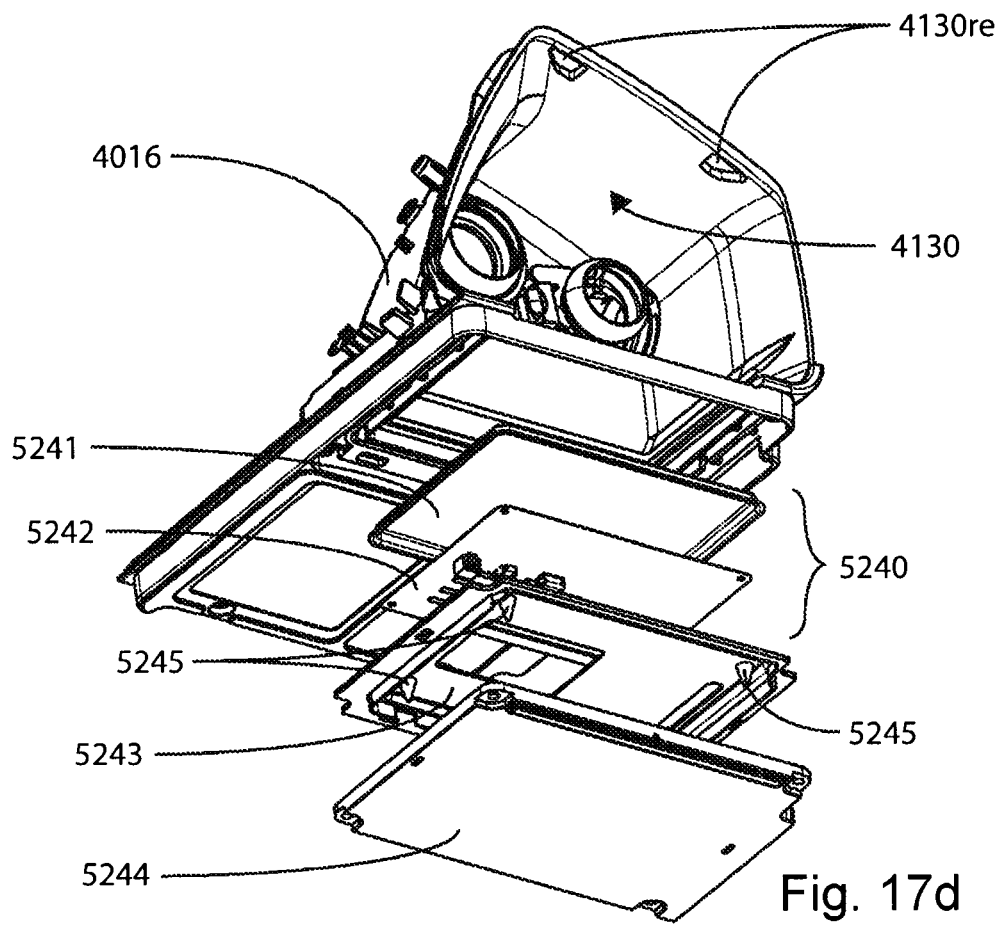

FIG. 17d shows a bottom perspective view of a chassis 4016 in accordance with one form of the present technology, showing the heating element 5240 in exploded view.

Figure 17E:
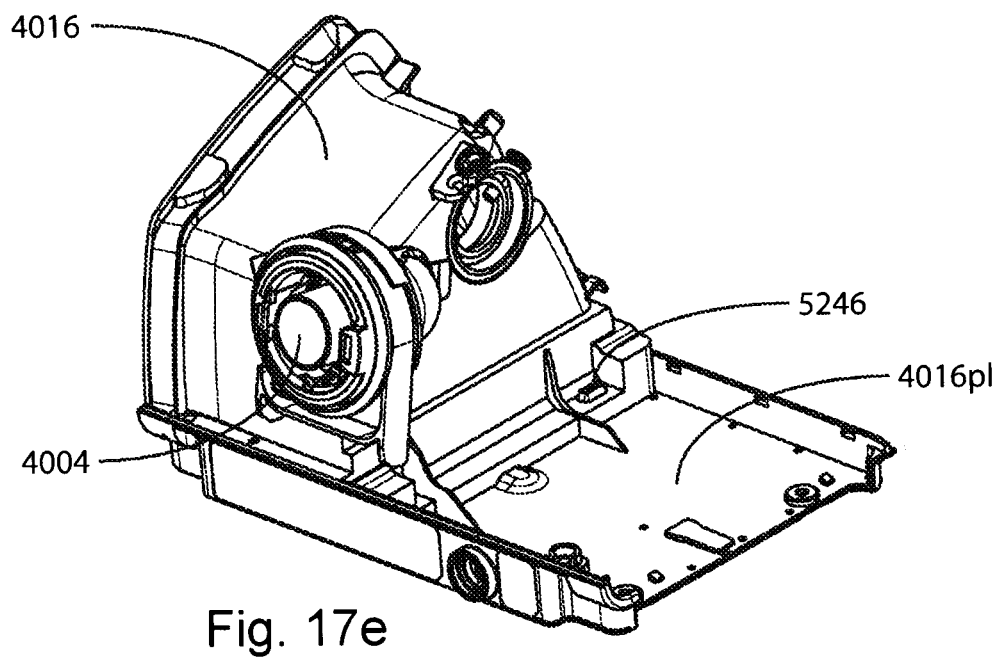

FIG. 17e shows a rear perspective view of a chassis 4016 in accordance with one form of the present technology.

Figure 17F:
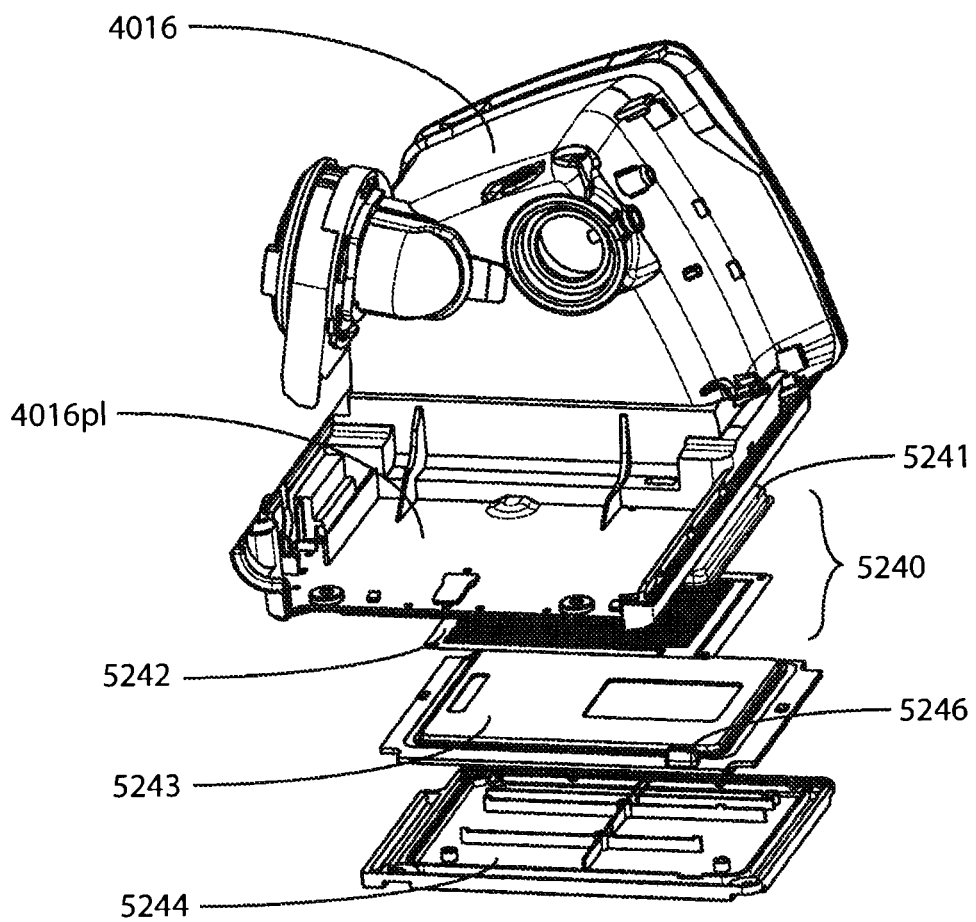

FIG. 17f shows a rear perspective view of a chassis 4016 in accordance with one form of the present technology, showing the heating element 5240 in exploded view.

Figure 17G:
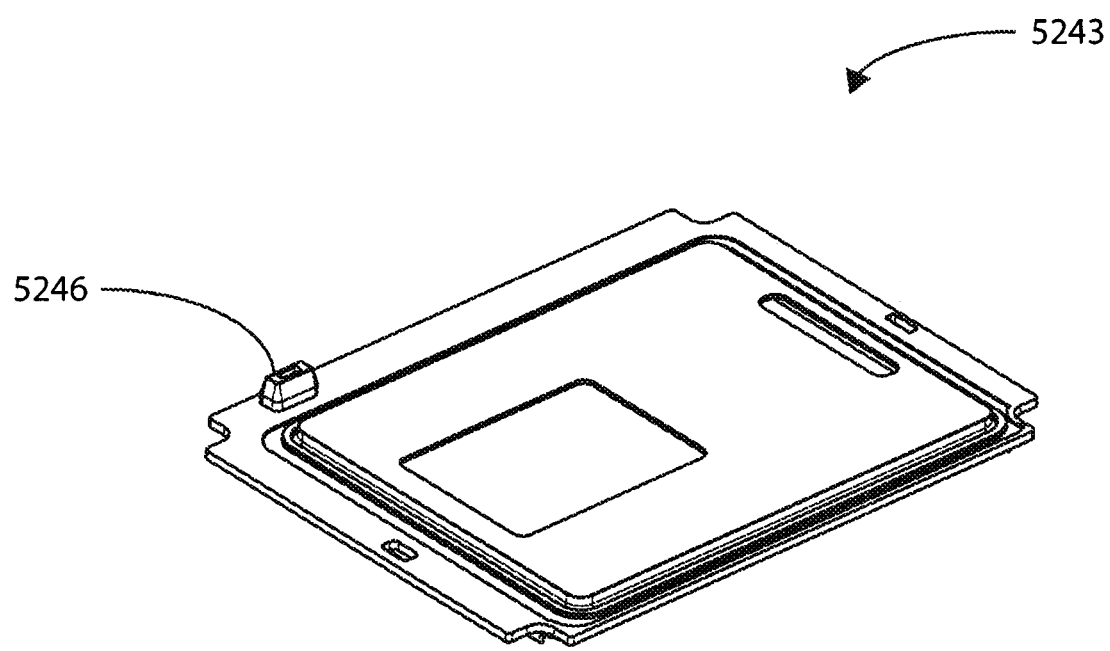

FIG. 17g shows a perspective view of a top of a HE seal 5243 in accordance with one form of the present technology.

Figure 17H:
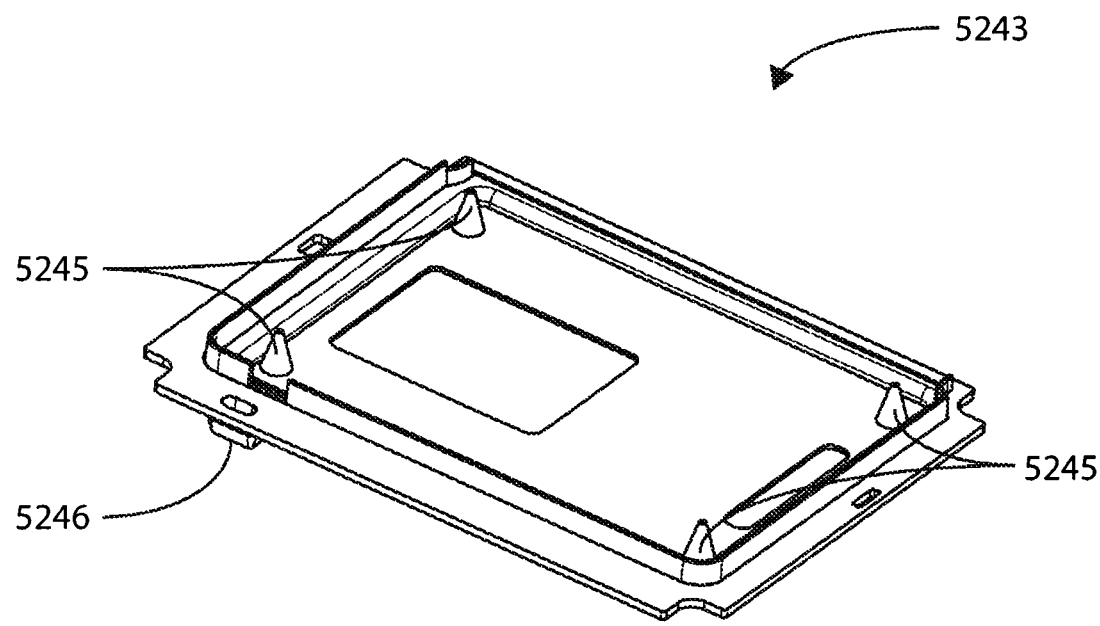

FIG. 17h shows a perspective view of a bottom a HE seal 5243 in accordance with one form of the present technology.

Figure 17I:
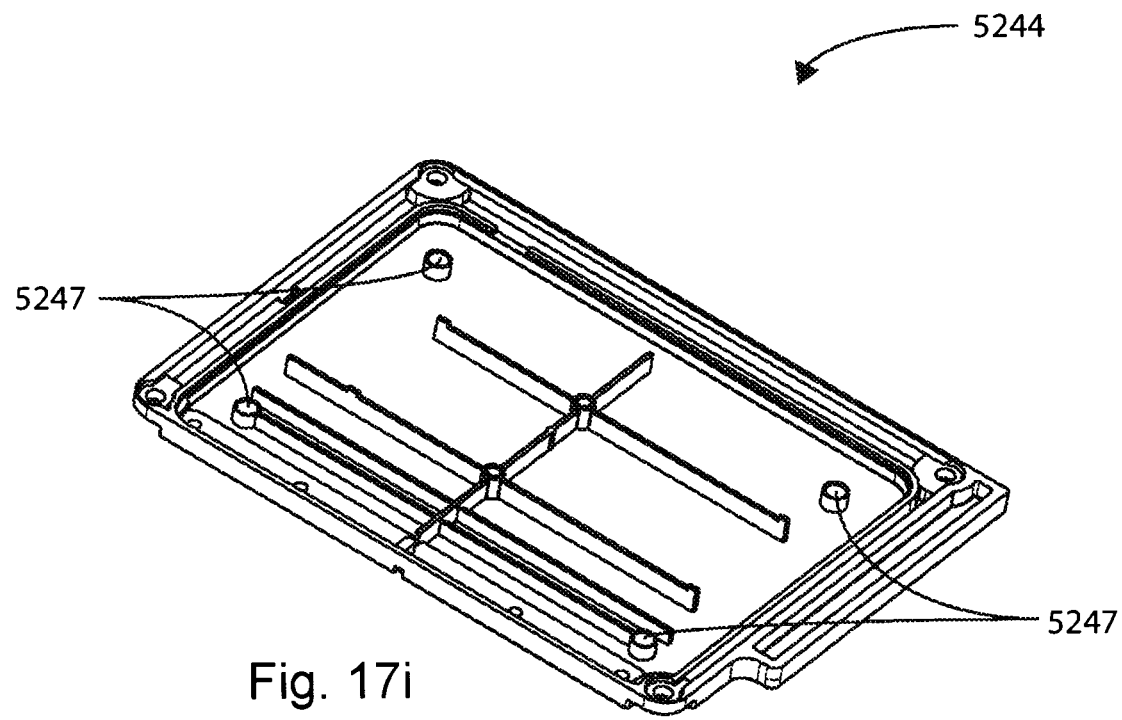

FIG. 17i shows a perspective view of a top of a HE base cover 5244 in accordance with one form of the present technology.

Figure 17J:
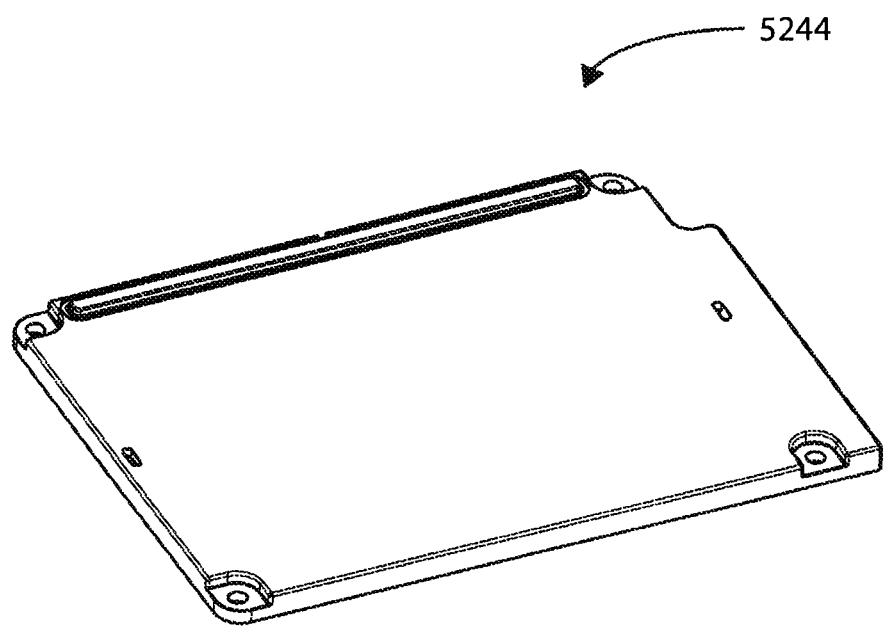

FIG. 17j shows a perspective view of a bottom of a HE base cover 5244 in accordance with one form of the present technology.

Figure 18A:
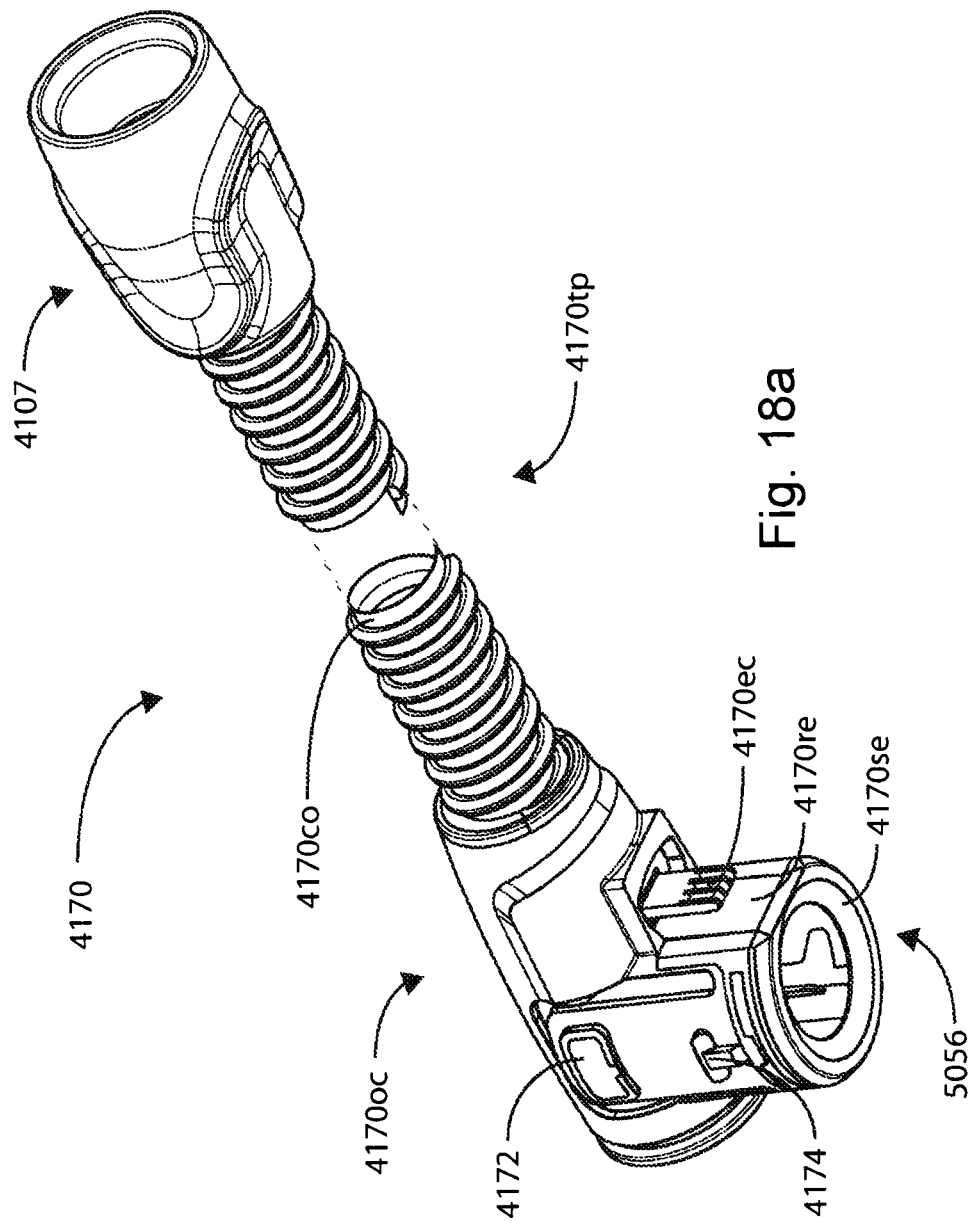

FIG. 18a shows a perspective view of an air circuit 4170 in accordance with one form of the present technology.

Figure 18B:
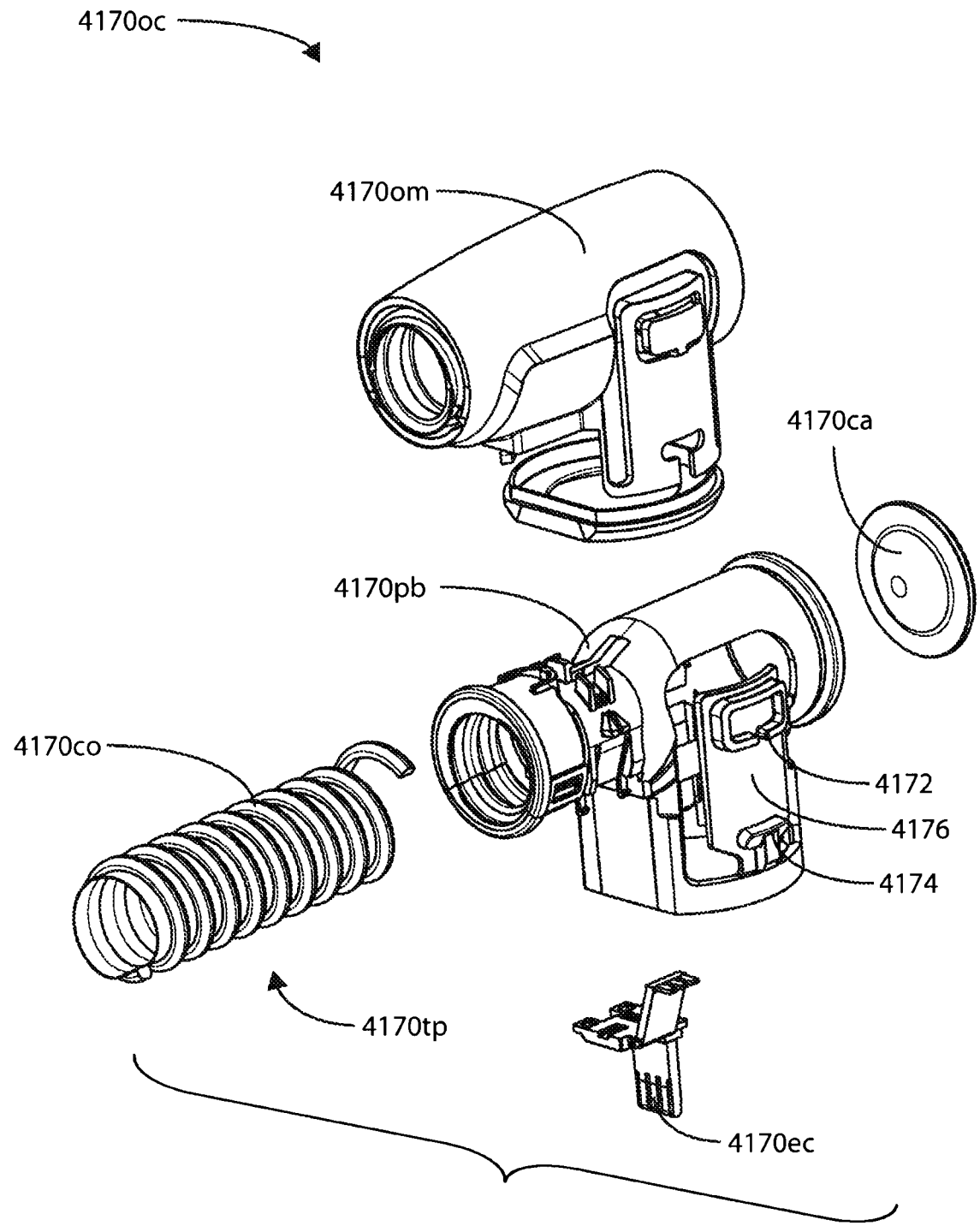

FIG. 18b shows an exploded perspective view of an air circuit 4170 in accordance with one form of the present technology.

Figure 18C:
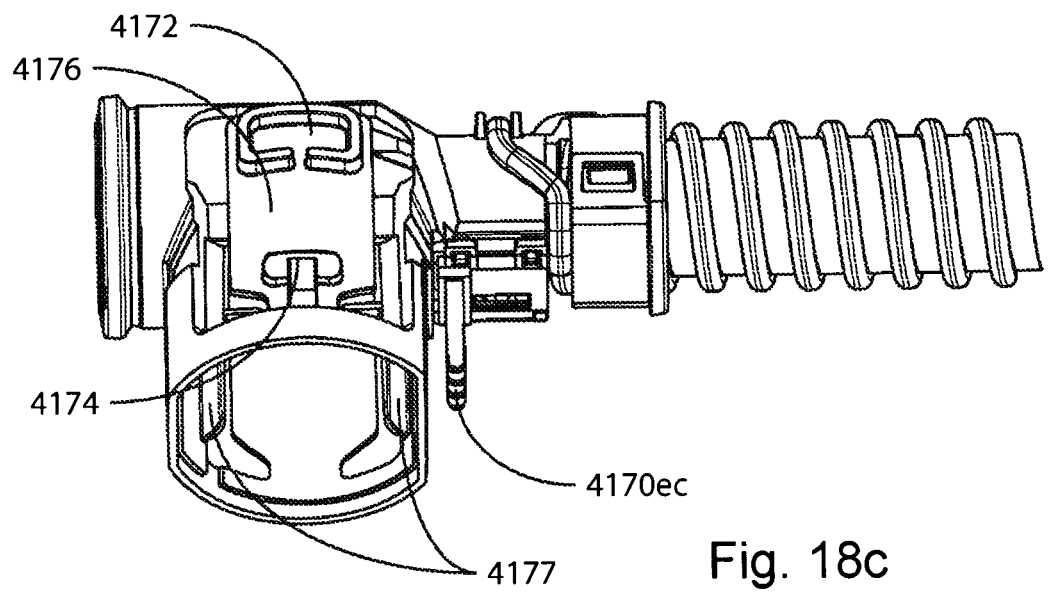

FIG. 18c shows a side perspective view of a portion of an air circuit 4170 in accordance with one form of the present technology.

Figure 18D:
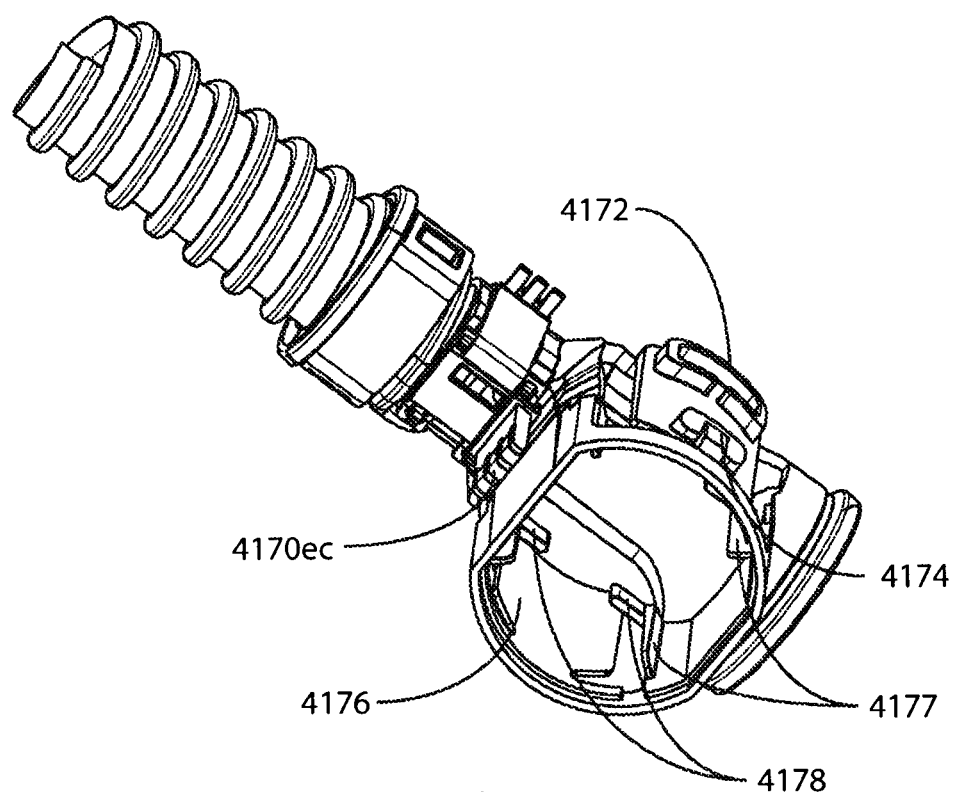

FIG. 18d shows a bottom perspective view of a portion of an air circuit 4170 in accordance with one form of the present technology.

Figure 18E:
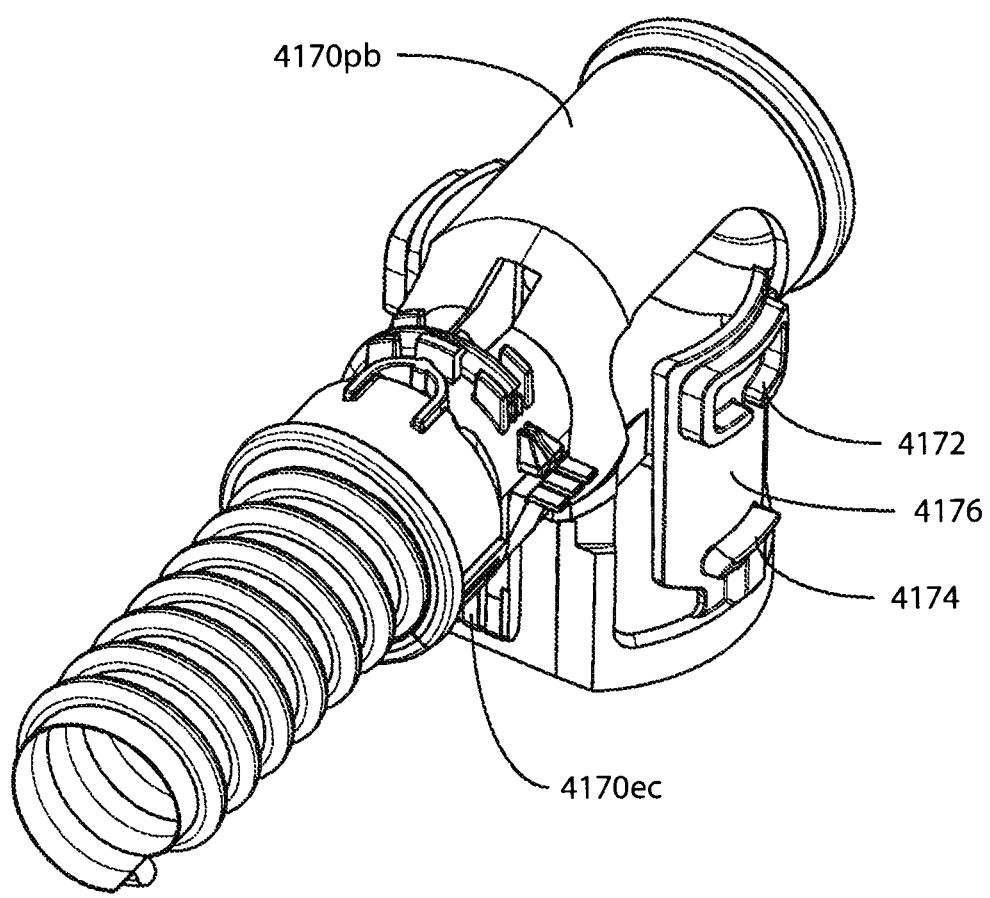

FIG. 18e shows a top perspective view of a portion of an air circuit 4170 in accordance with one form of the present technology.

Figure 18F:
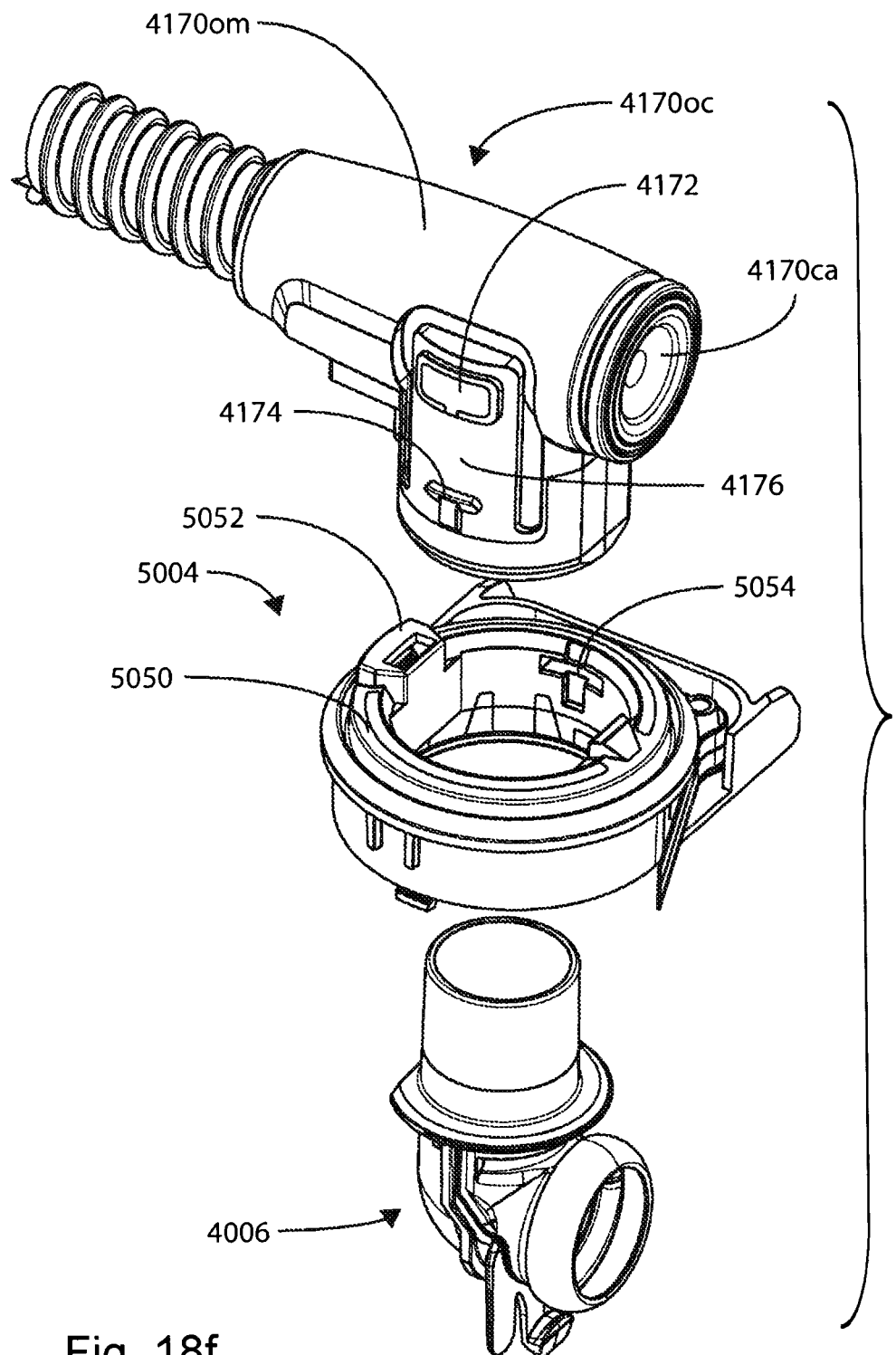

FIG. 18f shows an exploded perspective view of an air circuit 4170, an outlet assembly 5004 and an outlet tube 4006 in accordance with one form of the present technology.

Figure 18G:
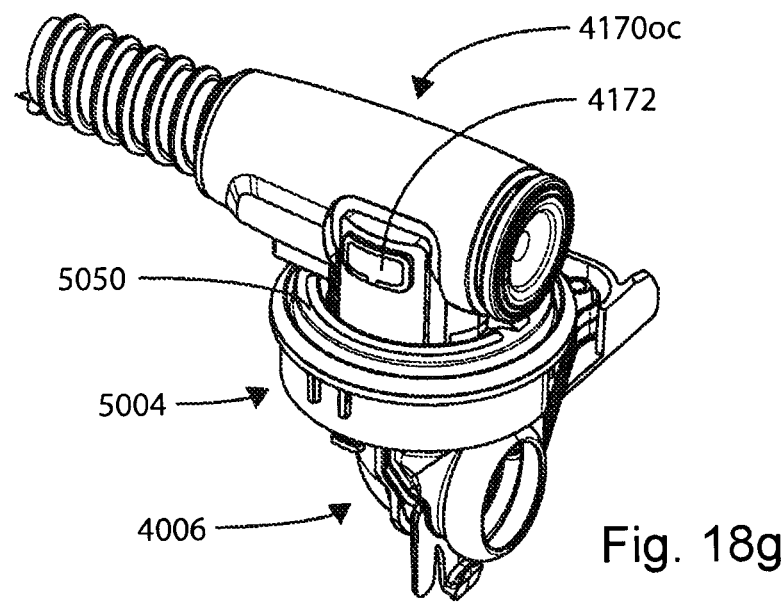

FIG. 18g shows a perspective view of an air circuit 4170, an outlet assembly 5004 and an outlet tube 4006 in accordance with one form of the present technology.

Figure 18H:
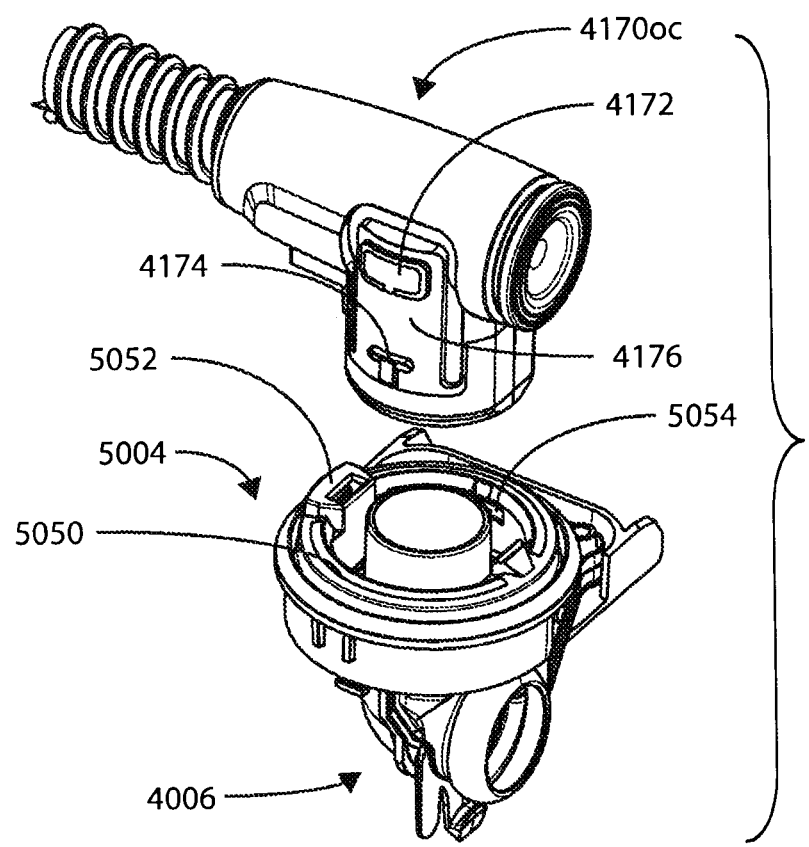

FIG. 18h shows a perspective view of an air circuit 4170, an outlet assembly 5004 and an outlet tube 4006 in accordance with one form of the present technology, showing the air circuit 4170 in exploded view.

Figure 18J:
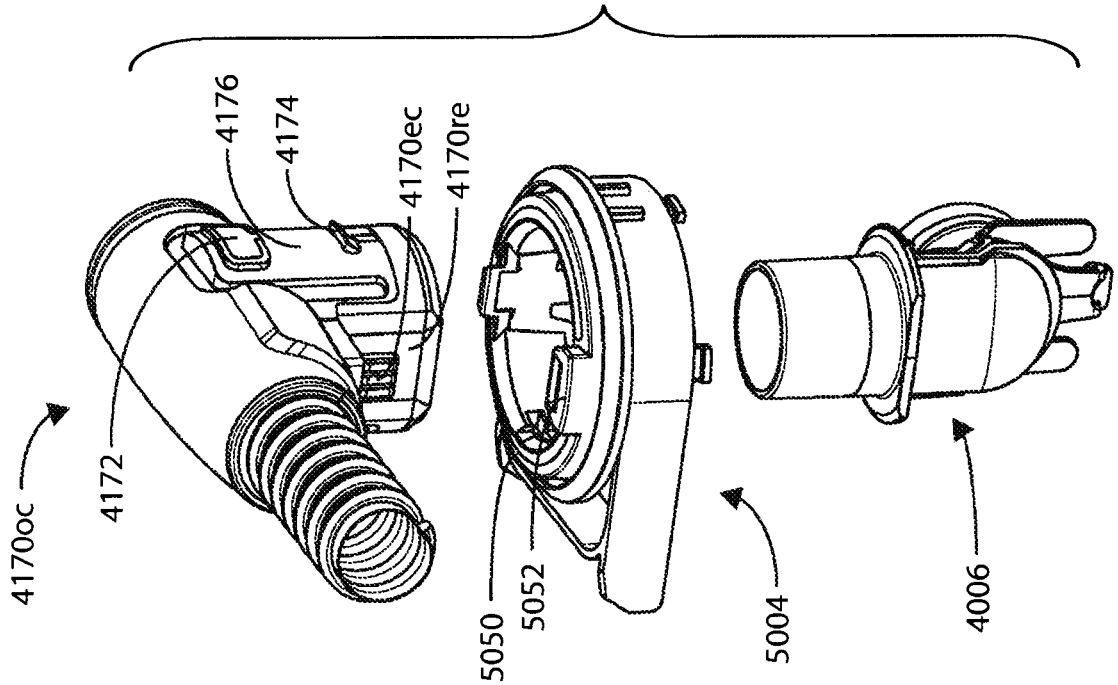
Figure 18I:
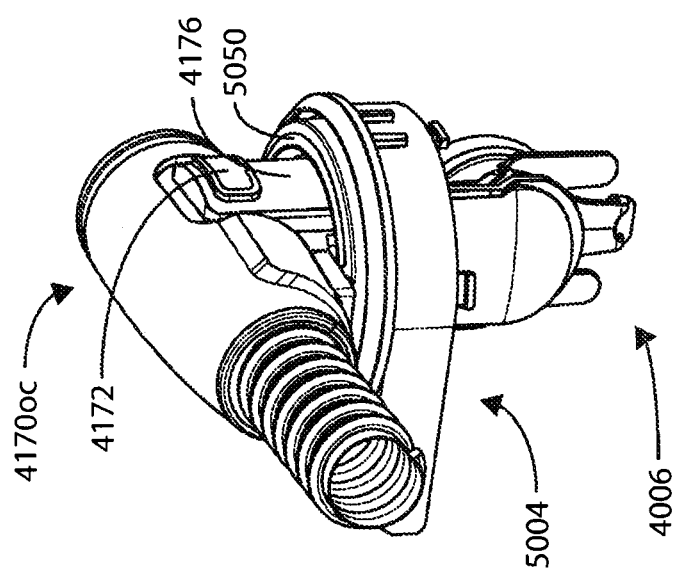

FIG. 18i shows another perspective view of an air circuit 4170, an outlet assembly 5004 and an outlet tube 4006 in accordance with one form of the present technology.

FIG. 18j shows another exploded perspective view of an air circuit 4170, an outlet assembly 5004 and an outlet tube 4006 in accordance with one form of the present technology.

Figure 18K:
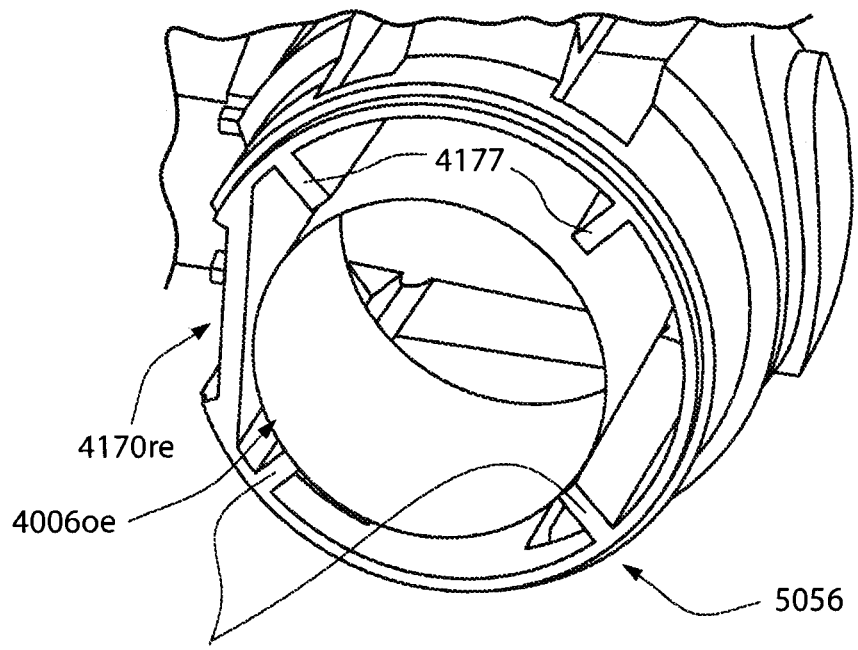

FIG. 18k shows a bottom perspective view of a portion of an air circuit 4170 and a portion of an outlet tube 4006 in accordance with one form of the present technology.

Figure 18L:
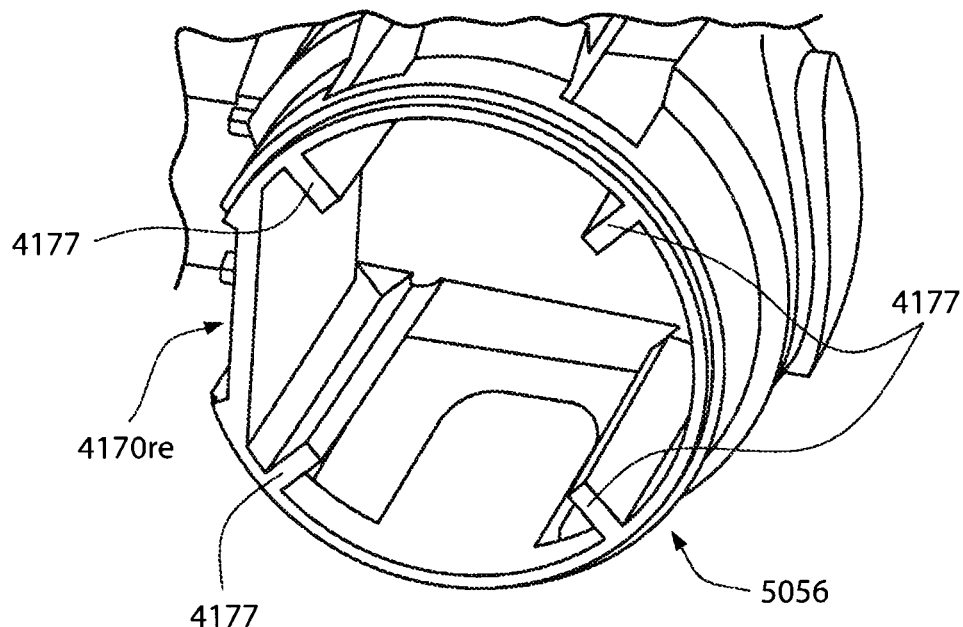

FIG. 18l shows a bottom perspective view of a portion of an air circuit 4170 in accordance with one form of the present technology.

Figure 18M:
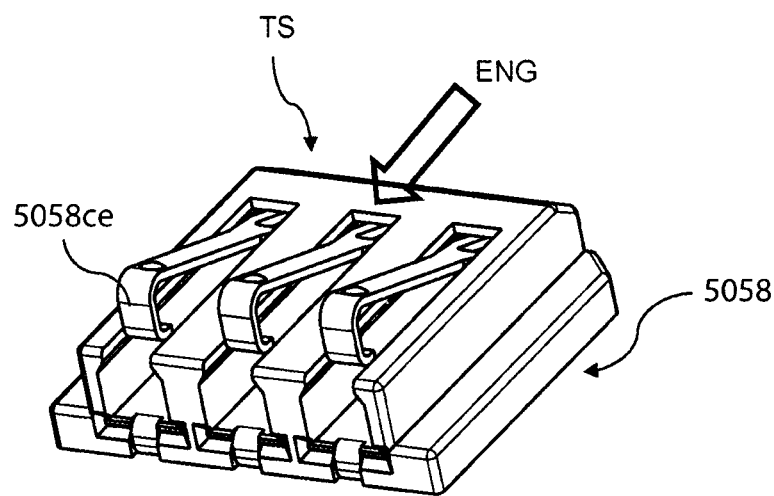

FIG. 18m shows a perspective view of a female electrical connector 5058 in accordance with one form of the present technology.

Figure 18N:
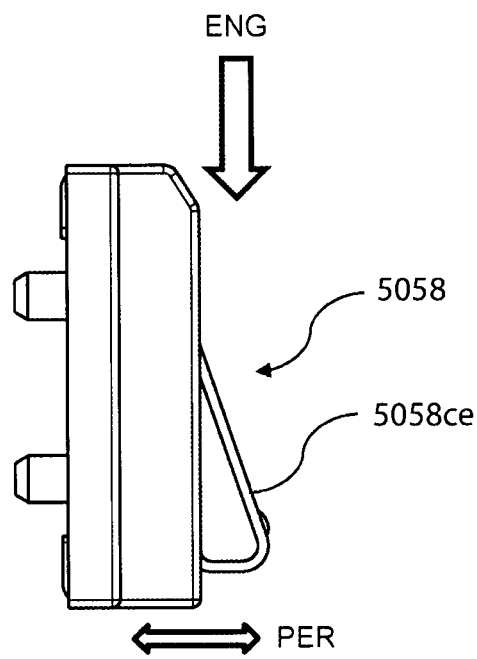

FIG. 18n shows a side view of a female electrical connector 5058 in accordance with one form of the present technology.

Figure 18O:
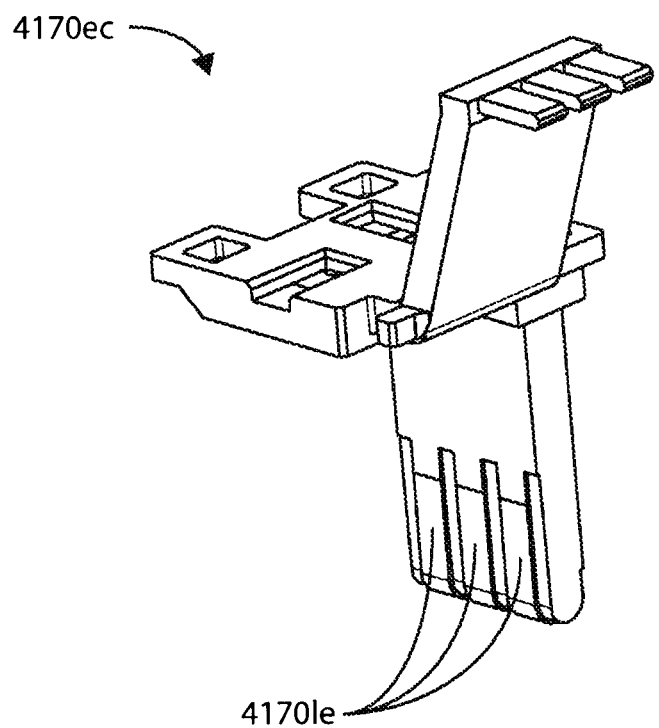

FIG. 18o shows a perspective view of an AC electrical connector 4170ec in accordance with one form of the present technology.

Figure 18P:
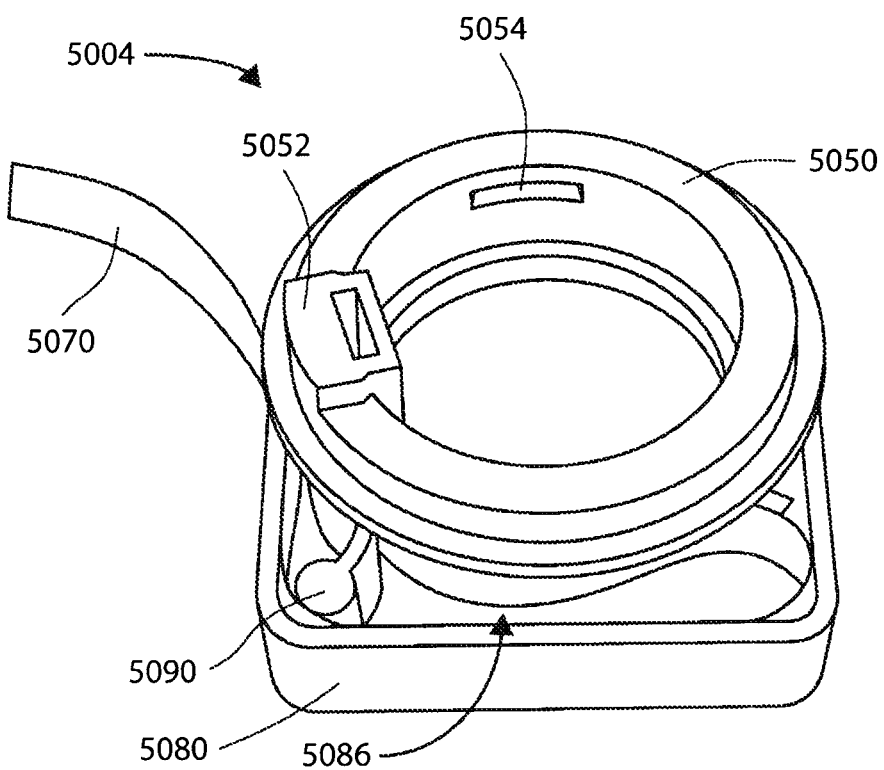

FIG. 18p shows a perspective view of an outlet assembly 5004 in accordance with one form of the present technology, showing the swivelling disc 5050 at a first position.

Figure 18Q:
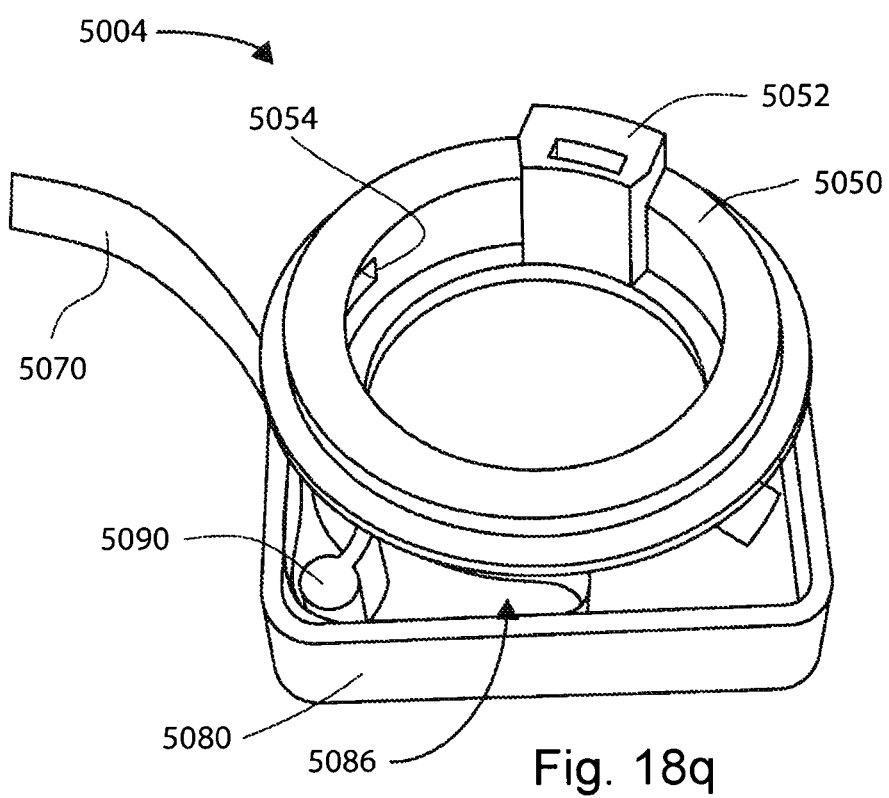

FIG. 18q shows a perspective view of an outlet assembly 5004 in accordance with one form of the present technology, showing the swivelling disc 5050 at a second position.

Figure 18R:
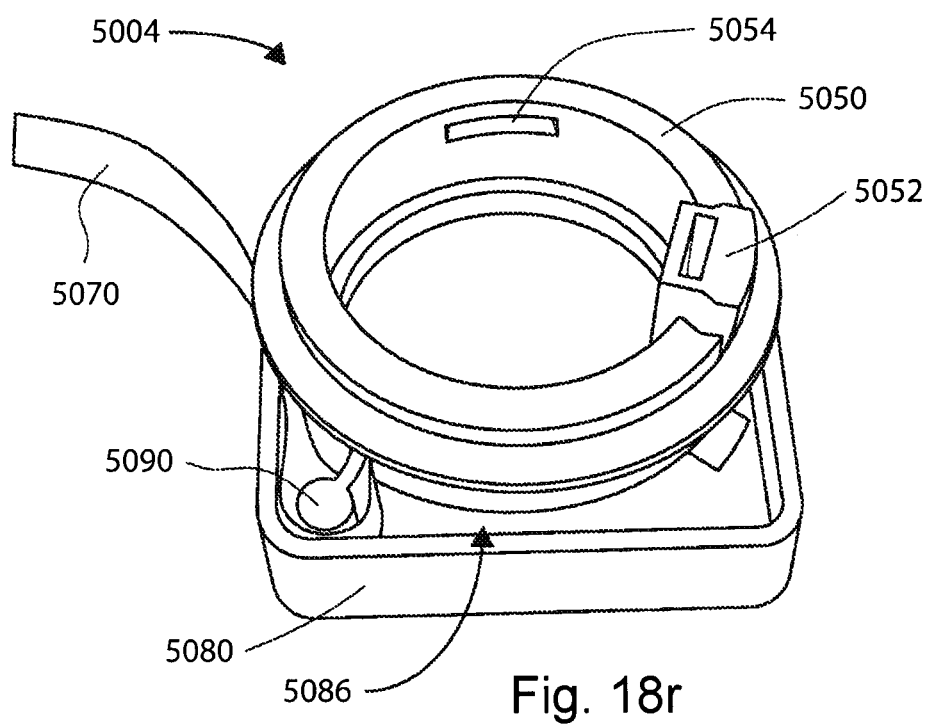

FIG. 18r shows a perspective view of an outlet assembly 5004 in accordance with one form of the present technology, showing the swivelling disc 5050 at a third position.

Figure 18S:
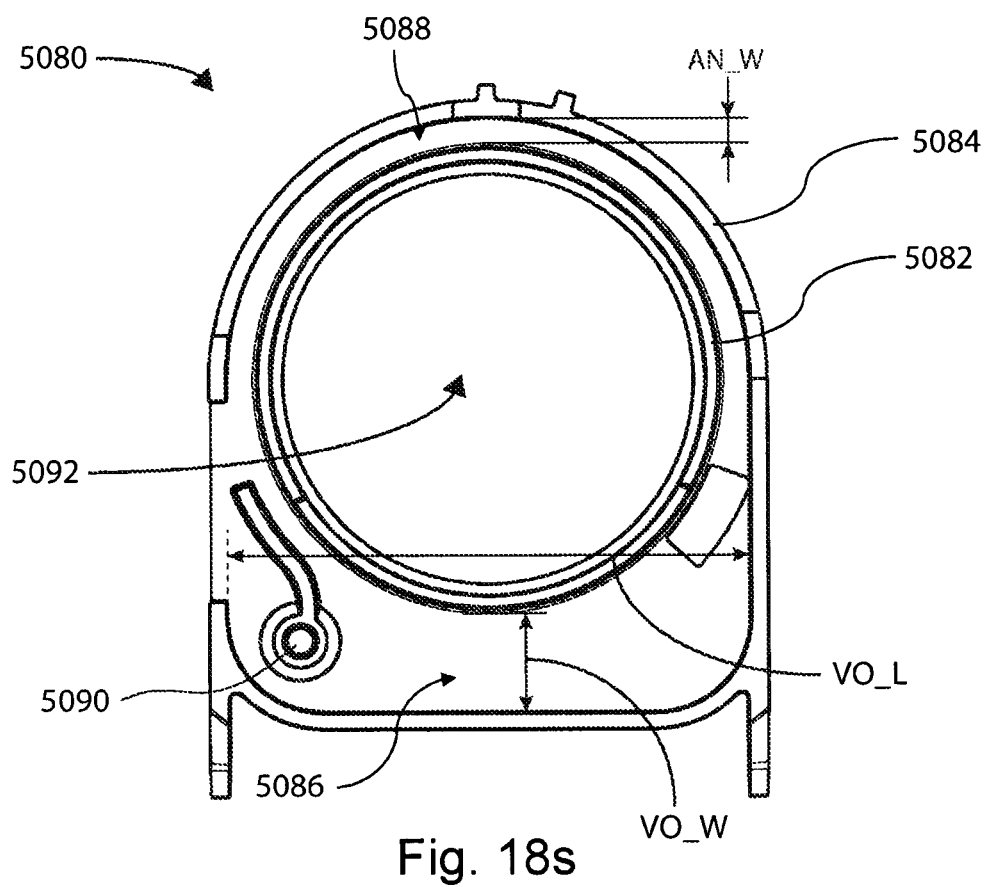

FIG. 18s shows a perspective view of a cable housing 5080 in accordance with one form of the present technology.

Figure 18T:
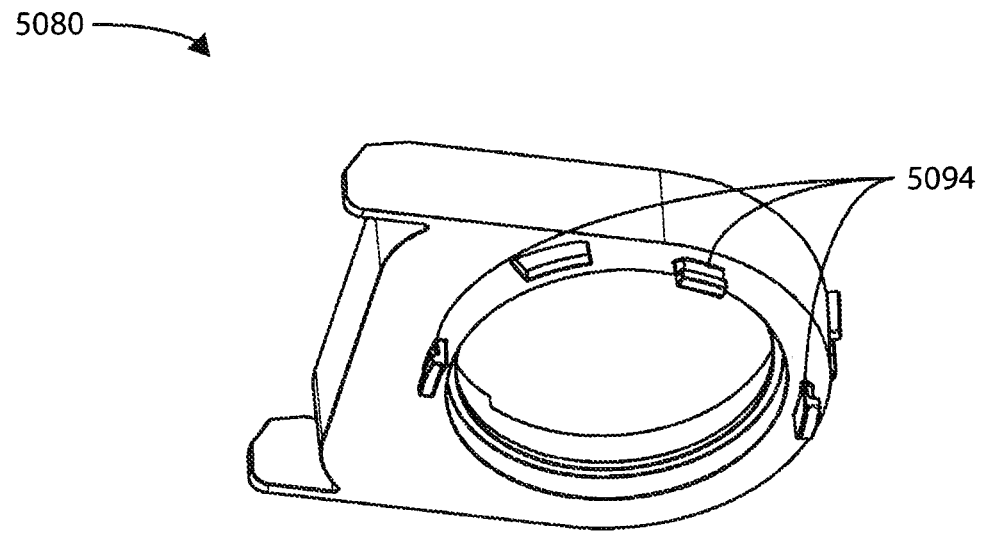

FIG. 18t shows a bottom perspective view of a cable housing 5080 in accordance with one form of the present technology.

Figure 18U:
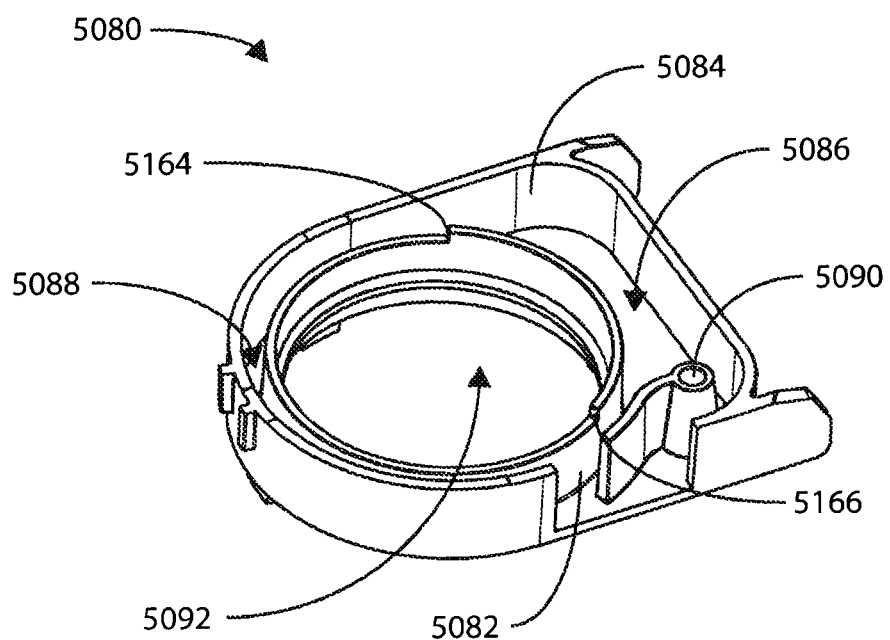

FIG. 18u shows a top perspective view of a cable housing 5080 in accordance with one form of the present technology.

Figure 18V:
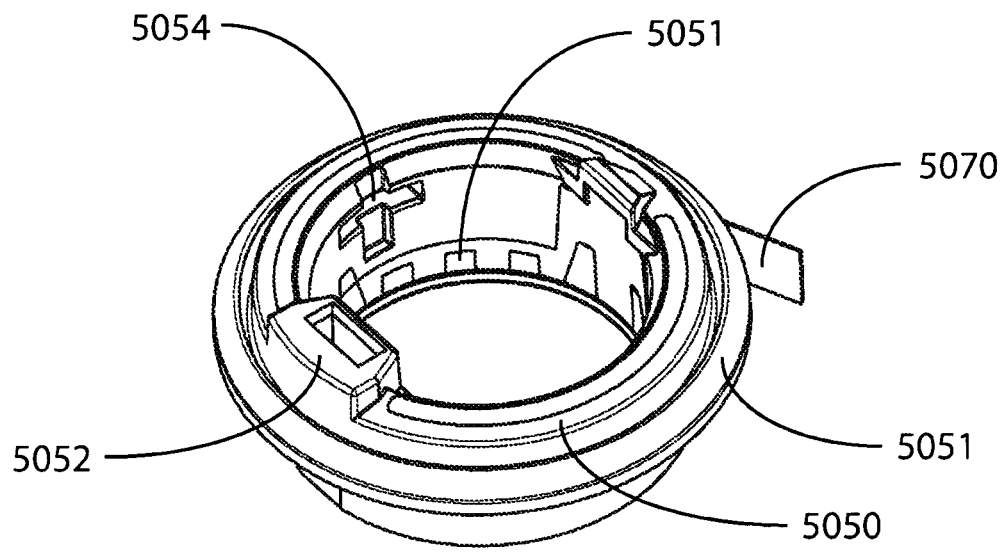

FIG. 18v shows a top perspective view of a swivelling disc 5050 in accordance with one form of the present technology.

Figure 18W:
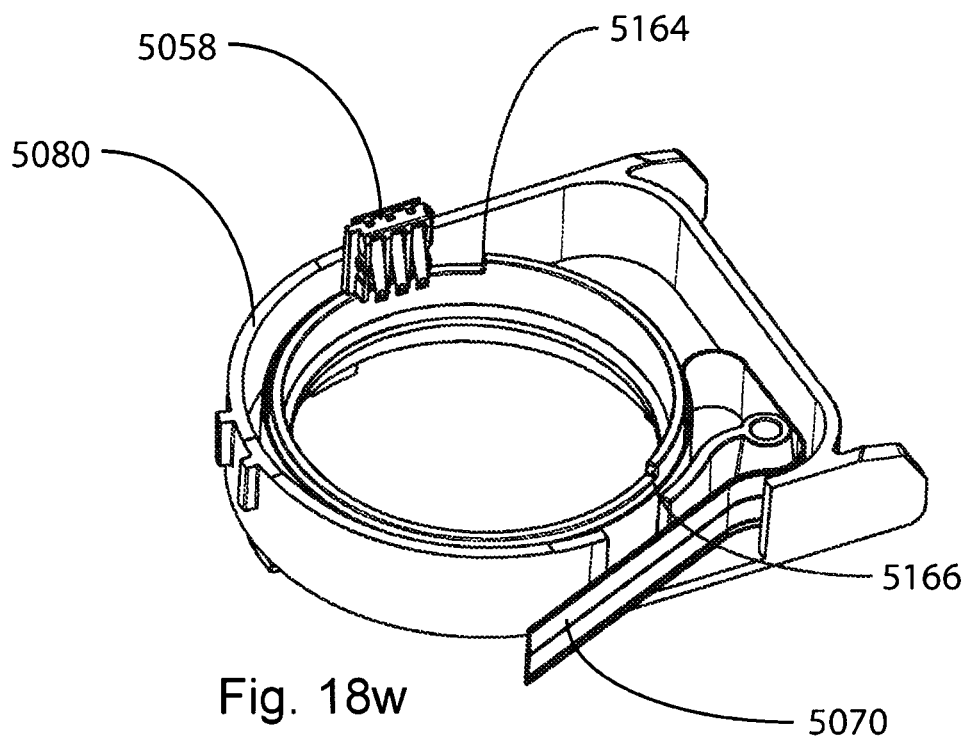

FIG. 18w shows a top perspective view of a cable housing 5080 and a cable 5070 in accordance with one form of the present technology.

Figure 18X:
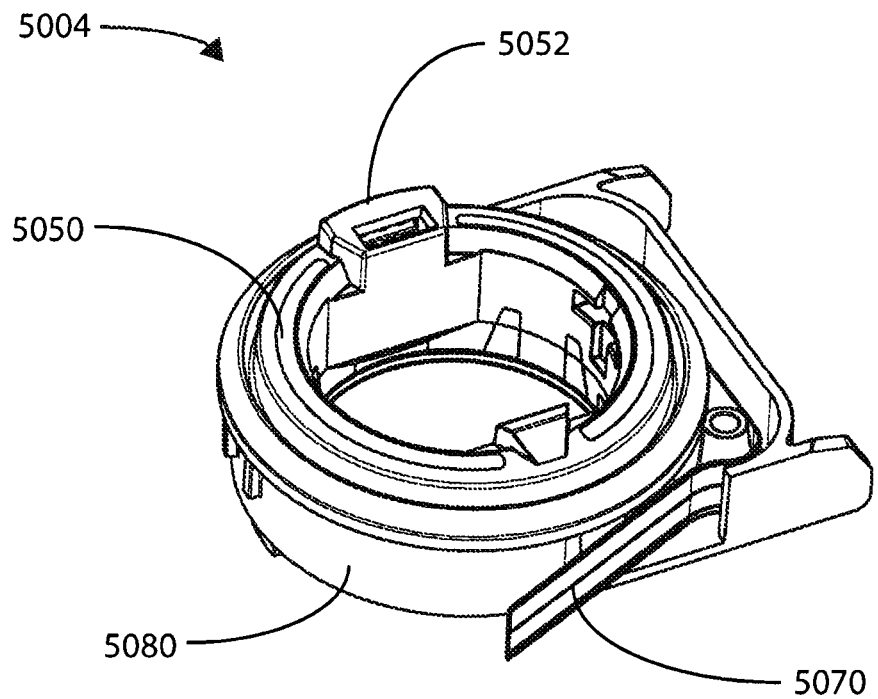

FIG. 18x shows a top perspective view of a cable housing 5080, swivelling disc 5050 and a cable 5070 in accordance with one form of the present technology.

Figure 18Y:
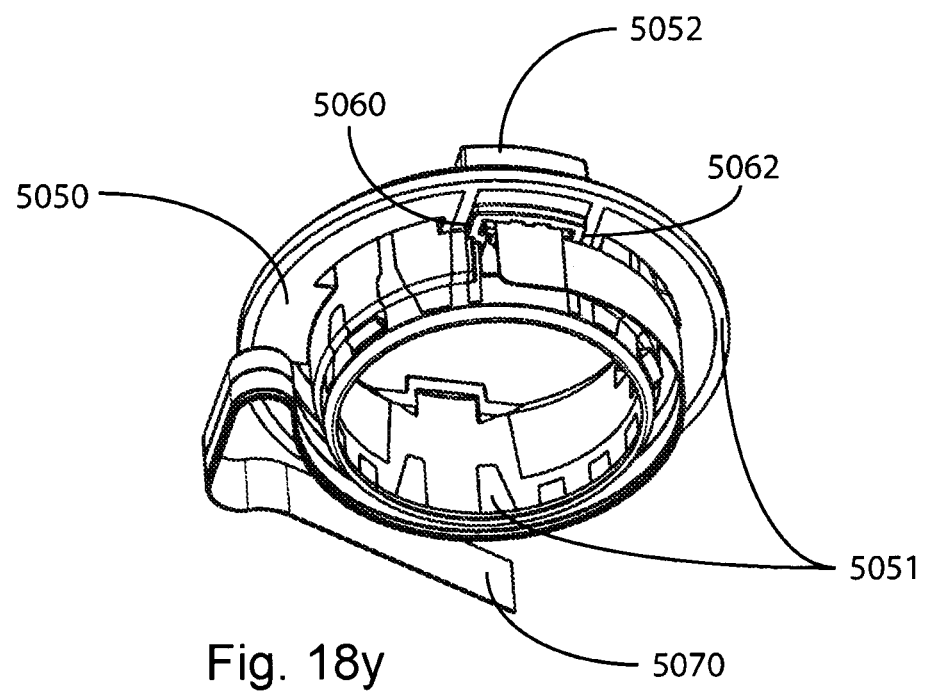

FIG. 18y shows a bottom perspective view of a swivelling disc 5050 and a cable 5070 in accordance with one form of the present technology.

FIG. 18z1 shows a rear view of a female electrical connector according to an example of the present technology.

FIG. 18z2 shows a perspective view of a female electrical connector according to an example of the present technology.

FIG. 18z3 shows a front-on view of a female electrical connector according to an example of the present technology, indicating the cross section taken for FIG. 18z4.

FIG. 18z4 shows a side cross-sectional view of a female electrical connector according to an example of the present technology.

FIG. 18z5 shows a rear perspective view of an electrical connector receiver contact element according to an example of the present technology.

FIG. 18z6 shows a front perspective view of an electrical connector receiver contact element according to an example of the present technology.

Figure 19:
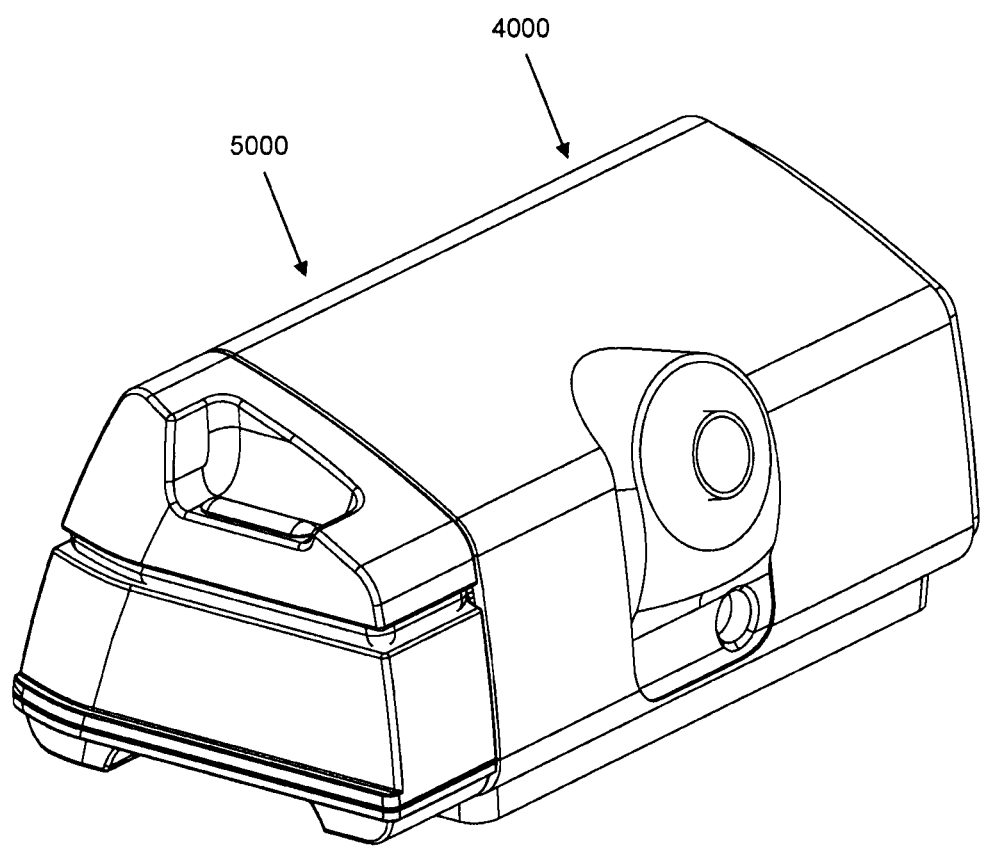

FIG. 19 shows an example of the present technology, showing a PAP device 4000 and an integrated humidifier 5000.

Figure 20:
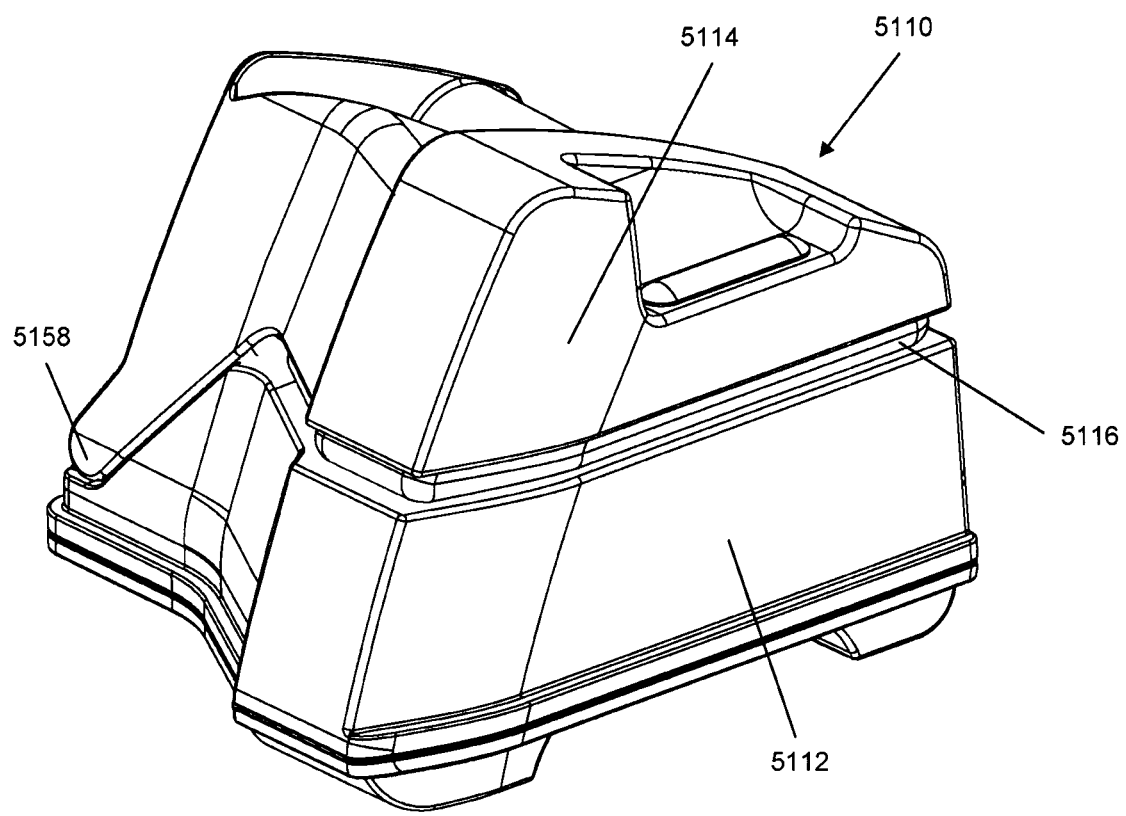
Figure 21:
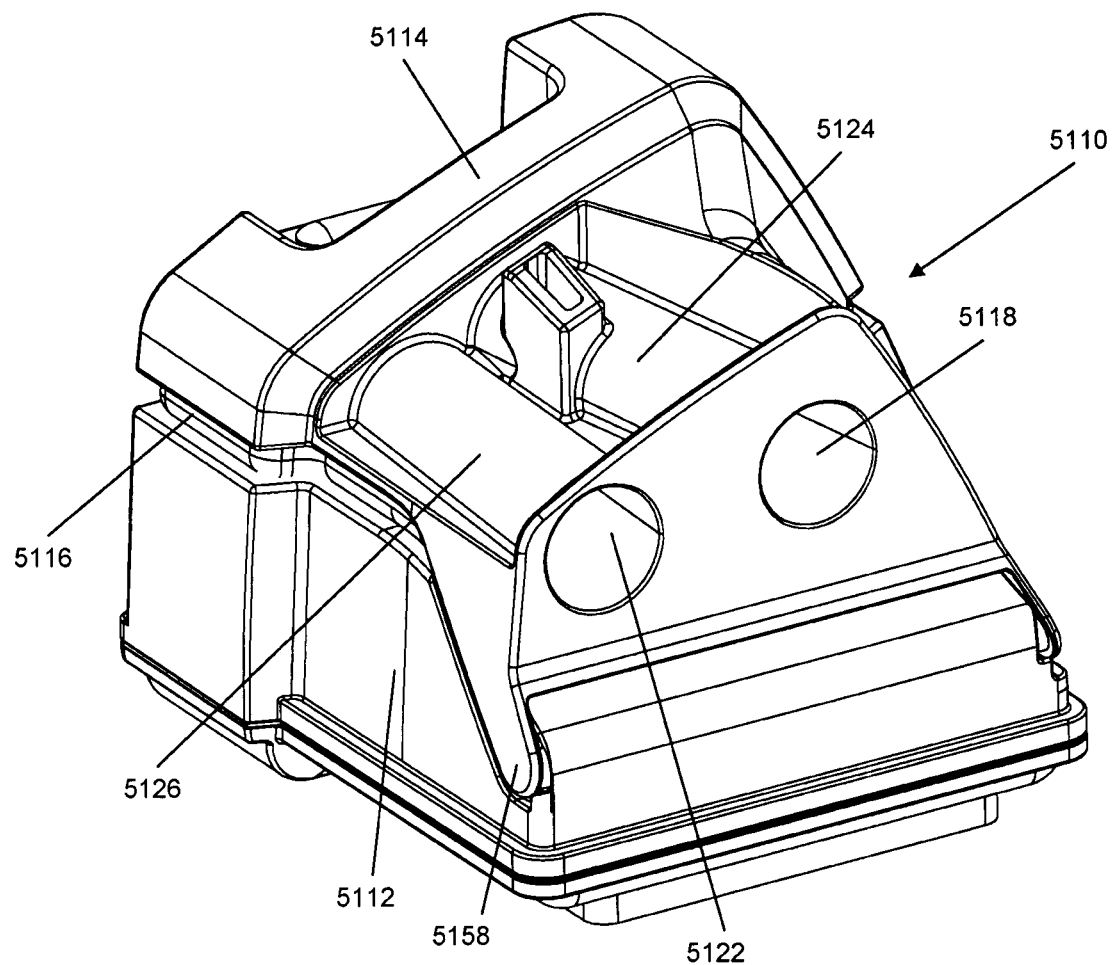
Figure 22:
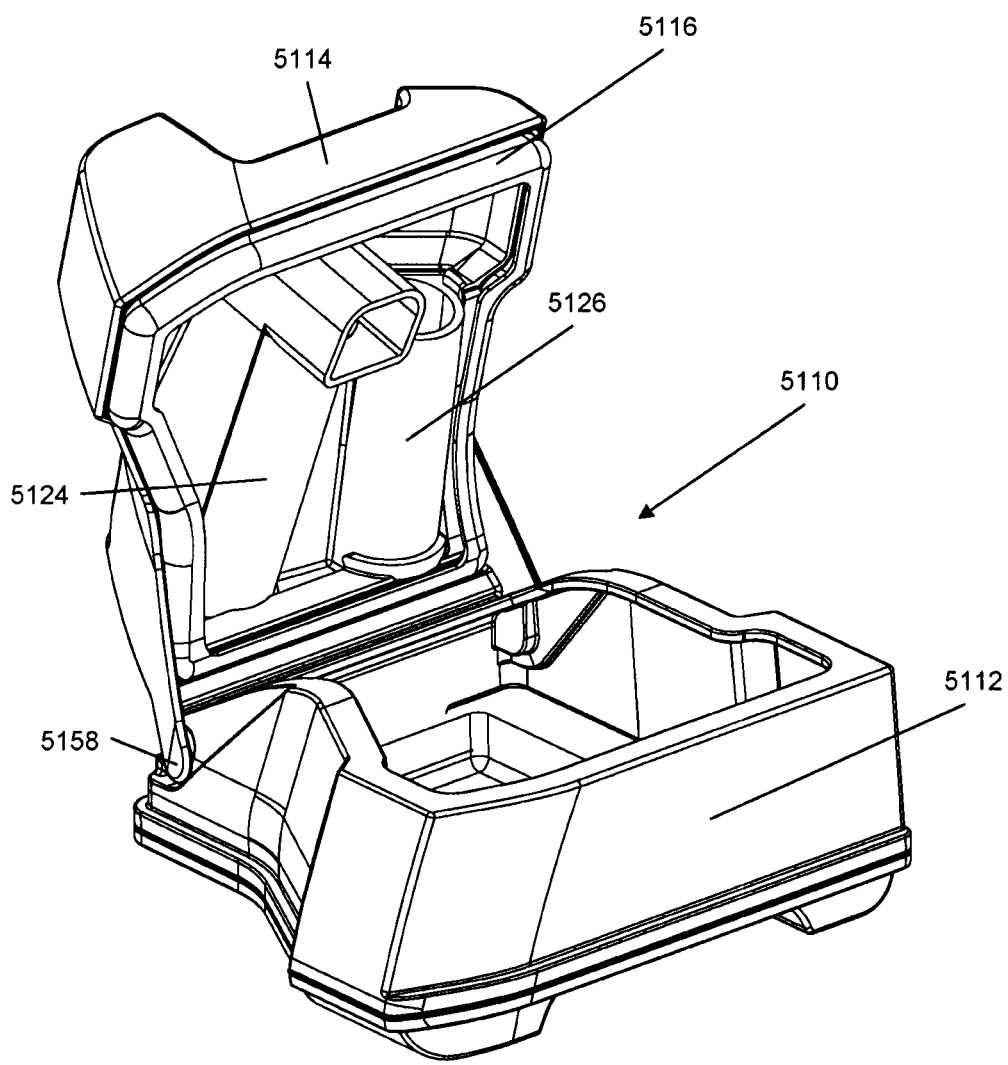
Figure 23:
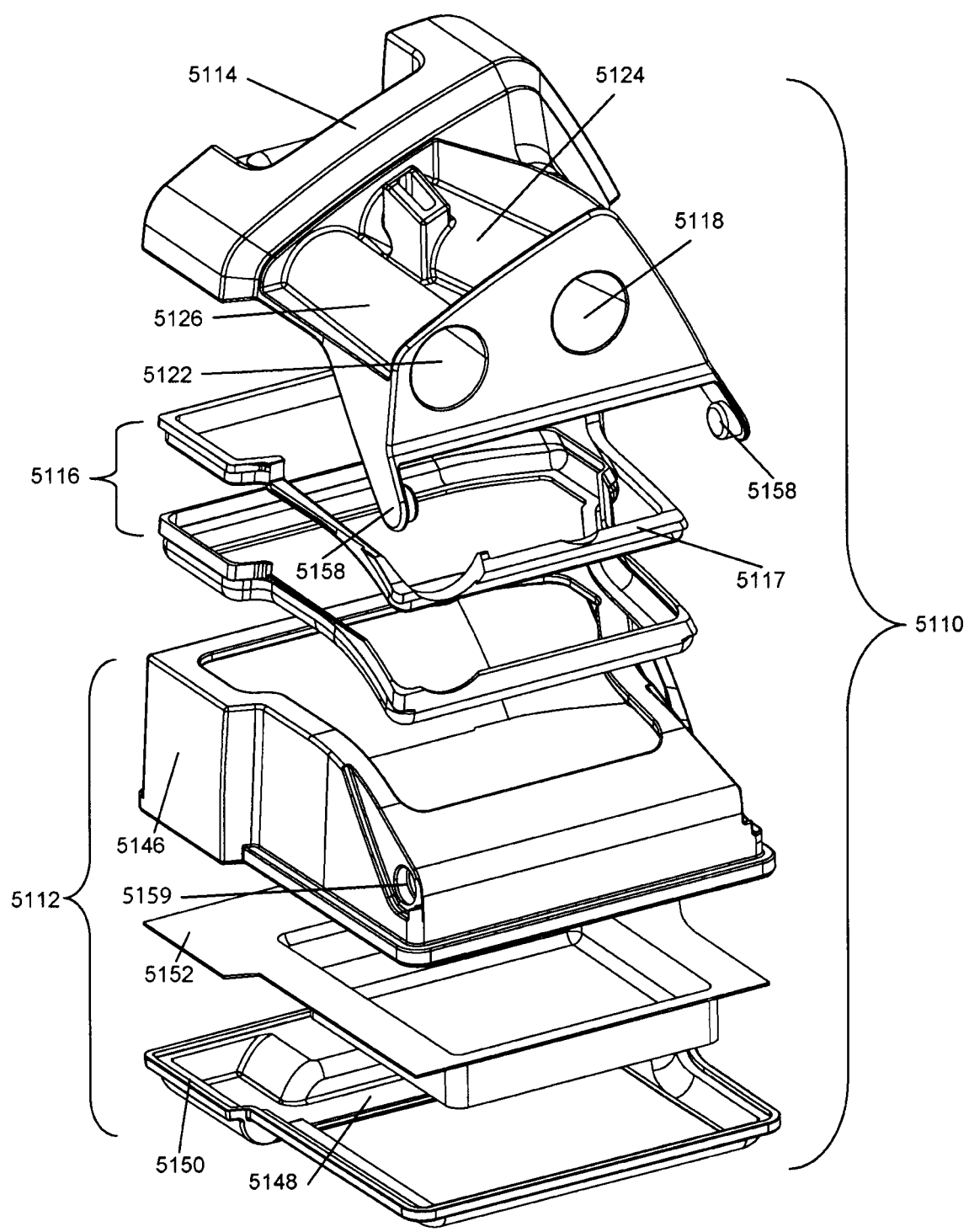
Figure 24:
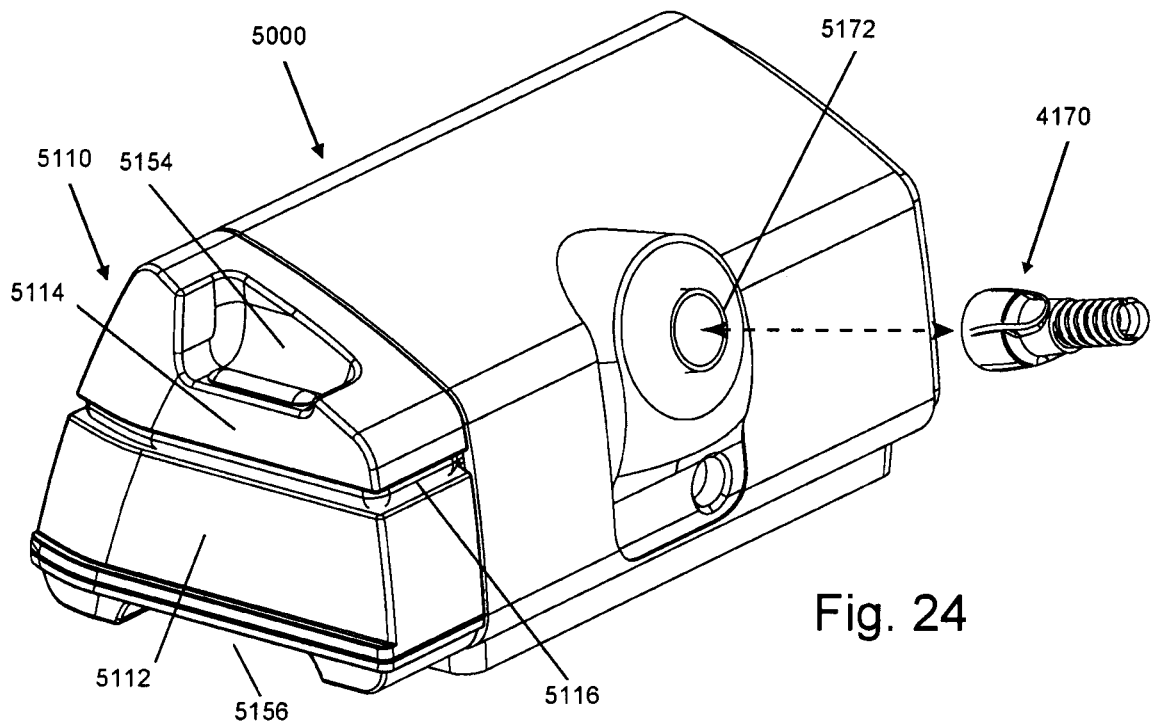

FIGS. 20-23 show various views of a humidifier reservoir 5110 in accordance with one aspect of present technology, wherein FIGS. 20-21 show the humidifier reservoir 5110 in a 'closed' configuration, FIG. 22 shows the humidifier reservoir 5110 in an 'open' configuration, and FIG. 23 is an exploded view of the humidifier reservoir 5110.

FIGS. 24-27 show the humidifier 5000 from various perspectives, demonstrating the engagement of the humidifier reservoir 5110 with the reservoir dock 5130 and/or engagement of the humidifier 5000 with the air circuit 4170.

FIGS. 28a-28c, 29a29c, and 30a-30c show a time-lapse chart of an exemplary flow path of gas as it enters the humidifier reservoir 5110 through the inlet 5118 and exits through the outlet 5122 after traversing through the inside of the humidifier reservoir 5110.

Figure 31:
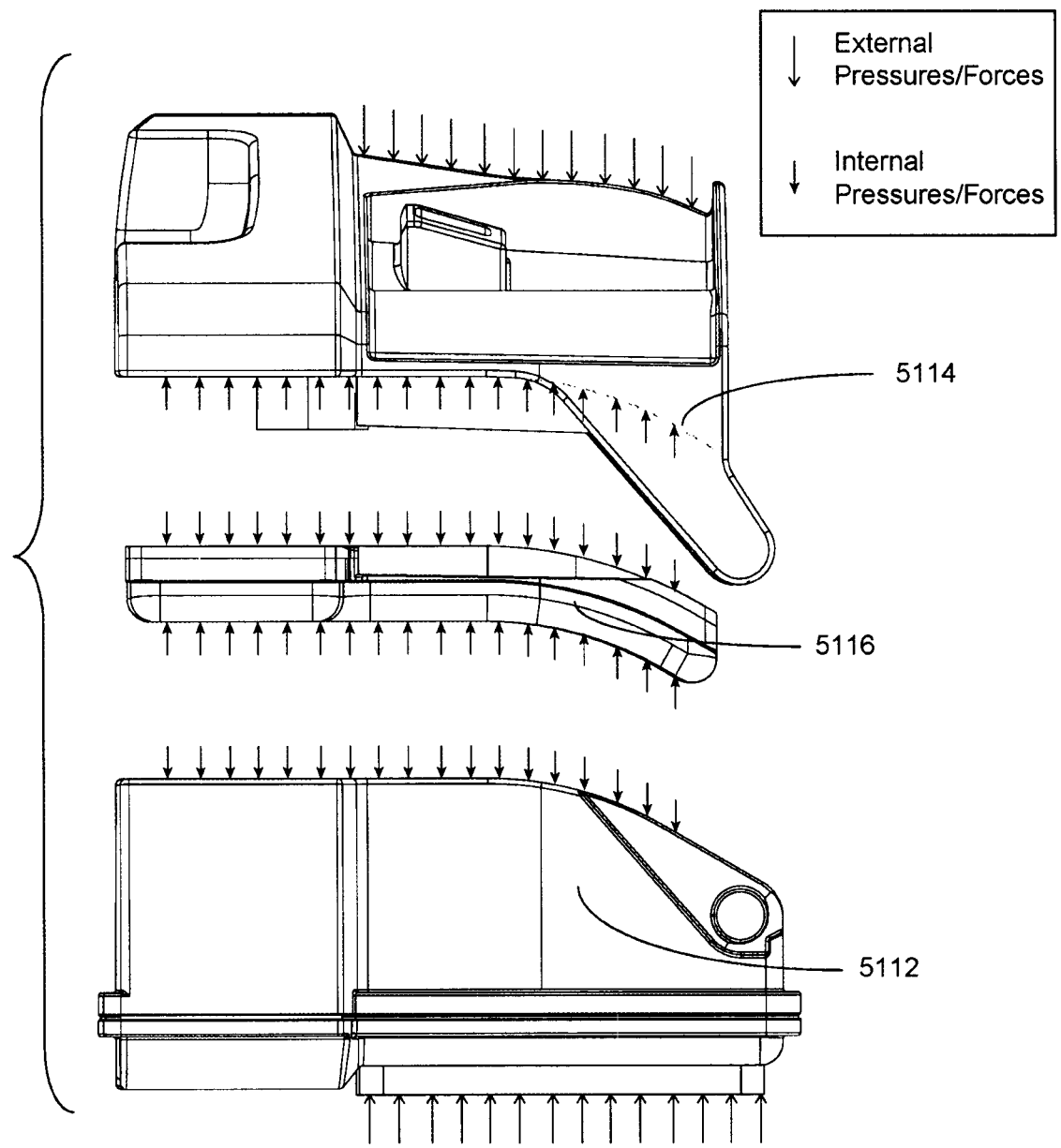
Figure 32:
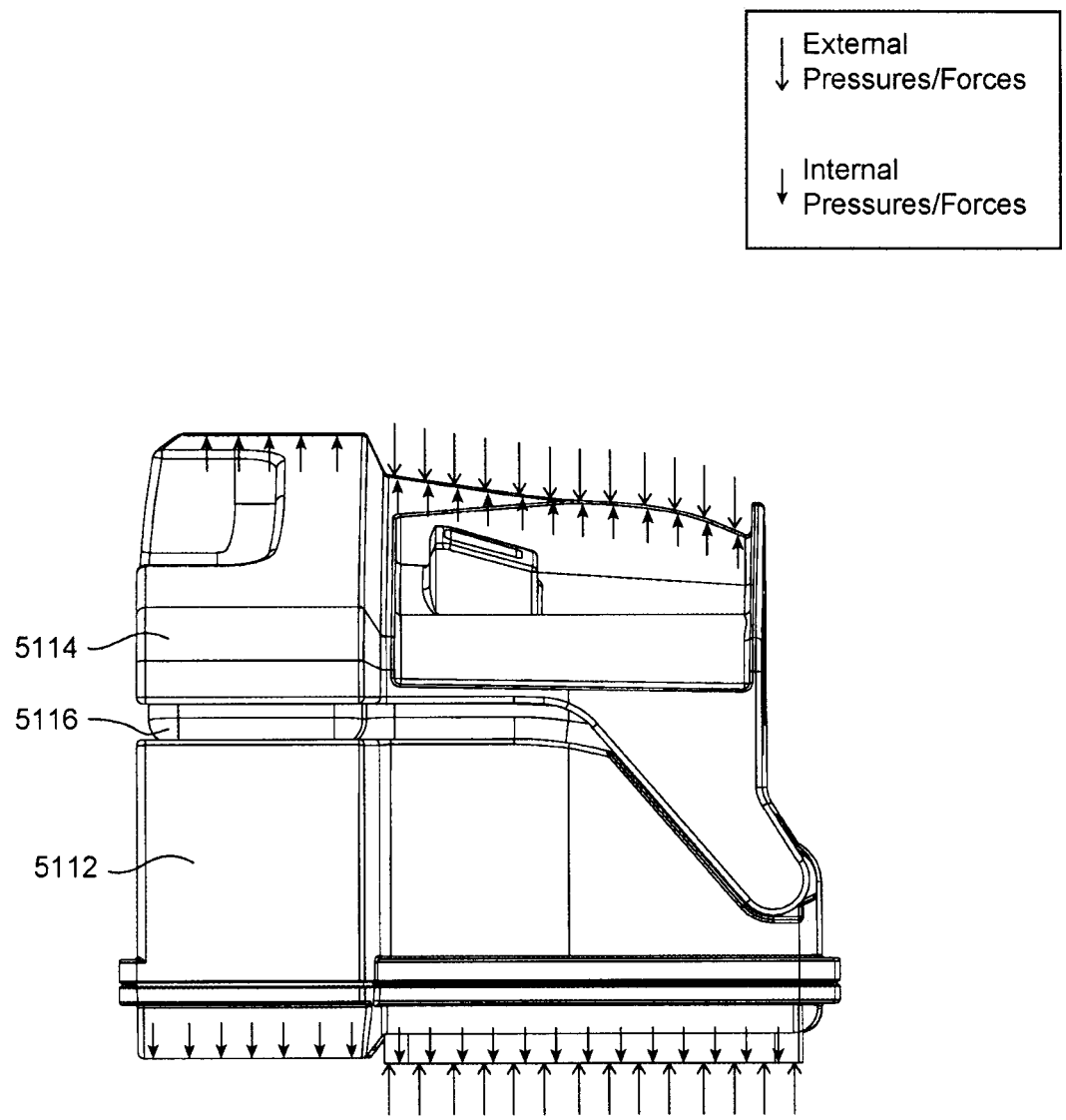

FIGS. 31-32 show exemplary distributions of pressure/force in the humidifier reservoir 5110 in various configurations.

FIGS. 33-40 show varying configurations of the reservoir lid 5114, in particular variations in configurations of the inlet tube 5124 and the outlet tube 5126 according to aspects of the present technology.

Figure 41A:
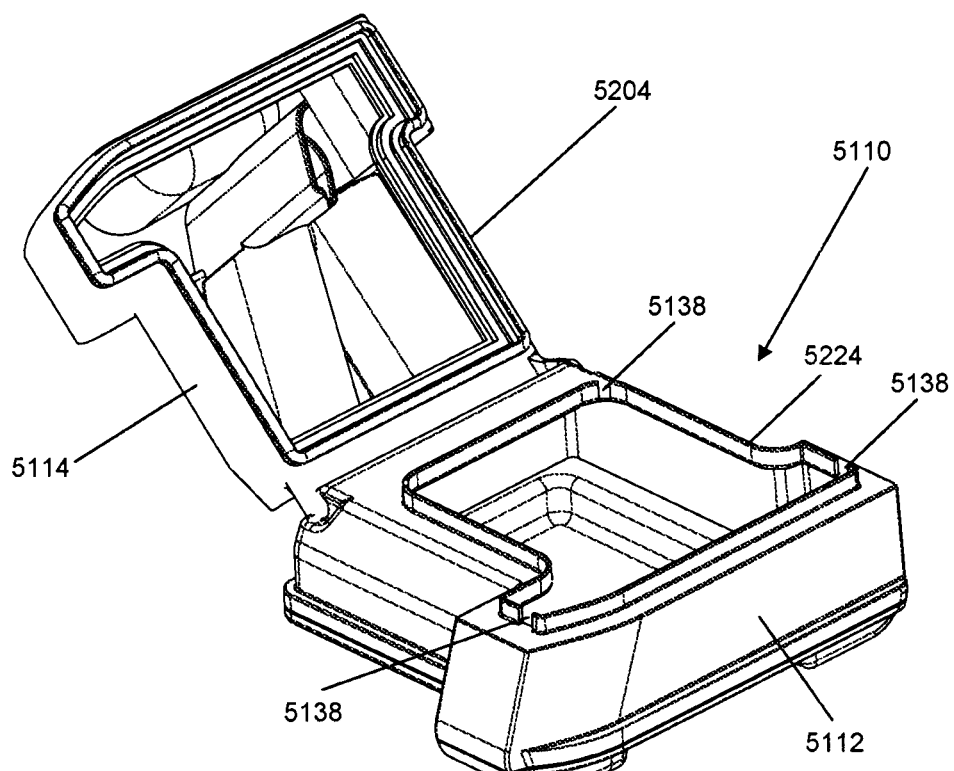
Figure 41B:
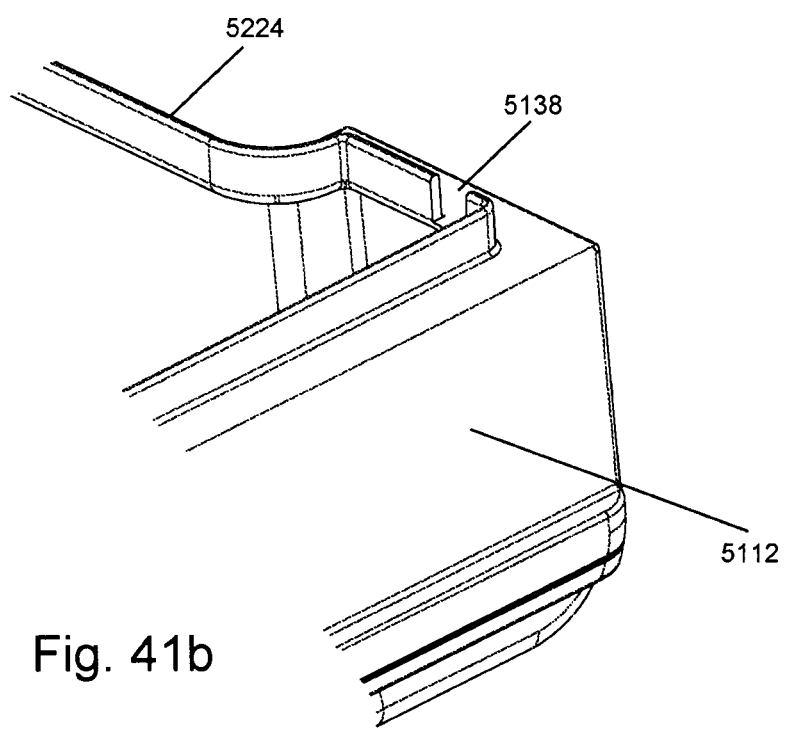
Figure 42:
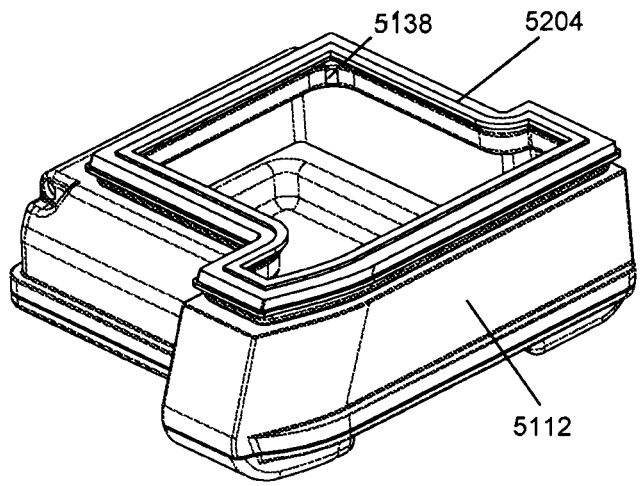

FIGS. 41a, 41b and 42 show the humidifier reservoir 5110 and in particular they aim to show the orifice 5138.

Figure 41C:
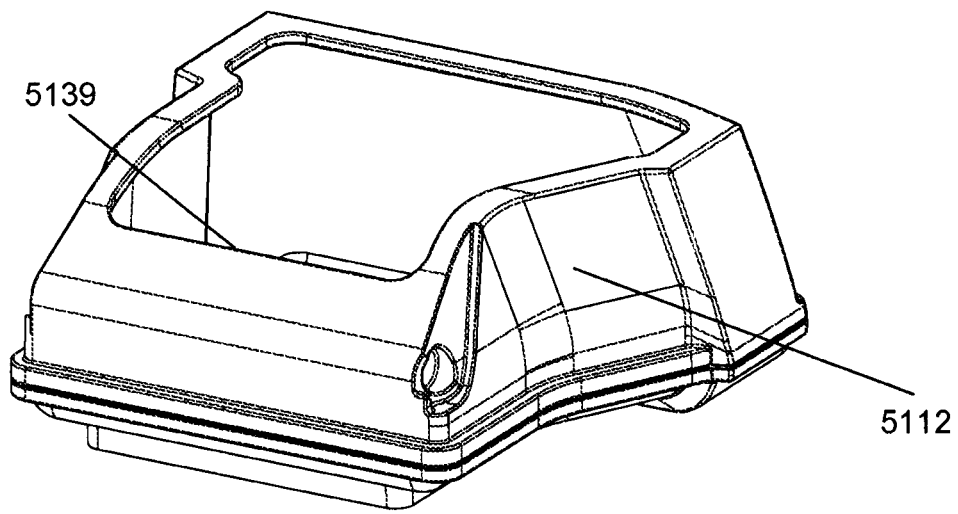
Figure 41D:
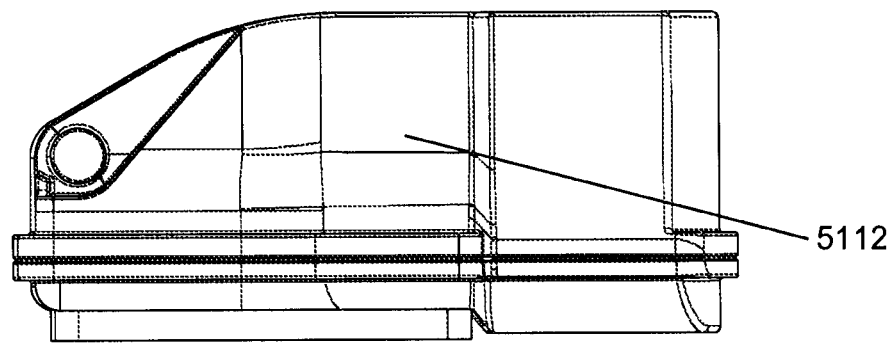

FIGS. 41c and 41d show the humidifier base 5112 and in particular they aim to show the sloped profile 5139.

Figure 43:
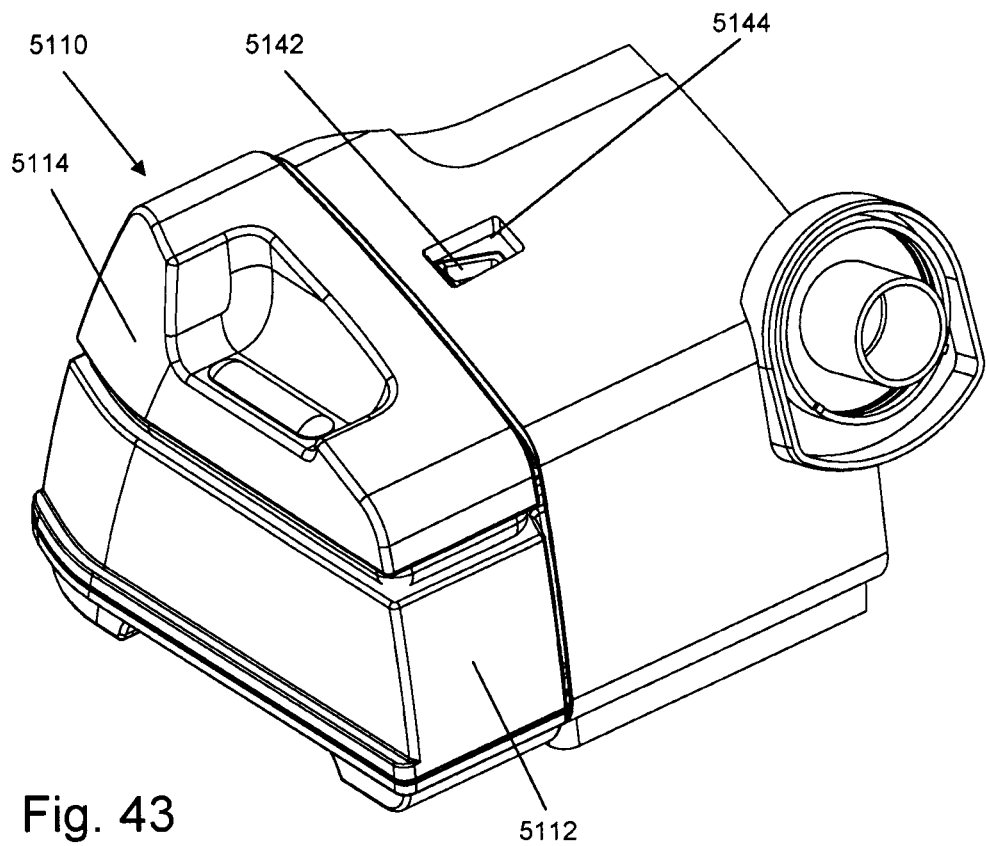
Figure 44:
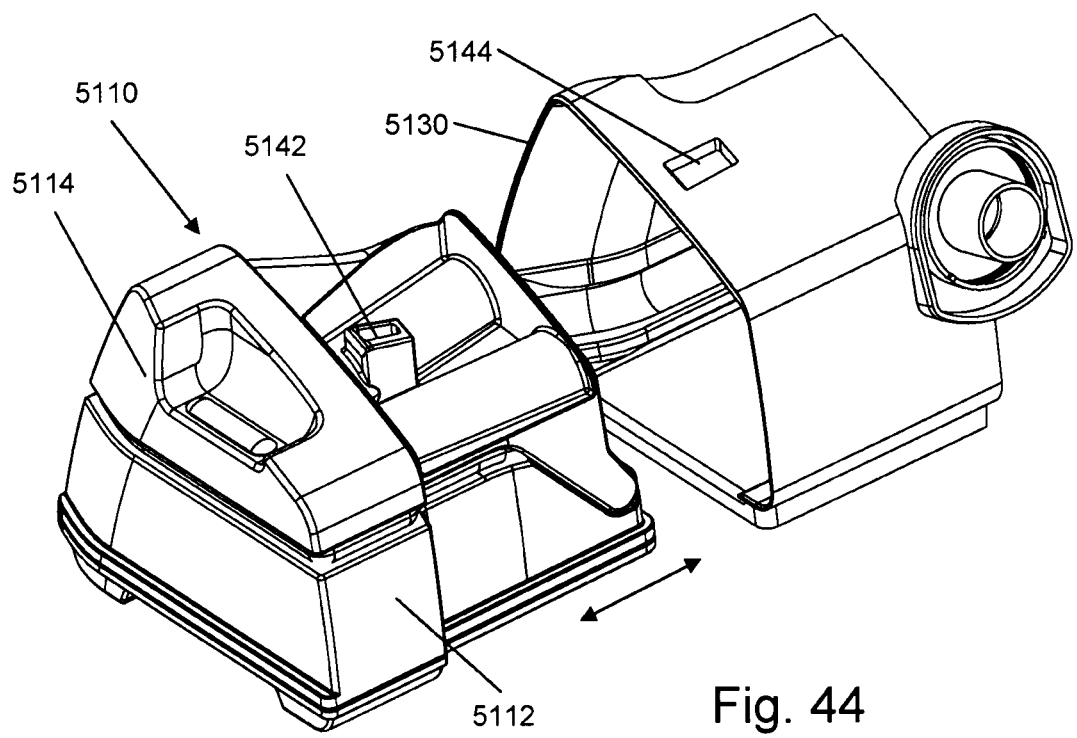

FIGS. 43-44 show the humidifier dock 5130 and the humidifier reservoir 5110, and in particular show the interaction between the lid retention protrusion 5142 and the dock locking recess 5144 according to one aspect of the present technology.

Figure 45:
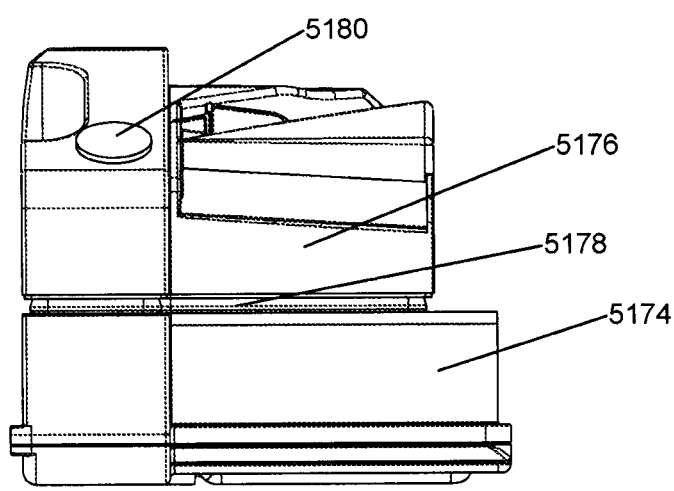

FIG. 45 shows the humidifier reservoir 5110 according to another example of the current technology, wherein it is configured with a re-filling cap 5180 and a base, top and variable portion may be affixed together.

FIGS. 46-49 shows other representations of a humidifier reservoir 5110 according to an aspect of the present technology, with particular regard to the arrangement of the inlet tube 5124 and the outlet tube 5126.

Figure 50:
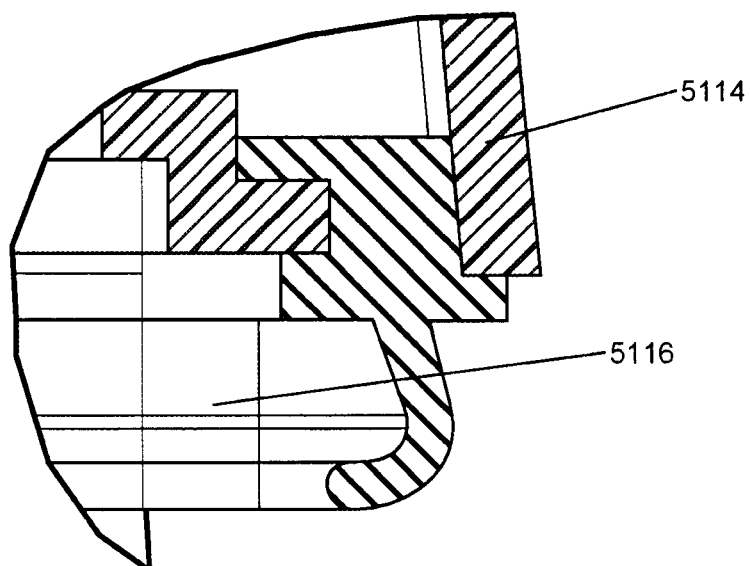

FIG. 50 shows a cross-sectional view of a reservoir lid 5114 and a variable portion in the form of a variable portion 5116 according to an aspect of the present technology.

Figure 51:
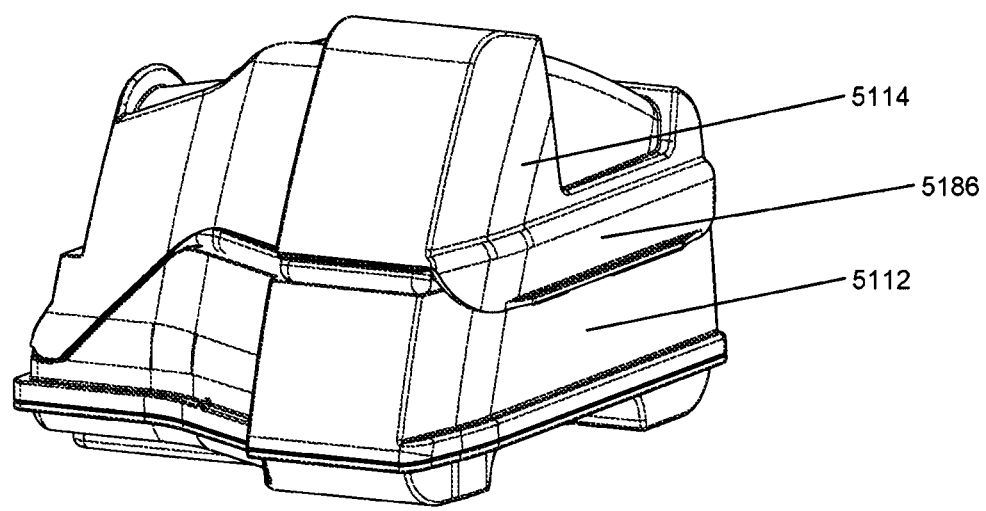

FIG. 51 shows an example of the humidifier reservoir 5110 according to another example of the current technology, wherein it is configured with a latch 5186.

Figure 52A:
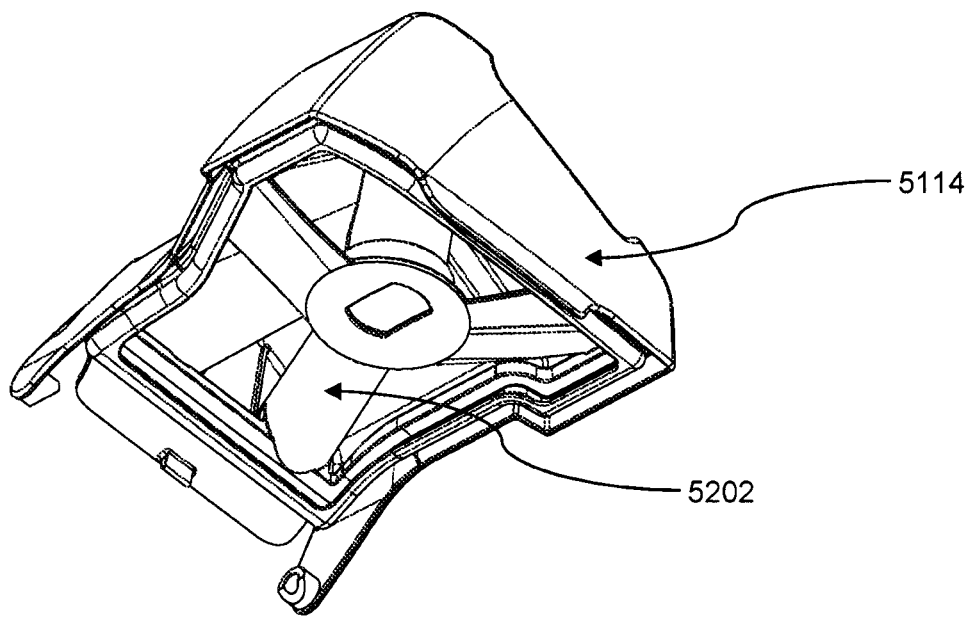
Figure 52B:
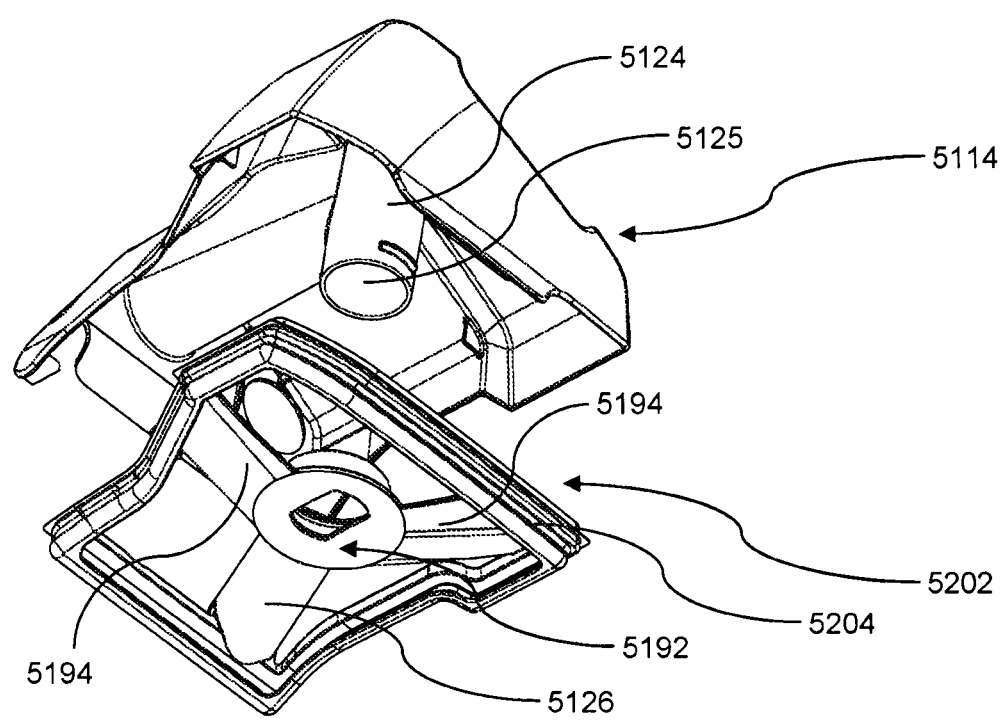
Figure 53:
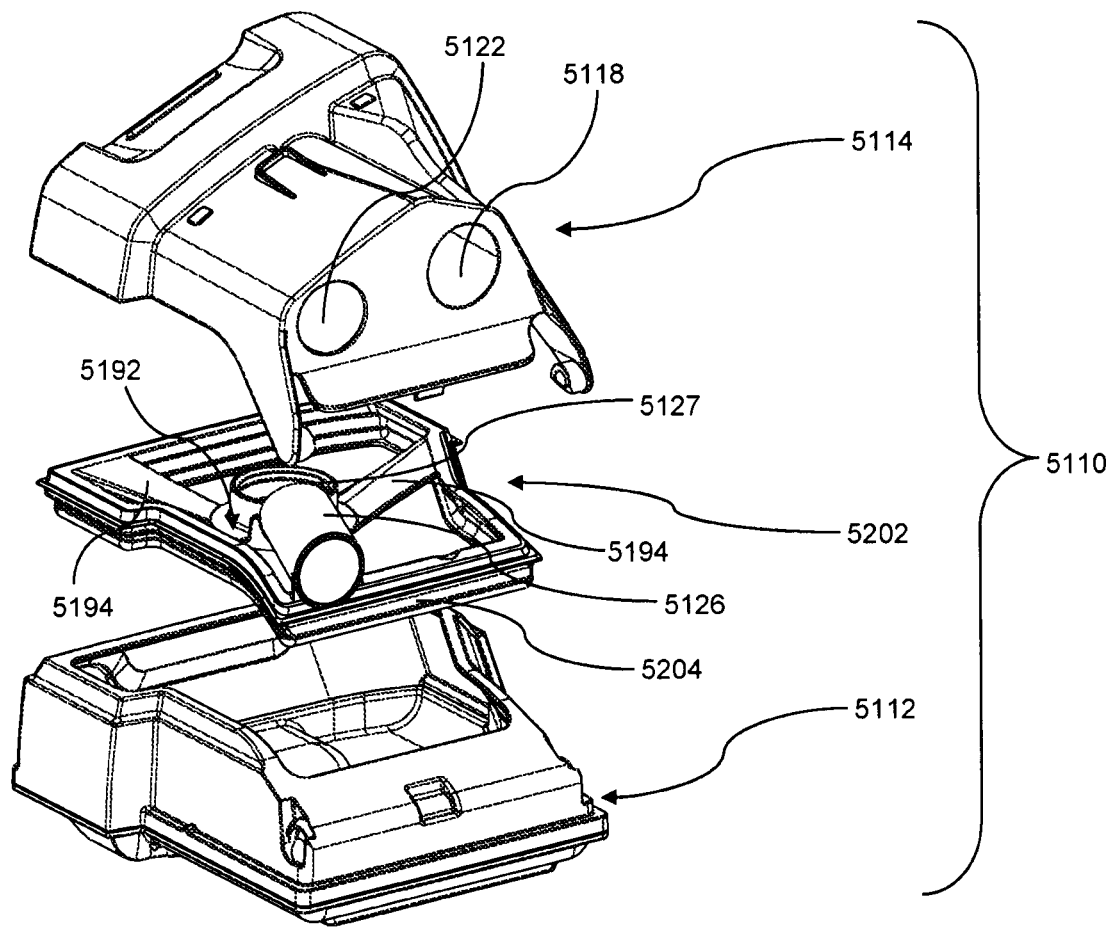

FIGS. 52a, 52b, and 53 show a portion of the humidifier reservoir 5110 according to another example of the current technology. In this configuration, the reservoir 5110 comprises a reservoir lid 5114 including an inlet tube 5124, an intermediate portion 5202 which comprises an outlet tube 5126 and a base portion 5112 (as seen in an exploded view shown in FIG. 53).

Figure 54A:
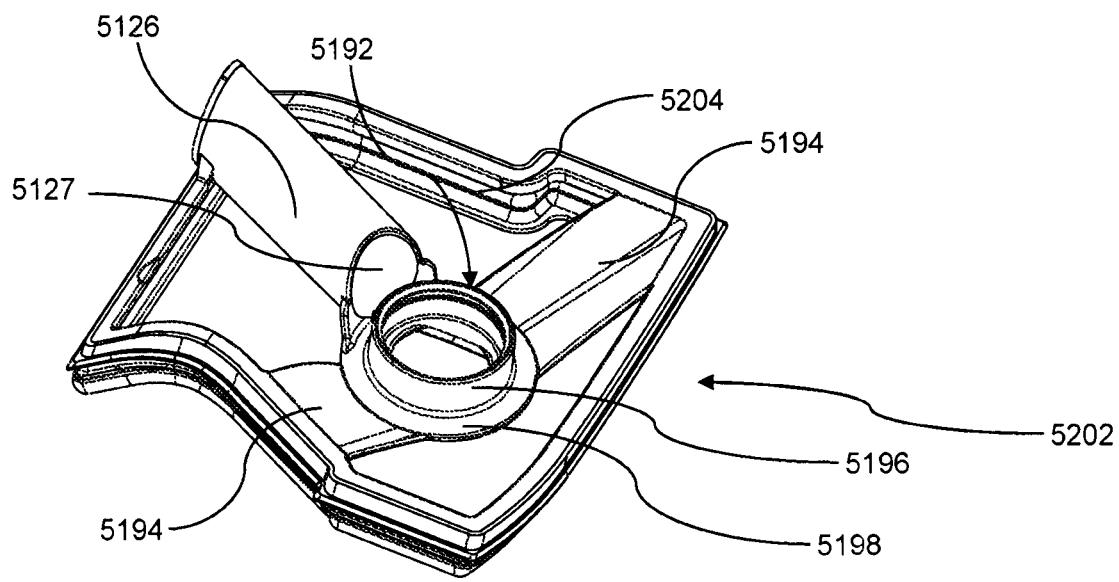
Figure 54B:
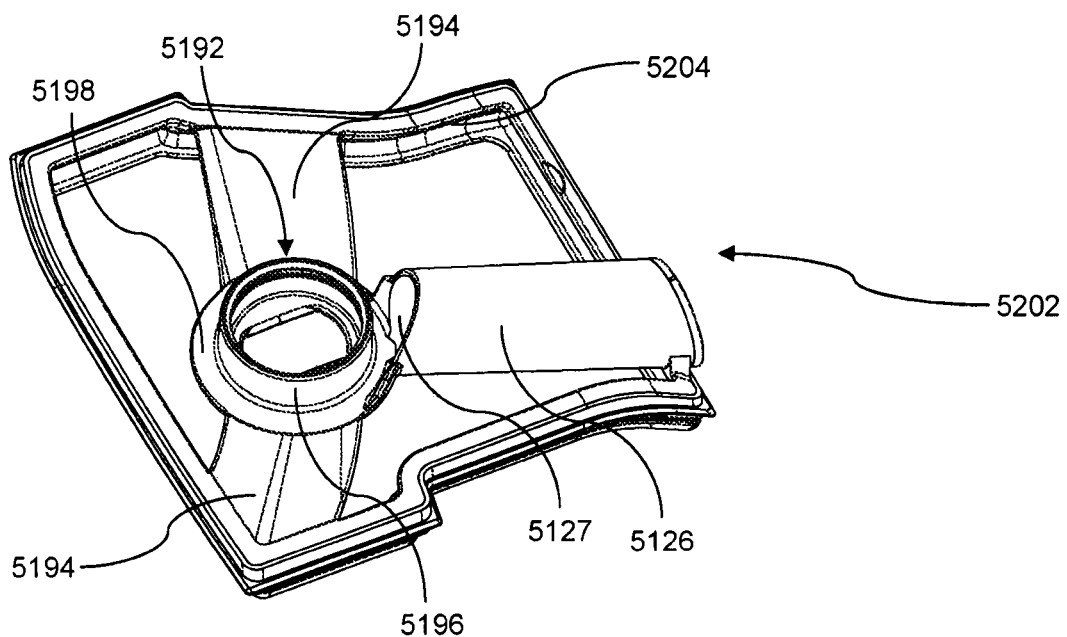

FIGS. 54a-54b show the intermediate portion 5202 of the reservoir 5110 from various angles. In particular they aim to show the baffle 5192, the outlet tube 5126 and the support spokes 5194.

Figure 55:
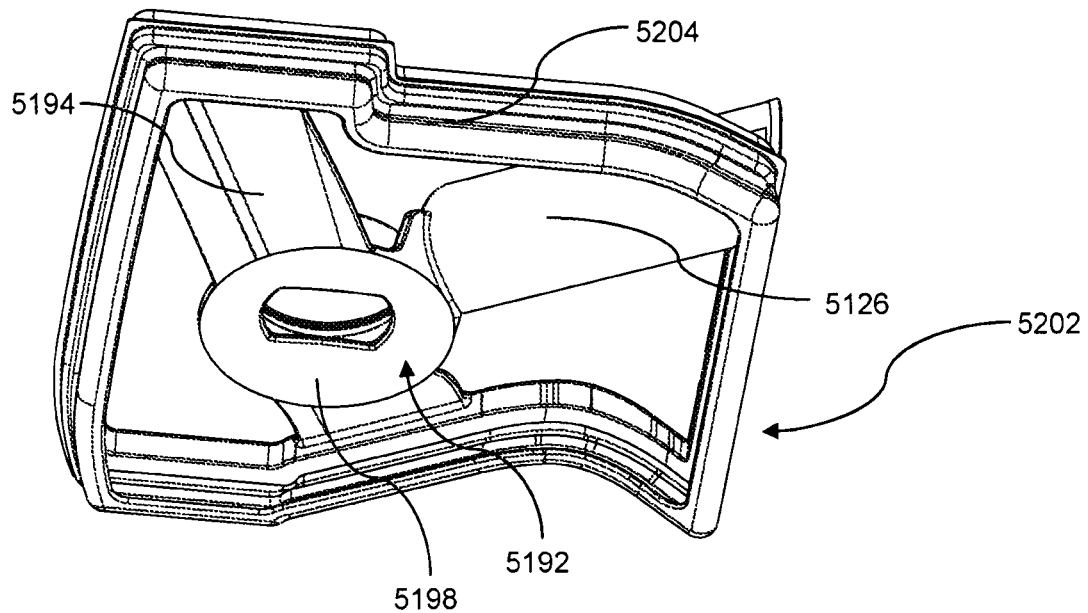

FIG. 55 shows a perspective bottom view of the intermediate portion 5202 of the reservoir 5110.

Figure 56A:
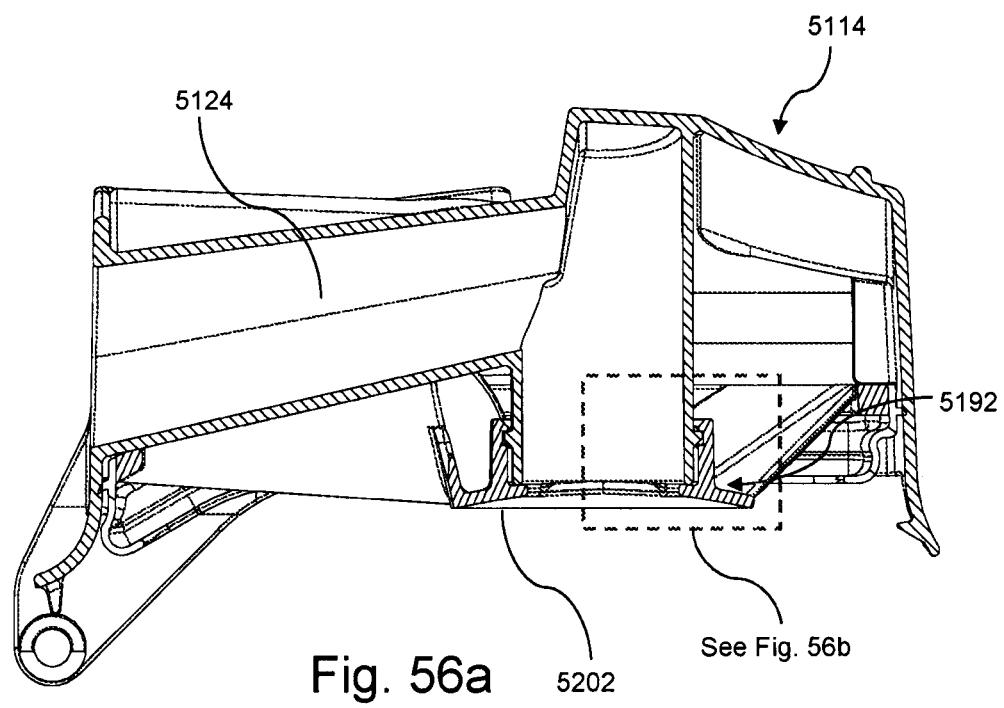
Figure 56B:
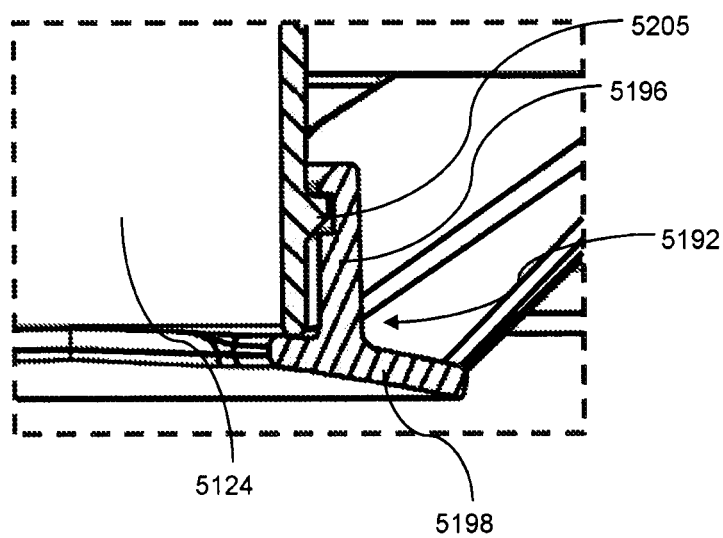

FIGS. 56a-56b show a cross section of the reservoir lid 5114 and the intermediate portion 5202 connected together. FIG. 56b shows the cross section of the baffle 5192 in further detail, in particular the arrangement of the vertical portion of the inlet tube 5124, the locating portion 5196 of the baffle 5192 and the deflector portion 5198 of the baffle 5192.

Figure 57:
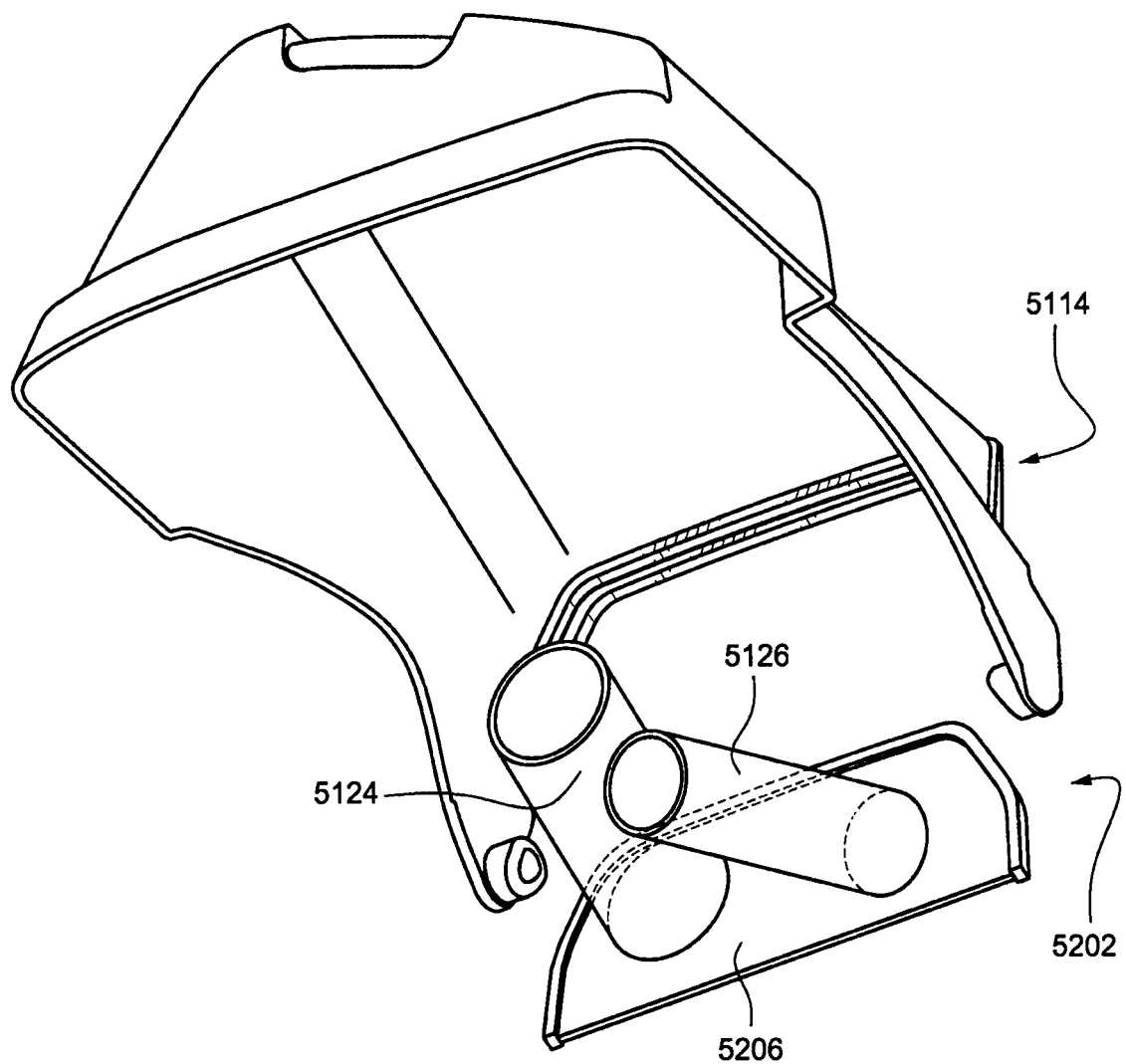

FIG. 57 shows an upper portion of the humidifier reservoir 5110 according to another example of the current technology. In this configuration, the reservoir 5110 comprises a reservoir lid portion 5114, a base portion (not shown), and an intermediate portion 5202 that comprises an outlet tube 5126, an inlet tube 5124 as well as a wall portion 5206.

Figure 58A:
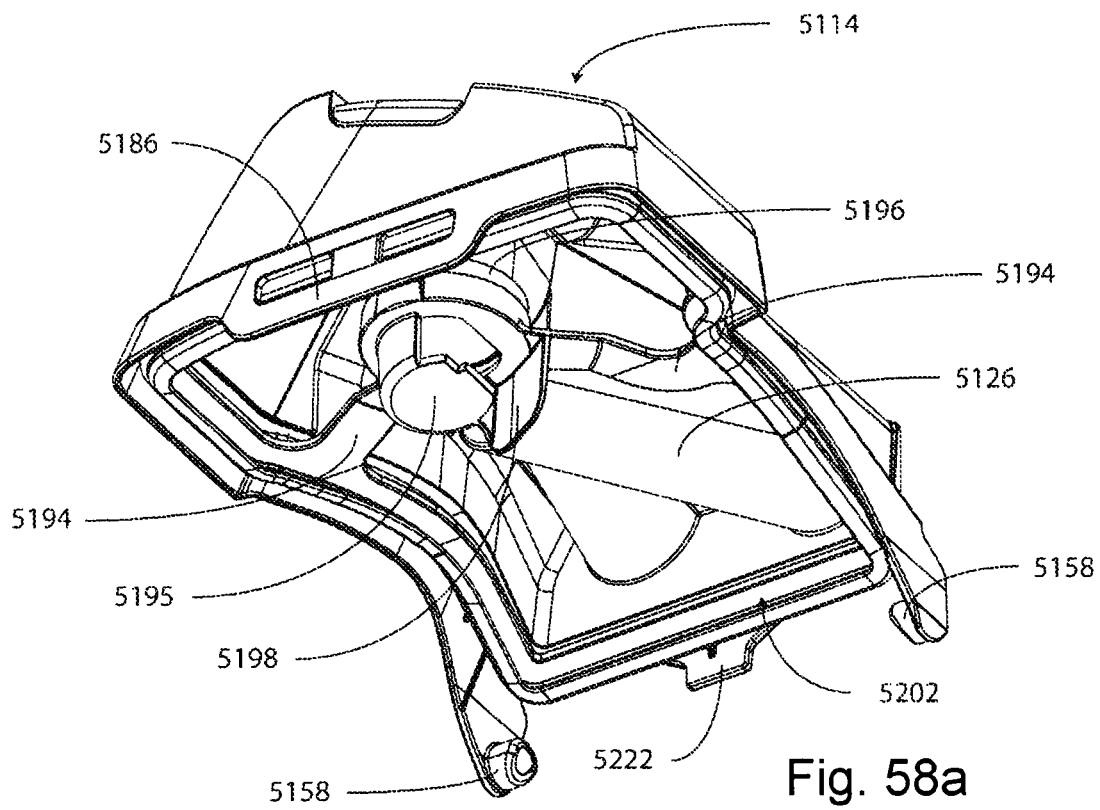
Figure 58B:
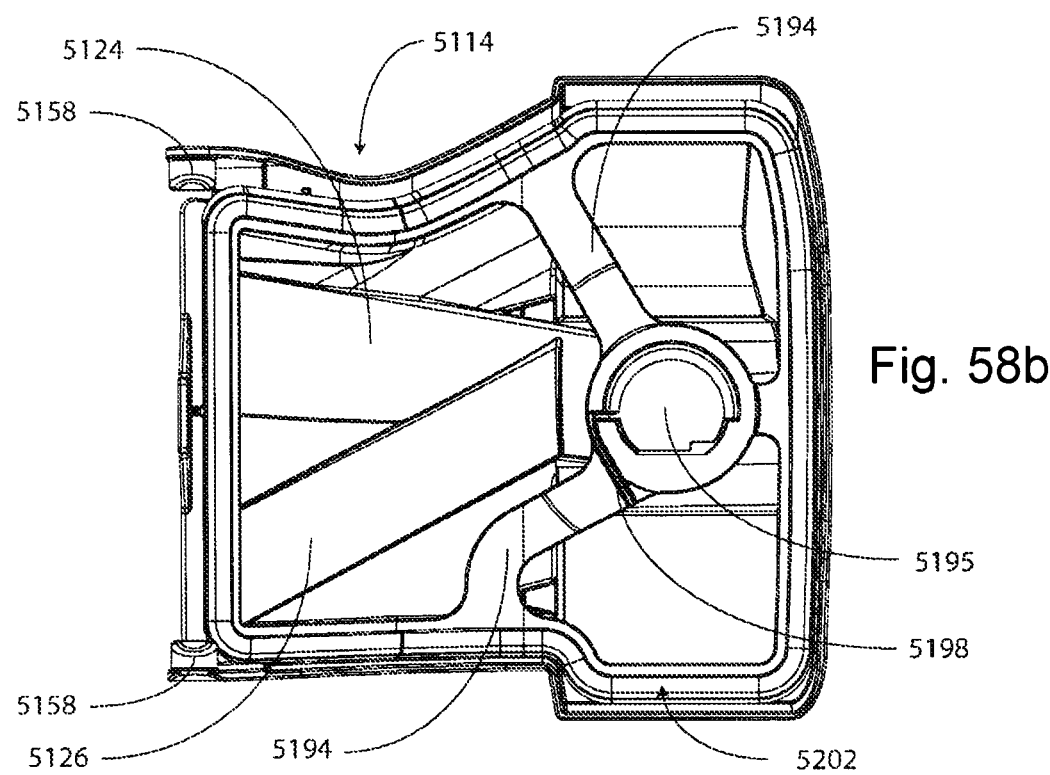

FIGS. 58a-58b show a portion of the humidifier reservoir 5110 according to another example of the current technology. FIGS. 58a-58b show the reservoir lid 5114 connected to the intermediate portion 5202, and in particular they aim to show the inlet tube 5124, the outlet tube 5126, the deflector portion 5198 and the flow director 5195.

Figure 59A:
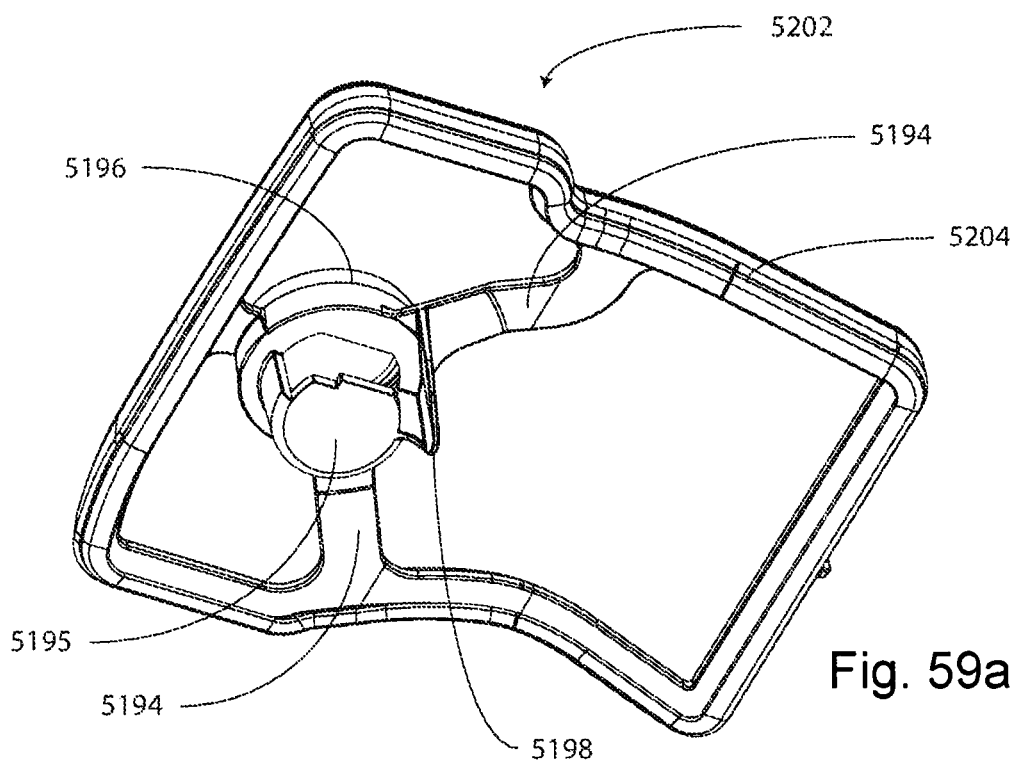
Figure 59B:
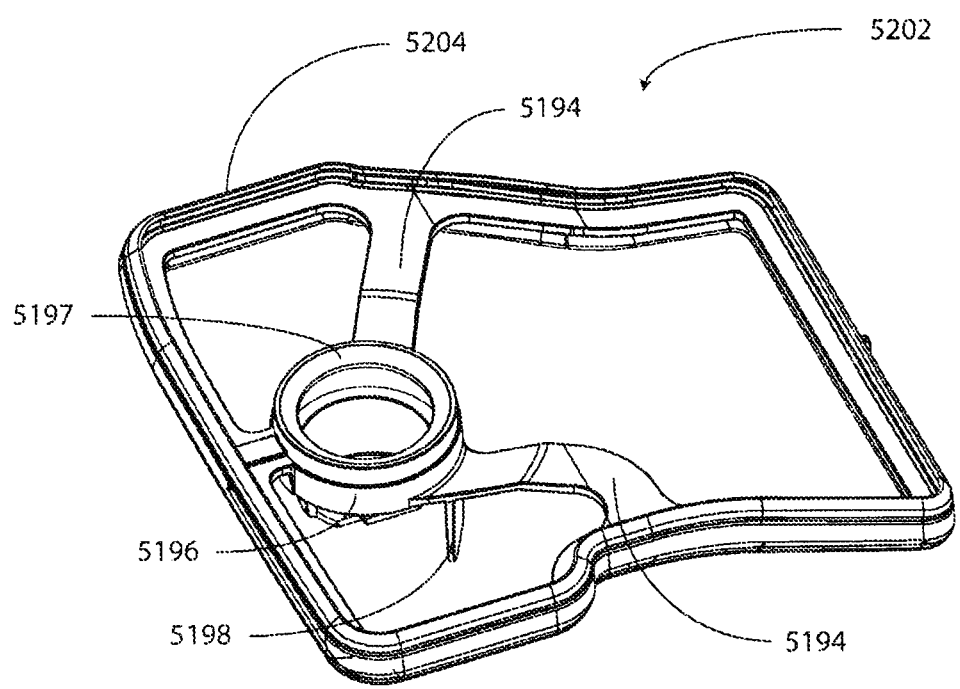

FIGS. 59a-59b show the intermediate portion 5202 according to another example of the current technology, and in particular they aim to show the deflector portion 5198, the flow director 5195, the locating portion 5196 and the seal 5204.

Figure 60:
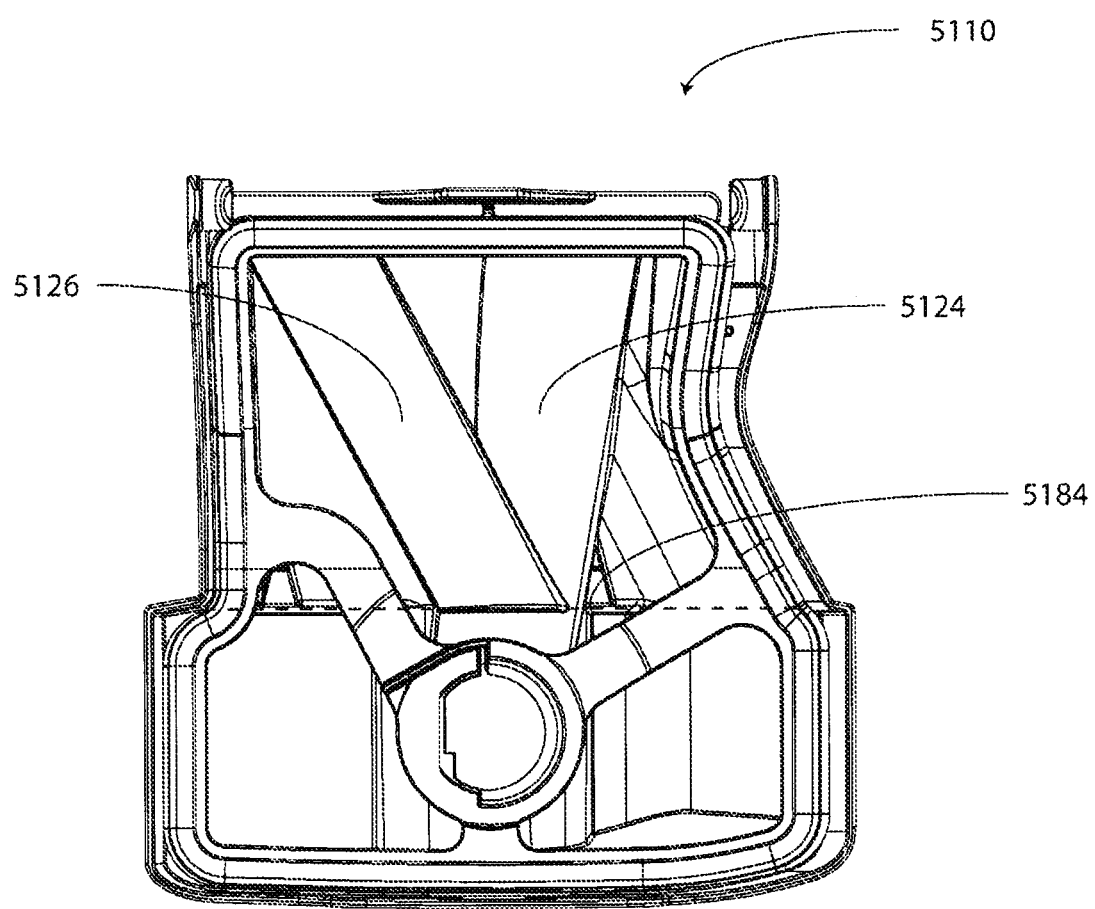
Figure 61A:
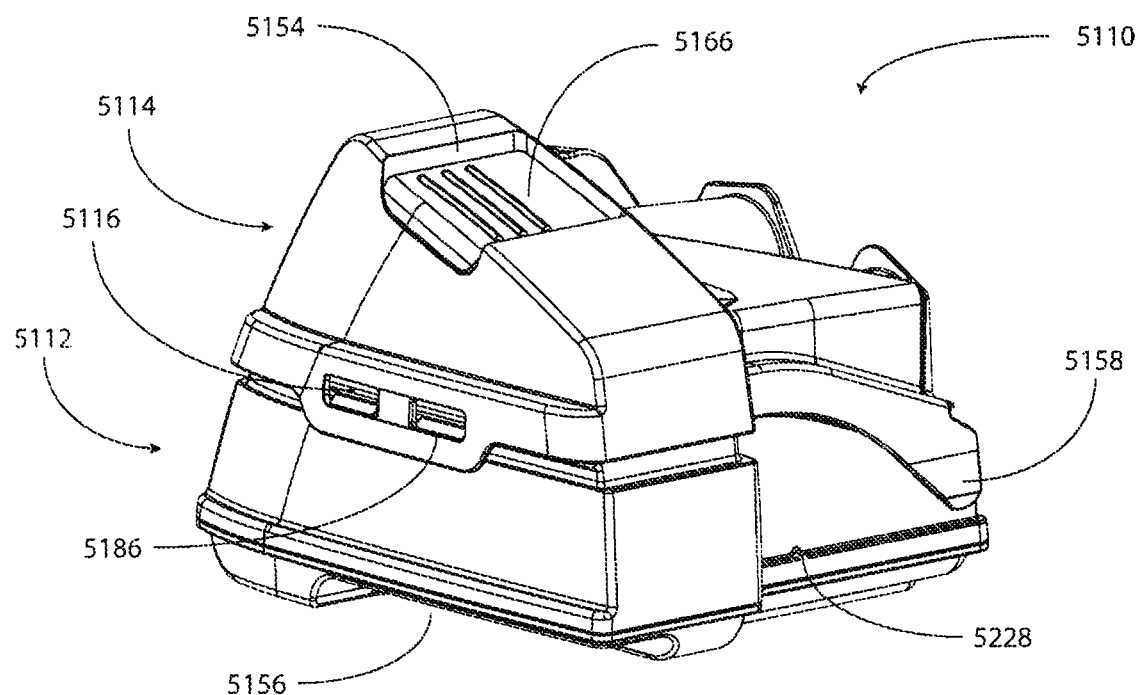
Figure 61B:
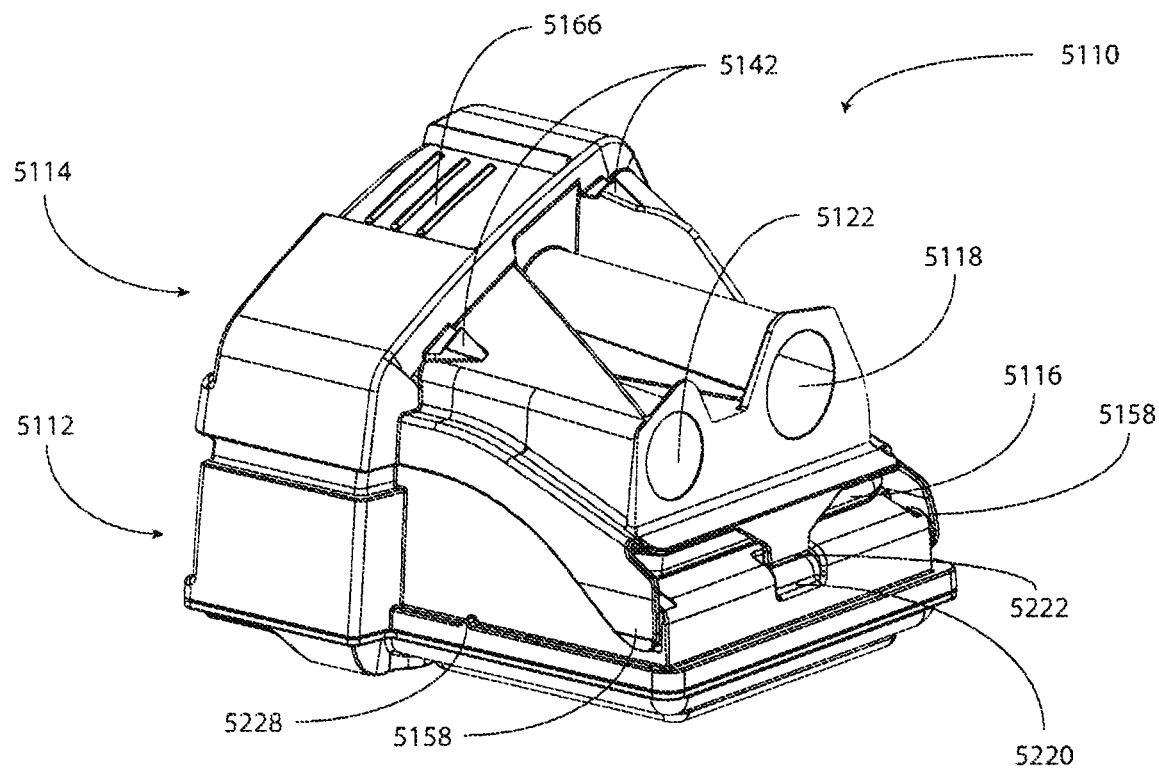

FIG. 60 shows a portion of the humidifier reservoir 5110 according to another example of the current technology. In particular, FIG. 60 shows a water level 5184 at which the air locks would be formed to prevent further ingress of liquid into the reservoir 5110 when the predetermined maximum volume of liquid is in the reservoir 5110.

Figure 62A:
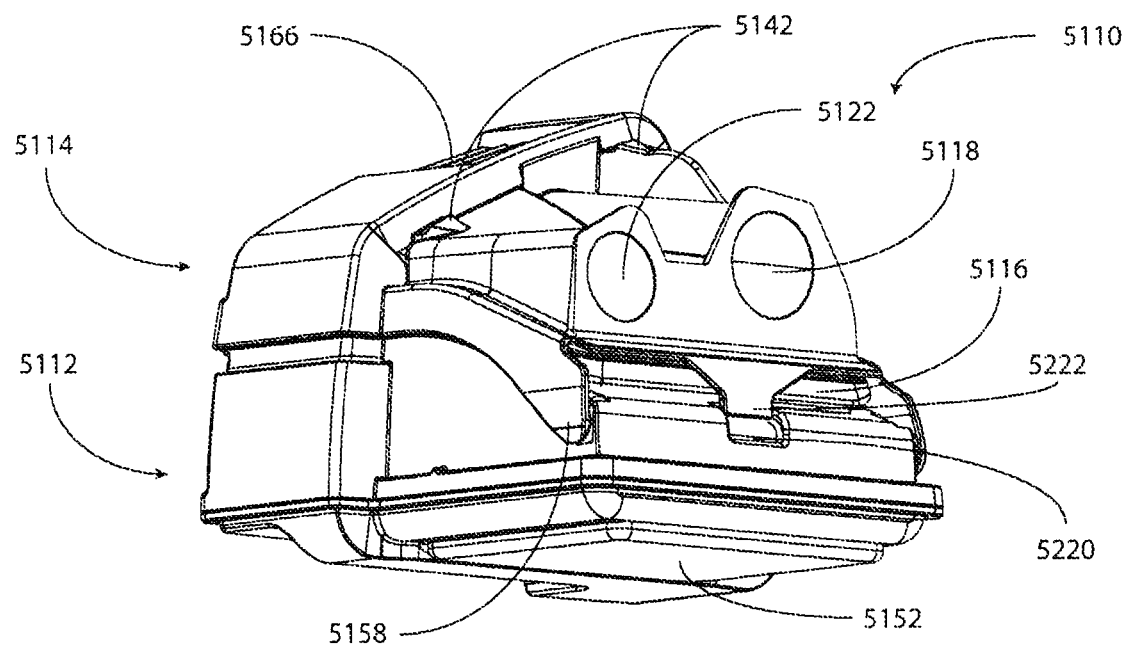
Figure 62B:
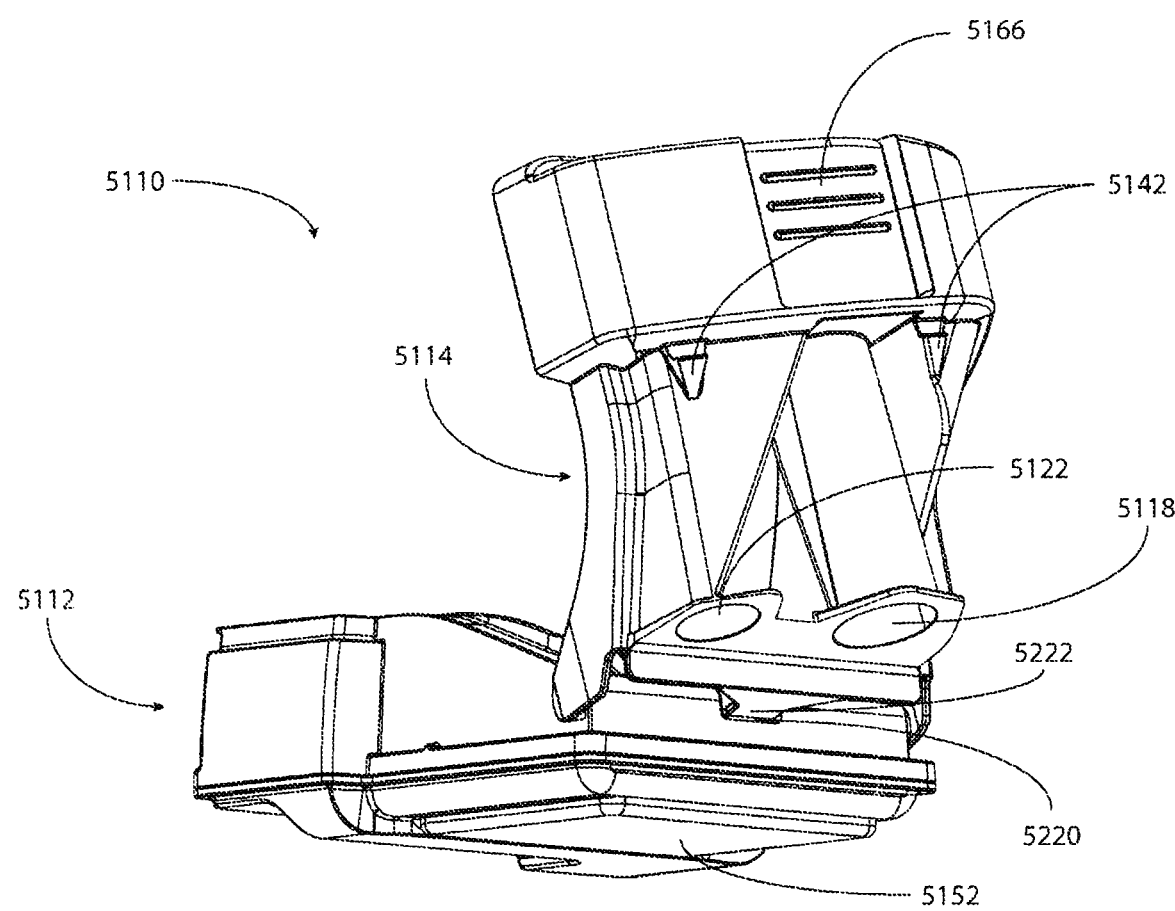

FIGS. 61a, 61b, 62a, and 62b show various views of a humidifier reservoir 5110 in accordance with one aspect of present technology, wherein FIGS. 61a-62a show the humidifier reservoir 5110 in a 'closed' configuration, FIG. 62b shows the humidifier reservoir 5110 in an 'open' configuration.

Figure 63A:
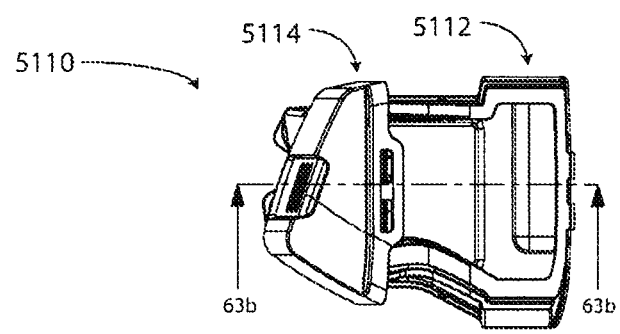
Figure 63B:
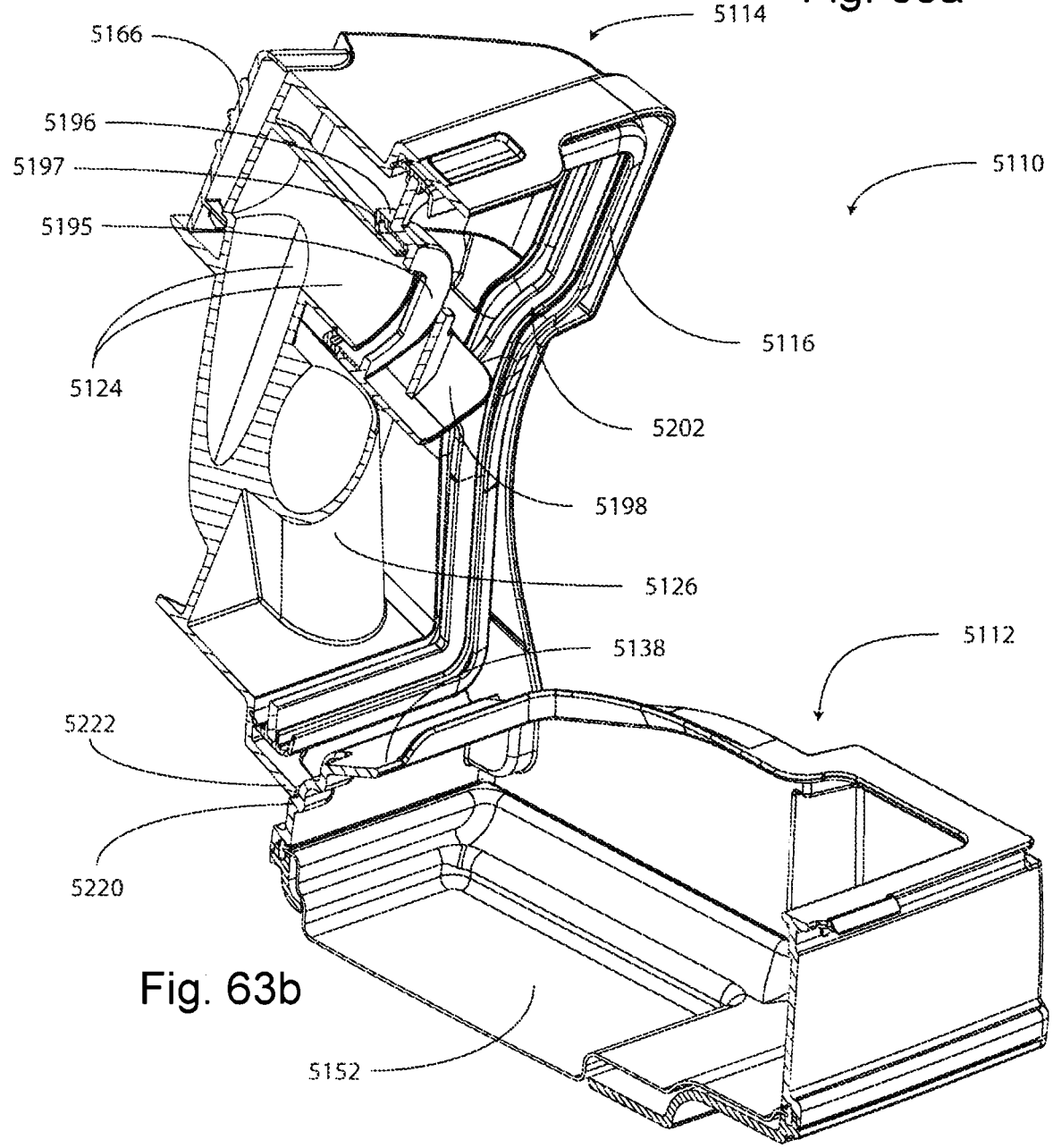

FIGS. 63a-63b show various views of a humidifier reservoir 5110 in accordance with one aspect of present technology. FIG. 63a shows a plan view of the humidifier reservoir 5110 in an 'open configuration', indicating a cross section to be shown in FIG. 63b, and FIG. 63b shows the reservoir 5110 with the cross section taken through line 63b-63b of FIG. 63a visible.

Figure 64:
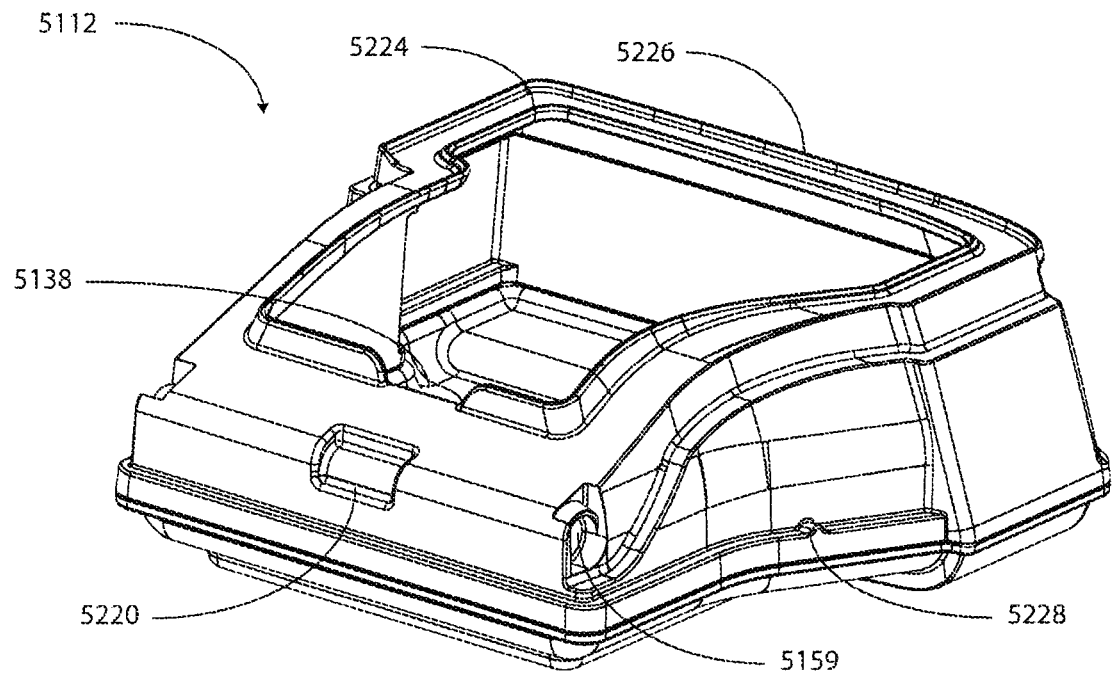
Figure 65:
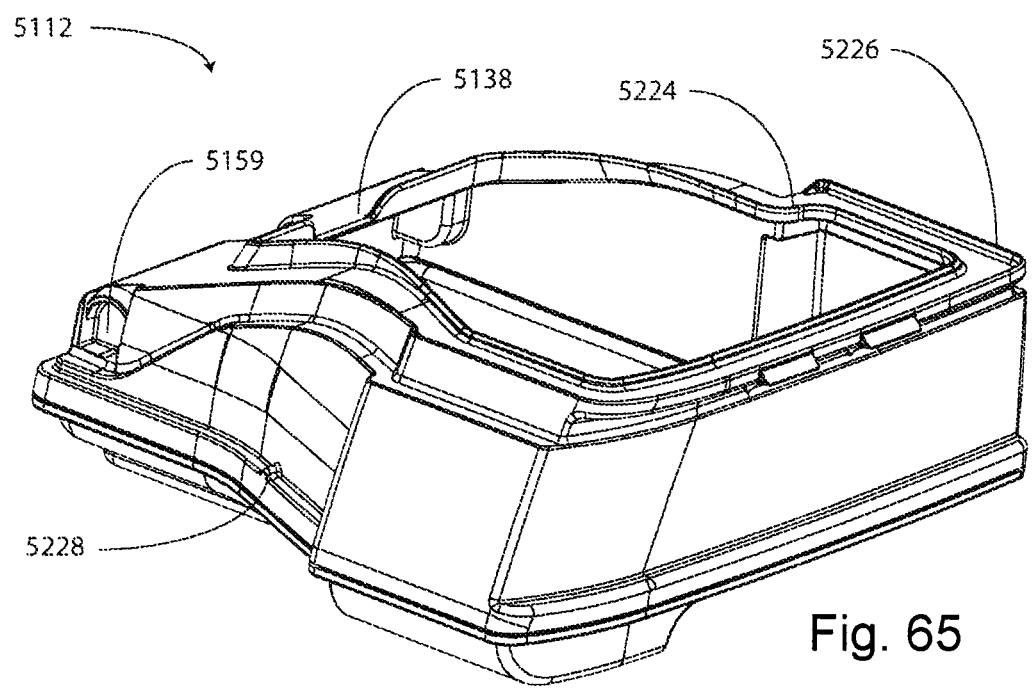

FIGS. 64-65 show various views of a reservoir base 5114 in accordance with one aspect of present technology.

FIG. 66 shows an exploded of an RPT device 4000, humidifier 5000, and end cap 5300 in accordance with one aspect of the present technology.

FIG. 67 shows a side perspective view of an end cap 5300 according to one aspect of the present technology.

Figure 68A:
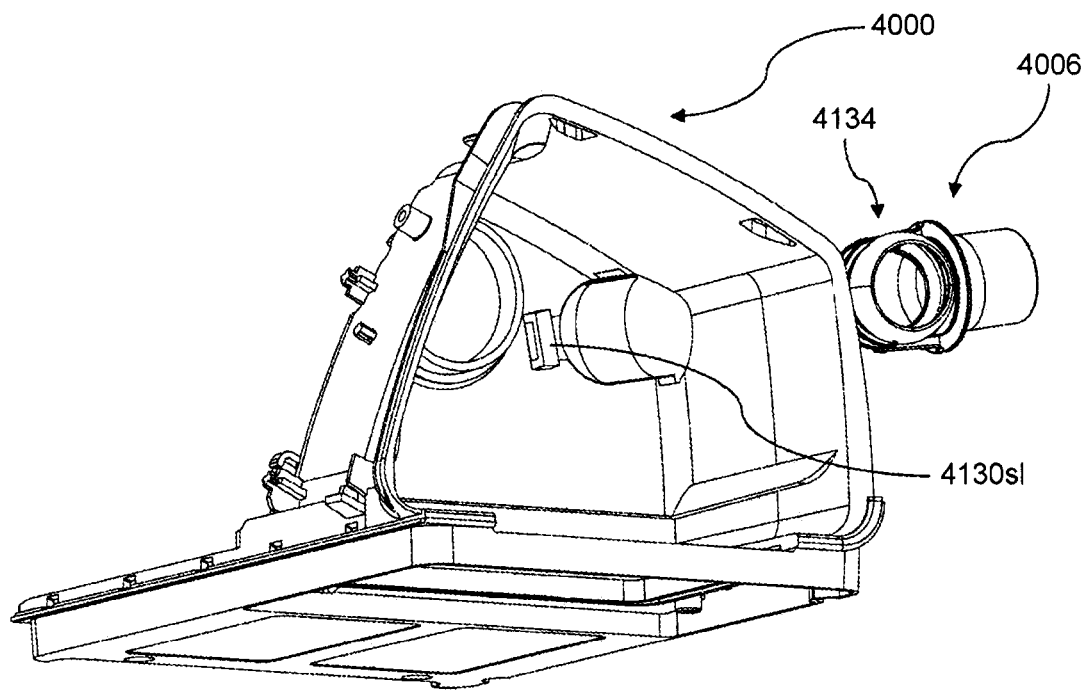

FIG. 68a shows an exploded bottom perspective view of a portion of a RPT device/humidifier and an airflow tube according to an example of the present technology.

Figure 68B:
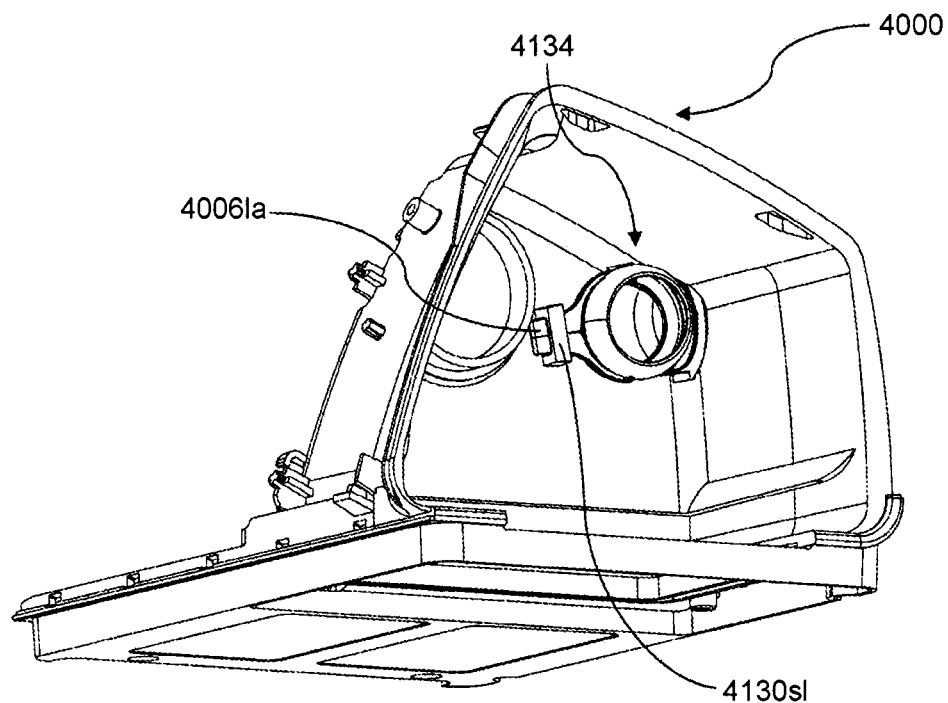

FIG. 68b shows a bottom perspective view of a portion of a RPT device/humidifier and an airflow tube according to an example of the present technology.

Figure 68C:
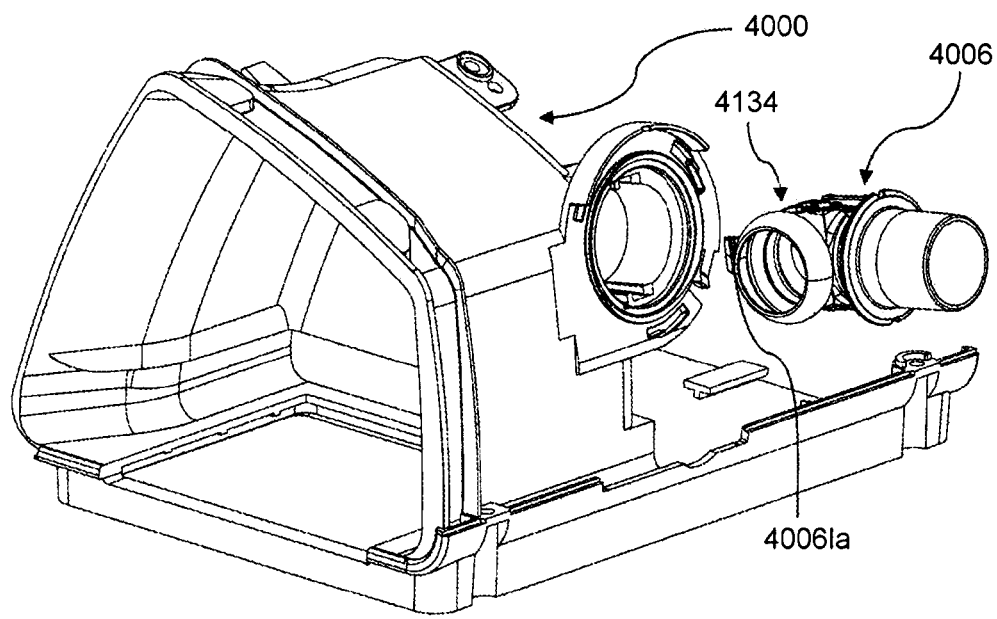

FIG. 68c shows an exploded rear perspective view of a portion of a RPT device/humidifier and an airflow tube according to an example of the present technology.

Figure 68D:
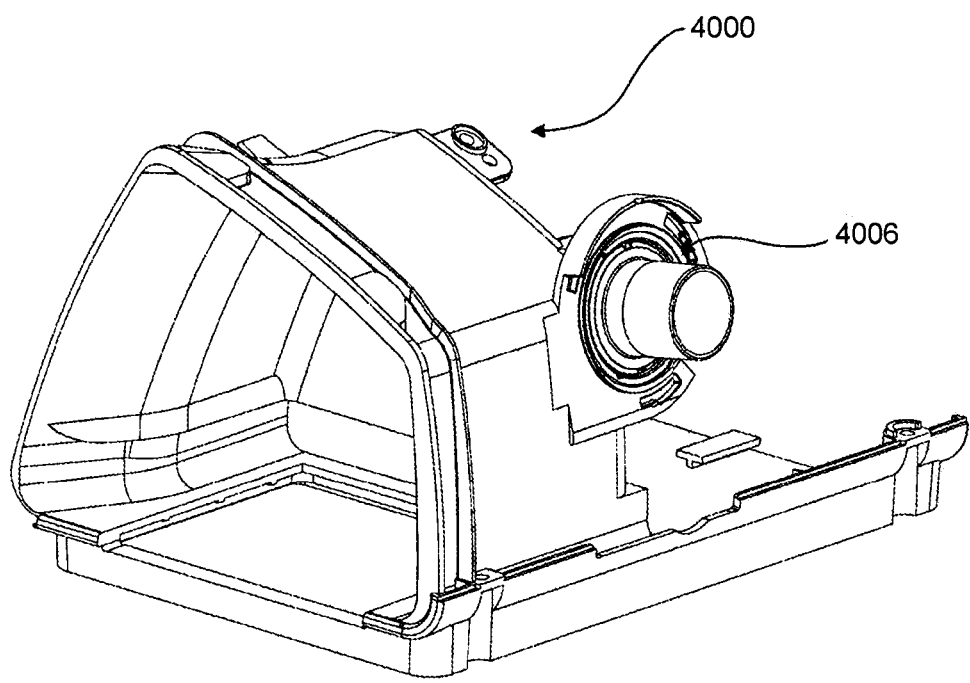

FIG. 68d shows a rear perspective view of a portion of a RPT device/humidifier and an airflow tube according to an example of the present technology.

Figure 68E:
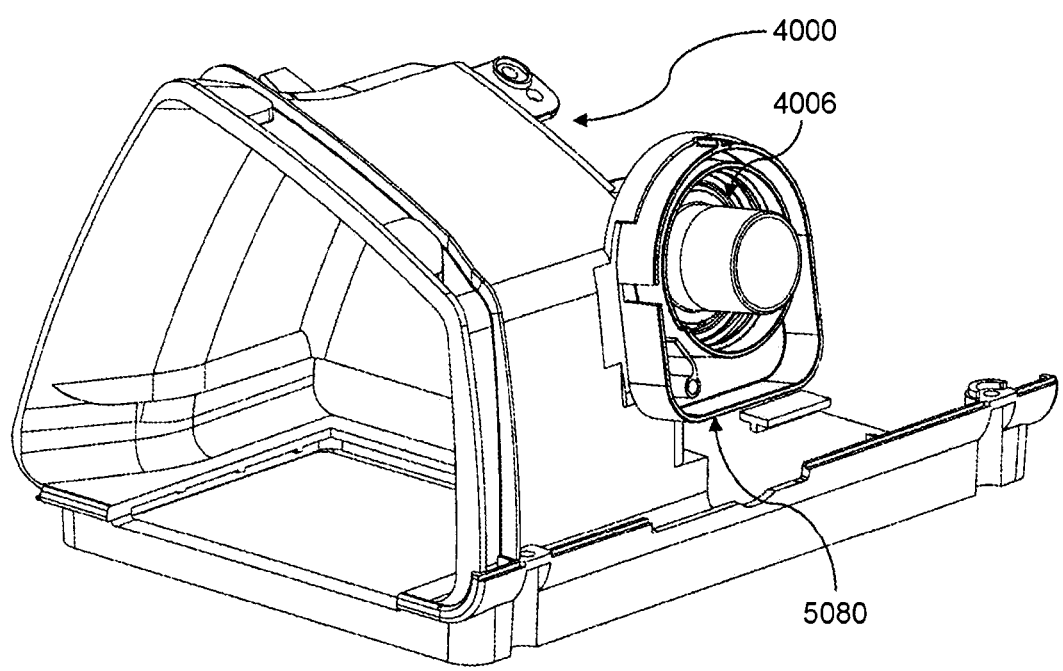

FIG. 68e shows a rear perspective view of a portion of a RPT device/humidifier, an airflow tube and a cable housing according to an example of the present technology.

Figure 69A:
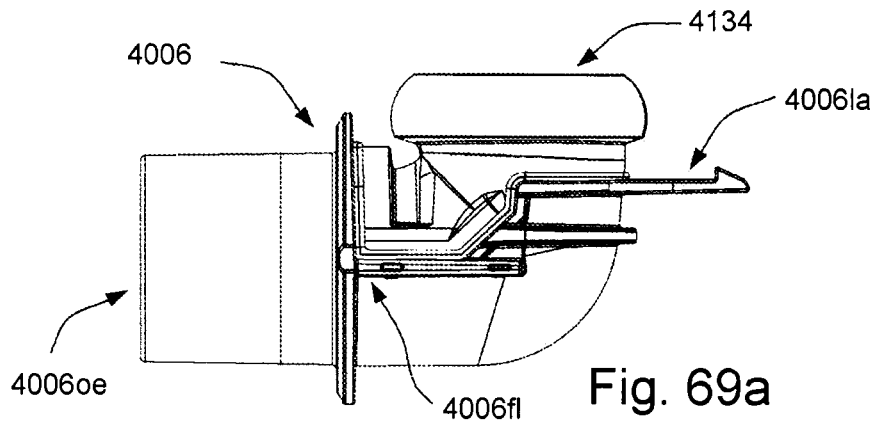

FIG. 69a shows a side view of an airflow tube according to an example of the present technology.

Figure 69B:
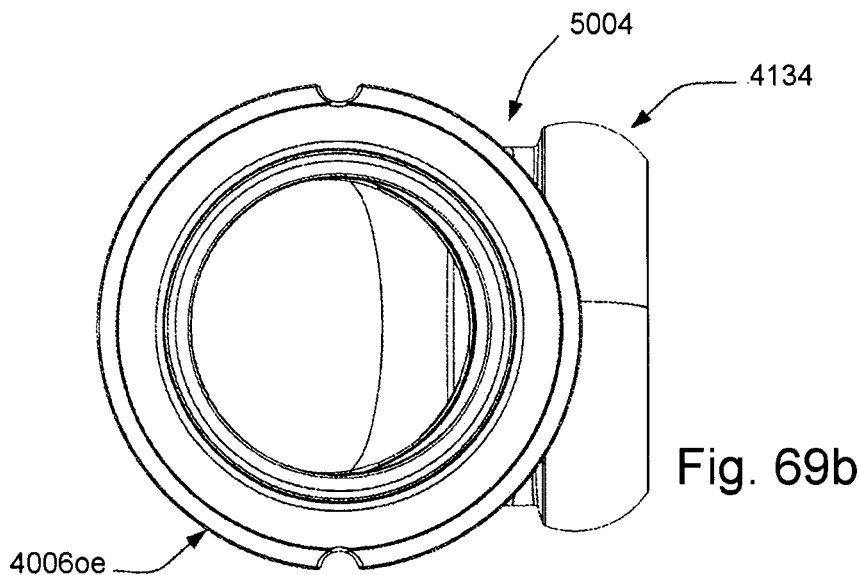

FIG. 69b shows another side view of an airflow tube according to an example of the present technology.

Figure 69C:
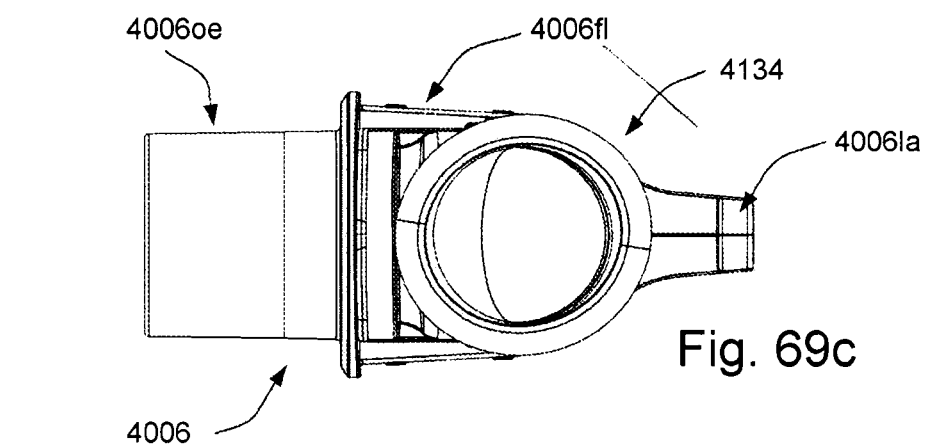

FIG. 69c shows another side view of an airflow tube according to an example of the present technology.

Figure 69D:
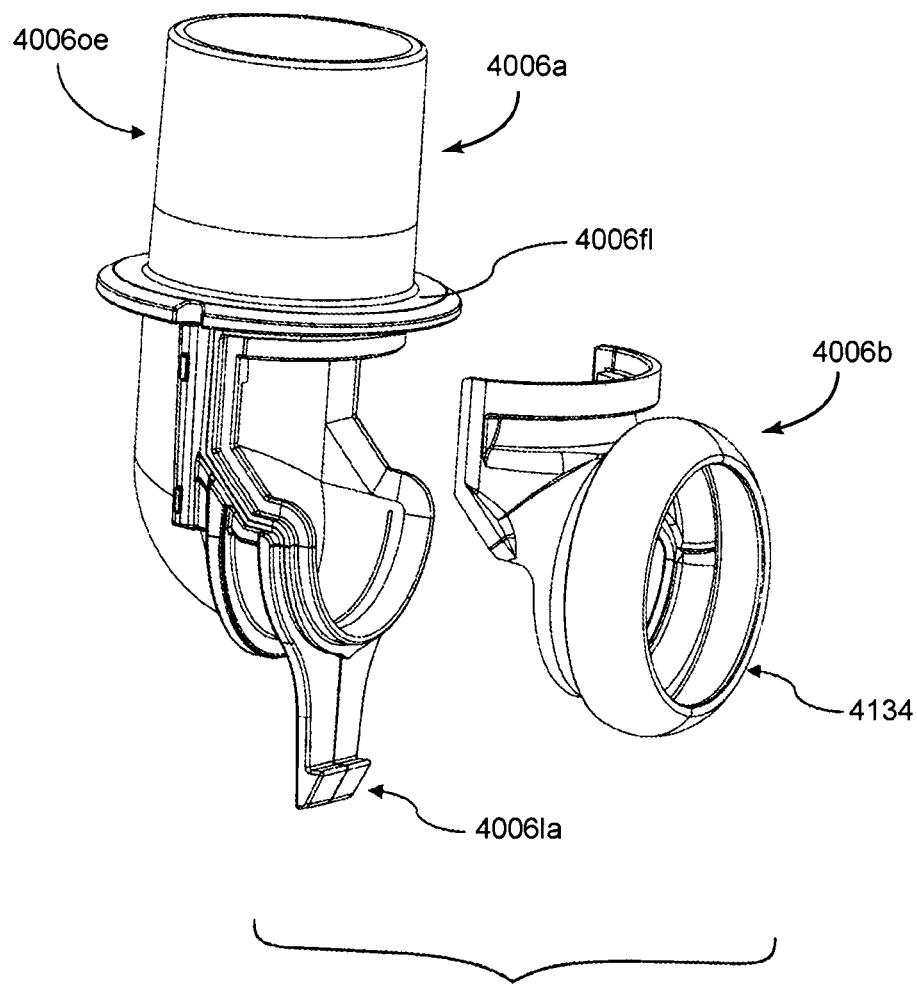

FIG. 69d shows an exploded perspective view of an airflow tube according to an example of the present technology.

Figure 70A:
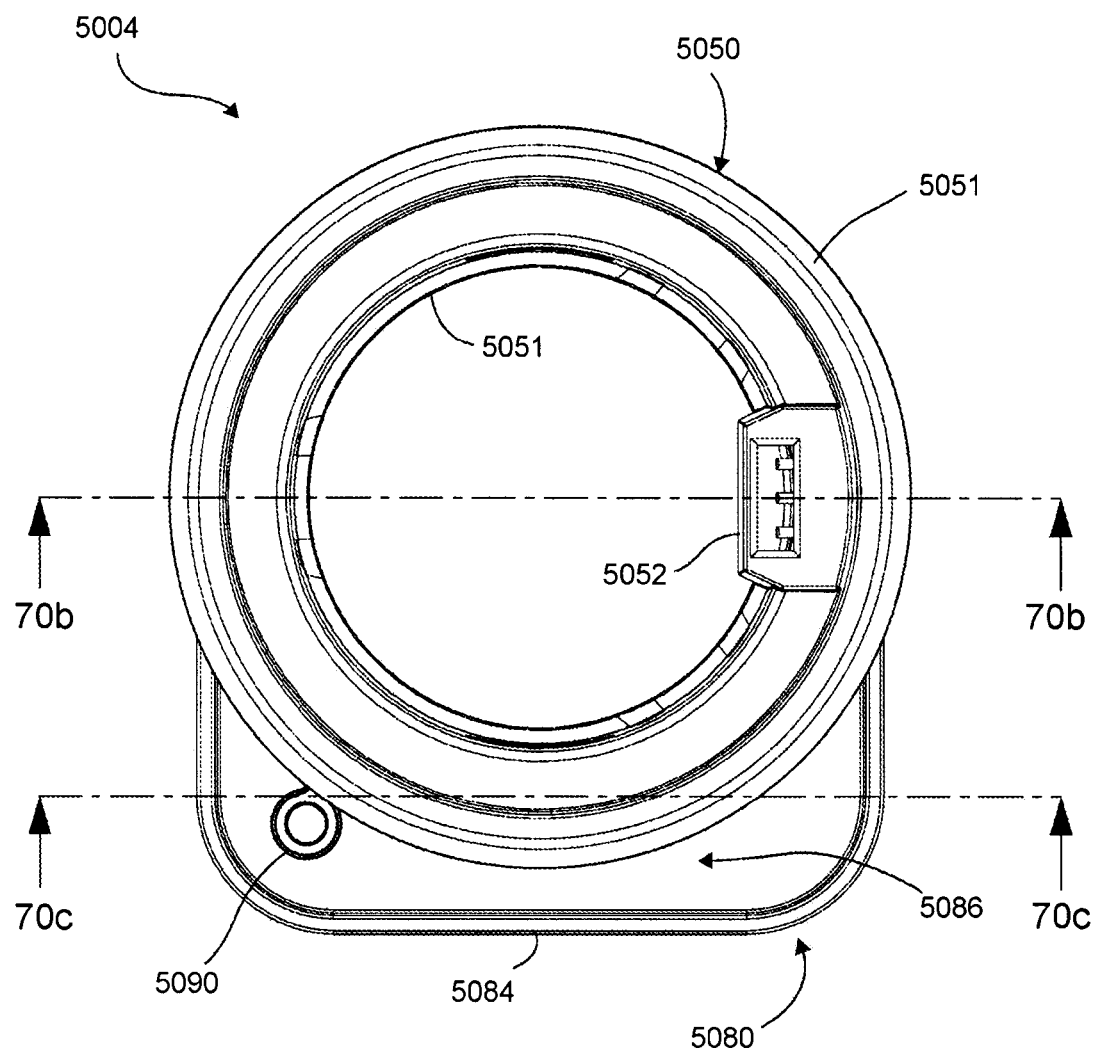

FIG. 70a shows a top view of an outlet assembly according to an example of the present technology.

Figure 70B:
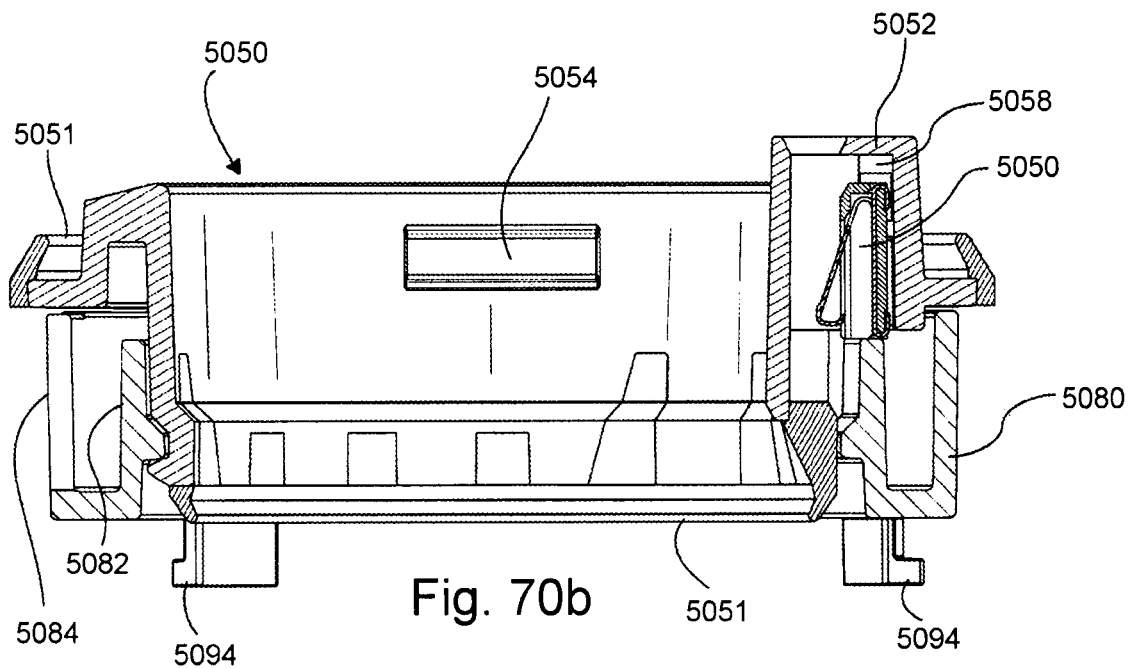

FIG. 70b shows a cross-sectional view of the outlet assembly of FIG. 70a taken through line 70b-70b according to an example of the present technology.

Figure 70C:
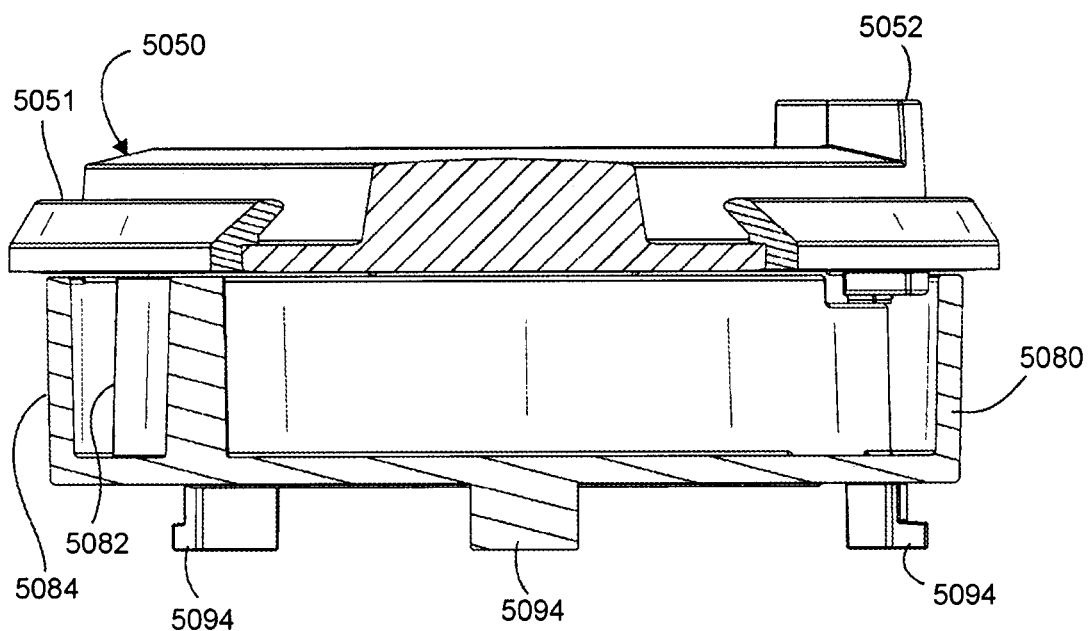

FIG. 70c shows a cross-sectional view of the outlet assembly of FIG. 70a taken through line 70c-70c according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised respiratory gas, such as air, to the patient 1000 via an air circuit 4170 to a patient interface 3000.

5.3 Patient Interface 3000

A non-invasive patient interface 3000 in accordance with one aspect of the present technology comprises the following functional aspects: a seal-forming structure 3100, a plenum chamber 3200, a vent 3400, a positioning and stabilising structure 3300 and one form of connection port 3600 for connection to air circuit 4170. The patient interface 3000 may optionally include a forehead support structure 3700 that couples with the stabilising structure 3300. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RPT Device 4000

An exploded view of an RPT device 4000 in accordance with one aspect of the present technology is shown in FIG. 5a. An RPT device 4000 may comprise mechanical and pneumatic components, electrical components and be configured to execute one or more algorithms. The RPT device may include one or more panel(s) such as a front panel 4012 and a side panel 4014. The RPT device 4000 may also comprise an outlet muffler 4124 as shown in FIGS. 5a and 5b. The outlet muffler 4124 may be removable and replaced with a water reservoir 5110 (see FIG. 5c). In such forms, the RPT device 4000 may be considered to include an integrated humidifier 5000. Thus, the RPT device 4000 may be used with or without humidification depending upon whether the water reservoir 5110 or the outlet muffler 4124 respectively is attached. Preferably the RPT device 4000 comprises a chassis 4016 that supports one or more internal components of the RPT device 4000. In one form the RPT device 4000 comprises a pressure generator 4140, which may be housed in a pneumatic block 4020 coupled to the chassis 4016.

The pneumatic path of the RPT device 4000 (e.g. shown in FIG. 5d) may comprise an inlet air filter 4112, an inlet muffler 4122, a pressure generator 4140 capable of supplying air at positive pressure (preferably a blower 4142) and an outlet muffler 4124 (or a water reservoir 5110 if humidification is required). One or more transducers 4270, such as pressure sensors 4272 and flow sensors 4274 may be included in the pneumatic path. The pneumatic path may also include anti-spill back valve 4160 to prevent water from the humidifier 5000 spilling back to the electrical components of the RPT device 4000.

The RPT device 4000 may comprise one or more electrical components which may be mounted on a single Printed Circuit Board Assembly (PCBA) such as the main PCBA 4202. In an alternative form, the RPT device 4000 may include more than one PCBAs.

5.4.1 RPT Device Components

An RPT device may comprise one or more of the following components in an integral unit. In an alternative form, one or more of the following components may be located as respective separate units.

5.4.1.1 Air Filter(s) 4110

An RPT device in accordance with one form of the present technology may include one or more air filters 4110.

In one form the pneumatic path may comprise an inlet air filter 4112 (e.g. upstream of a pressure generator 4140) and another air filter 4114 (e.g. downstream of the pressure generator 4140) such as an antibacterial filter placed within the pneumatic path at a location between an outlet of the pneumatic block 4020 and a patient interface 3000. See FIG. 5d.

5.4.1.2 Side Panel 4014

In one form, the RPT device 4000 may comprise a side panel 4014 as shown in FIGS. 6a-6c. The side panel 4014 may comprise one or more RPT device inlets 4002 configured to receive a flow of air into the RPT device 4000. As shown in FIG. 6a, the RPT device inlet 4002 may comprise a plurality of apertures configured to allow a flow of air therethrough.

The side panel 4014 (see FIG. 6a) may be configured to house the inlet air filter 4112, and comprise a side panel frame 4014f and an inlet air filter cover 4014fc configured to secure the inlet air filter 4112 relative to the side panel frame 4014f. The inlet air filter cover 4014fc may be coupled, preferably removably coupled or pivotably coupled, (as shown in FIGS. 6b-6c) to the side panel frame 4014f so as to allow replacement of the inlet air filter 4112. The inlet air filter cover 4014fc may further comprise a filter cover handle (e.g. a recess) 4014ch for the user to access to open and close the inlet air filter cover 4014fc, and a retaining feature (e.g. a latch, not shown) to secure the inlet air filter cover 4014fc in its closed configuration.

The side panel 4014 may comprise an air filter housing 4014h configured to locate the inlet air filter 4112 therein, for example as a part of the inlet air filter cover 4014fc as shown in FIG. 6c. The air filter housing 4014h comprises a plurality of walls 4014w configured to locate the inlet air filter 4112, for example as the inlet air filter cover 4014fc is pivoted relative to the side panel frame 4014f.

The RPT device inlet 4002 may be configured with a plurality of apertures as shown in FIGS. 6a-6c. The plurality of aperture may allow a flow of air therethrough in a direction parallel to an inlet of the pneumatic block 4020 as described in further detail below.

The side panel 4014 may further comprise one or more connection ports 4014cp (e.g. as shown in FIG. 6d) to allow access to removable storage media and accessories such as communication devices or USB ports. Accordingly, the side panel 4014 may comprise one or more access covers 4014ac (e.g. as shown in FIGS. 6a, 6c and 6d) for protection of the connection ports 4014cp, from one or more of: ingress of water/dust/contaminants and accidental removal of the removable storage media or accessories. The access covers 4104ac may also be used for aesthetic purposes.

The access cover 4014ac may comprise one or more access cover anchoring portions 4014an which may be used to couple the access cover 4014ac to the side panel frame 4014f (e.g. by insertion into a slot—not shown). The cover portions 4014co may protect the connection ports 4014cp, for example by including one or more complementary recesses 4014re to receive any protruding portions of the connection ports 4014cp. The access cover 4014ac may further comprise one or more access cover hinge portions 4014hi. In some forms, the access cover hinge portion 4014hi may be integrally formed with the cover portions 4014co and the anchor portion 4014an of the access cover 4014ac for improved manufacturability and lower cost.

5.4.1.3 Muffler(s) 4120

In one form of the present technology, an inlet muffler 4122 is located in the pneumatic path upstream of a pressure generator 4140. See FIG. 5d.

In one form of the present technology, an outlet muffler 4124 is located in the pneumatic path between the pressure generator 4140 and a patient interface 3000. See FIG. 5d.

The outlet muffler 4124 may be a removable component of the RPT device 4000 as shown in FIGS. 7a-7b. The RPT device 4000 may comprise a corresponding dock 4130 (described in further detail below) configured to receive the outlet muffler 4124 or a water reservoir 5110. Such an arrangement may allow a manufacture of the RPT device 4000 and the integrated humidifier 5000 to easily convert between a first configuration, in which no humidification is provided when the outlet muffler 4124 in located in the dock 4130, to a second configuration that enables humidification, where the water reservoir 5110 is located in the dock 4130 and vice versa. For instance, where humidification is desired, the outlet muffler 4124 may be removed using the muffler lever 41241e to allow the RPT device 4000 to receive a water reservoir 5110. In one form, insertion of the water reservoir 5110 into the dock 4130 would allow humidification of the flow of air from the pneumatic block 4020 before delivery to the patient 1000 as will be described in further detail below.

The outlet muffler 4124 may comprise an identification element, to allow a controller, such as the central controller 4230 or the humidity controller 5250, to detect its presence (or absence), for example in the dock 4130. The dock 4130 may comprise a complementary detection element, to detect the presence (or absence) of the outlet muffler 4124. In one form, detection of the presence or absence of the outlet muffler 4124 in the reservoir dock 5130 may cause the controller to perform one more functions including: switch off/on the heating element 5240, adjust the power output of the heating element 5240, switch off/on a heating element in the air circuit 4170, adjust the power output of the heating element in the air circuit 4170, adjust the pressure drop estimation between the pressure generator 4140 and the patient interface 3000, disable/enable user interface elements relating to operation of the humidifier 5000, or disable/enable data logging/data reporting relating to operation of the humidifier 5000. In one form, the outlet muffler 4124 may comprise an identification element (shown in the form of a magnet 5340) disposed thereon, such as in an end cap magnet holder 5345. The identification element may be used for detection of the outlet muffler 4124 by the controller via the detection element. For example the detection element may include a Hall Effect sensor (not shown) located in or near the dock 4130 such as on the PCBA 4202.

One advantage of an outlet muffler 4124 comprising an identification element, may be to allow reduced power consumption or customised operation of the humidifier 5000 where an outlet muffler 4124 is used. A further advantage of having the heating element on by default and turned off by engagement of the outlet muffler 4124 is in a single step of installing the outlet muffler 4124 both the heating element 5240 is deactivated and access to the heater plate is prevented.

In one form, the outlet muffler 4124 receives a flow of air from the pneumatic block 4020, and delivers the flow of air to the RPT device outlet 4004. Thus the outlet muffler 4124 may comprise a muffler entry 4124in and a muffler exit 4124ou. The outlet muffler 4124 may also comprise additional components such as a muffler cap 4124ca, a muffler body 4124bo, a muffler damper 4124da and a muffler foam 4124fo shown in FIGS. 7e-7f.

The outlet muffler 4124 may comprise a muffler lever 41241e for disengaging the outlet muffler 4124 from the rest of the RPT device 4000, for example by releasing a latch. The muffler lever 41241e is configured (in FIGS. 7a-7f) to be depressed from above to disengage the outlet muffler 4124, for example by releasing one or more muffler clips 4124cl from the one or more complementary recesses 4130re in the dock 4130 (shown in FIG. 7b, and in more detail in FIG. 16i). It would be understood that the outlet muffler 4124 could comprise one or more of any number of known means to removably couple the outlet muffler 4124 to the RPT device 4000. The outlet muffler 4124 may further comprise one or more muffler clips 4124cl with the RPT device 4000, for example comprising a muffler hinge 4124hi. In some forms, the outlet muffler 4124 may comprise a muffler travel limiter 4124tl configured to prevent damage to the muffler hinge 4124hi, which may occur for example due to plastic deformation where the muffler hinge 4124hi is of a 'living hinge' configuration. Yet further, the muffler travel limiter 4124tl may be configured to engage with the muffler lever 41241e and deform as the muffler lever 41241e is activated (e.g. depressed). In such an arrangement, the travel limiter 4124tl may provide feedback to the user upon engagement of the muffler lever 41241e with the muffler travel limiter 4124t, and may provide a varying degree of resistance to indicate the extent of deformation occurred. As shown in FIGS. 7e-7f, the muffler damper 4124da may be integrally formed with the muffler travel limiter 4124tl. In some forms, the muffler damper 4124 may be configured to engage the muffler cap 4124ca and/or the muffler body 4124bo by friction.

Similarly, the outlet muffler 4124 may be configured so that the muffler lever 41241e must be depressed to allow the outlet muffler 4124 to be inserted into the dock 4130. In one form, the one or more muffler clips 4124cl may be configured to interfere with the dock 4130 if the outlet muffler 4124 is inserted without depression of the muffler lever 41241e. Upon insertion of the outlet muffler 4124 into the dock 4130, the one or more muffler clips 4124cl moves to engage with the dock 4130 (e.g. by upwards motion), thereby securing the outlet muffler 4124 into the dock 4130.

The outlet muffler 4124 may comprise one or more acoustic features to reduce the noise output of the RPT device 4000, such as muffler foam 4124fo and a muffler damper 4124da as shown in FIGS. 7e-7f. The muffler damper 4124da may be coupled with the muffler cap 4124ca and may be formed of a flexible material, such as silicone, to dampen noise. Furthermore, the outlet muffler 4124 may comprise a muffler expansion chamber 4124ex formed therein to reduce noise. In the form shown in FIG. 7e, the muffler expansion chamber 4124ex may be a cavity formed in the muffler body 4124bo.

5.4.1.4 Pressure Generator 4140

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be preferably capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.5 Pneumatic Block 4020

In one form, a pneumatic block 4020 comprising a pressure generator 4140 (e.g. blower 4142) may form a part of the RPT device 4000. The pneumatic block may for example comprise a configuration described in PCT patent application publication umber WO 2013/020167, the entire contents of which is incorporated herewithin in its entirety by reference.

A pneumatic block 4020 according to one aspect of the present technology is shown in FIGS. 11a-11d. The pneumatic block 4020 may comprise a PB inlet 4020in, a PB outlet 4020ou, and house a blower 4142. According to one aspect of the present technology, the pneumatic block 4020 may provide a compact, enclosed pneumatic path for the air flow while minimising noise and vibration outputs due to the said air flow. Furthermore, such a pneumatic block 4020 may allow the external housing 4010 to be arranged independently thereof for added flexibility in the aesthetics of the RPT device 4000 in relation to the pneumatic block 4020.

The pneumatic block 4020 may also comprise one or more of a flow plate 4020fp, a blower sleeve 4020bs, one or more sensor ports such as flow sensor port 4020sp and acoustic foam 4020af. The pneumatic block 4020 may include an outer housing, for example including a first PB housing 4020h1 and a second PB housing 4020h2. The PB inlet 4020in and the PB outlet 4020ou may be arranged on the first PB housing 4020h1 and the second PB housing 4020h2 respectively.

The flow plate 4020fp may divide the interior of the pneumatic block 4020 into a first chamber 4020c1, a second chamber 4020c2 and the interior of the blower sleeve 4020bs. In one form, the flow of air would be received into the pneumatic block 4020 through the PB inlet 4020in, and enter the PB inlet tube 4020it (shown in FIG. 11d and FIG. 11h). The PB inlet tube 4020it delivers the flow of air to the first chamber 4020c1, from which the flow of air travels to the second chamber 4020c2. In one form, a plurality of flow tubes 4020ft located on the flow plate 4020fp (e.g. as shown in FIG. 11d-11f) may deliver the flow of air from the first chamber 4020c1 to the second chamber 4020c2. The flow plate 4020fp may comprise a cavity through which the PB inlet tube 4020it may travel to deliver the flow of air to the first chamber 4020c1. The flow tubes 4020ft may additionally be used to determine the rate of flow as will be described in further detail below. The second chamber 4020c2 then delivers the flow of air to the blower 4142 through the blower inlet 4142in (see FIG. 11c), wherein the flow of air is pressurised and exits through the blower outlet 4142ou before exiting the pneumatic block 4020 through the PB outlet 4020ou as shown in FIG. 11j. In one form, the flow plate 4020fp may comprise approximately 10-15 flow tubes 4020ft, such as 11-14, such as 12 flow tubes as shown in FIG. 11e. The flow tube 4020ft may be tapered in one form, such as shown in FIG. 11*j*, in a converging direction from the first chamber 4020*c*1 to the second chamber 4020*c*2.

The PB inlet 4020*in* may comprise a flexible portion, such as the PB inlet insert 4020*ii* as shown in FIG. 11*h*. The flexible portion may help the PB inlet 4020*in* to be correctly aligned with the RPT device inlet 4002, by for example resiliently conforming to allow for any axial or radial misalignment therebetween. Yet further, the flexible portion may reduce mechanical load or stress on the pneumatic block 4020 while allowing for the axial or radial misalignment, as the modulus of the flexible portion may be significantly smaller than that of the housing of the pneumatic block such as the first PB housing 4020*h*1 and the second PB housing 4020*h*2. In one form, the flexible portion may be constructed from flexible materials such as silicone, and the housing of the pneumatic block, including the first PB housing 4020*h*1 and the second PB housing 4020*h*2, may be constructed from a more rigid material such as polypropylene, although it will be understood that a range of other materials may be suitable for both.

The blower sleeve 4020*bs* (as shown in FIGS. 11*k* and 11*l*) may be made from a flexible, resilient material such as silicone. In one form, the blower sleeve 4020*bs* may act as a suspension member to reduce noise and vibration output from the blower 4142 which may be transmitted to the patient 1000 (or the bed partner 1100). The blower sleeve 4020*bs* may also comprise a chamber configured to receive the flow of air from the blower outlet 4142*ou* and deliver the flow air to the PB outlet 4020*ou* as shown in FIG. 11*j*. In one form, the blower sleeve 4020*bs* is configured to accept the blower 4142, and sealingly engage the flow plate 4020*fp*, for example, by one or more sleeve tabs 4020*st* located on the blower sleeve 4020*bs*.

The blower sleeve 4020*bs* may also comprise a sleeve pull tab 4020*pt* configured to assist in assembly of the blower sleeve 4020*bs* with other parts of the pneumatic block such as the second PB housing 4020*h*2. The sleeve pull tab 4020*pt* may be configured as an elongated tab suitable for manual gripping, such that a person (or automated device) assembling the pneumatic block 4020 may hold the sleeve pull tab 4020*pt*, and pull through the PB outlet rim 4020*or* (as shown in FIG. 11*d*) to locate the PB outlet 4020*ou* with respect to the second PB housing 4020*h*2. One advantage of such an arrangement would be reduced assembly time, while another would be accurate location of the PB outlet 4020*ou* while achieving desired suspension characteristics of the blower sleeve 4020*bs*.

The flow sensor ports 4020*sp* may be accessible from an exterior of the pneumatic block 4020 and fluidly couple to a flow transducer 4274 (not shown). The flow sensor ports 4020*sp* may also be fluidly coupled to the flow path, such as in the pneumatic block 4020 to allow the flow transducer 4274 to measure the rate of flow through the RPT device 4000. In one form, the flow sensor ports 4020*sp* may be connected to the first chamber 4020*c*1 and the second chamber 4020*c*2 so that the flow sensor would measure the drop in pressure between the first chamber 4020*c*1 and the second chamber 4020*c*2. The flow sensor ports 4020*sp* may be integrally formed with an enclosure of the pneumatic block 4020 such as the first PB housing 4020*h*1, or alternatively may be a part of a separate component such as the PB sensor coupler 4020*sc*. Some or all of the flow sensor ports 4020*sp* may be flexibly configured to assist in correctly aligning and engaging the flow transducer 4274 with the pneumatic block 4020.

Introduction of any water onto the flow sensor ports 4020*sp* may adversely affect operation of the flow transducer 4274, for example by at least partially occluding a port for sensing of air pressure. It is also known that there may be a risk of water ingress into the RPT device 4000, for example when the RPT device 4000 is used with a humidifier 5000, as the RPT device 4000 may be in close proximity to water, and as the humidifier 5000 may contain water therein. Accordingly, each flow sensor flow path connecting respective flow sensor ports 4020*sp* to the chambers 4020*c*1 and 4020*c*2 may comprise one or more water ingress prevention features, such as a PB water trap 4020*wt*, or a PB water shield 4020*ws* (see FIG. 11*o*). According to one form, the PB water trap 4020*wt* may be a recessed portion in the flow sensor flow path configured to hold a predetermined volume of water, while allowing air flow through the flow sensor flow path. A PB water shield 4020*ws* may comprise a port of small cross section area configured to allow a flow of air therethrough, however prevent ingress of water due to the higher surface tension of water. To further discourage any water from interfering with operation of the flow sensor, the port of the PB water shield 4020*ws* may be horizontally oriented and/or be located towards a top portion of the pneumatic block 4020. In one form, the port of the PB water shield 4020*ws* may be approximately 1 mm, for example at its smallest diameter, although it will be understood that other sizes may be also suitable to prevent ingress of water through the port. In one form the PB water shield 4020*ws* may be located such that the port is arranged to be substantially flat and/or vertical at its outermost surface, at which point its diameter may be the smallest. Furthermore, the flow sensor port 4020*sp* may be arranged perpendicularly to the respective port of the PB water shield 4020*ws* that the flow sensor port 4020*sp* is fluidly connected to. In one form, the flow sensor port 4020*sp* may be configured that any water which does make its way through the port of the PB water shield 4020*ws* (or an equivalent air path) must rotate (e.g. through 90 degrees) to travel to the flow sensor, such as by travelling upwards in the normal, working orientation of the RPT device 4000. The PB water shield 4020*ws* may be formed integrally with the enclosure of the pneumatic block 4020 (e.g. first PB housing 4020*h*1), or alternatively may be formed separately, to be inserted into the enclosure (e.g. by interference fit, as shown in FIG. 11*n*) or connected to the enclosure (e.g. by welding, not shown). Yet further, the flow sensor flow path 4020*fp* may be configured so that the flow sensor port 4020*sp* may be located above the height of the corresponding openings of the flow sensor flow path in each chamber 4020*c*1 and 4020*c*2. This may further prevent ingress of water into the flow sensor 4274.

5.4.1.6 Chassis 4016

The RPT device 4000 may comprise a chassis 4016 as shown in FIGS. 8*a*-8*f*, wherein the chassis 4016 may provide a structural frame for the RPT device 4000. The platform 4016*pl* may comprise an external wall of the RPT device 4000 in some forms as shown in FIG. 5*a* and FIG. 8*b*. The chassis 4016 may also locate one or more components such as the external housing 4010, the pneumatic block 4020, the PCBA 4202, and the outlet muffler 4124 as seen in FIG. 5*a*.

In one form, the chassis 4016 may comprise a platform 4016*pl* (see FIGS. 8*a*-8*b*) configured to support the pneumatic block 4020. The chassis 4016 may comprise a dock 4130 configured to receive the outlet muffler 4124 (or the water reservoir 5110), for example into a cavity therein, to connect the outlet muffler 4124 or the water reservoir 5110 to the pneumatic path. The dock 4130 may receive a portion of the outlet muffler 4124 as shown. The dock 4130 may include a dock outlet 4132 configured to deliver a flow of air into the outlet muffler 4124 or the water reservoir 5110 when inserted, and a dock inlet 4134 to receive a flow of air from the outlet muffler 4124 or the water reservoir 5110 when inserted as shown in FIGS. 8c-8d. The chassis 4016 may also comprise an RPT device outlet 4004 as shown in FIG. 8e, wherein the RPT device outlet 4004 may be removably coupled to the chassis 4016. The dock outlet 4132 may be configured to fluidly couple with the muffler entry 4124in or the water reservoir inlet 5118. The dock inlet 4134 may be configured to fluidly couple with the muffler exit 4124ou or the water reservoir outlet 5122.

In one form, the dock inlet 4134 and the dock outlet 4132 may each comprise a bellows type face seal. The seal may be engaged to abut the complementary portion of the outlet muffler 4124 (e.g. 4124ou or 4124in as shown in FIG. 7e) or the water reservoir 5110 (e.g. 5118 or 5222 as shown in FIG. 16d) or as described in U.S. Pat. No. 8,544,465, the entire contents of which is incorporated herewithin by reference. One advantage of such a bellows type face seal may be that it allows for misalignments in axial and radial directions. As such a seal would abut the complementary portion, this configuration may be radially more tolerant to misalignment than an arrangement where, for example, one male connector is inserted into a female connector. Furthermore, the flexibility of such a seal would allow for axial misalignments to be present without adversely affecting performance of the RPT device 4000 (or the humidifier 5000).

An outlet tube 4006 may comprise the RPT device outlet 4004 and the dock inlet 4134, as well as being removably coupled to the dock 4130. In some forms, a separate intermediate tube 4008 may comprise the dock outlet 4132. The intermediate tube 4008 may be configured to couple to the pneumatic block 4020 to receive a flow of air from the pneumatic block 4020 for delivery to the dock 4130. The intermediate tube 4008 may further comprise a dock outlet pressure port 4132pp for measuring the air pressure at the dock outlet 4132.

The outlet tube 4006 may comprise an outlet tube latch portion 40061a configured to engage with a complementary feature in the dock 4130, such as the dock outlet slot 4130s1. The outlet tube 4006 may further comprise one or more outlet tube guide portions 4006gu, which may assist in correct insertion of the outlet tube 4006 into the dock 4130 by engagement with one or more corresponding dock guide portions 4130gu. An outlet tube guide portion 4006gu may comprise a flat plate in one form as shown in FIG. 8g, configured to be engaged and directed by the dock guide portions 4130gu, which may be sloped to direct the outlet tube 4006 to its intended position, such as to engage the outlet tube latch portion 40061a with the dock outlet slot 4130s1.

The outlet end 4006oe may also be formed with an ISO taper, such as a 22 mm outer diameter ISO taper, to allow connection of standard non-heated air circuit.

As seen in FIGS. 8g and 8h the outlet tube 4006 may comprise a flow bend, having an internal circular or curved cross-section configured to reduce the impedance of the air flow through the outlet tube 4006. The outlet tube 4006 may be constructed in two-parts as shown in FIG. 8h, wherein a first portion 4006a is moulded from rigid material such as Bisphenol A (BPA) free polycarbonate/acrylonitrile butadiene styrene (PC/ABS), and the second portion 4006b comprising at least a part of the flow bend is overmoulded from a compliant material such as silicone. Use of a compliant material to form the second portion 4006b that comprises a portion of the bend may allow withdrawal of a moulding tool that comprises the internal bend from the internal cavity at the end of the moulding process by deforming the second portion 4006b.

The outlet tube 4006 may also include a retaining flange 4006fl to assist in at least one of locating or securing the outlet tube 4006 to the RPT device 4000 or the humidifier 5000, or a housing or chassis thereof. The retaining flange 4006fl may assist in correctly locating or positioning the outlet end 4006oe of the outlet tube 4006 within the outlet of the RPT device 4000 or humidifier 5000 as shown in FIG. 8e, for example by abutting a locating flange in the RPT device 4000 and/or humidifier 5000. It should be understood that the retaining flange 4006fl may allow for fixed attachment of the outlet tube 4006. The retaining flange 4006fl may, alternatively, allow for removable attachment of the outlet tube 4006 so that it may be cleaned or replaced.

The outlet tube 4006 may include an inlet end 4006ie that connects to the humidifier 5000 or the RPT device 4000 as shown in FIG. 8b-8f. The inlet end 4006ie may comprise a pressure activated face seal or bellows seal to provide sealed pneumatic connection from an outlet of the RPT device 4000 and/or the humidifier 5000, such as the dock outlet 4132 described above. In another example of the present technology, the outlet tube 4006 may be connected at the inlet end 4006ie to at least one conduit that is in turn connected to a RPT device 4000 and/or a humidifier 5000. In any of these scenarios one function of the outlet tube 4006, and specifically the inlet end 4006ie, may be to receive the flow of gas from the RPT device 4000 and/or the humidifier 5000 and direct it outside of the device to the air circuit 4170 via the outlet connector 4170oc. The outlet tube 4006 also facilitates rotation of the outlet connector 4170oc of the air circuit 4170 by allowing the outlet connector 4170oc to rotate around the outlet end 4006oe.

A portion of the RPT device 4000 is shown in FIGS. 8g-8h and 18i-18j with the outlet tube 4006 and/or the cable housing 5080. The outlet tube 4006 may also incorporate a latch portion 40061a to connect with a complementary receiving portion (such as the dock outlet slot 4130s1) of the RPT device 4000 and/or the humidifier 5000 to locate and/or retain the airflow tube in a correct position within the RPT device 4000 and/or the humidifier 5000 as described above. The engagement of the latch portion 40061a with the dock outlet slot 4130s1 may provide a sensory feedback, such as a click, to indicate correct connection. The latch portion 40061a may be further configured so that the outlet tube 4006 would be dislodged from receiving portion as it disengages therefrom. The latch portion 40061a may be a different colour to the complementary receiving portion or RPT device 4000 and/or the humidifier 5000 component for improved visibility. In certain circumstances, the outlet tube 4006 and/or the complementary receiving portion may be configured so that a button such as at the end of the latch portion 40061a may be used to release the outlet tube 4006 from the complementary receiving portion. A tool may be used to release the outlet tube 4006 from the receiving portion.

The outlet tube 4006 may be configured so that engagement of the latch portion 40061a with the complementary receiving portion also completes a pneumatic connection between the air circuit 4170 and the RPT device 4000 and/or the humidifier 5000 when the air circuit 4170 is attached to the RPT device 4000 and/or humidifier 5000. Accordingly, it may be possible to detect the absence or incorrect connection of the outlet tube 4006 or a disengagement thereof by detection of air leak.

In a further optional arrangement, when the outlet connector 4170oc of the air circuit 4170 is connected to the RPT device 4000 and/or the humidifier 5000 the connection action may be configured to ensure the correct connection of the outlet tube 4006 with the complementary receiving portion. Incorrect connection of the outlet tube 4006 to the complementary receiving portion may prevent the outlet connector 4170oc from being able to connect correctly to the outlet tube 4006, which may be indicated by the RPT device 4000 through detection of a high leak flow, for example. In a further alternative the outlet connector 4170oc of the air circuit 4170 may be used to facilitate insertion and/or removal of the outlet tube 4006 from the RPT device 4000 and/or the humidifier 5000.

As discussed above, when the air circuit 4170 is attached to the RPT device 4000 and/or humidifier 5000, the outlet end 4006 of the outlet tube 4006 may be coupled to the outlet connection region 5056 of the outlet connector 4170oc.

The dock 4130 may comprise one or more features configured to engage a component (e.g. outlet muffler 4124) which is inserted therein. For example, the dock 4130 may comprise one or more flanges 4130fl as shown in FIGS. 8c-8f, the flanges being adapted to engage and guide the outlet muffler 4124 or the water reservoir 5110 as they are inserted into the dock 4130.

In one form, the dock 4130 may comprise one or more components of a humidifier 5000, where the humidifier 5000 is integrally constructed with the RPT device 4000. For example, a base of the dock 4130 may comprise a heating element 5240 as will be described in greater detail below.

5.4.1.7 Transducer(s) 4270

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the present technology, one or more transducers 4270 may be constructed and arranged to measure properties such as a flow rate, a pressure or a temperature at one or more points in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.7.1 Flow Transducer 4274

A flow transducer 4274 in accordance with the present technology may be based on a differential pressure transducer, for example, an SDP600 Series differential pressure transducer from SENSIRION.

In one form, a signal representing a flow rate such as a total flow Qt from the flow transducer 4274 is received by the central controller 4230.

5.4.1.7.2 Pressure Transducer 4272

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

5.4.1.7.3 Motor Speed Transducer 4276

In one form of the present technology a motor speed transducer 4276 is used to determine a rotational velocity, such as of the motor 4144 or the blower 4142. A motor speed signal from the motor speed transducer 4276 is preferably provided to the therapy device controller 4240. The motor speed transducer 4276 may, for example, be a speed sensor, such as a Hall effect sensor.

5.4.1.7.4 Ambient Light Sensor 4278

As the RPT device 4000 is often used in a bedroom environment, for example to be used while the patient 1000 is about to go to sleep, or is asleep, it may be important to ensure that any light-emitting features of the RPT device 4000 is not excessively bright.

In one form of the present technology an ambient light sensor 4278 is used to determine the light level in the ambient area around the RPT device 4000. An ambient light signal from the ambient light sensor 4278 may be provided as an input to the central controller 4230, for example to adjust a brightness of a display or any other light-emitting features, such as a backlight for input devices 4220 or any notification lights.

The ambient light sensor 4278 may be connected to an aperture such as the external housing light port 4101p as shown in FIG. 9a. In such a configuration, light level detected by the ambient light sensor 4278 would correspond to the light level at or near the aperture. In one form, the external housing light port 4101p may be located adjacent to the display 4294 such that the brightness of the display 4294 may be adjusted according to the detected light level. The ambient light sensor 4278 may be connected to the aperture by a light well (also referred to as a light pipe) to assist in accurately determining the light level at the aperture.

The display 4294 may be configured to operate at one of a plurality of predetermined brightness settings. The brightness setting may be chosen according to a signal output of the ambient light sensor 4278. For instance, the display 4294 may be configured to operate at a lower brightness setting if the light measured by the ambient light sensor 4278 is at or below a threshold (e.g. 10, 15 or 20 lux), and the display 4294 may be configured to operate at a higher brightness setting where the light measured by the ambient light sensor 4278 is above the threshold (e.g. 10, 15 or 20 lux). Thus, in such an arrangement a lower the level of the ambient light may result in a lower brightness setting.

5.4.1.8 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.9 Air Circuit 4170

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

As shown in FIG. 18*a*, the air circuit 4170 may include an AC tube portion 4170*tp* and an AC outlet connector 4170*oc* at one end of the tube portion 4170*tp* to connect the air circuit to the RPT device 4000 or the humidifier 5000. In one form, the AC outlet connector 4170*oc* may comprise an AC pre-block 4170*pb*, an AC overmould 4170*om* and an AC electrical connector 4170*ec*. The electrical connector 4070*ec* may be oriented parallel to a centre axis of the outlet connection region 5056 and extend downward from an underside of the outlet connector 4170*oc* and out from an opening in the AC overmould 4170*om* for protection, such as from water ingress.

The AC tube portion 4170*tp* may also include a helical coil 4170*co* to provide support for the AC tube portion 4170*tp*. The air circuit 4170 may also incorporate a heating element to prevent rainout (condensation of water vapour, for example, within the AC tube portion 4170*tp* or the patient interface 3000), which may be provided within the AC helical coil 4170*co*. When a heating element is provided in the AC helical coil 4170*co* electrical power or signalling or both may be necessary if, for example, the heating element is an electrical resistance heater. In some instances, an electrical connection may be required between the patient interface 3000 and the RPT device 4000 or the humidifier 5000 for electrical power or communication therebetween.

The air circuit 4170 may require both pneumatic and electrical connections to be formed to the humidifier 5000 (or the RPT device 4000), as well as a mechanical connection. These connections may be formed through the AC outlet connector 4170*oc* to allow the pressurized gas to flow to the patient interface 3000, to provide electrical power and signalling to the heating element in the AC helical coil 4170*co* and to locate and secure the air circuit 4170 relative to the humidifier 5000 (or the RPT device 4000). These connections may be formed simultaneously or in series such that one of the mechanical, pneumatic or electrical connections is completed before others. The air circuit 4170 may comprise a patient interface connector 4107 to couple to a patient interface 3000 at the opposite end of the tube portion 4170*tp*. In some forms, the patient interface connector 4107 may be different to the AC outlet connector 4170*oc* as shown in FIG. 18*a*.

FIGS. 18*b*-18*e* depict air circuits or portions thereof according to examples of the present technology. FIGS. 18*f*-18*j* also depict exemplary air circuits that are connected to an outlet assembly 5004. As can be seen in FIG. 18*a*-18*b*, an AC tube portion 4170*tp* having an AC helical coil 4170*co* may be connected to an AC outlet connector 4170*oc*. The AC helical coil 4170*co*, as discussed above, may include a heating element and it may also function as a support structure for the AC tube portion 4170*tp*. An electrical connection may be formed by inserting the AC outlet connector 4170*oc* on the outlet assembly 5004 (to be discussed in greater detail below) so that an AC electrical connector 4170*ec* comes into electrical contact with electrical components of the outlet assembly.

5.4.1.9.1 Formation of Pneumatic and Electrical Connections

The air circuit 4170 may require both pneumatic and electrical connections to be formed to the humidifier 5000 (or the RPT device 4000), as well as a mechanical connection. These connections may be formed through the outlet connector 4170*oc* to allow the pressurized gas to flow to the patient interface 3000, to provide electrical power and signalling to the heating element in the helical coil 4170*co* and to locate and secure the air circuit 4170 relative to the humidifier 5000 (or the RPT device 4000). These connections may be formed simultaneously or in series such that one of the mechanical, pneumatic or electrical connections is completed before others. The air circuit 4170 may comprise on another end a patient interface connector 4107 to couple to a patient interface 3000.

The AC outlet connector 4170*oc* may comprise a recess 4170*re* configured to couple to an electrical connector receiver 5052 of a swivelling disc 5050 (see FIGS. 18*i*-18*j* and further discussion below) to aid in releasably securing the AC outlet connector 4170*oc* to the humidifier 5000, for example at the outlet assembly 5004. The recess 4170*re* may also provide a visual aid to the patient to locate the outlet connector 4170*oc* in relation to the outlet assembly 5004 by being shaped to correspond to the electrical connector receiver 5052 (see FIG. 18*j*). The electrical connector receiver 5052 may house a female electrical connector 5058 such as that shown in FIGS. 18*m*-18*n*. The AC outlet connector 4170*oc* may also include an actuator 4172 that controls a retention feature 4174. When the AC outlet connector 4170*oc* is inserted onto the outlet assembly 5004, the retention feature 4174 may engage with a corresponding notch 5054 of the swivelling disc 5050 (see FIG. 18*i*-18*j*). The actuator 4172 in conjunction with the notch 5054 may produce an audible sound or provide tactile feedback or both at the actuator 4172 upon engagement. The actuator 4172 or the retention feature 4174 may be produced with higher wear characteristics than the swivelling disc 5050 to allow wear to occur on the air circuit 4170, which may be a consumable component. This may be achieved by use of a material with lower hardness to form the retention feature 4174 compared to the material from which the swivelling disc 5050 is formed. The retention feature 4174 and notch 5054 may engage by a snap-fit and the actuator 4172 may be depressible to bring in the retention feature to release it from the notch 5054. In some cases, the retention feature 4174 and the notch 5054 may be configured so that when they are not completely engaged, they may be forced into place at commencement of therapy by the therapy pressure, for example by being configured so that the therapy pressure acting on the tab 4176 urges the retention feature 4174 towards the notch 5054. As shown in FIG. 18*c*-18*e*, the actuator 4172 and the retention feature 4174 may both be located on an AC tab 4176 such that pushing the actuator inward also causes the retention feature to be moved inward, thereby freeing it from the notch 5054. In one form, the actuator 4172 may be located further from a pivot of the tab 4176 than the retention feature 4174, which would impart a mechanical advantage to the user and increase the travel required to depress the actuator 4172 to improve the resolution of movement of the retention feature 4174 to the user. This arrangement may further improve the feedback provided to the user during engagement/disengagement of the outlet connector 4170*oc*. An outlet connection region 5056

(as shown in FIG. 18a) may be shaped to correspond with the shape of the swivelling disc 5050, as shown in FIG. 18f-18j, for example.

As shown in FIG. 18d, a travel stop 4178 located at the inner ends of the ribs 4177 may be used in some examples of this technology in order to limit the travel, or level of squeezing, of the actuator 4172 during insertion and removal to prevent plastic deformation of the surrounding portions, to prevent tear of the AC outlet connector 4170oc in a periphery of the AC tab 4176 or both. The travel stops 4178 extend from the inner ends of the ribs 4177 and are aligned with the inner surface of the AC outlet connector 4170oc in the location of the actuator 4172. When the actuator is squeezed or pushed inwards the inner surface of the AC outlet connector 4170oc is correspondingly squeezed or pushed inwards until it contacts the travel stop 4178. The travel stop prevents further squeezing or pushing of the actuator.

In a further example of the technology, the notch may be replaced with a radial slot that is capable of retaining the outlet connector via the retention feature(s) but allowing rotation thereof. In such an example the swivelling disc may be fixed relative to the outlet housing or it may be eliminated completely such that the radial slot is located on the housing. Furthermore, it should be understood that such examples would retain the need for a movable electrical connector within the outlet assembly such that the electrical connection may be maintained while the outlet connector rotates.

FIGS. 18k and 18l show detailed bottom views of examples of the AC outlet connector 4170oc and specifically the outlet connection region 5056. FIG. 18k shows the AC outlet connector 4170oc connected at the outlet connection region 5056 to an outlet end 4006oe of an outlet tube 4006. (shown in FIGS. 19xx and discussed further below). The outlet tube 4006 may be formed as a multiple patient multiple user (MPMU) tube that is one or more of removable, replaceable and cleanable. It should be noted that for the sake of clarity the outlet end 4006oe is shown in this view and reference should be made to FIGS. 18f-18j for further depiction. The outlet tube 4006 may function as a removable intermediate pneumatic coupling between the AC outlet connector 4170oc of the air circuit 4170 and the air outlet of RPT device 4000 or the humidifier 5000.

5.4.1.9.2 Internal Ribs of the Outlet Connector 4170Oc

FIG. 18k shows a plurality of ribs 4177 disposed around the inner periphery of the outlet connection region 5056 of the AC outlet connector 4170oc. In the illustrated example four ribs 4177 are shown but a different number of ribs such as two, three, five or more ribs may be utilised. The ribs 4177 may function to support and position the AC outlet connector 4170oc relative to the outlet end 4006oe of the outlet tube 4006. The ribs 4177 may function to guide the AC outlet connector 4170oc during insertion to couple to the outlet end 4006oe of the outlet tube 4006 in the outlet assembly 5004 to form the pneumatic connection. This guidance may also assist in aligning the outlet connection region 5056 to facilitate the electrical connection between the AC electrical connector 4170ec and the electrical connector receiver 5052 on the swivelling disc 5050 of the outlet assembly 5004. In this arrangement, although the insertion or connection of the air circuit AC outlet connector 4170oc to the RPT device outlet assembly 5004 may be achieved in one movement by the user, the pneumatic connection is formed first and the electrical connection is formed second. The AC outlet connector 4170oc, the outlet assembly 5004 and the outlet tube 4006 may be configured such that outlet tube 4006 engages the seal 4170se of the AC outlet connector 4170oc prior to the electrical connector receiver 5052 forming an electrical connection with the AC electrical connector 4170ec. Accordingly, during removal or disconnection, the electrical connection is the first to be disconnected and the pneumatic connection is disconnected second. This may be advantageous to ensure that a pneumatic seal is maintained from the RPT device 4000 or the humidifier 5000 to the air circuit 4170 and, more specifically, between the AC outlet connector 4170oc and the outlet tube 4006. Furthermore, this may provide improved safety, for example, if supplemental oxygen is added to the flow of air delivered by the humidifier 5000, as this arrangement may prevent oxygen from being exposed during connection or disconnection of the electrical connections. FIG. 18l shows a similar view to FIG. 18k, however, the outlet end 4006oe of the outlet tube 4006 is not shown to provide a clearer depiction of an example of the ribs 4177. Both of these views also show the profile of the recess 4170re.

In some cases, a non-heated air circuit 4170 may be used that does not incorporate a heating element. Accordingly, the diameter of the central opening 5092 in the swivelling disc 5050 may be sufficiently large to accept such a non-heated air circuit 4170. Accordingly, in one example of the current technology, the external diameter of the airflow tube may be approximately 22 mm to allow connection to a standard 22 mm external diameter non-heated air circuit, and the external diameter of the AC outlet connector 4170oc may be approximately 36 mm. However, it is recognised that other external diameter sizes may be utilised.

Internal ribs 4177 may be used to reduce any radial gaps between the interior of the outlet connection region 5056 and the outlet tube 4006. Still further, the ribs 4177 and the outlet tube 4006 may be configured so that the gaps therebetween are relatively smaller than the gap between the exterior of the outlet connection region 5056 and the swivelling disc 5050. This may allow more of the wear from rotation to occur on the outlet tube 4006 in comparison to the swivelling disc 5050, which may be advantageous as the outlet tube 4006 may be more readily replaced than the swivelling disc 5050.

Another advantage of the ribs 4177 may be to allow a greater portion of any mechanical load that may result from tilting or non-axial movement to be transferred from the AC outlet connector 4170oc to the outlet tube 4006. This may be advantageous in that this may help wear occur on the consumable components such as the air circuit 4170 and/or the outlet tube 4006 than the non-consumable components of the humidifier 5000, such as the swivelling disc 5050. Yet another advantage of the ribs 4177 may be to maintain or restrict the deformation of the base seal 4170se (as shown in FIG. 18a) during engagement of the AC outlet connector 4170oc with the outlet assembly 5004 by limiting the maximum axial deformation that the base seal 4170se can undergo towards the interior of the AC outlet connector 4170oc.

5.4.1.9.3 Electrical Connection

The AC electrical connector 4170ec may include one or more lead-in features, such as chamfers, or curved radii on its edges on the leading surface in the direction of insertion such as shown in FIG. 18o. This may assist insertion of the AC electrical connector 4170ec into the electrical connector receiver 5052 to provide a surface wipe connection and prevents damage to the conductors on the AC electrical connector 4170ec. The thickness of the electrical leads 41701e on the AC electrical connector 4170ec may be approximately between 0.2 mm to 1.2 mm, for example 0.4 mm, 0.6 mm, 0.8 mm or 1 mm. The thickness may vary according to a number of parameters such as, the design life of the AC electrical connector 4170ec, material chosen for the electrical leads 41701e and the material chosen for the receiver contact elements 5058ce. One suitable example of material for the electrical leads 41701e may be high temper phosphor bronze, that is nickel plated and then gold plated. In some circumstances, an increased amount of conductive material and/or high conductivity plating (such as gold and/or platinum) may be used on the electrical leads 41701e. This may have the advantage of improving wear characteristics and/or dissipating heat from the electrical connector 4170ec. The electrical leads 41701e may have exposed conductive surfaces on the lower end of the electrical connector 4170ec to ensure full insertion is required to make the electrical connection.

Another feature provided by the connection of the AC electrical connector 4170ec to the electrical connector receiver 5052 on the swivelling disc 5050 may be that when assembled together, the electrical connector receiver 5052 is covered by the AC outlet connector 4170oc as shown in FIG. 18i and FIG. 18j. FIG. 18j shows an exploded view wherein the AC outlet connector 4170oc is shown above the swivelling disc 5050, and FIG. 18i shows the AC outlet connector 4170oc in engagement with the swivelling disc 5050. When the outlet connector 4170oc is inserted onto the swivelling disc 5050, as shown in FIGS. 18g and 18i, the region of the outlet connector that surrounds the AC electrical connector 4170ec may cover over the opening in the electrical connector receiver 5052 to prevent debris and contaminants (such as liquids) from entering into the electrical connector receiver.

As mentioned above, the electrical connector 4170ec and the electrical connector receiver 5052 are configured so that the electrical connection between them is to be made after the AC outlet connector 4170oc is mechanically engaged with the swivelling disc 5050. This reduces the proportion of any deformation or load from misalignment between the AC outlet connector 4170oc and the swivelling disc 5050 that is supported by the AC electrical connector 4170ec and the electrical connector receiver 5052. In one example, such an arrangement may be achieved by configuring the AC outlet connector 4170oc into the swivelling disc 5050 so that during insertion of the AC outlet connector 4170oc with the swivelling disc 5050, the outlet tube 4006 and the ribs 4177 engage prior to engagement of the AC electrical connector 4170ec and the electrical connector receiver 5052. This configuration may also be advantageous in cases where the gas provided via the air circuit 4170 includes supplementary oxygen, as it may prevent occurrence of electrical arcing while the pneumatic circuit is not isolated.

A yet another feature of the current technology may be found in the arrangement of the receiver contact elements 5058ce on the female electrical connector 5058 in the electrical connector receiver 5052 as shown in FIG. 18m-18n. The electrical leads 41701e may engage the receiver contact elements 5058ce as the AC electrical connector 4170ec is inserted into the electrical connector receiver 5052 from the top of the connector TS. This engagement may occur via a sliding action in the direction of the arrow ENG shown in FIG. 18a-18b. The receiver contact elements 5058ce may be configured in a sloped, triangular profile as shown in FIG. 18n and/or to be compliant in a perpendicular direction PER to the sliding plane to assist in their engagement with the electrical leads 41701e.

The aforementioned triangular profile and/or compliance may allow improved engagement between the electrical leads 41701e on the AC electrical connector 4170ec and the receiver contact elements 5058ce as the AC electrical connector 4170ec is progressively inserted into the electrical connector receiver 5052. During engagement with the AC electrical connector 4170ec, as the AC electrical connector 4170ec slides along the length of the female electrical connector 5058 the contact elements 5146 may be depressed inwards and maintain contact to the electrical leads 41701e. This may allow improved accommodation of mechanical tolerances from such sources as manufacturing variance or in-use deformation.

Still further, the receiver contact elements 5058ce may be biased, so that when deformed from its original configuration (as shown in FIG. 18n) and depressed inwards, the receiver contact elements 5058ce may be biased towards returning to the undeformed position, thereby improving the fidelity of its connection with the electrical leads 41701e. Another advantage of such an arrangement of the female electrical connector 5058 may be that it is self-cleaning. As the female electrical connector 5058 and the AC electrical connector 4170ec may engage each other in a slide-on, slide-off action, it may prevent build-up of contaminants which, if left uncleaned, may affect the fidelity of the electrical connection formed between the two parts.

Any contaminants that have been removed by the wiping action may be prevented from entering the air path, for example by a swivel disc seal 5051. In addition when the female electrical connector 5058 is arranged in a vertical position and the connection is made in a vertical direction any contaminants that are wiped off the electrical contacts will fall down below the connector. A cavity may be formed below the female electrical connector 5058 within the electrical connector receiver 5052 into which the contaminants may collect. This cavity is not in communication with the pneumatic path of the RPT device or the humidifier 5000.

FIG. 18z1 shows the surface of the female electrical connector 5058 that may be connected to the cable 5070. The connector comprises a plurality of weld points 5058w1, 5058w2, 5058w3, for example such that there may be two weld points for each of the conductive tracks, which allows for improved mechanical strength against load. The connector may also incorporate one or more pegs, rivets or pins 5058pe for alignment during assembly and/or mechanical bonding. Optionally the one or more pegs, rivets or pins 5058pe may be heat staked to provide a mechanical restraint. In certain arrangements a washer or plate may be provided between the one or more pegs, rivets or pins 5058pe and the cable 5070 to spread the mechanical restraint force over a larger surface of the connector.

FIG. 18z2-18z4 show another example of the female electrical connector 5058, including another example of receiver contact elements 5146, shown in further detail in FIG. 18z5-18z6. A feature of this example of the receiver contact element 5058ce is that a bifurcated retention feature 5058rf is formed from the base portion 5058bp rather than the contact portion 5058co and/or the curved portion 5058cu. The receiver contact elements 5058ce may be made from a material of high electrical and thermal conductivity with high strength and hardness, such as beryllium copper.

Having the exposed electrical connections on the outlet connector 4170oc of the air circuit 4170 provides additional electrical safety as the air circuit does not include a power supply but requires connection to swivelling disc 5050 on the RPT device 4000 and/or humidifier 5000 to receive power. Also, the exposed electrical connections that may be exposed to cleaning processes are also on the replaceable air circuit 4170 component.

5.4.1.9.4 Elbow Outlet Connector

Figure 1A:
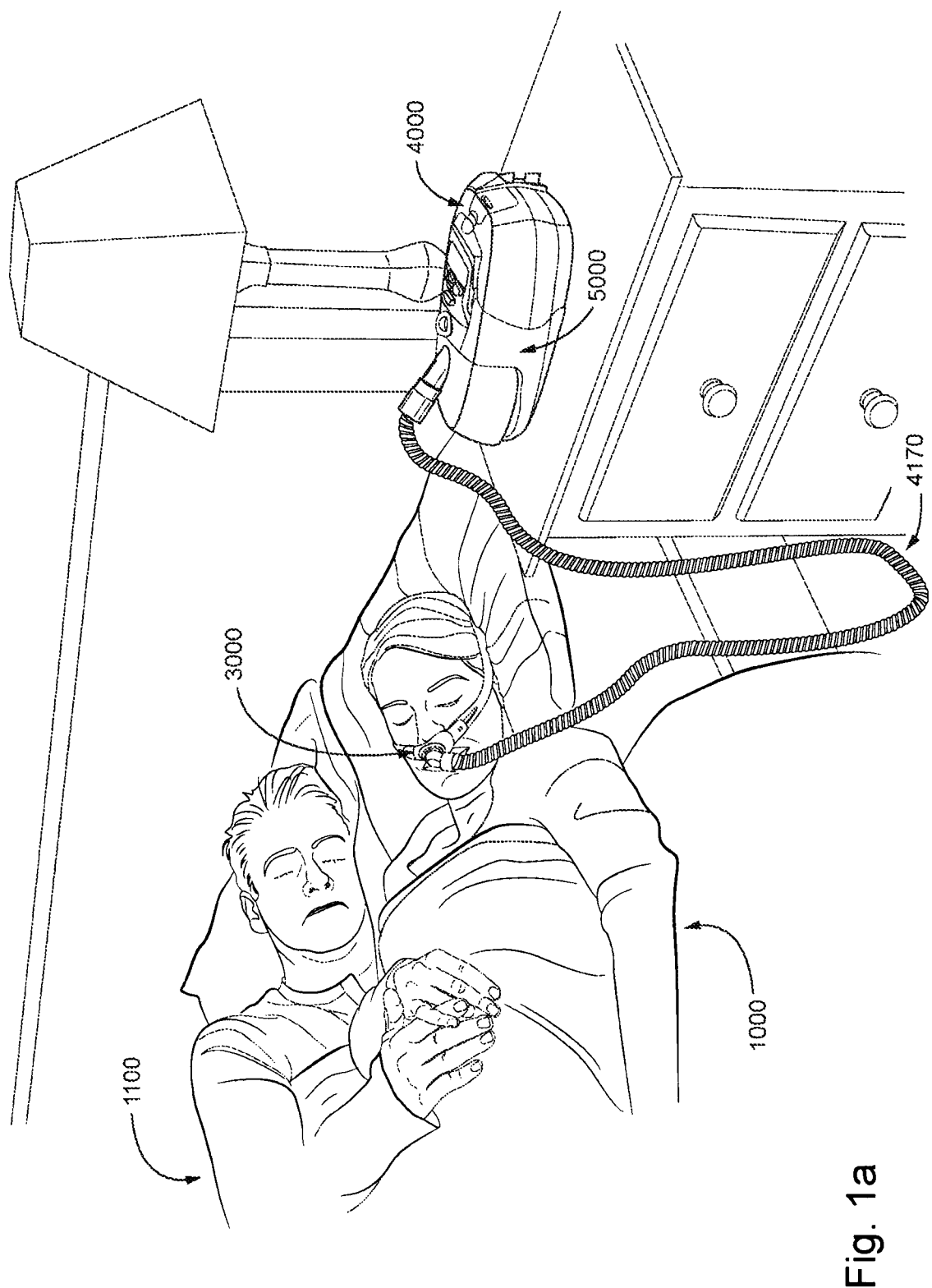
FIG. 1b shows a system including a patient 1000 wearing a patient interface 3000, in the form of a nasal mask, receives a supply of air at positive pressure from an RPT device 4000. Air from the RPT device is humidified in a humidifier 5000, and passes along an air circuit 4170 to the patient 1000.
FIG. 1 shows a system including a patient 1000 wearing a patient interface 3000, in the form of a full-face mask, receives a supply of air at positive pressure from an RPT device 4000. Air from the RPT device is humidified in a humidifier 5000, and passes along an air circuit 4170 to the patient 1000.
Figure 1B:
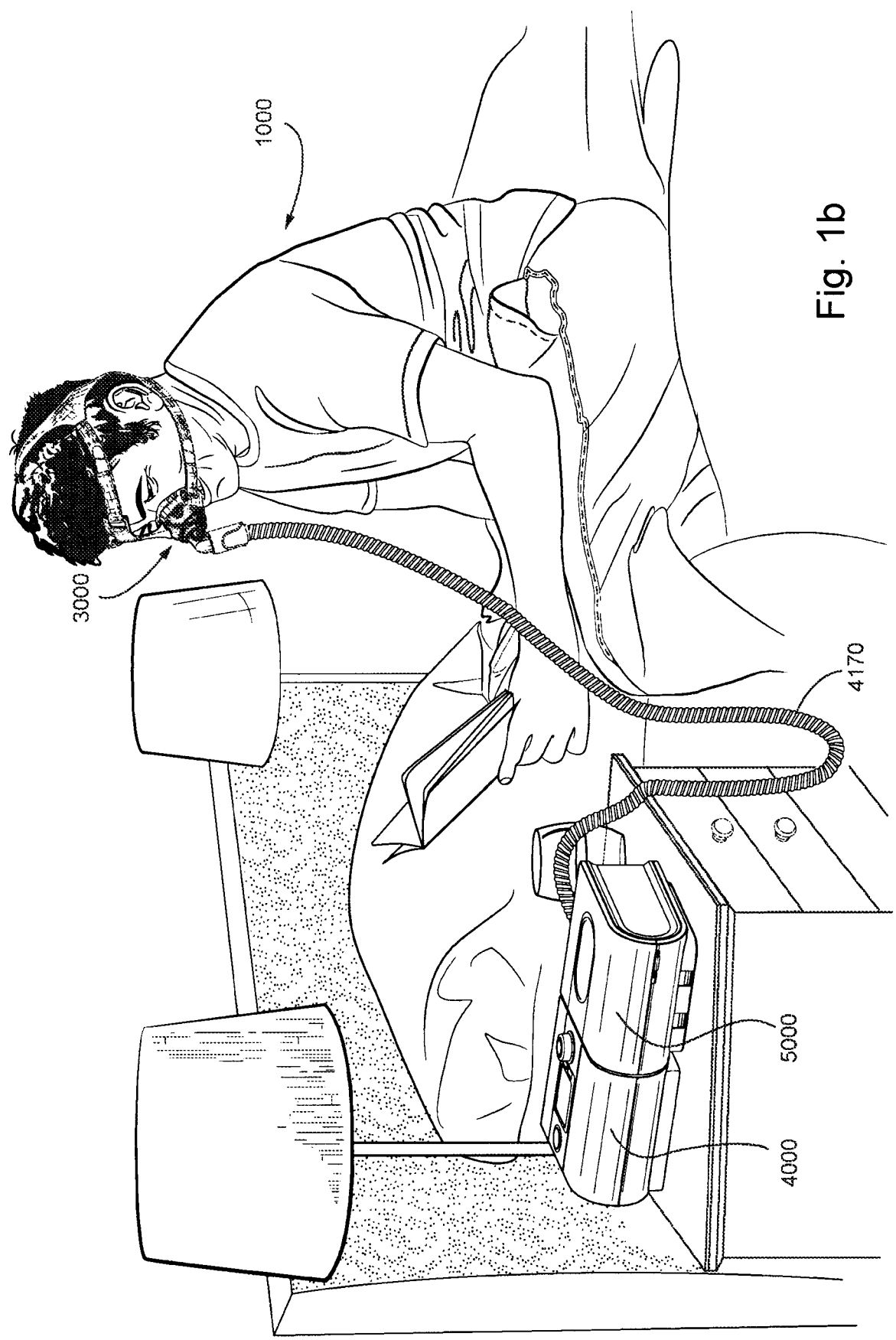
Figure 1C:

By forming the AC outlet connector 4170*oc* with an elbow, as can be seen in FIG. 18*a*-18*j*, the patient may be prevented from inadvertently pulling the air circuit 4170 off of the RPT device 4000 or the humidifier 5000, because the direction of the tension force vector of the air circuit will be located at an angle (e.g., perpendicular) to the direction of engagement of the air circuit 4170 with RPT device 4000 or the humidifier 5000. Also, as shown in FIG. 1*a*-*c*, the RPT device 4000 or the humidifier 5000 may be located on a nightstand, for example, during treatment such that the patient lying in bed is at substantially the same height as the RPT device or the humidifier. In such a situation, the inclusion of an elbow as part of the AC outlet connector 4170*oc* may allow the air circuit 4170 to be pointed more directly at the patient such that bend angles of the air circuit may be reduced, particularly at or near the elbow, which in turn may reduce stress on the air circuit. In one example of the present technology, the AC outlet connector 4170*oc* may include an elbow having an angle of about 90°. It should be understood, however, that any number of angles may be possible, such as for example between 0° and 120°, including 20°, 40°, 60°, 800 or 100°. The choice of this angle may be affected by any number of design requirements such as flow impedance, convenience, location of the AC outlet connector 4170*oc* or noise implications.

5.4.1.9.5 Rotatable Outlet Connector

As the patient may move during treatment, thus pulling the air circuit 4170, it may be advantageous to further reduce the bend angles of the air circuit and reduce stress on the assembly, in particular the air circuit, as well as the connection thereto from the AC outlet connector 4170*oc*. This may be accomplished by allowing the AC outlet connector 4170*oc* to rotate relative to the RPT device 4000 or the humidifier 5000 while the mechanical, pneumatic and electrical connections are maintained. The outlet tube 4006 also facilitates rotation of the AC outlet connector 4170*oc* of the air circuit 4170 by allowing the AC outlet connector 4170*oc* to rotate around the outlet end 4006*oe*.

As described above, the air circuit 4170 may be connected to the RPT device 4000 or the humidifier 5000 by inserting the AC outlet connector 4170*oc* onto the outlet assembly 5004, as shown in FIGS. 16*a*-16*b* and 18*f*-18*j*. Rotatability may be provided by features shown in FIGS. 18*p*-18*r* for example.

FIGS. 18*p*-18*r*, 18*v* and 18*w* show various views of the swivelling disc 5050 according to various examples of the technology. It has been described above that the swivelling disc 5050 may be the component that receives the AC outlet connector 4170*oc* when connecting the air circuit 4170 to the RPT device 4000 or the humidifier 5000. The swivelling disc 5050 may also provide rotatability relative to the RPT device and/or the humidifier.

FIG. 18*y* shows a perspective view of the bottom of the exemplary swivelling disc 5050 and the cable 5070. In other words, this view depicts features of the swivelling disc 5050 that are located opposite the side to which the AC outlet connector 4170*oc* may connect. A cable 5070, to be discussed in greater detail below, can be seen extending from an underside of the electrical connector receiver 5052. The end of the cable 5070 that is inside of the electrical connector receiver 5052 may be in electrical communication with the AC electrical connector 4170*ec* when the AC outlet connector 4170*oc* is inserted onto the swivelling disc 5050. The free end of the cable 5070 shown may be in electrical communication with at least one component of the RPT device 4000 or the humidifier 5000 (e.g., the central controller 4230, PCBA 4202 or a power supply 4210). It should also be understood that the cable 5070 may be of any sufficient length to perform its connective function, as will be discussed in greater detail below.

The swivelling disc 5050 may also incorporate a swivel disc seal 5051 as shown in FIG. 18*w*-18*x*-18*y* that may comprise a compliant material such as TPE. The swivel disc seal 5051 may function to maintain a seal between the swivelling disc 5050 and the outlet tube 4006 to prevent any contaminants from entering the air path, for example by extending around a periphery of the top of the swivelling disc 5050 and towards the base of the swivelling disc 5050 as shown in FIGS. 18*v* and 18*y*. In one form, the swivel disc seal 5051 may be an overmoulded portion of the swivelling disc 5050.

As described above, the AC outlet connector 4170*oc* may be releasably coupled to the swivelling disc 5050 by engagement of the retention features 4174 in corresponding notches 5054 and by engagement of the recess 4170*re* onto the electrical connector receiver 5052. When connected to the swivelling disc 5050, the AC outlet connector 4170*oc* may be able to rotate in unison with the swivelling disc and relative to the cable housing 5080.

FIGS. 70*a*-*c* show views of the swivelling disc 5050 joined to the cable housing 5080. FIG. 70*a* shows a top view of an outlet assembly according to an example of the present technology. In FIGS. 70*a*-*c* the swivelling disc 5050 may be in an intermediate rotational position relative to the cable housing 5080.

FIG. 70*b* shows a cross-section of the outlet assembly 5004 across the symmetrical plane of the female electrical connector 5058 taken through line 70*b*-70*b* of FIG. 70*a*. This example of the current technology shows an internal shoulder 5160 that recesses the female electrical connector 5058 from the opening of the electrical connector receiver 5052, which may improve the electrical safety of the electrical connector receiver 5052 when engaging with and/or disengaging from the connector 4170*ec*. Recessed placement of the female electrical connector 5158 from the opening of the electrical connector receiver 5052 may also prevent occurrence of any electrical arcing at or near an exposed area. The current arrangement of the female electrical connector 5058 and the electrical connector receiver 5052 may also prevent any powered components from being touched by a user.

FIG. 70*c* shows another cross-sectional view of the outlet assembly 5004 taken through line 70*c*-70*c* of FIG. 70*a*. Inner wall 5082 of the swivelling disc 5050 can be seen within the outer wall of the cable housing 5280. The tabs 5094 of the cable housing 5080 can also be seen. The flange 5112 of the swivelling disc 5050 can also be seen above the outer wall 5084 of the cable housing 5080.

5.4.1.9.6 Limited Rotation

The disc stop surfaces 5060, 5062 (shown in FIG. 18*y*18*x*), discussed above, have a pair of complementary housing stop surfaces 5164, 5166 (shown in FIG. 18*w*18*t*) that may be located on an inner wall 5082 of the cable housing 5080. By connecting the swivelling disc 5050 (as shown in FIG. 18*v*) to and within the inner wall 5082 of the cable housing 5080 (as shown in FIG. 18*w*), for example as shown in FIG. 18*x*, the rotation of the swivelling disc 5050 relative to the cable housing 5080 may be limited by engagement of the disc stop surfaces 5060, 5062 to corresponding housing stop surfaces 5164, 5166 at or near its extreme positions. Rotation of the swivelling disc 5050, in one example of the technology, may be limited to less than about 360°. Rotation may also be limited to an amount that is greater than about 180°. In a further example, rotation may be limited to about 270°. The desired range of rotation of the swivelling disc 5050 may be determined by a number of factors, such as the location of the swivelling disc 5050 with respect to the RPT device 4000 and/or humidifier 5000, the elbow angle of the AC outlet connector 4170*oc*, and material properties of the components.

The depicted examples show two pairs of complementary stop surfaces, as discussed above, that may represent opposite ends or surfaces of one structure. It may be possible to have multiple stop structures formed on respective components. For example, the stop surfaces on the inner wall of the housing may be provided with two separate protrusions thereon and likewise for the swivelling disc. It is also envisioned that multiple configurations of stop surfaces may be provided on a single combination of housing and swivelling disc such that one combination may include a number of available rotational limits.

FIG. 18*p* shows the swivelling disc 5050 rotated into one extreme position in the counter-clockwise direction relative to the cable housing 5080. FIG. 18*r* shows the swivelling disc 5050 rotated into another extreme position towards the other limit of travel in the clockwise direction relative to the cable housing 5080. FIG. 18*q* shows the swivelling disc 5050 in a position relative to the cable housing 5080 that is between the extreme positions shown in FIGS. 18*p* and 18*r*. Although the swivelling disc 5050 does not allow the stop surfaces 5060, 5062, 5164, 5166 to be seen in FIG. 18*p*-18*r*, it should be understood that when the swivelling disc 5050 is in either extreme position shown in FIGS. 18*p* and 18*r* that one of the disc stop surfaces 5060, 5062 is engaged and/or abutted against a corresponding housing stop surface 5164, 5166.

It should be understood that each AC tab 4176 of the AC outlet connector 4170*oc* includes a retention feature 4174 that is engaged with a corresponding notch 5054 of the swivelling disc 5050 to releasably connect the substructure to the swivelling disc so that they may rotate in unison relative to the cable housing 5080.

5.4.1.9.7 Electrical Cable Connection

As discussed above, the cable 5070 may be provided to electrically connect the AC electrical connector 4170*ec* to at least one component of the RPT device 4000 or the humidifier 5000. The cable 5070 (e.g. shown in FIG. 18*v*-18*y*, 18*u*-18*x*) may be a flexible circuit board (FCB) or a ribbon cable. The cable 5070 may also include multiple wires to provide multiple electrical connections for powering and signalling functions. The cable 5070 may be oriented such that the major or longer side is oriented in parallel to the axis of rotation of the swivelling disc. If an FCB is used as the cable 5070, it may be oriented so that the surface of the FCB where the conductive tracks are located is protected from frictional contact with the cable housing 5080 as it rotates with the swivelling disc 5050, in order to help prolong the life of the cable 5070. Still further, the contacting surface (away from the conductive tracks) may comprise a low-friction surface so that when it slides relative to the cable housing 5080 the friction force created is minimised. This may have the effect of reducing the amount of wear occurring on the cable 5070, as well as reducing the load imposed on the solder/mounting joints between the cable 5070 and any electrical connectors connected thereto, such as the female electrical connector 5058. An example of such a low-friction surface may be a polyamide substrate.

5.4.1.9.8 Cable Management

In accordance with an example of the present technology, the cable 5070 may be fixed at one end to the electrical connector receiver 5052 of the swivelling disc 5050. Although not shown, it should be understood that the opposite end of the cable 5070 may be fixedly connected to at least one component of the RPT device 4000 or the humidifier 5000 such as a PCBA 4202 to provide power to the cable. Thus, the cable 5070 may have a fixed length between the connection to the swivelling disc 5050 and the connection to at least one component of the RPT device 4000 or the humidifier 5000.

The cable 5070, in an example of the present technology shown in FIG. 18*p*-18*r*, may also include a slack portion that may be contained within either an annular section between the inner wall 5082 and the outer wall 5084, or a recess or void 5086 defined, at least in part, by the cable housing 5080 depending upon the position of the swivelling disc 5050. The flange 5112 of the swivelling disc 5050 may also contribute to defining the upper cover of the annular section, however, the flange 5112 does not contact the cable 5070 within the annular section. The cable housing 5080 (see FIG. 18*s*) may also include the inner wall 5082 and an outer wall 5084, both of which may further define the void 5086. The cable housing 5080 may also include a retainer 5090, which may help to maintain the cable 5070 in the proper orientation by reducing the chance of entanglement or pinching and to prevent the slack portion from being pushed out of the cable housing 5080. The outer diameter of the retainer 5090 may be designed to provide a minimum diameter for bend of the cable 5070 without damaging the electrical elements of the cable 5070, for example an outer diameter of approximately 4 mm, 4.5 mm, 5 mm or some other outer diameter. It is to be understood that the outer diameter size of the retainer 5090 may be varied depending upon the size and type of cable used. As can be seen in FIG. 18*s*, the exemplary cable housing 5080 depicted may include an opening that may be formed in the shape of a slot and through which the cable 5070 may pass, while maintaining a substantially fixed length of the cable 5070 within the cable housing 5080.

The cable 5070 is at least partially wrapped around the inner wall 5082 within the annular section 5174 when the swivelling disc is rotated towards the extreme position shown in FIG. 18*r*. The cable 5070 does not wrap around the swivelling disc 5050 but moves with the swivelling disc within the annular section as the swivelling disc 5050 is rotated.

FIGS. 18*p*-18*r* depict another feature of the depicted examples of the technology. As the swivelling disc 5050 is rotated between extreme positions the cable 5070 may be pushed and pulled between the void 5086 and annular section of the cable housing 5080 due to its connection to the swivelling disc 5050. For example, when the swivelling disc 5050 is rotated from the position shown in FIG. 18*p* to the position shown in FIG. 18*r* it can be seen that a portion of the cable 5070 is pulled out of the void 5086 and into the annular section 5088. It should be understood that the portion of the cable 5070 shown doubled back in the void 5086 in FIG. 18*p*, for example, may be considered the slack portion. In other words, the slack portion may be the excess cable that represents a length of the cable beyond what is necessary for direct connection to the swivelling disc 5050. Thus, as the swivelling disc 5050 is rotated from the position shown in FIG. 18*p* to the position shown in FIG. 18*q* the slack portion may be progressively removed from the void 5086 so that the slack portion of the cable 5070 may be progressively pulled into the annular section 5088 and begin to wrap around the inner wall 5082 as the cable is pulled. As the swivelling disc 5050 is rotated further, from the position shown in FIG. 18*q* to the position shown in FIG. 18*r*, the portion of the cable 5070 that is pulled into the annular section 5088 increases and the slack portion may be pulled completely or nearly completely from the void 5086. The recess or void 5086 and the annular section 5088 may be formed on opposing sides of the inner wall 5082.

Rotation of the swivelling disc 5050 in the opposite direction, from the position in FIG. 18*r* to the position in FIG. 18*q* to the position in FIG. 18*p*, may cause the cable 5070 to be progressively pushed from the annular section 5088 and unwrapped from around the inner wall 5082 such that the slack portion in the void 5086 may increase and begin to double back. In an example of the present technology, the maximum slack portion of the cable 5070 may be of a fixed length. In another example, that fixed length may be less than about the circumference of the swivelling disc 5050 and/or about equal to the distance of an arc swept out by the electrical connector receiver 5052 as the swivelling disc rotates between extreme positions. It should also be understood that in an example of the present technology when the swivelling disc 5050 is in the position shown in FIG. 18*p* the largest amount of the slack portion of the cable 5070 is gathered or contained in the void 5086.

5.4.1.9.9 Cable Housing

FIGS. 18*s*-18*t* depict features of the cable housing 5080 according to examples of the present technology. As described above, the cable housing 5080 may include the inner wall 5082 and the outer wall 5084 that together may define the void 5086 and the annular section 5088. The inner wall 5082 may define an opening 5092 through which the outlet tube 4006 may extend when the outlet assembly 5004 is assembled onto the RPT device 4000 or the humidifier 5000. Further facilitating this assembly, housing tabs 5094 (see FIG. 18*t*) may be located on the cable housing 5080 to attach the cable housing to the RPT device 4000 or the humidifier 5000. This may improve the manufacturability and serviceability of the cable housing 5080. The housing tabs 5094 may be configured so that they are, by themselves and/or as a set, able to support the weight of the humidifier 5000 and the RPT device 4000. This may prevent damage from occurring to the humidifier 5000, the RPT device 4000 or the cable housing 5080 when the assembly is accidentally lifted by the air circuit 4170 or the AC outlet connector 4170*oc*. In some instances, the air circuit 4170 or the AC outlet connector 4170*oc* may be configured to mechanically fail if the humidifier 5000 and/or the RPT device 4000 is held in place and a force is imposed onto the air circuit 4170 and/or the AC outlet connector 4170*oc* in the upwards direction.

Returning to the inner wall 5082 and the outer wall 5084, in an example of the present technology, the slack portion of the cable 5070 can be seen (for example, in FIG. 18*p*) to form a radius in the void 5086. This radius may affect the stress imposed on the cable 5070 (and therefore potentially its operating life) and is defined in part by the distance (VO_W in FIG. 18*s*) between the inner wall 5082 and the outer wall 5084 in the void 5086. Therefore, these walls may be separated by a distance in the range of 2 mm to 5 mm across the void 5086 based on a desired minimum radius of the cable 5070. In one example, the distance is in the range of 4 mm to 5 mm. It should be understood that the desired minimum radius of the cable may change as a function of the properties of the cable 5070 and its design parameters such as design life, or usage cases. Similarly, the length (VO_L in FIG. 18*s*) of the void 5086 may be lengthened or shortened according to the maximum slack length of the cable 5070, which may be driven by the maximum rotation of the swivelling disc 5050.

The width (AN_W in FIG. 18*s*) of the annular section 5088 between the inner wall 5082 and the outer wall 5084 may be minimised as the cable 5070 travels therein as the swivelling disc 5050 rotates from one extreme position to the other. This may have the benefit of reducing noise produced by the cable and preventing buckling of the cable in the annular section. The width of the annular section may be between approximately 1 mm and 4 mm, such as 2 mm or 3 mm, and it should be understood that the width may depend on various characteristics and/or properties of the assembly, such as the characteristics of the cable chosen or the radius of the inner wall 5082. In some arrangements the inner wall 5082 of the annular section 5088 and/or the outer wall 5084 of the annular section 5088 may include dampening material to help improve sound performance when the swivelling disc is rotated. A dampening material may also ensure the cable moves around the inner wall 5082 rather than the outer wall 5084 or vice versa.

In an example of the present technology, the cable housing 5080 may be formed from polypropylene, or polycarbonate/acrylonitrile butadiene styrene (PC/ABS). The swivelling disc 5050 may be formed from a combination of polycarbonate/acrylonitrile butadiene styrene (PC/ABS) and a thermoplastic elastomer (TPE).

5.4.1.10 Oxygen Delivery Port 4180

In one form of the present technology, one or more oxygen delivery ports 4180 may be used to deliver supplementary oxygen to one or more points in the pneumatic path, such as upstream of the pneumatic block 4020, to the air circuit 4170 or to the patient interface 3000.

5.4.1.11 Power Supply 4210

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.1.12 Central Controller 4230

In one form of the present technology, the central controller 4230 is one or a plurality of processors suitable to control an RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.1.13 Clock 4232

Preferably RPT device 4000 includes a clock 4232 that is connected to the central controller 4230.

5.4.1.14 Therapy Device Controller 4240

In one form of the present technology, therapy device controller 4240 is a control module 4330 that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

5.4.1.15 Protection Circuits 4250

The one or more protection circuits 4250 in accordance with the present technology may comprise an electrical protection circuit, a temperature and pressure safety circuit.

5.4.1.16 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which are stored computer program instructions expressing the one or more methodologies described herein, such as the one or more algorithms.

5.4.1.17 Data Communication Interface 4280

In one preferred form of the present technology, a data communication interface 4280 is provided, and is connected to the central controller 4230. The data communication interface 4280 may allow the RPT device 4000 to connect to another device or a network, such as a remote external communication network 4282, a local external communication network 4284, remote external device 4286 or a local external device 4288. The data communication interface 4280 may communicate data with the other device/network that it is connected to, for example transmitting data from the RPT device 4000 regarding the patient's 1000 previous night's sleep, or receiving a message.

The remote external communication network 4282 or the local external communication network 4284 may be further connectable to another network or device, such as a remote external device 4286 or a local external device 4288 respectively as shown in FIG. 5d.

Examples of the remote external communication network 4282 may include the Internet and cellular telephone networks. The data communication interface 4280 may connect to the remote external communication network 4282 using one or more communication methods (wired or wireless) such as Ethernet, USB, optical fibre, CDMA, GSM, LTE. In some forms, the data communication interface 4280 may connect to a network via another network or device (not shown).

Examples of the local external communication network 4284 may include a home computer network and a hospital computer network. In one form, the local external communication network 4284 utilises one or more communication standards, such as Wi-Fi, Bluetooth, or a consumer infrared protocol.

In one form, the data communication interface 4280 may communicate with one or more servers containing one or more processors, memory and incorporating with other components typically present in general purpose computing devices. The data communication interface 4280 may communicate with a server as disclosed in the Australian provisional patent applications AU 2014901998, AU 2014901999 and AU 2014901997 the entire contents of which is incorporated herewithin by reference.

In one form, the remote external device 4286 is one or more computers. Such a remote external device 4286 may be accessible to an appropriately authorised person such as a clinician. Examples of local external device 4288 may include a personal computer, mobile phone, tablet or remote control.

In one form (shown in FIG. 10a-10b), the data communication interface 4280 may be a wireless communication module located on a separate PCBA to the main PCBA. The data communication interface 4280 may comprise an antenna 4280an, and an antenna ground plane 4280gp. The antenna ground plane 4280gp in this form may comprise the PCB, and may improve performance of the antenna 4280an (and thus performance of the data communication interface 4280).

The antenna 4280an may receive and transmit signal to allow the data communication interface 4280 to communicate, for example with a server as described above. The antenna 4280*an* may be an elongate member engaged with the antenna ground plane 4280*gp* (described in further detail below). The antenna 4280*gp* may be located towards an outer periphery of the RPT device 4000 so as to improve fidelity and strength of any signal to and from the antenna 4280*gp*, for example adjacent to an edge of the side panel 4014 as shown in FIG. 10*a*. In one form, the antenna 4280*gp* may be arranged so that its major axis is substantially oriented vertically for improved efficiency.

The geometry (e.g. a length) of the antenna ground plane 4280*gp*, particularly in a direction perpendicular to the long axis of the antenna 4280*an*, may affect a performance level of the ground plane 4280*gp* (and in turn the antenna 4280*an*). Typically, an increase to the length of the antenna ground plane 4280*gp* may be beneficial to its performance. Preferably, an antenna ground plane is arranged in a rectangular shape (not shown), extending in a direction perpendicular to a major axis of the antenna. The length of the antenna ground plane 4280*gp* is preferably such that a minimum performance requirement of the antenna ground plane 4280*gp* is met. Similarly to the antenna 4280*an* described above, the antenna ground plane 4280*gp* may be arranged substantially vertically, and located toward a periphery of the RPT device 4000, for example engaged with the side panel 4014 as shown in FIG. 10*a*.

However, in some cases, the configuration of the RPT device 4000 (such as its overall size and arrangement of components therein) may prevent the antenna ground plane 4280*gp* from comprising (or exceeding) the length required to meet the minimum performance requirements without an accompanying increase to a size of the RPT device 4000. Yet further, in some cases the RPT device 4000 may comprise one or more sources of radiation (such as a motor or others) which may raise the performance level required for the data communication interface 4280 to perform adequately.

According to one aspect of the present technology, the antenna ground plane 4280*gp* comprises one or more notches configured to increase the effective length of the ground plane 4280*gp*. In such forms, the effective length of the ground plane 4280*gp* may be increased by the lengths of each side of the one or more notches. The one or more notches may allow a ground plane 4280*gp* to be arranged as a more complex geometric shape than a rectangle, such as that shown in FIG. 10*b*, while improving the performance of the ground plane 4280*gp*.

The effective total length ($L_{eff}$) of the ground plane 4280*gp* may be determined from the length of the antenna ground plate and the length of each side wall of each notch within the antenna ground plane 4280*gp*. For example as shown in FIG. 10*b*, the antenna ground plane 4280*gp* may comprise a notch having a first side 4280*n*1 and a second side 4280*n*2. In this configuration, the effective total length ($L_{eff}$) of the antenna ground plane 4280*gp* is the sum of: the length of the antenna ground plane 4280*gp* ($L_1$), the length of the first side ($L_{n1}$), and the length of the second side ($L_{n2}$). Thus the effective length ($L_{eff}$) of the antenna ground plane 4280*gp* would be $L_{eff}=L_1+L_{n1}+L_{n2}$.

The notches may improve a performance of the wireless data communication interface, for example by more than 25% (e.g. by 35%, 50%, 65%, 80%), which may otherwise be achieved through an increase in a size of the antenna ground plane 4280*gp*. As discussed above, inclusion of notches may thus beneficially allow a reduction in a size of the RPT device 4000 which may not be otherwise possible.

5.4.1.18 Input Devices 4220

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value or a menu option.

In one form as shown in FIG. 9*a*, the RPT device 4000 may comprise a first button 4222, for example to start or stop therapy, a second button 4224, and a first dial 4226. The first dial 4226 in some forms may be depressible to function as a button.

5.4.1.19 Output Devices Including Optional Display, Alarms 4290

An output device 4290 in accordance with the present technology may take the form of one or more of a visual, audio and haptic unit. A visual display 4294 may include a Liquid Crystal Display (LCD) or Light Emitting Diode (LED) display.

5.4.1.19.1 Display Driver 4292

A display driver 4292 receives as an input the characters, symbols, or images intended for display on the display 4294, and converts them to commands that cause the display 4294 to display those characters, symbols, or images.

5.4.1.19.2 Display 4294

A display 4294 is configured to visually display characters, symbols, or images in response to commands received from the display driver 4292. For example, the display 4294 may be an LCD screen which is located on the front of the RPT device 4000 as shown in FIG. 9*a*. In another example, the display 4294 may be an eight-segment display, in which case the display driver 4292 converts each character or symbol, such as the figure "0", to eight logical signals indicating whether the eight respective segments are to be activated to display a particular character or symbol.

In some forms, the display 4294 may be provided separately to the RPT device 4000, or another device such as a smartphone may be used as the display 4294. In such forms, the display 4294 may be in communication with the RPT device 4000 via the data communication interface 4280.

5.4.1.20 User Interface Panel 4190

In one form, the RPT device 4000 may comprise a user interface panel 4190, for example as shown in FIG. 12*a*-12*d*. The user interface panel 4190 may include one or more of: a shield for the display 4294, actuating mechanisms for the buttons 4222 and 4224, an external housing light port 4010*1p* (and a light well 41901*w*) for the ambient light sensor 4278 and one or more seals to prevent water ingress into an interior the RPT device 4000.

The user interface panel 4190 may comprise a display cover 4294*co*. The display cover 4294*co* may be configured to protect the display 4294 from damage while allowing an unobstructed view of the display 4294, for example by being formed from a rigid, transparent material. In one form, the display cover 4294*co* may be formed with a curvature to act as a lens to assist viewing of the display 4294. The user interface panel 4190 may further comprise a resilient material such as thermoplastic elastomer (TPE) or silicone, for example to perform as a seal.

The user interface panel 4190 may provide a dial aperture 4226ap to accept an encoder shaft 4226sh for the dial 4226 (see FIG. 13a-13b) therethrough. The user interface panel 4190 may comprise one or both of a dial seal 4226se and a dial cover 4226co to prevent ingress of water into the interior of the RPT device 4000 (as shown in FIG. 12a-12d). In one form, the dial cover 4226co is configured with a greater height at or near a top of the dial 4226 to encourage any water incident in the area to run downwards without ingress into the RPT device 4000 or even towards the dial seal 4226se. The dial seal 4226se may further prevent water ingress by sealing around the encoder shaft 4226sh for the dial 4226, while allowing rotation thereof.

According to one aspect, the user interface panel 4190 may comprise a UI base 4190ba and a UI seal 4190se as shown in FIG. 12b and FIG. 12d. The UI base 4190ba may perform one or more of the functions described above, for example as a shield for the display 4294, actuating mechanisms for the buttons 4222 and 4224 and an external housing light port 40101p for the ambient light sensor 4278. Accordingly, the UI base 4190ba may be constructed from a transparent material such as acrylonitrile butadiene styrene (ABS) or polycarbonate material. Such a construction may allow the UI base 4190ba to integrally comprise a light well 41901w (or a light pipe) configured as described above, in one form as a prism or a protrusion extending from under a first surface of the UI base 4190ba proximate to the ambient light sensor 4278 to above another, opposite surface facing the exterior of the RPT device 4000 as shown in FIG. 12a-12d. In one form, one end of the light well 41901w may terminate to form the external housing light port 40101p.

The UI seal 4190se may seal one or more areas such as between the UI base 4190ba and the external housing 4010, between the encoder shaft 4226sh and the UI base 4190ba, between the display 4294 and the UI base 4190ba, or between the UI base 4190ba and the buttons 4222 and 4224. The UI seal 4190se4 may be engaged with the UI base 4190ba as an overmould, resulting in one integral user interface panel 4190 as shown in FIG. 12a and FIG. 12c for example, onto which buttons 4222 and 4224 may be coupled. The user interface panel 4190 may be then coupled with the main PCBA 4202 as for example shown in FIG. 5a.

As the RPT device 4000 may be used with a humidifier 5000 (discrete or integrated), the patient 1000 may often be interacting with the humidifier and the user interface sequentially, for example by filling up a water reservoir and then starting the RPT device 4000 or navigating a user menu. Accordingly, it may be advantageous for the user interface panel 4190 to effectively prevent or discourage water ingress into the RPT device 4000. Furthermore, constructing the UI base 4190ba from one material, and to perform multiple functions as described above may lead to reduced manufacturing costs.

5.4.1.21 Front Panel 4012

One example of the front panel 4012 may be configured as shown in FIG. 14a-14b. The front panel 4012 may be removable from the RPT device 4000, for instance to allow the patient 1000 to customise the visual look of the RPT device 4000, or to differentiate one model of the RPT device 4000 from another, where a plurality of models are available for example. In one form, the front panel 4012 may communicate with the central controller 4230 to customise an aspect of the RPT device 4000, for example to provide one of a plurality of different modes of operation as described in U.S. patent application Ser. No. 14/204,041, the entire contents of which is incorporated herewithin by reference.

The front panel 4012 may comprise one or more retention features to allow the front panel 4012 to be secured onto the RPT device, such as by engagement with the external housing 4010. In one form, the front panel 4012 may comprise one or more internal shoulders 4012sh (as shown in FIG. 14b) configured to engage with one or more complementary features on the external housing 4010, such as the protrusions 4010pr (as shown in FIG. 13a-13b). The external housing 4010 may comprise an access point such as a front panel cutout 4010co, configured to accept a finger of the patient 1000 for example to allow the patient 1000 to remove the front panel 4012, such as by levering the front panel 4012 up from the external housing 4010. The front panel 4012 may further comprise a cavity to allow access to light by the external housing light port 40101p.

5.4.2 RPT Device User Interface

The RPT device 4000 may comprise a user interface, for example comprising a visual interface shown through the display 4294. The user (e.g. the patient 1000) may interact with the RPT device 4000 using the input devices 4220 as described above.

5.4.2.1 Visual Interface

The visual interface may comprise a menu of user-selectable items. The user may interact with the menu by selecting one of a plurality of items presented on the menu using the input devices 4220 such as a dial or by touching areas of a touchscreen. The user may confirm a selection by depressing a button or touching a touchscreen for example.

5.4.2.1.1 First Menu Screens

According to one aspect, a first menu screen 4295m1 presented to the user may be configured as shown in FIG. 15a-15b. The first menu screen 4295m1 may present a limited number of sub-menu options to the user, for example two sub-menu options. According to another aspect, the sub-menu options may be arranged by a particular type of an interaction the user may have with the RPT device 4000. For example, the first menu screen 4295m1 may comprise a selectable menu 4295se and a report menu 4295re. The selectable menu 4295se may substantially comprise menu items with which a user may interact, and the report menu 4295re may substantially comprise menu items which may report information to a user. By substantially dividing the user interface into categories based on interactivity with the user, the user may be able to more effectively interact with the user interface and navigate through the sub-menu items.

In some instances, the first menu screen 4295m1 may be the very top level of a menu hierarchy or structure. Accordingly, the first menu screen 4295m1 may advantageously present the user with sub-menu options which are arranged by the particular type of interaction possible.

FIGS. 15c-15d show another example of a first clinical menu screen 4295m2, showing a 'clinical' menu comprising a selectable menu 4295se and a report menu 4295re. The clinical menu may be activated by a predetermined operation, such as pressing particular user interface buttons in a particular sequence. Similarly to the first menu screen 4295m1, first clinical menu screen 4295m2 may be the very top level of a menu hierarchy or structure for an alternative set of menu items (and sub-menu options). Although the first clinical menu screen 4295m2 presents different visual icons (and titles) to the first menu screen 4295m1, arrangement of the two sub-menu options may be advantageously arranged by the particular type of interaction possible therewith, so that the layout of the user interface would remain consistent for improved usability.

Thus, in one form, the top level menu, regardless of whether it is a first menu screen 4295m1 or a first clinical menu screen 4295m2 may comprise a predetermined, consistent, number of sub-menu items, such as two, as shown in FIG. 15a-15d. For instance, by arranging the very top level menu hierarchy to comprise a predetermined sub-menu items that are arranged by the type of interaction possible, the user may be able to advantageously maintain familiarity with the interface. This may be particularly advantageous as a significant percentage of users of medical devices such as RPT devices may not be proficient with high-technology gadgets or devices.

The selectable menu 4295se may comprise items which may be individually selected by the user, for example to make changes to a behaviour or a functionality of the RPT device 4000 (or the humidifier 5000), or to enter a sub-menu item. For example, the selectable menu 4295se may be displayed as shown in FIG. 15a-15d, and once entered may comprise one or more configurable items such as therapy mode, ramp time, humidity level, language, date, units, mask type or pressure levels. In one example, the user may navigate to the sub-menu of the selectable menu 4295se, and arrive at a selectable sub-menu 4295o1 or 4295o2, depending on whether the navigation was from the first menu screen 4295m1 or the first clinical menu screen 4295m2 respectively as shown in FIG. 15e or FIG. 15f. In both cases, however, the user would have arrived at a series of selectable items.

The report menu 4295re may comprise items which relate to reporting of data. For example, the report menu 4295re (e.g. as shown in FIG. 15a or 15c) once entered may comprise one or more report items such as total usage hours, events per hour, report of mask seal or report of humidifier performance. In another example, while the device is operating, the report menu 4295re (e.g. as shown in FIG. 15b or 15d) once entered may comprise one or more statuses such as current pressure levels, leak level, remaining ramp time or humidifier status. In one example, the user may navigate to the sub-menu of the report menu 4295re, and arrive at a report sub-menu 4295r1 or 4295r2, depending on whether the navigation was from the first menu screen 4295m1 or the first clinical menu screen 4295m2 respectively as shown in FIG. 15g and FIG. 15h. In both cases, however, the user would have arrived at a series of selectable items as shown.

According to another aspect, the visual interface 4295 may be configured so that the items displayed on the first menu screen 4295m1 (or the first clinical menu screen 4295c1) may vary according to the context of the operation of the device, while the layout remains consistent, as seen in FIG. 15a-15d. The first menu screen 4295m1 shown in FIG. 15a may change to that shown in FIG. 15b (and from FIG. 15c to FIG. 15d) if the RPT device 4000 is in operation, changing the image displayed for the report menu 4295re.

Similarly, the selectable menu 4295se appear at substantially same location in FIGS. 15a and 15c, although the image displayed may vary depending on whether the first menu screen 4295m1 or the first clinical menu screen 4295c1 is displayed on the visual interface 4295.

A composition of the first menu screen 4295m1 (or the first clinical menu screen 4295c1) which includes one sub-menu item comprising configurables, and another sub-menu item comprising reports may be beneficial in one or more respects. In one respect, the user may be able to navigate through the menu items with greater ease, as the structure of the menu would remain consistent despite any variations to the menu according to its operating conditions (e.g. operation of the RPT device 4000, or differences between a clinical menu and a patient menu). Still further, maintaining a consistency of layout while varying images displayed thereon may effectively indicate a change in one or more operating conditions of the RPT device to the user without potentially causing confusion by a change in a menu structure.

5.4.2.1.2 Subsequent Menu Screens

Examples of sub-menus for the selectable menu 4295se are shown in FIGS. 15e and 15f. It can be seen here that the contents of the selectable sub-menu 4295o1 and 4295o2 are selectable items, which may be actionable by the user, save for headings. For example, the user may scroll down to contents such as 'Mask' as shown in FIG. 15e to change a type of mask that the RPT device 4000 is coupled to, or to 'Humidity Level' as shown in FIG. 1f to change a level of desired humidity output of the humidifier 5000.

Examples of sub-menus for the report menu 4295re are shown in FIGS. 15g and 15h. The report sub-menus 4295r1 and 4295r2 may be configured so as to display information, in contrast to the contents of the selectable sub-menu 4295o1 or 4295o2 described above.

In one form, the sub-menus such as selectable sub-menu 4295o1 or 4295o2 or the report sub-menu 4295r1 or 4295r2 may comprise a greater number of items than can be displayed on the screen of the RPT device 4000 (or the humidifier 5000). The sub-menus may be thus configured so that a movable portion of the sub-menu (e.g. window portion 4295w in FIG. 15e-15g) is displayed on the screen by scrolling. Such an arrangement may be particularly useful in an arrangement wherein the user interface may comprise a relatively small screen, to reduce the amount of backwards and forwards navigation between different levels of sub-menus.

In one form, the report sub-menus 4295r3 or 4295r4 may display one or more aspects of an operation of the RPT device 4000 and the humidifier 5000 as for example shown in FIG. 15i-15j. The one or more aspects may include, for example, a status of the humidifier 5000, a fidelity of connection between the data communication interface 4280 and the other device/network that it is connected to, a quantity of leak or one or more settings of the RPT device 4000 and the humidifier 5000.

In one form, the report sub-menus 4295a1-4295a8 may display one or more sequential images such as an animated arcuate portion shown in FIG. 15k-15p. In one form, the report sub-menu may change to indicate a change of a status to the user. For example, the animated arcuate portion shown in FIGS. 15k-15p may be displayed to the user to indicate that the RPT device 4000 is in a 'ramp' period. Subsequently, at an end of the ramp period, the report sub-menu may change to one shown in FIG. 15q to indicate an end of the ramp period to the user.

5.5 Humidifier 5000

5.5.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways. In one form, the humidifier 5000 may be a discrete unit that is connectable to an RPT device 4000. In another form, the humidifier 5000 may be integrated with the RPT device 4000, for example as shown in FIG. 5c and as described in further detail below.

A humidifier 5000 may comprise a water reservoir 5110, heating element 5240 and one or more transducers. The humidifier 5000 may be configured to receive a flow of air from a RPT device 4000 and deliver a flow of humidified air to a patient interface 3000 for example via an air circuit 4170.

5.5.2 Humidifier Components

5.5.2.1 Water Reservoir 5110

According to one arrangement, the humidifier 5000 may comprise a water reservoir 5110 configured to hold, or retain, a volume of liquid (e.g. water) to be used for humidification of the flow of air. FIGS. 16c-16d show one form of a water reservoir 5110, which comprises a reservoir base 5112, a reservoir lid 5114, and an intermediate portion 5202 including a compliant portion 5116. The water reservoir 5110 is configured to hold a predetermined maximum volume of water in order to provide adequate humidification for at least the duration of respiratory therapy, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

The reservoir 5110 may also be configured to discourage egress of liquid therefrom, such as when the reservoir 5110 is displaced or rotated from its normal, working orientation, such as through any apertures or in between its sub-components. As the flow of air to be humidified by the humidifier 5000 is typically pressurised, the reservoir 5110 may also be configured to prevent losses in pneumatic pressure through leak or flow impedance.

The water reservoir 5110 may comprise an inlet 5118 for receiving the flow of air into the reservoir 5110, and an outlet 5122 for delivering a flow of air from the reservoir 5110. The reservoir 5110 may include to an reservoir inlet tube 5124 and an reservoir outlet tube 5126 (e.g., see FIG. 16e). In one configuration, the inlet 5118 and reservoir inlet tube 5124 are integrally formed as one inlet component and the outlet 5122 and the reservoir outlet tube 5126 are integrally formed as one outlet component.

FIG. 20-23 show one form of a water reservoir 5110, which comprises a reservoir base 5112, a reservoir lid 5114, and a variable portion 5116. The reservoir 5110 is configured to hold a given, maximum volume of liquid (e.g. water), typically several hundred millilitres, e.g. 300 millilitres (ml), 325 ml, 350 ml or 400 ml, although it is to be understood that other volumes of liquid may be utilised such as 100 ml, 200 ml, 250 ml, 500 ml or more or less. In one form, the reservoir 5110, may comprise a cavity formed by a plurality of walls to hold the given, maximum volume of liquid as shown in FIG. 22-23.

5.5.2.2 Water Reservoir Dock 5130

Figure 25:
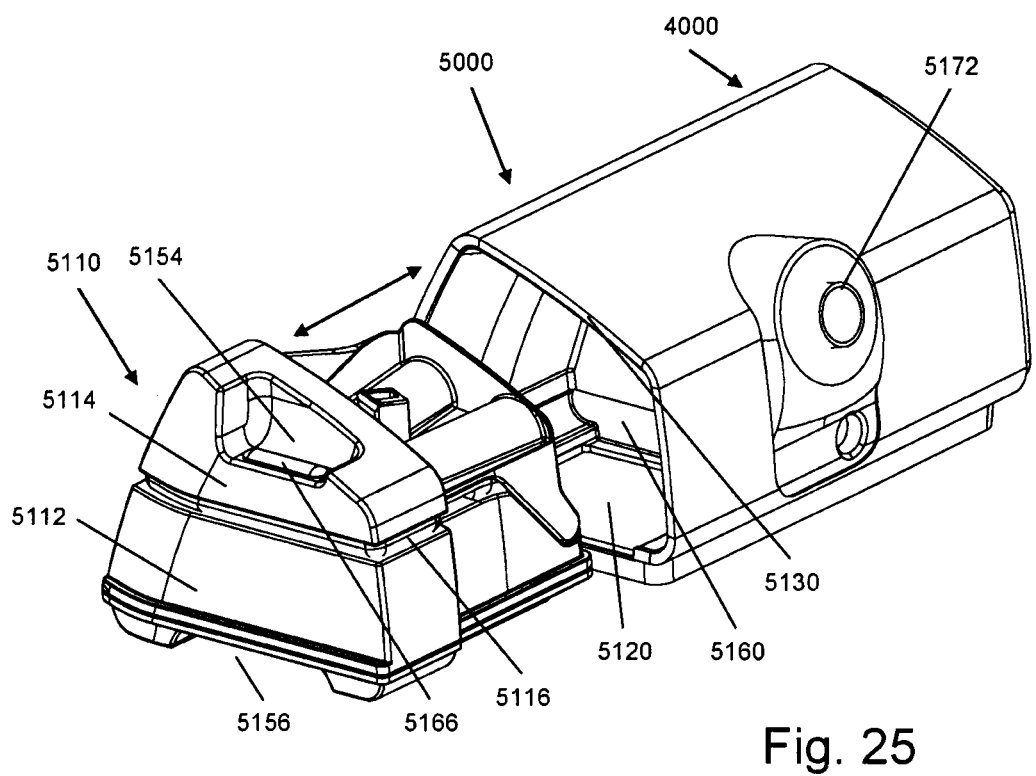

A humidifier 5000 may comprise a water reservoir dock 5130 to receive a water reservoir 5110. As shown in FIG. 25, the water reservoir dock 5130 may form a cavity 5160 to receive the water reservoir 5110. In one form, the water reservoir dock 5130 may be integrated with the humidifier 5000 as shown in FIG. 24-27. The water reservoir dock 5130 may also connect the water reservoir 5110 to the pneumatic path. In this arrangement, the reservoir dock 5130 comprises a dock gas outlet 5168 to output a flow of breathable gases to a water reservoir 5110, a dock gas inlet 5170 to receive the flow of breathable gases that has been humidified in the water reservoir 5110, and a humidifier outlet 5172 to transfer the flow of humidified breathable gases to the air circuit 4170. The cavity 5160 may include a top portion configured to cover at least a portion of the lid of the reservoir 5110 and a bottom portion including the heater plate 5120.

It should be understood that the reservoir dock 5130 may be provided separately to a humidifier 5000 in an alternate arrangement. In such an arrangement, additional interfaces may be used to connect the reservoir dock 5130 to the humidifier 5000.

In another arrangement, a water reservoir dock 5130 may comprise an opening in a substantially horizontal plane, so that the water reservoir 5110 may be inserted from above or below the water reservoir dock 5130.

5.5.2.3 Water Reservoir Lid 5114

In one form, the water reservoir lid 5114 is pivotably connected to the base 5112 (e.g. by hinges 5158 as shown in FIG. 16e) to allow the reservoir 5110 to be converted between an open configuration and a closed configuration (see FIGS. 16k and 16k). When the water reservoir 5110 is in its closed configuration, the compliant portion 5116 is put into sealing engagement between the base 5112 and the lid 5114 to seal the base 5112 and the lid 5114. The hinges 5158 may couple to complementary hinge recess portions 5159 (shown in FIG. 16f) located in the reservoir base 5112. In one form, the lid 5114 may be constructed from a biocompatible material, such as a plastic or thermoplastic polymer, for example, acrylonitrile butadiene styrene (ABS) or polycarbonate material. The pivotable connection may further allow the water reservoir lid 5114 and the base 5112 to be compressed towards each other in comparison to their normal operating configuration, for example for insertion of the reservoir 5110 into the dock 4130 as will be described in further detail below.

Another aspect of the present technology relates to the operation of the pivoting action in the lid 5114 in relation to the base 5112. As the lid 5114 rotates about the hinges 5158, a range of rotation may be defined as shown in FIG. 62a and FIG. 62b. In one form, two ends of the range of rotation may be defined by closure of the lid 5114 with respect to the base 5112, where one of the two ends may be a fully open position defined by a rotation guide 5220, which may interfere with a rotation stop 5222 at the fully open position.

According to another aspect, the lid 5114 may configured so that when a user attempts to open the lid 5114 further than the rotation stop 5222 and the rotation guide 5220, the lid 5114 would disconnect from the base 5112. As shown in FIG. 62b and FIG. 63b, at the fully open position the rotation guide 5220 may be in contact with the rotation stop 5222. In this form, attempts to further open the lid 5114 with respect to the base 5112 would cause the rotation stop 5222 to act as a pivot of a cantilever, and cause the lid 5114 to separate from the base 5112 at the hinges 5158, whereby damage to the reservoir 5110, for example from application of excessive force thereto, may be avoided. In one form, the hinges 5158 may be configured to allow disconnection more easily at one orientation of the lid 5114 with respect to the base 5112 (e.g. then the reservoir 5110 is in the fully open position) than at another orientation. This may be achieved by, for example, introduction of a taper to the hinges 5158 on the lid 5114 as shown in FIGS. 58a and 58b.

The water reservoir lid 5114 may comprise the inlet 5118, the reservoir inlet tube 5124, the outlet 5122 and the reservoir outlet tube 5126 in one form as shown in FIG. 16e. The reservoir 5110 may further comprise flow elements, such as a baffle (e.g. inlet cap 5125 shown in FIG. 16e and FIG. 16k and/or a plate 5123 as shown in FIG. 16e and FIG. 16k), configured to increase the length of the tortuous flow path and/or to prevent ingress of water into the inlet tube 5124 and/or the outlet tube 5126. In one example, the water reservoir lid 5114 may further comprise one or more baffles configured to direct the air through a tortuous path in the water reservoir 5110. In one form, the baffle may be coupled to an end of the reservoir inlet tube 5124 as an inlet cap 5125 (as shown in FIG. 16e and FIG. 16k), and in another form, the baffle may be arranged as a plate 5123 (as shown in FIGS. 16e and 16k).

5.5.2.4 Compliant/Variable Portion 5116

In one form, when the water reservoir 5110 is in use, the compliant portion 5116 may act as a seal between the reservoir base 5112 and the reservoir lid 5114. The compliant portion 5116 may be provided as part of the reservoir lid 5114 or as part of the reservoir base 5112, or independently of both, for example as part of an intermediate portion 5202 (see FIGS. 16l-16m). The compliant portion 5116 may be engaged with the reservoir lid 5114 or the reservoir base 5112 by any number of means including, and not limited to, ultrasonic welding, friction fitting, gluing or by using an intermediate component.

The compliant portion 5116 preferably includes a sufficiently resilient construction so as to be able to resist forces and/or pressures generated in the reservoir 5110, such as those generated by the user, the reservoir dock 5130 and/or the flow of air flowing through the reservoir 5110. The compliant portion 5116 is also preferably compliant to be able couple to the lid 5114 and/or the base 5112, and conform to its shape to form a seal. In one form, a rigid portion of the intermediate portion may be constructed from a nylon material of approximately 2 mm thickness (such as 1 mm, 1.5 mm, 2.5 mm or 3 mm), and a silicone material may be used to overmould onto the rigid portion to form the compliant portion 5116.

In some arrangements, the compliant portion 5116 may couple to the lid 5114 and/or the base 5112, and the base 5112 and/or the lid 5114 may be formed as two separate parts that are able to be assembled with the compliant portion 5116 coupled therebetween.

In an alternative arrangement, the compliant portion 5116 may be located within a wall of the reservoir base 5112 and/or a wall of the reservoir lid 5114, for example integrally by overmoulding or as a separate component connected as a sub-assembly. In such an arrangement the compliant portion would not be located between the reservoir base 5112 and the reservoir lid 5114 but within the reservoir base 5112 and/or the reservoir lid 5114. There may be more than one compliant portion 5116 or the compliant portion may be formed in multiple parts to provide more compliance in movement of the reservoir 5110.

In one form, when the water reservoir 5110 is in use, the variable portion 5116 may act as a seal between the reservoir base 5112 and the reservoir lid 5114. The variable portion 5116 may also perform other functions, such as to improve thermal contact between the reservoir 5110 and the heater plate 5120, as will be described in further detail below.

The variable portion 5116 may be provided as part of the reservoir lid 5114 or as part of the reservoir base 5112, or independently of both. The variable portion 5116 may be engaged with the reservoir lid 5114 or the reservoir base 5112 by any number of means including, and not limited to, ultrasonic welding, friction fitting, gluing or by using an intermediate component. The variable portion 5116 may comprise a carrier 5117 (as shown in FIG. 23).

The variable portion 5116 is preferably constructed sufficiently resiliently so as to be able to resist compressive forces and/or pressures generated in the reservoir 5110, such as by the user, the reservoir dock 5130 and/or the flow of breathable gas flowing through the reservoir 5110. It is also preferably compliant in the planar direction to be able couple to the lid 5114 and/or the base 5112, and conform to its shape. In one form, the carrier 5117 may be constructed from a nylon material of approximately 2 mm thickness (such as 1 mm, 1.5 mm, 2.5 mm or 3 mm), and a silicone material may be used to overmould onto the carrier 5117 to form the variable portion.

In some arrangements, the variable portion 5116 may couple to the lid 5114 and/or the base 5112, and the base 5112 and/or the lid 5114 may be formed as two separate parts that are able to be assembled with the variable portion 5116 coupled therebetween.

In an alternative arrangement the variable portion 5116 may be located within a wall of the reservoir base 5112 and/or a wall of the reservoir lid 5114, for example integrally by overmoulding or as a separate component connected as a sub-assembly. In such an arrangement the variable portion would not be located between the reservoir base 5112 and the reservoir lid 5114 but within the reservoir base 5112 and/or the reservoir lid 5114. There may be more than one variable portion 5116 to provide more compliance in movement of the reservoir 5110.

5.5.2.5 Water Reservoir Base 5112

According to one arrangement, the reservoir base 5112 comprises a conductive portion 5120 (such as the base conductor plate 5152, e.g., see FIG. 16f) configured to thermally couple with a heating element 5240 of the humidifier 5000. The conductive portion 5152 improves efficiency of heat transfer from the heating element 5240 to the volume of liquid in the reservoir 5110. All or a part of the base conductor plate 5152 may be made of a heat conducting material such as aluminium (e.g. approximately 2 mm thick, such as 1 mm, 1.5 mm, 2.5 mm or 3 mm) or another heat conducting material such as metal. In some cases, suitable heat conductivity may be achieved with less conductive materials of suitable thickness.

The reservoir base 5112 may also be configured as a receptacle to retain the given, maximum volume of liquid that the reservoir 5110 is configured to hold. In one form, the base 5112 may comprise further features such as an overfill prevention feature.

In one form, the reservoir base 5112 may further comprise an inner lip 5224 and/or an outer lip 5226, for example as shown in FIG. 64 and FIG. 65. According to one aspect, the inner lip 5224 and/or outer lip 5226 may prevent egress of liquid from the reservoir 5110 through the interface between an intermediate portion 5202 (e.g. the compliant portion 5116) and the base 5112, for example when the intermediate portion 5202 is compressed, or when the intermediate portion 5202 is under vibration.

It should be appreciated that the reservoir base 5112 may be constructed in any number of parts. The reservoir base 5112 may be constructed as a single part made of, for example, aluminium or another heat conducting material such as metal. In another arrangement, the reservoir base 5112 may be constructed in two parts, for example comprising a lower component and an upper component.

According to one arrangement, the reservoir base 5112 comprises a conducting portion (such as the base conductor plate 5152) configured to thermally couple with a heater plate 5120 of the humidifier 5000. The conducting portion improves efficiency of heat transfer from the heater plate 5120 to the volume of liquid in the reservoir 5110. All or a part of the base conductor plate 5152 may be made of a heat conducting material such as aluminium (e.g. approximately 2 mm thick, such as 1 mm, 1.5 mm, 2.5 mm or 3 mm) or another heat conducting metal. In some cases, suitable heat conductivity may be achieved with less conductive materials of suitable thickness.

The reservoir base 5112 may also be configured as a receptacle to retain the given, maximum volume of liquid that the reservoir 5110 is configured to hold. In one form, the base 5112 may comprise further features such as an overfill prevention feature as will be described in further detail below. The reservoir base 5112 may also comprise a base upper body 5146 and a base bottom plate 5148, which together with the base conductor plate 5152 may form a receptacle.

The base upper body 5146 and/or the base bottom plate 5148 may be constructed from a bio-compatible material suitable for retaining the body of liquid, such as a plastic or thermoplastic polymer, for example, ABS or polycarbonate material. The base conductor plate 5152 may comprise of a sealing element 5150, which may be integrated to, and/or sealingly connected to both the base upper body 5146 and the base bottom plate 5148 to prevent egress of water from the water reservoir 5110, particularly from the base 5112. For example, the sealing element 5150 may be overmoulded onto the base conductor plate 5152, and the resulting component may be secured between the base upper body 5146 and the base bottom plate 5148.

In one form as shown in FIG. 23, the base 5112 may comprise a base upper body 5146, a base bottom plate 5148, and a base conductor plate 5152. However, it should be appreciated that the reservoir base 5112 may be constructed in any number of parts. The reservoir base 5112 may be constructed as a single part made of, for example, aluminium or another heat conducting material such as metal. In another arrangement, the reservoir base 5112 may be constructed in two parts, for example comprising a lower component and an upper component. In such an arrangement, the lower component may be constructed from a heat conducted material and perform the roles of the base conductor plate 5152, sealing element 5150 and base bottom plate 5148, and the upper component may be equivalent to the base upper body 5146, and be constructed a polycarbonate material.

In one form, the reservoir base 5114 may further comprise an inner lip 5224 and/or an outer lip 5226, for example as shown in FIG. 65-FIG. 65. According to one aspect, the inner lip 5224 and/or outer lip 5226 may prevent egress of liquid from the reservoir 5110 through the interface between an intermediate portion 5202 (e.g. the seal 5204) and the base 5114, for example when the intermediate portion 5202 is compressed, or when the intermediate portion 5202 is under vibration.

5.5.2.6 Reservoir Handles 5154 5156

FIG. 24-27 show an upper handle 5154 that is located on the reservoir lid 5114, and a lower handle 5156 that is located on the reservoir base 5112. These handles are intended to assist the patient (or user) 1000 to grip and hold the water reservoir 5110. In the shown arrangement, the handles 5154, 5156 are located away from the hinges 5158 such that by holding the reservoir 5110 by the handles 5154 5156 the patient 1000 imparts forces onto the reservoir 5110 compressing the variable portion 5116, which pushes the lid 5114 and the base 5112 towards each other. A compression force may also help maintain the variable portion 5116 in sealing engagement between the reservoir base 5112 and the reservoir lid 5114, such as during transport to/from re-filling the reservoir 5110 with liquid. It is to be understood that the handles 5154 and 5156 may be placed on other components or areas of the water reservoir 5110.

A friction grip 5166 may be provided on a surface of either or both of the handles 5154 5156 as shown in FIG. 25. The friction grip 5166 may be constructed to assist the patient 1000 to hold the reservoir 5110, such as by being made from a higher friction material, made in a higher friction texture and/or made into an easier-to hold shape than the surrounding areas of the reservoir 5110. For example, the friction grip 5166 may be constructed from an elastomeric material such as silicone whereas the water reservoir 5110 may primarily be constructed from a polycarbonate material.

5.5.2.7 Air Flow Path

It is one of the aims of the present technology to force the flow of breathable gas to travel through the reservoir 5110 in a tortuous path between the inlet 5118 and the outlet 5122. This prevents any 'short-circuiting' of the flow of breathable gas, which may lead to inadequate humidity in the flow of breathable gas which is delivered to the patient 1000.

FIG. 28a-30c show an exemplary path of the flow of breathable gas through the reservoir 5110 as it enters through the inlet 5118 and exits through the outlet 5122. The figures are arranged chronologically in three distinct orthogonal views per figure to visually demonstrate the exemplary flow path. In this arrangement the flow of breathable gas received through the inlet 5118 passes through the inlet tube 5124 (FIG. 28a-28c), into the internal volume of the water reservoir 5110 (FIG. 29a-29c). The flow of breathable gas then passes through the outlet tube 5126 to exit the water reservoir 5110 at the outlet 5122 (FIG. 30a-30c) as humidified breathable gas. FIG. 28a-30c show the reservoir 5110 with the lid 5114 and the base 5112 in exploded view orientation for clarity, and any flow of gas that occurs in the internal volume of the reservoir 5110 is shown in dotted lines. The dotted arrows shown indicate the general direction of the exemplary flow of breathable air, although it is noted that the nature of gas or air flow means that any gas flow path includes swirling (e.g. turbulence) of the gas rather than a straight and direct air flow path.

In some forms of the present technology, the reservoir 5110 may comprise flow elements, or a baffle 5192, configured to increase the length of the tortuous flow path and/or to prevent ingress of water into the inlet tube 5124 and/or the outlet tube 5126. For instance, the reservoir 5110 may comprise a deflector portion 5198 as shown in FIG. 52a-55, or a deflector portion 5198 or a flow director 5195 FIG. 58a-58b. In some arrangements, the baffle 5192 may further comprise a locating portion 5196 as will be described in further detail below.

In the arrangement shown in FIG. 52a-55, the deflector portion 5198 is configured to prevent the flow of breathable gas from entering the outlet tube 5126 immediately after exiting the inlet tube 5124 through the inlet tube outlet 5125 (i.e. short-circuiting). When assembled together as seen in FIG. 52a, the deflector portion 5198 may be located close to the inlet tube inner end 5125, such as by abutting it. In this arrangement, the deflector portion 5198 forms a cover between the inlet tube outlet 5125 and a base of the outlet tube inner end 5127. This cover may be further advantageous in that it forces the flow of breathable gas to travel in a channel created by the cover and the volume of water for improved humidity pickup.

In the arrangement shown in FIG. 58a-58b, the reservoir 5110 includes a flow director 5195 as well as a deflector portion 5198. The deflector portion 5198 is configured to prevent short-circuiting of the flow of breathable gas, and the flow director 5195 is further configured to direct the flow of breathable gas that exits the inlet tube 5124 in a direction approximately parallel with the volume of liquid in the reservoir 5110. This may ameliorate occurrence of 'spitting', which can occur when the flow of breathable gas exits the inlet tube 5124 in a direction normal to the surface of the volume of liquid.

Figure 33:
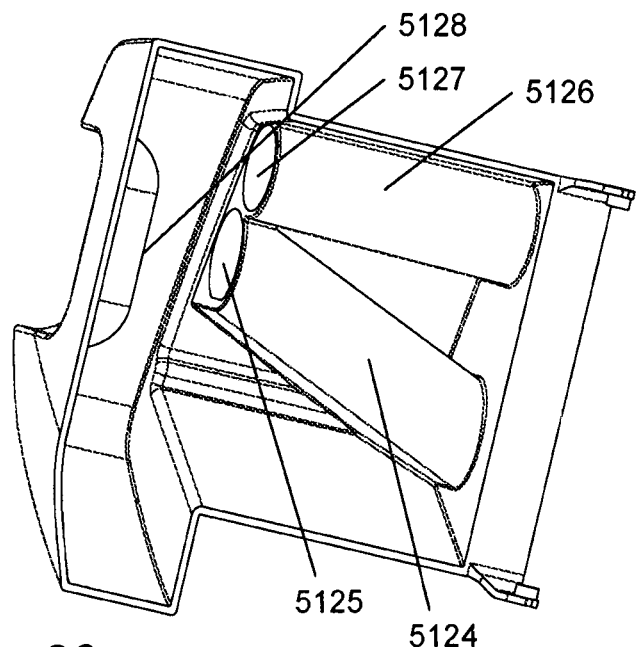
Figure 34:
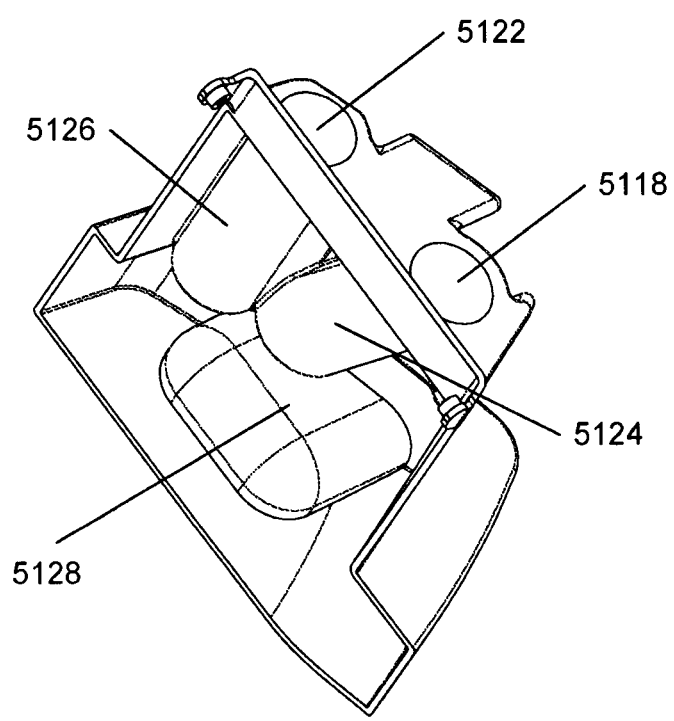
Figure 35:
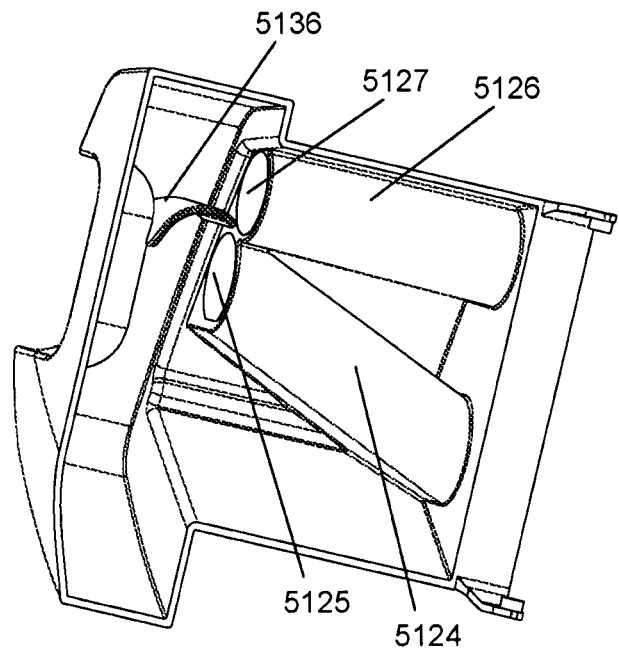
Figure 36:
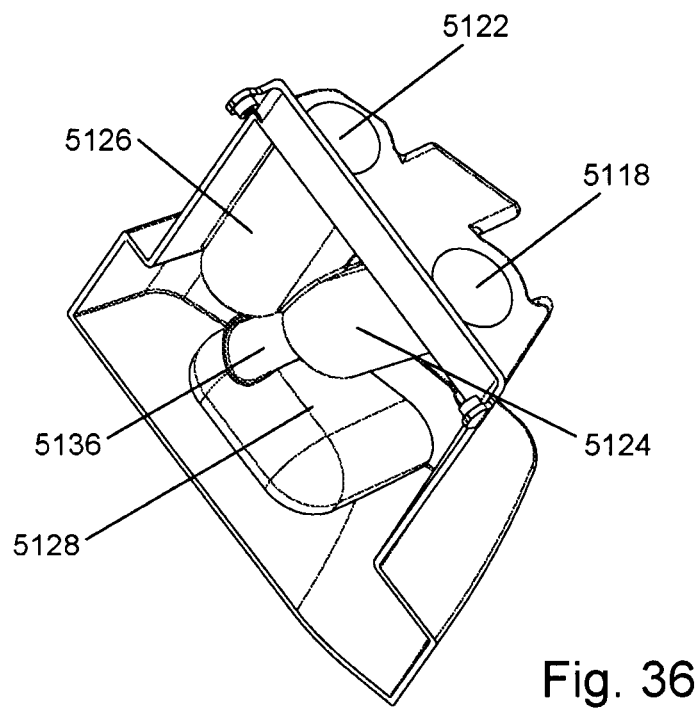
Figure 37:
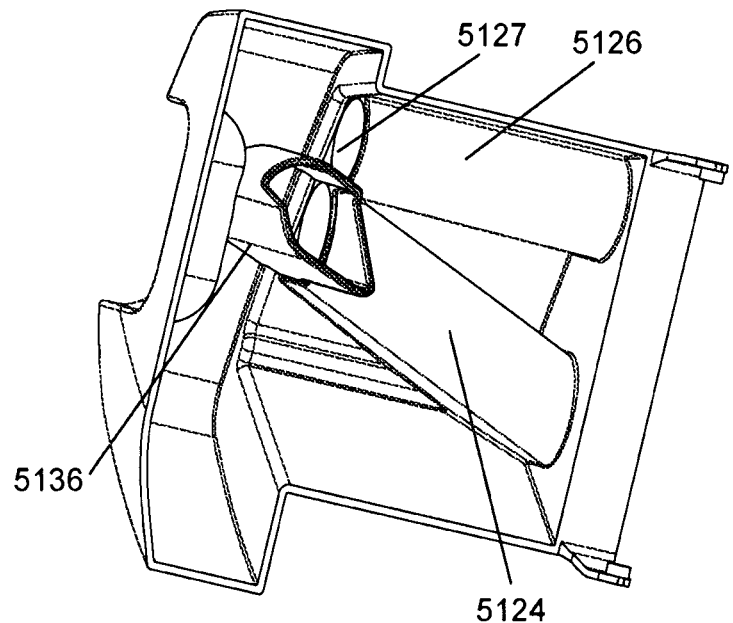
Figure 38:
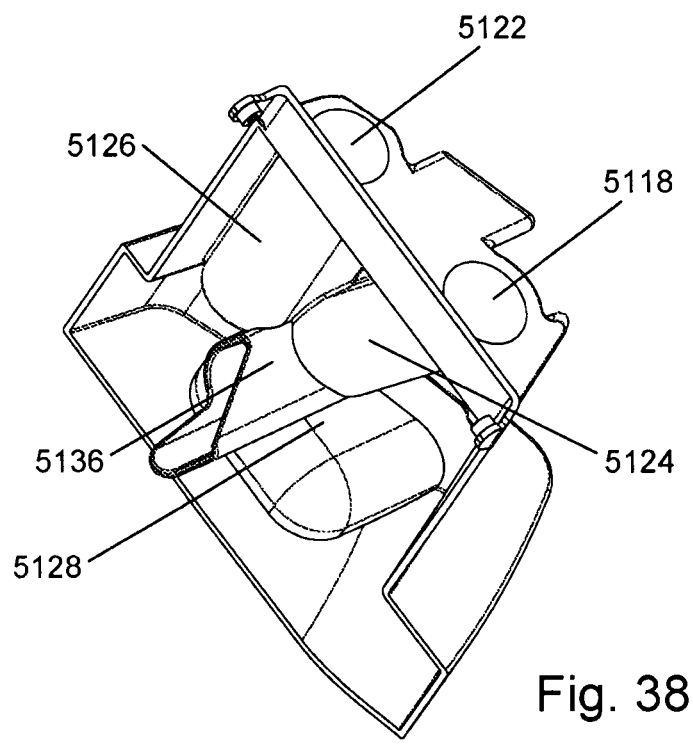

As shown in FIG. 33-34, the reservoir 5110 may include an end wall 5128 that is near and opposed to an interior end 5125 of the inlet tube 5124. The inner end wall 5128 of the reservoir 5110 directs air exiting the inlet tube 5124 to flow across the water surface before it reaches an interior end 5127 of the outlet tube 5126 and flows out of the outlet 5122 through the outlet tube 5126. FIG. 35-38 show examples of other arrangements of flow elements, wherein the reservoir 5110 may include a turning vane 5136 which is placed near the interior end 5125 of the inlet tube 5124. The turning vane 5136 may be formed as an extension of the inlet tube 5124 as shown in FIG. 37-38, or the turning vane 5136 may be a separate component located adjacent to or coupled with the inlet tube 5124. The turning vane may also be profiled as shown in FIG. 37-38.

The path of the flow of breathable air demonstrated in FIG. 28a-30c is exemplary only, and is aimed to demonstrate one of many paths that the flow of breathable gas may traverse through, namely that it enters the water reservoir 5110 through the inlet 5118 and exits through the outlet 5122 after experiencing some degree of swirling within the volume of the water reservoir 5110. A person skilled in the art would understand that the particles or molecules that form the flow of breathable air may not follow a single path within the water reservoir 5110 due to a number of factors, including, for example, localised turbulence (eddies) or pressure gradients within the water reservoir 5110. As a result the cumulative path of the flow of breathable air may comprise any number of paths wherein it experiences various degrees of 'swirling' within the water reservoir 5110 prior to exiting via the outlet tube 5126 at the outlet 5122. It is also possible that some small portion of the flow of breathable air may escape the water reservoir 5110 as a leak.

5.5.2.8 Reservoir Inlet/Outlet

As described above, the reservoir inlet 5118 is configured to receive the flow of breathable gas into the reservoir 5110, and the reservoir outlet 5122 is configured to output the humidified flow of breathable gas. The inlet 5118 and/or the outlet 5122 are preferably further configured to prevent egress of liquid from the reservoir 5110 when the reservoir 5110 is displaced and/or rotated from its normal, working orientation. Still further, the inlet 5118 and/or the outlet are preferably configured to prevent short-circuiting of the flow of breathable gas as described above. In one form, the inlet 5118 may be configured to prevent 'spitting', or splashing, of liquid which may be caused by a jet of air impinging on the volume of liquid in the reservoir 5110.

In one arrangement as shown in FIG. 33, the reservoir inlet 5118 includes an inlet tube 5124 to provide a flow path for the inlet flow of breathable gas into the reservoir 5110, and the reservoir outlet 5122 includes an outlet tube 5126 to provide a flow path for the outlet flow of humidified breathable gas from the reservoir 5110.

In one configuration as shown in FIGS. 37-38, it may be advantageous to configure the turning vane 5136 so that the lowest portion of the turning vane 5136 extends below the lowest portion of the outlet tube 5126. This may further prevent ingress of water into the inlet tube 5124 from any 'spitting' of water.

The water reservoir 5110 is preferably configured to provide tilt spillback protection from the water flowing back through the outlet tube 5126 or the inlet tube 5124. Water egress through the inlet tube 5124 may be particularly undesirable as it may introduce water into the PAP device 4000 and damage electronic components (such as an electric motor, a flow sensor or a printed circuit board) from exposure to water.

In one arrangement of the present technology, the reservoir 5110 achieves spillback protection by arranging the inlet tube outlet 5125 so that when the reservoir 5110 is rotated by 90 degrees in any direction from its working, horizontal orientation the given maximum volume of water is able to be stored in the reservoir 5110 without reaching the inlet tube inner end 5125.

Figure 39:
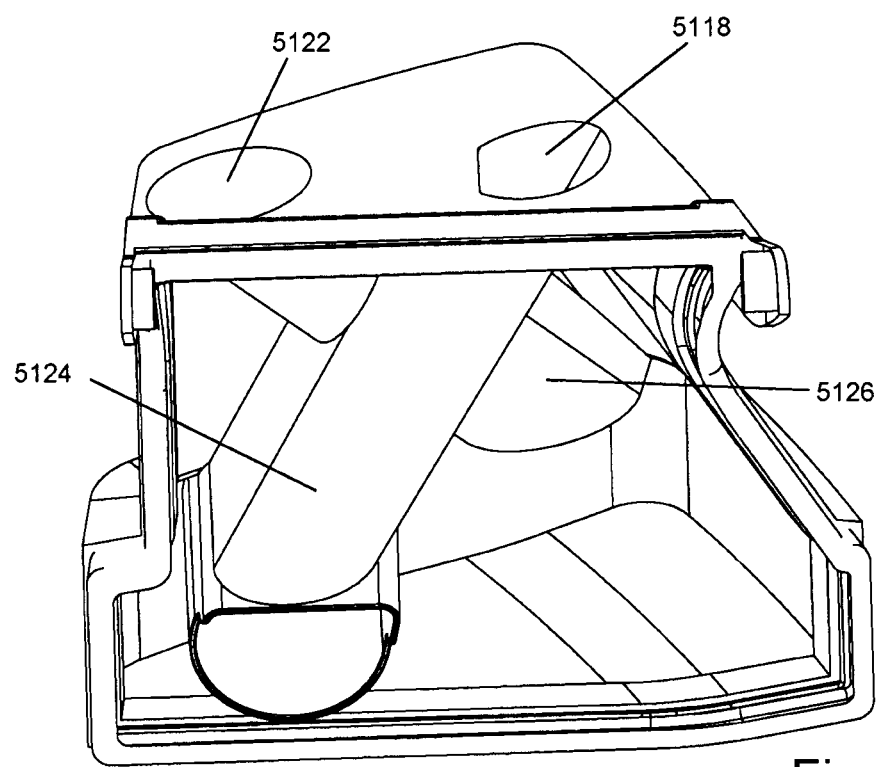
Figure 40:
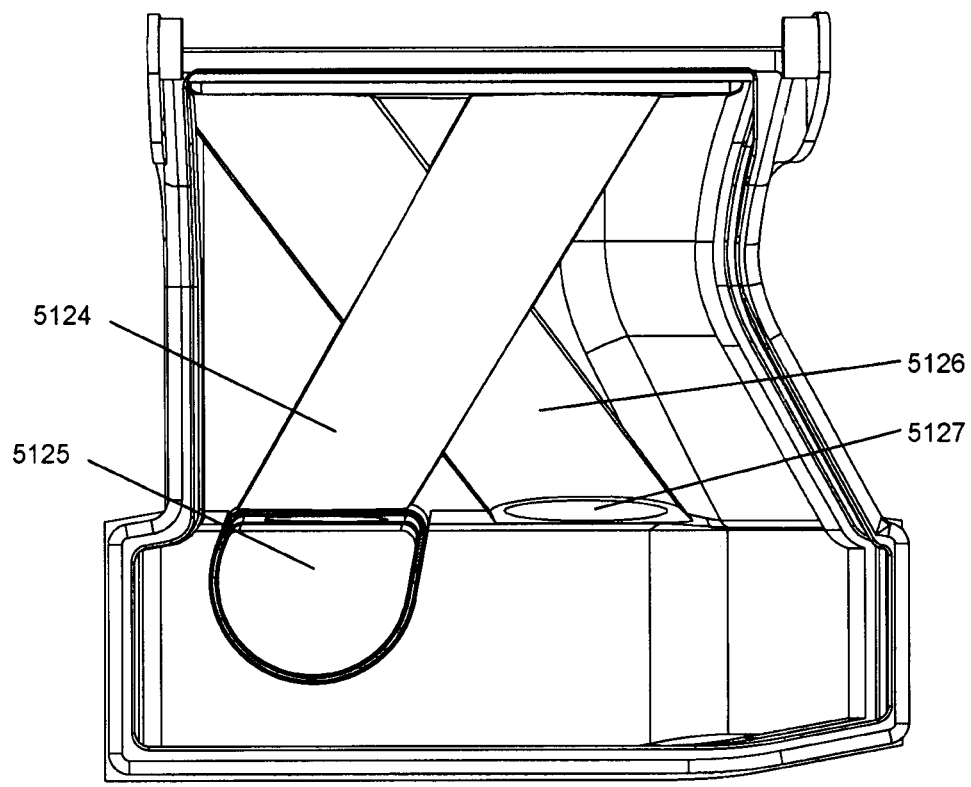

In another arrangement of the reservoir 5110, the axes of inlet tube 5124 and the outlet tube 5126 may intersect when viewed from above as shown in FIG. 39-40. The inlet tube 5124 and outlet tube 5126 may not be connected to each other as one of the tubes passes below the other tube, such as the inlet tube 5124 passes below the outlet tube 5126.

This configuration may improve the tilt spillback protection by arranging the inlet tube 5124 and the outlet tube 5126 such that when the reservoir 5110 is tilted away from its working orientation, water must reach the higher end of the inlet tube 5124 or the outlet tube 5126 to exit the reservoir 5110. For example, if the reservoir 5110 was tilted such that the water reaches the lower of the interior end 5125 of the inlet tube 5124, the water must still rise higher to reach the exterior end of the inlet tube 5124 to exit the reservoir 5110 as shown in FIG. 40.

Figure 46:
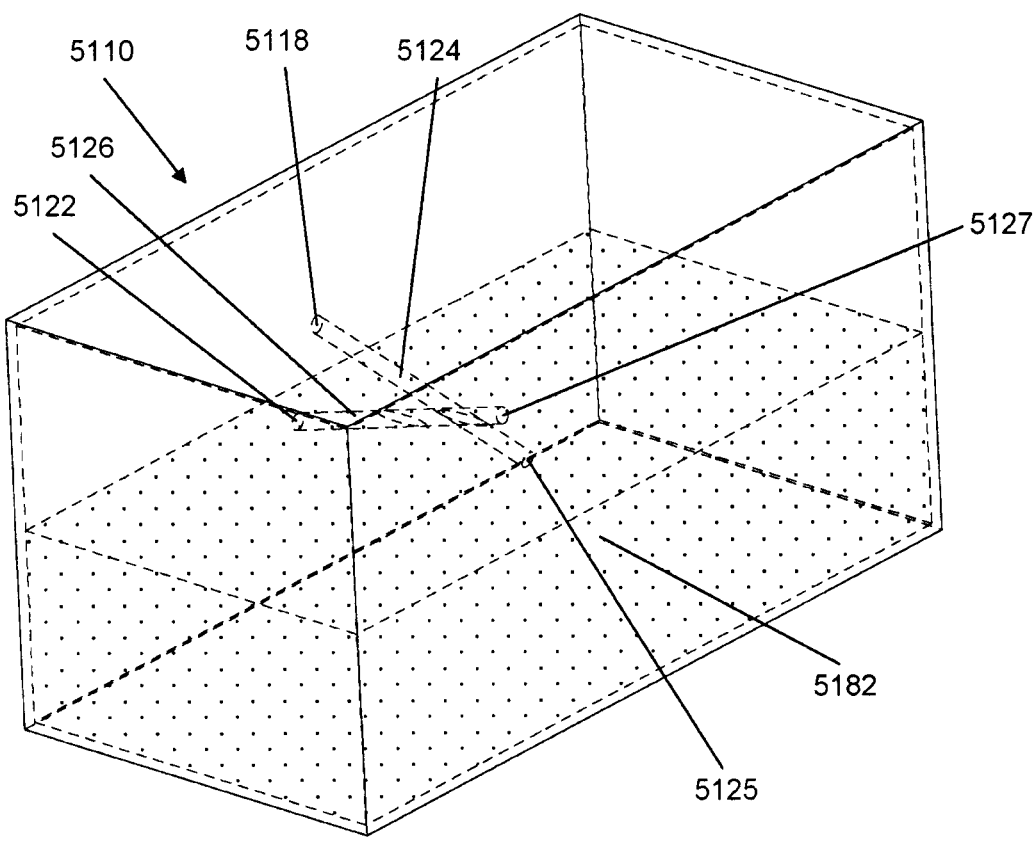
Figure 47:
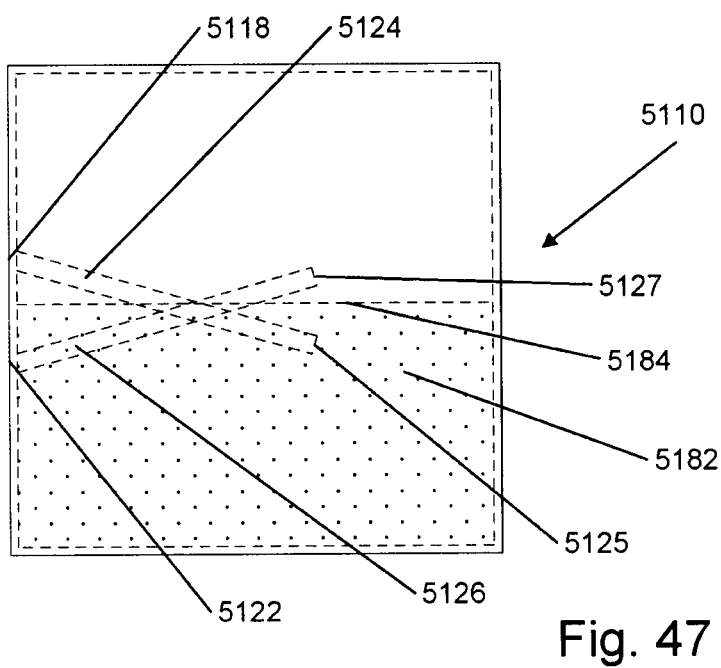
Figure 48:
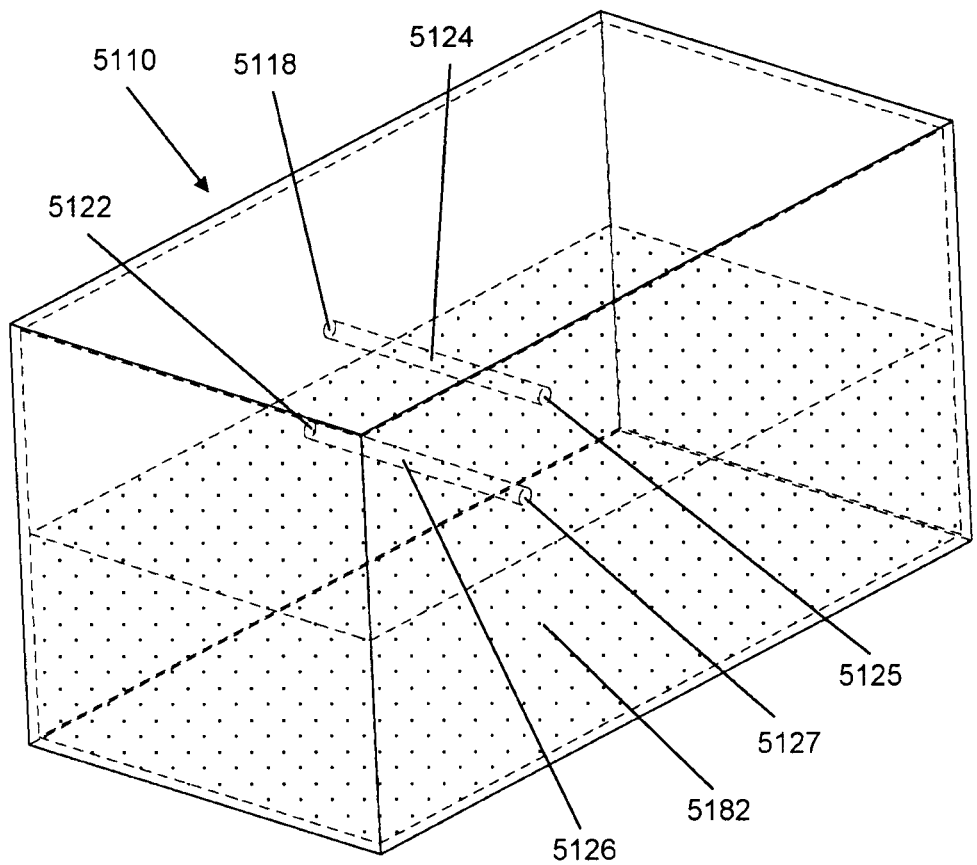
Figure 49:
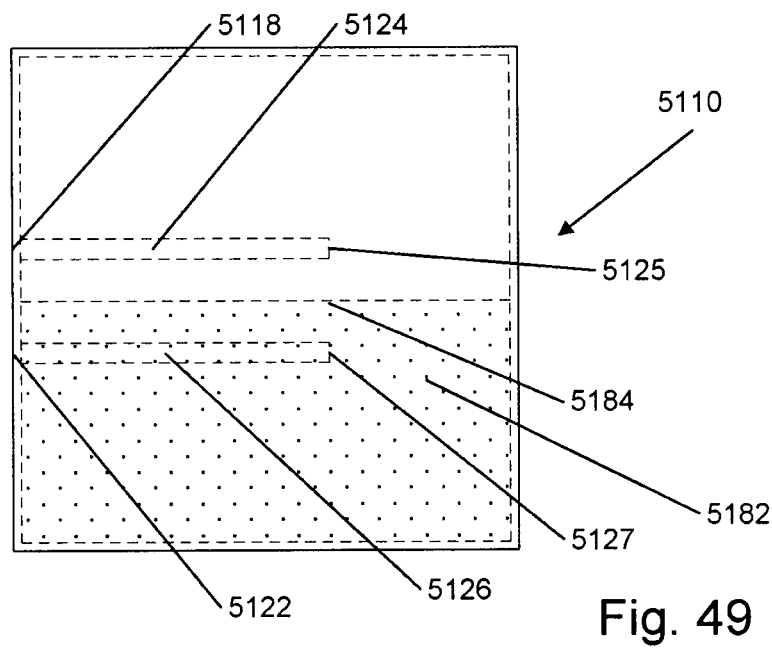

Simplified representations of the effects created by crossed inlet and outlet tubing are shown in FIG. 46-49, wherein the internal surfaces are shown by dotted lines. These figures show alternate arrangements of a water reservoir 5110, with an inlet 5118 and an outlet 5122 that respectively include an inlet tube 5124 and an outlet tube 5126. FIG. 46-47 show a configuration wherein the axes of the tubing intersect when viewed from the side (as shown in FIG. 47), and FIG. 48-49 show an alternate configuration wherein the axes of the tubing are substantially parallel when viewed from the side (as shown in FIG. 49). In FIG. 46-49, a volume of water 5182 is assumed to fill approximately half of the volume of the reservoir 5110, and the water level 5184 is indicated by the dotted lines extending horizontally.

When the water reservoir 5110 is oriented as shown in FIG. 46-47, the arrangement of the inlet tube 5124 and the outlet tube 5126 requires the water level 5184 to rise above the higher end of the inlet tube 5124 or the higher end of the outlet tube 5126 if any water 5182 is to exit the water reservoir 5110. On the other hand, in the arrangement shown in FIG. 47-48 the water level 5184 only needs to rise as high as a lower end of the inlet tube 5124 or the outlet tube 5126 in order to exit the water reservoir 5110.

As the water level 5184 will change as a function of the orientation of the water reservoir 5110, this effect of crossing the inlet tube 5124 and the outlet tube 5126 may be re-created at any orientation as required by re-orienting the inlet tube 5124 and the outlet tube 5126 to suit the shape of the water reservoir 5110. In some forms, the inlet tube 5124 and the outlet tube 5126 may be crossed when viewed from multiple angles orthogonal to each other.

In the forms shown in FIG. 39-40 and FIG. 46-49, inlet interior end and the outlet interior end are located within the cavity and the inlet exterior end and the outlet exterior end are located in one of the plurality of walls of the cavity. A first axis (inlet tube axis) is defined by the inlet interior end and the inlet exterior end and a second axis (outlet tube axis) is defined by the outlet interior end and the outlet exterior end. When the reservoir is tilted (for example by approximately 90 to normal working orientation) the first axis is on a first angle such that the inlet interior end and the inlet exterior end are positioned at different heights, such that the predetermined maximum volume of water is below at least one of the inlet interior end or the inlet exterior end to prevent spillback of water through the inlet tube. Furthermore, when the reservoir is tilted (for example by approximately 90° to normal working orientation) the second axis is on a second angle such that the outlet interior end and the outlet exterior end are positioned at different heights, such that the predetermined maximum volume of water is below at least one of the outlet interior end or the outlet exterior end to prevent spillback of water through the outlet tube. This effect may be also created wherein the reservoir is tilted at any other angles, to suit the design and/or tilt conditions of the humidifier 5000 and/or reservoir 5110.

5.5.2.9 Reservoir Arrangement with Removable Inlet/Outlet Tubes

In a yet further example of the current technology, the reservoir 5110 may be configured as shown in FIG. 52a-53. In this example, the reservoir 5110 comprises a lid portion 5114, an intermediate portion 5202 and a base portion 5112 (base portion not shown in FIG. 52a-52b for clarity). The lid portion 5114 and the intermediate portion 5202 may be configured to be releasably engaged to each other. They may be further configured to comprise a number of features when engaged to each other, such as an inlet 5118, an outlet 5122, an inlet tube 5124 and an outlet tube 5126, while being releasably engaged to each other. For example, the lid portion 5114 may comprise an inlet 5118, an outlet 5122 and an inlet tube 5124, and the intermediate portion 5202 may comprise an outlet tube 5126 as shown in FIG. 52b.

As shown the intermediate portion 5202 may also comprise a baffle 5192 and at least one support spoke 5194. The support spokes 5194 may be provided for structural support and/or to position the outlet tube 5126 and/or the baffle 5192 on the intermediate portion. The baffle 5192 is arranged to block a direct air path (or short-circuiting as described above) between the inlet tube inner end 5125 and the outlet tube inner end 5127 to encourage movement of the airflow within the reservoir to improve humidity uptake by the airflow within the reservoir 5110. In addition a seal 5204 may be either integrated with the intermediate portion 5202 as shown or may be formed as separate component to the intermediate portion.

An advantage of this arrangement may be improved cleanability of the reservoir 5110 by separating some of the components from the reservoir, such as the inlet tube 5124 and/or the outlet tube 5126. This arrangement may be particularly advantageous in such situations as when at least one of the inlet tube 5124 or the outlet tube 5126 extends into the internal volume of the reservoir 5110, as such features may hinder access the interior of the reservoir 5110. It can be seen in FIG. 52a-52b that the intermediate portion 5202 is engaged with the lid portion 5114 in its normal working orientation. However, as the intermediate portion 5202 is separable from the lid portion 5114, the inlet tube 5124 and the outlet tube 5126 may be separated to improve access to the interior of the lid portion 5114.

By using two separable portions 5114, 5202 to construct the upper portion of the reservoir and/or configuring the inlet/outlet tubes 5124, 5126 to be releasably engaged to the reservoir 5110, the number of small, difficult-to-access areas may be reduced, which may improve cleanability of the reservoir 5110. Furthermore, the removable inlet tube 5124 and/or the removable outlet tube 5126 may be themselves more easily accessible for cleaning as well.

In another example of the current technology (not shown), the lid portion 5114 and the intermediate portion 5202 may each comprise parts of a feature, wherein they would combine to form a complete feature. For instance, the lid portion 5114 may comprise a part of the inlet tube 5124 and a part of the outlet tube 5126, and the intermediate portion 5202 may comprise another part of the inlet tube 5124 and another part of the outlet tube 5126. Those skilled in the art will understand that the reservoir may be further sub-divided into any number of separable portions, and separable features such as the inlet tube 5124 and/or the outlet tube 5126 may be located in any number of arrangements in relation to the separable portions.

Another advantage of the current arrangement may be to improve spillback performance (prevention of liquid egress through the inlet tube 5124 and/or outlet tube 5126) of the reservoir 5110. Spillback performance may be improved by increase of the internal volume of the reservoir 5110, which may be achieved by introduction of a void above the inlet tube 5124 and/or the outlet tube 5126. Another method of improving spillback performance is to arrange the inlet tube inner end 5125 and/or the outlet tube inner end 5127 proximal to the center of the reservoir 5110. As a reservoir 5110 is typically produced by injection molding, forming an inlet tube 5124 and/or an outlet tube 5126 as a part of the lid 5114 prohibits introduction of a void above the inlet tube 5124 and/or the outlet tube 5126. In such a configuration, a molding tool comprising the internal volume of the lid 5114 would be pinned in place by the inlet tube 5124 and/or the outlet tube 5126 and thus molding would not be possible, or require a complex and costly tooling arrangement. In such a case, the ability to separate the inlet tube 5124 and the outlet tube 5126 may be further advantageous.

It will be understood that the lid portion 5114, the intermediate portion 5202 and the base portion 5112 may be configured in any number of ways. For instance, the relative sizes of the lid portion 5114 and the base portion 5112 may vary, and the lid portion 5114 and/or the base portion 5112 may further comprise multiple materials or components in its construction. One or more of the inlet tube 5124 and the outlet tube 5126 may be removably or releasably coupled to the lid portion 5114 or the base portion 5112, for example as a part of the intermediate portion. The intermediate portion may also be configured to initially engage the lid portion 5114 and/or the base portion 5112, for example by being configured to be inserted into the lid portion 5114 or the base portion 5112.

Another feature of this arrangement is the use of support spokes 5194 in order to provide structural rigidity to the intermediate portion 5202 of the lid 5114. The spokes 5194, by themselves or in combination with the baffle 5192, may provide a handle for disassembly of the lid 5114 from the intermediate portion 5202. This may improve usability of the lid 5114 as the user may grip the baffle 5192 and/or the spokes 5194 to separate the intermediate portion 5202 from the lid portion 5114. It should be understood that a number of other configurations may be possible wherein the support spokes 5194 are arranged alternatively to the exemplary arrangement as shown in FIG. 54a-55.

In an example of the current technology, the baffle 5192 may comprise a locating portion 5196 and a deflector portion 5198 as seen in FIG. 54a-55. The locating portion 5196 may be in the form of a cylinder to assist in accurately locating the baffle 5192 in relation to the inlet tube 5124 by fitting around the outside of the vertical portion of the inlet tube 5124. In some forms, the baffle 5192 may further comprise a baffle seal 5197 to seal between the baffle 5192 and the inlet tube 5124, for example as shown in FIG. 59b. The baffle 5192 may also be configured in combination with the spokes 5194 so that at least some portions of the baffle 5192 may act as a spoke 5194 or vice versa.

An exemplary cross-section of the assembled lid 5114 is shown in FIG. 56a-56b. The diameter of the inlet tube 5124 or the locating portion 5196 may be varied along its length, for example in a frustro-conical arrangement, so as to progressively engage with each other. The two components 5124, 5196 may also incorporate a complementary retaining mechanism such as a protrusion/slot combination 5205 as shown in FIG. 56a-56b.

It is also to be understood that the seal 5204 may be located at an alternative location to the exemplary arrangements shown in FIG. 52a-55. For example, the seal 5204 may be formed as a part of the lid portion 5114, as a part of the reservoir base portion 5112, or as a separate component by itself that is not integrally formed to any of the lid portion 5114, the intermediate portion 5202 and the base 5112. One exemplary method of forming the seal 5204 with the lid portion 5114 or the base 5112 may be by overmoulding or use of a chemical adhesive.

FIG. 57 shows an exploded view of another example of the current technology. In this arrangement, the reservoir 5110 comprises a lid portion 5114, an intermediate portion 5202 and a base portion 5112 (not shown in FIG. 57 for clarity). The intermediate portion 5202 comprises the inlet tube 5124 and the outlet tube 5126 as well as a wall portion 5206 that is configured to be coupled with the lid portion. Alternatively the intermediate portion 5202 may engage the base portion 5112, and may comprise one or both of the inlet tube 5124 and the outlet tube 5126. In some cases, the wall portion 5206 that is configured to couple with the lid portion may connected with one or more of the inlet tube 5124 and the outlet tube 5126.

This configuration may allow removal of the inlet tube 5124 and/or the outlet tube 5126 for improved cleanability of the reservoir 5110. Furthermore, this configuration may improve spillback performance of the reservoir 5110 by increasing the internal volume of the reservoir 5110.

In some cases, the inlet tube 5124 and the outlet tube 5126 may be arranged so that removal of either or both of the tubes 5124, 5126 from the reservoir 5110 does not affect the predetermined maximum volume of water that the reservoir 5110 may retain. Such a configuration may allow cleaning of the tubes 5124, 5126 without removing any water from the reservoir 5110.

5.5.2.10 Overfill Prevention

In some prior art humidifier water reservoirs, overfilling of the water reservoir 5110 may reduce effectiveness of a spill prevention feature. For example, overfilling may allow the liquid in the reservoir 5110 to reach the inlet 5118 at a lower angle of tilt than if the reservoir 5110 had not been over-filled. As a result, some prior art humidifier water reservoirs have included a water filling indication mark to reduce occurrence of such overfilling, however this may only go some way towards ameliorating this risk.

Another aspect of this technology is the inclusion of one or more overfill protection features configured to prevent filling the reservoir above the maximum volume of water when filling the humidifier reservoir in its open configuration and/or the closed configuration.

In one arrangement as seen in FIGS. 41a and 41b, an overfill protection feature may include at least one orifice 5138 in the water reservoir 5110 to indicate over-filling. According to this aspect of the technology, when the water reservoir 5110 is being re-filled with the reservoir lid 5114 open, over-filling beyond a predetermined maximum volume of the reservoir 5110 would cause water to spill out from the orifice 5138. This would indicate to the user that the reservoir 5110 is full, as well as preventing such overfilling. Advantageously water would spill out only through the at least one orifice 5138 rather than from all areas of the water reservoir resulting in less overflow spillage for the user to clean up. Thus, the at least one orifice defines an egress path of water when the predetermined maximum volume of water is exceeded. FIG. 41a show the water reservoir 5110 in its open configuration, wherein an upper flange of the base 5112 does not span the perimeter of the entire opening, creating an orifice 5138. FIG. 41b shows a portion of the base 5112 indicating the at least one orifice 5138. The at least one orifice 5138 may be in the form of one or more apertures, holes, slits or slots, or any other form that allows communication of fluid into and out of the water reservoir 5110. The at least one orifice 5138 may be formed in one or more positions around the upper flange of the base 5112.

In an alternate arrangement, the overfill protection feature may include a sloped profile 5139. As shown in FIGS. 41c and 41d, the reservoir base 5112 may be arranged so that its side profile has a sloped profile 5139 in one or more directions. This arrangement may also indicate over-filling when the reservoir base 5112 is re-filled with liquid or water. In this arrangement, when the reservoir lid 5114 is in its open configuration, water may spill out at the base of the sloped profile 5139 rather than from all areas of the reservoir. Thus, the sloped profile defines an egress path of water when the predetermined maximum volume of water is exceeded. Advantages of the above methods may be that over-filling may become more difficult than has been in the prior art, and presents another advantage that in response to attempted over-filling, spillage may occur at more predictable locations.

Another aspect of this technology is that when the water reservoir 5110 is in its closed position, a seal 5204 sealingly engages the base 5112 and the reservoir lid 5114 and blocks or seals the orifice 5138 or sloped profile 5139 preventing fluid communication into and out of the water reservoir 5110. One arrangement of this feature is shown in FIG. 42, which shows that when the reservoir lid 5114 is closed (lid not shown in this image), the seal 5204 sealingly engages with the base 5112 on the outside of the orifice 5138 and no longer allows communication of liquid or air into and out of the water reservoir 5110 through the orifice 5138. Similarly the seal 5204 would engage with the base 5112 to surround the edges of the sloped profile preventing communication of liquid or air into and out of the water reservoir 5110 through the sloped profile 5139. In some arrangements the seal 5204 may be integrated with the variable portion 5116 as described above. Alternatively the seal 5204 may be a separate seal that may be used in a reservoir with or without a variable portion.

According to another aspect of the present invention, an overfill prevention feature may be configured to prevent overfilling when a user is attempting to fill the reservoir 5110 while in its closed configuration.

In one form (shown in FIG. 60 without the reservoir base 5112), the overfill prevention feature may form one or more air locks to prevent further ingress of liquid into the reservoir 5110 when the predetermined maximum volume of liquid is in the reservoir 5110. In this form, when filling the reservoir 5110 in its closed configuration, the one or more air locks would form an enclosure of gas in the reservoir 5110 that is not displaced by the volume of liquid in the reservoir 5110. In an example shown in FIG. 60, the reservoir 5110 is in an orientation such that the normal to the inlet 5118 and the outlet 5122 are oriented vertically, as a user would orient the reservoir 5110 while filling it with water. The water level 5184 would rise, and reach the level shown on FIG. 60, whereupon the remaining volume of gas in the reservoir 5110 is no longer able to access the inlet tube 5124 or the outlet tube 5126, therefore would no longer be able to escape from the reservoir 5110. The reservoir 5110 would thus not be able to receive any further volume of water into its interior volume.

Preferably, the volume of water in the reservoir 5110 when any further ingress of water into the reservoir 5110 is prevented by formation of the one or more air locks is substantially equal to the predetermined maximum volume of liquid to be retained in the reservoir 5110. In some cases, the reservoir 5110 may allow further filling of the inlet tube 5124 and/or the outlet tube 5126 although further ingress of water into the interior volume is prevented by the air locks. In such cases, the volume of liquid in the reservoir 5110 when the air locks are formed, as well as the volume of the inlet tube 5124 and/or the outlet tube 5126 may be configured so that when added together, they are substantially equal to the predetermined maximum volume of liquid to be retained in the reservoir 5110.

In some cases, for example where the normal to the inlet 5118 and the outlet 5122 may not be parallel, a user may fill the reservoir 5110 in one of a multiple orientations while closed. In such cases, the reservoir 5110 may be configured such that the appropriate air locks are formable at one of, or a plurality of the multiple orientations. The air locks need not be formed solely by occlusion of the inlet tube 5124 and/or the outlet tube 5126. In some forms (not shown), one or more air locks may be formed by occlusion of any cavities or ports which may allow fluid communication between the interior and the exterior of the reservoir 5110. Furthermore, the occlusion need not be performed by the volume of liquid in the reservoir 5110. In some forms, the volume of liquid, as it is increased, may deform or move another component to form a seal (and thus an air lock) in the reservoir.

5.5.2.11 Retaining Clip

The reservoir lid 5114 may include a feature by which the water reservoir 5110 is to be retained in the water reservoir dock 5130 once the two members are engaged with each other. In one arrangement a retaining feature may be a protrusion, or a clip, 5142 on the reservoir lid 5114 as shown in FIGS. 43-44. FIGS. 43-44 show a water reservoir 5110 and the reservoir dock 5130. Here, a protrusion, or a clip, 5142 on the reservoir lid 5114 removably engages with a corresponding dock locking recess 5144 in the water reservoir dock 5130 when the water reservoir 5110 is inserted into the water reservoir dock 5130. This connection secures the water reservoir 5110 relative to the water reservoir dock 5130.

As described above the variable portion 5116 of the reservoir is compressed to enable insertion of the reservoir into the dock 5130. The compression of the variable portion 5116 allows a portion of the reservoir 5110 to slide into the dock 5130 and allows the protrusion or clip 5142 to slide initially under the outer edge surface of the dock 5130 to reach the dock locking recess 5144. The compression force applied to the reservoir for insertion may then be released to allow the protrusion or clip 5142 to engage with the dock locking recess 5144 and securing of the reservoir 5110 within the dock 5130. When the reservoir 5110 is secured within the dock 5130 the variable portion 5116 is no longer in or in a reduced compressed state. Similarly, in order to be able to remove the water reservoir 5110 from the water reservoir dock 5130, the variable portion 5116 must be compressed as to disengage the lid retention protrusion 5142 from the dock locking recess 5144.

The retention protrusion 5142 may be further configured with a taper as shown in FIG. 44. The taper may be directed to increase in height away from the direction of insertion, to increase the amount of interference between the retention protrusion 5142 and the dock 5130 progressively during insertion. It would be clear to those skilled in the art that in an alternative arrangement the lid retention protrusion 5142 may be a recess, and the dock locking recess 5144 may be a corresponding protrusion. Alternatively one of any number of retaining features that are known in the art may be used to achieve the same outcomes as described above.

5.5.2.12 Water Reservoir-to-Humidifier Connection

In one form, the water reservoir 5110 in use receives a flow of air output by the RPT device 4000 at the dock outlet 4132. The water reservoir 5110 is removably coupled with the humidifier 5000, for example configured (as shown in FIG. 16g-16h) to be insertable into the dock 4130. When the water reservoir 5110 is engaged with the dock 4130, the reservoir inlet 5118 may receive the flow of air output by the RPT device 4000, and direct the flow of air into the water reservoir 5110. Humidity (i.e. water vapour) is added to the flow of air as the air travels through the reservoir 5110, and the humidified flow of air exits the reservoir 5110 through the reservoir outlet tube 5126 and to the reservoir outlet 5122. The reservoir outlet 5122 is connectable to an air circuit 4170 to deliver the flow of humidified air to the patient 1000.

The double-ended arrows in FIG. 16h show the direction of relative motion, i.e. generally horizontal movement, between the humidifier 5000 and the water reservoir 5110 in connection and disconnection with each other in this arrangement. In the arrangement shown in FIG. 16g-16h, the water reservoir 5110 is connected with the humidifier 5000 by placing the water reservoir 5110 in the dock 4130. In this arrangement, the heights and shapes of the cavity in the dock 4130 and the water reservoir 5110 are such that to engage the water reservoir 5110 with the dock 4130 the compliant portion 5116 is compressed, for example by between about 1 mm and about 5 mm, for example by about 2 mm, about 3 mm or about 4 mm. Thus, the shape of the portion of the water reservoir 5110 that is inserted into the dock 4130 is complementary to the shape of the dock cavity 5160 and the height of the water reservoir 5110 when compliant portion 5116 is compressed is slightly less than the height of the dock cavity 5160 to enable the insertion of the water reservoir 5110 into the dock cavity 5160.

In one form, a compressive force is required to sufficiently compress the compliant portion 5116 and allow relative movement (i.e. sliding) between the water reservoir 5110 and the dock 4130. For example a compression force as measured at the handle recesses 5154, 5156 of between about 10 N and about 30 N, or about 20 N, or some other compression force is required to allow insertion of the water reservoir 5110 into the dock 4130. The vertical gap achieved between the water reservoir 5110 and the cavity of the dock 4130 during insertion (or removal) may be between about 1 mm and about 5 mm, for example about 2 mm, 3 mm or 4 mm, when this compressive force is applied at the handle recesses 5154, 5156 and the water reservoir 5110 is inserted into the dock 4130. The water reservoir 5110 and the dock 4130 may be arranged so that the amount of compression in the compliant portion 5116 is reduced once the water reservoir 5110 is connected with the dock 4130 and the patient 1000 is no longer applying a compressive force. The reduction in compression may be between about 0.5 mm and about 2.5 mm, for example about 1 mm, 1.5 mm or 2 mm.

In the illustrated arrangement (see FIG. 16a-16b) the reservoir outlet 5122 is connectable to the dock inlet 4134, through which the humidified flow of air travels to the humidifier outlet 5172. The humidifier outlet 5172 is connectable to the air circuit 4170 as indicated in FIG. 13 by the double-ended dotted arrow (see FIG. 13). An advantage of such an arrangement is that the water reservoir 5110 can be removed from the dock 4130 while the air circuit 4170 remains attached to the device outlet 4004. Thus the insertion and removal of the water reservoir 5110 is independent of the connection of the air circuit 4170. A further advantage is that the water reservoir 5110 must be removed from the dock 4130 to fill the water reservoir 5110 with liquid. In this form, neither of the inlet 5118 and the outlet 5122 of the reservoir 5110 are exposed while the reservoir 5110 is inserted in the humidifier 5000 in an operating configuration, while the reservoir 5110 itself remains accessible to the patient 1000, for example to allow easy removal from the humidifier 5000. This arrangement may reduce the likelihood of the user over-filling the water reservoir 5110 over the predetermined, maximum volume of liquid, as the water reservoir 5110 incorporates features to prevent over-filling. Still further, as the user is encouraged to remove the water reservoir 5110 to fill the reservoir 5110 with liquid, the likelihood of spillage of water onto, or into, the humidifier 5000 and/or the RPT device 4000 is reduced.

The compliant portion 5116 may be constructed from an elastomeric material such as silicone, thermoplastic elastomer (TPE), TPE polyester, TPE polyurethane or natural rubber. In choosing the material to be used for the compliant portion 5116 it may be advantageous to choose one that does not experience mechanical relaxation across the range of storage and operational temperatures that the compliant portion 5116 may be exposed to. One example of a material for the compliant portion 5116 which meets these requirements may be silicone.

A reservoir latch 5186 may be provided on the water reservoir 5110, as shown in FIG. 40, so that when the reservoir latch 5186 is engaged, it secures the reservoir lid 5114 and reservoir base 5112 together. The latch 5186 may prevent the reservoir lid 5114 and the reservoir base 5112 from separating and maintain the compliant portion 5116 in sealing engagement between the lid 5114 and the base 5112, for example by compression. In one form, the latch 5186 may be configured to restrict relative movement of the lid 5114 in relation to the base 5112 in one direction only, thus allow further compression of the compliant portion 5116 while preventing separation of the lid 5114 and the base 5112. This may allow insertion of the water reservoir 5110 into the dock 4130, and/or allow the compliant portion 5116 to assist thermal engagement between the reservoir 5110 and the heating element 5240 as described elsewhere in this disclosure.

When in use, the water reservoir 5110 receives the flow of breathable air for example output by the PAP device 4000. In one form, the water reservoir 5110 is removably coupled with the humidifier 5000 as shown in FIG. 24-27 by inserting the water reservoir into the water reservoir dock 5130, for example by sliding. The inlet 5118 of the water reservoir 5110 is configured to receive the flow of breathable gas that is output by the PAP device 4000, and to direct the flow of breathable gas into the water reservoir 5110. Humidity (i.e. water vapour) is added to the flow of breathable gas as the breathable gas travels through the reservoir 5110, and the humidified flow of breathable gas exits the reservoir 5110 through the outlet tube 5126 and to the reservoir outlet 5122. The reservoir outlet 5122 is connectable to an air circuit 4170 to deliver the flow of humidified breathable gas to the patient 1000.

Figure 27:
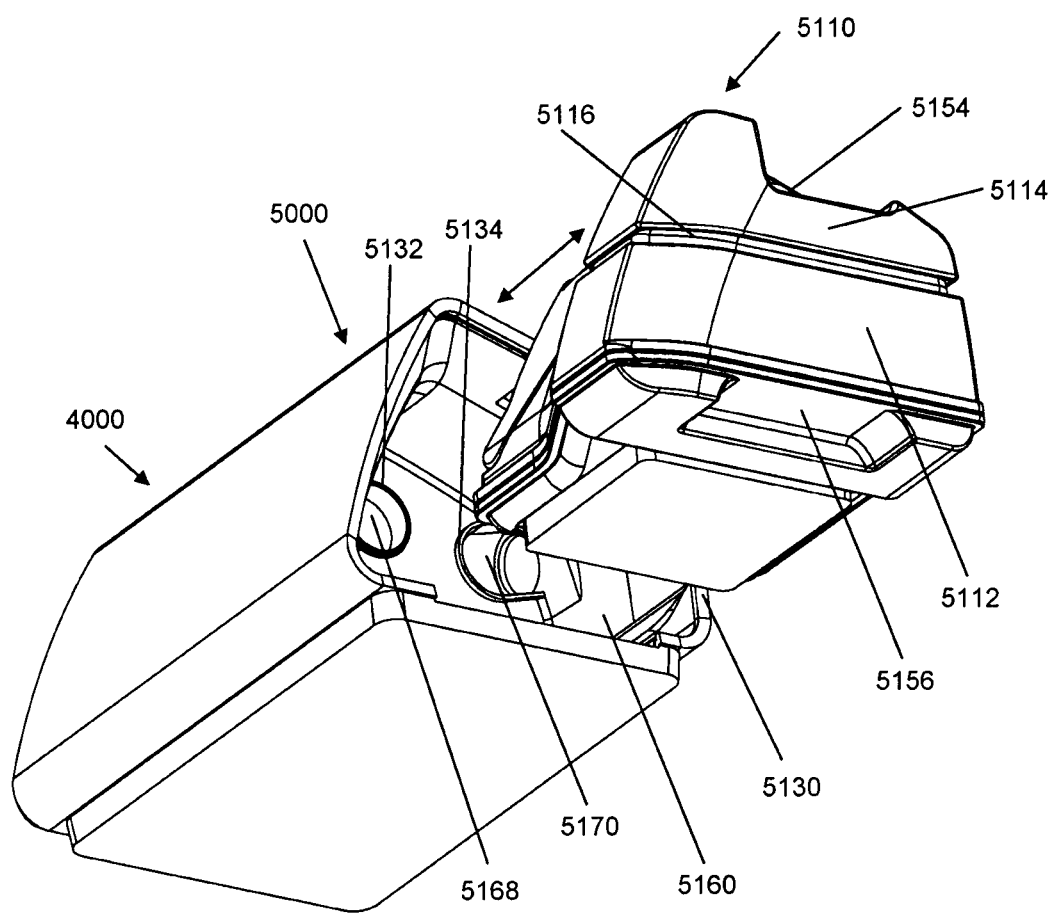
Figure 28B:
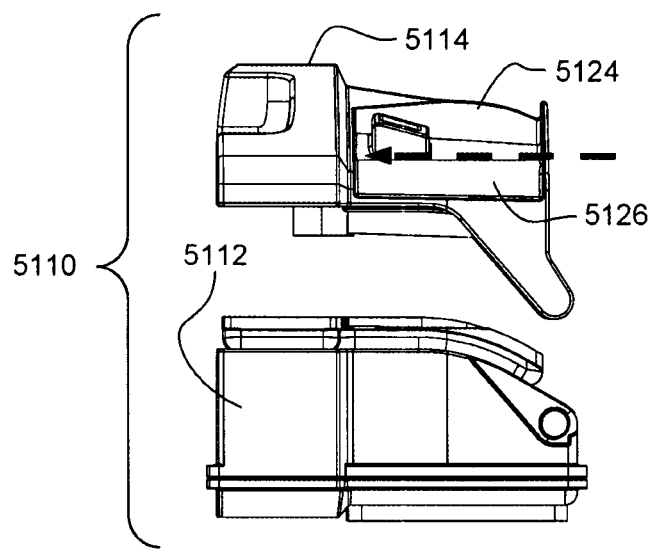
Figure 28A:
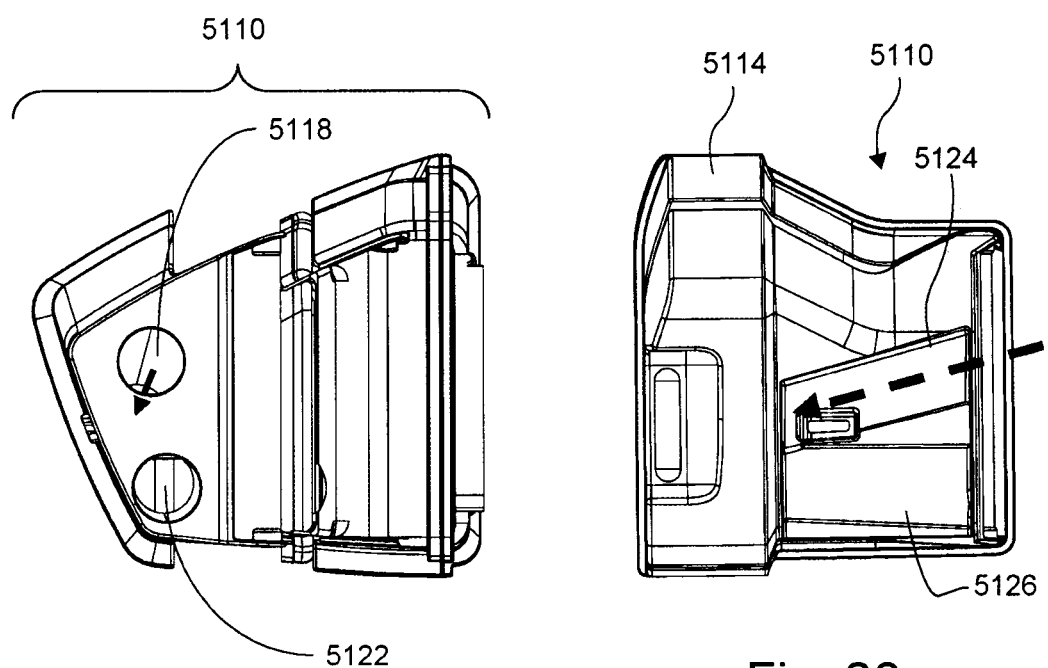
Figure 28C:
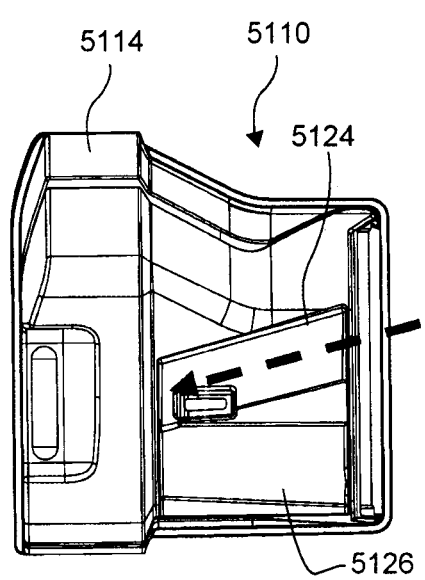
Figure 30B:
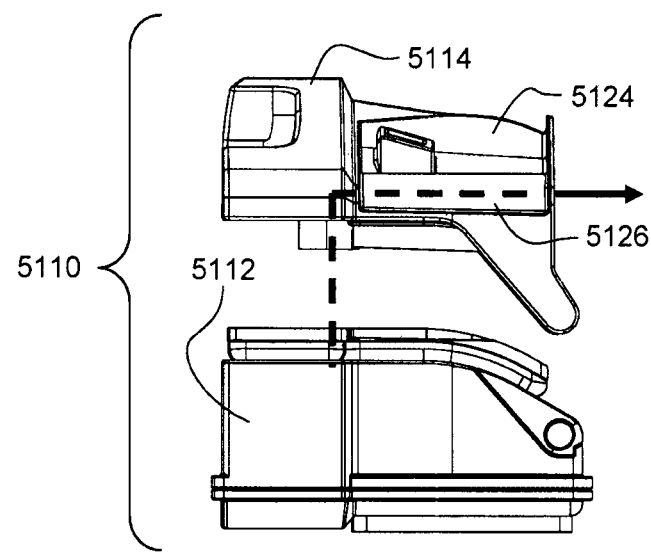
Figure 30A:
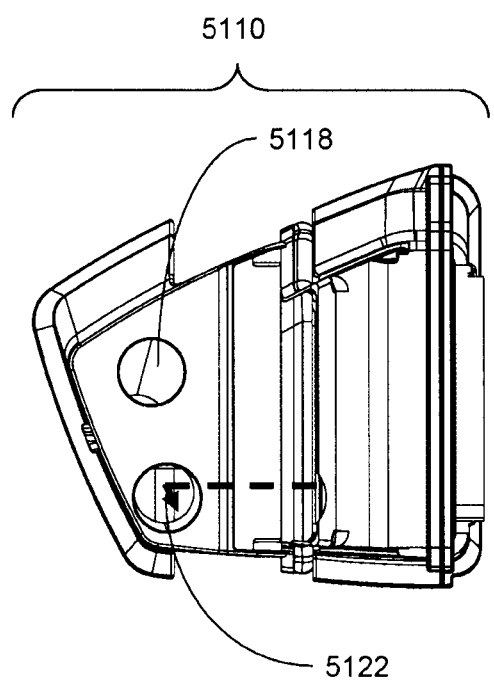
Figure 30C:
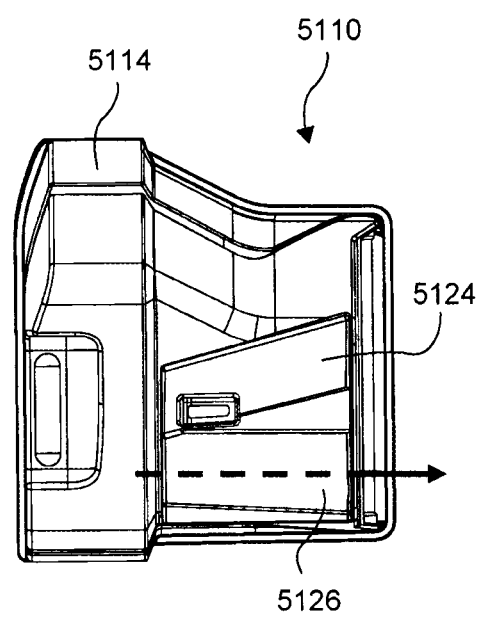

The double-ended arrows in FIG. 25 and FIG. 27 show the direction of relative motion, i.e. generally horizontal movement, between the humidifier 5000 and the water reservoir 5110 in connection and disconnection with each other in this arrangement. However, the water reservoir 5110 may be coupled to the humidifier 5000 by other methods such as insertion in a generally vertical direction, connection by one or more intermediate components (e.g. tubes) or being integrally formed with a humidifier.

In an alternative arrangement, not shown, the water reservoir 5110, may be inserted into the dock cavity 5160 from a vertical direction rather than using a sliding motion. In such an arrangement the dock cavity of the humidifier 5000 may comprise a moveable cover portion, such as a lid or top portion, which is at least partially opened to allow insertion of the water reservoir 5110 and closed following insertion to secure the water reservoir 5110 within the dock cavity 5160.

In the illustrated arrangement (see FIG. 27) the reservoir outlet 5122 is connectable to the reservoir dock gas inlet 5170, through which the humidified flow of breathable air travels to the humidifier outlet 5172. The humidifier outlet 5172 is connectable to the air delivery circuit or air circuit 4170 as indicated in FIG. 13 by the double-ended dotted arrow (see FIG. 24). One advantage of such an arrangement is that the humidifier reservoir 5110 must be removed from the reservoir dock 5130 to fill the humidifier reservoir 5110 with liquid. This arrangement generally prevents access to any openings in the humidifier reservoir 5110 while it is connected to the humidifier 5000, and may reduce the likelihood of the user over-filling the water reservoir 5110 over the given, maximum volume of liquid, as the humidifier reservoir 5110 incorporates features to prevent over-filling as described further below. Still further, as the user is encouraged to remove the water reservoir 5110 to fill the reservoir 5110 with liquid, the likelihood of spillage of water onto, or into, the humidifier 5000 and/or the PAP device 4000 is reduced.

As shown in FIG. 27, first and second dock seals 5132, 5134 may be provided to help seal the connection between the reservoir inlet 5118 and the dock 5130 and the connection between the reservoir outlet 5122 and the dock 5130.

Figure 26:
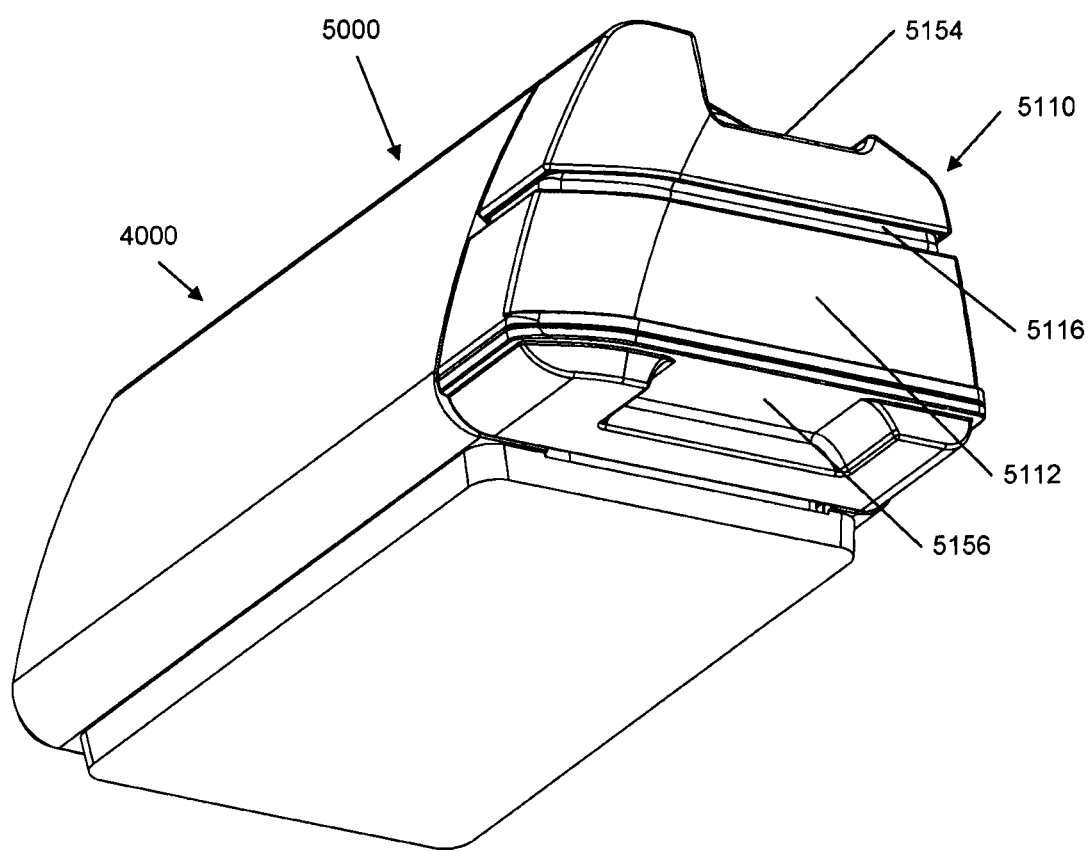

In the arrangement shown in FIG. 26-27, the water reservoir 5110 is connected with the humidifier 5000 by placing the water reservoir 5110 in the water reservoir dock 5130. In this arrangement, the heights and shapes of the dock internal cavity 5160 and the water reservoir 5110 are such that to engage the water reservoir 5110 with the water reservoir dock 5130 the variable portion 5116 is compressed, for example by between about 1 mm and about 5 mm, for example by about 2 mm, about 3 mm or about 4 mm. Thus, the shape of the portion of the water reservoir 5110 that is inserted into the dock 5130 is complementary to the shape of the dock cavity 5160 and the height of the water reservoir 5110 when variable portion 5116 is compressed is slightly less than the height of the dock cavity 5160 to enable the insertion of the water reservoir 5110 into the dock cavity 5160.

The variable portion 5116 may be constructed with a cross-section shape such as one shown in FIG. 50. A compressive force is required to sufficiently compress the variable portion 5116 and allow relative movement (i.e. sliding) between the water reservoir 5110 and the water reservoir dock 5130. For example a compression force as measured at the handle recesses 5154, 5156 of between about 10 N and about 30 N, or about 20 N, or some other compression force is required to allow insertion of the water reservoir 5110 into the dock cavity 5160. The vertical gap achieved between the water reservoir 5110 and the dock internal cavity 5160 during insertion (or removal) may be between about 1 mm and about 5 mm, for example about 2 mm, 3 mm or 4 mm, when this compressive force is applied at the handle recesses and the water reservoir 5110 is inserted into the reservoir dock 5130. The water reservoir 5110 and the reservoir dock 5130 may be arranged so that the amount of compression in the variable portion 5116 is reduced once the water reservoir 5110 is connected with the reservoir dock 5130 and the patient 1000 is no longer applying a compressive force. The reduction in compression may be between about 0.5 mm and about 2.5 mm, for example about 1 mm, 1.5 mm or 2 mm.

The variable portion 5116 may be constructed from an elastomeric material such as silicone, TPE, TPE polyester, TPE polyurethane or natural rubber. In choosing the material to be used for the variable portion 5116 it may be advantageous to choose one that does not experience mechanical relaxation across the range of storage and operational temperatures that the variable portion 5116 may be exposed to. One example of a material for the variable portion 5116 which meets these requirements may be silicone.

A reservoir latch 5186 may be provided on the water reservoir 5110, as shown in FIG. 40, so that when the reservoir latch 5186 is engaged, it secures the reservoir lid 5114 and reservoir base 5112 together. The latch 5186 may prevent the reservoir lid 5114 and the reservoir base 5112 from separating and maintain the variable portion 5116 in sealing engagement between the lid 5114 and the base 5112, for example by compression. In one form, the latch 5186 may be configured to restrict relative movement of the lid 5114 in relation to the base 5112 in one direction only, thus allow further compression of the variable portion 5116 while preventing separation of the lid 5114 and the base 5112. This may allow insertion of the water reservoir 5110 into the reservoir dock 5130, and/or allow the variable portion 5116 to assist thermal engagement between the reservoir 5110 and the heater plate 5120 as described elsewhere in this disclosure.

5.5.2.12.1 Pre-Compression for Improved Thermal Contact

According to one aspect of this technology, the water reservoir 5110 and the heater plate 5120 of the humidifier are in thermal contact, or thermal engagement, as described above. A degree of thermal contact, for example measured in thermal conductivity or thermal contact resistance, between two components may vary according to a number of parameters.

In the prior art, additional components have been used to improve thermal contact between a water reservoir and a heater plate by increasing the contact pressure therebetween. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

In the present technology, pre-compression of the water reservoir 5110, for example in engagement with the water reservoir dock 4130, may be used to help improve thermal contact between the reservoir 5110 and the heating element 5240.

In one arrangement, the water reservoir 5110 may be configured so that in its operating configuration, such as when it is placed in the water reservoir dock 41305130, the compliant portion 5116 is compressed as described above. The reservoir 5110 and the reservoir dock 4130 may be further configured so that a reaction force to the compression of the compliant portion 5116 pushes the base 5112 of the water reservoir 5110 against the heating element 5240 to improve the thermal contact therebetween.

Thus, the compliant portion 5116 may act as a spring that is biased to push the reservoir base 5112 and/or the reservoir lid 5114 in a direction perpendicular to the heating element 5240. As the reservoir 5110 is secured externally, such as confined within the reservoir dock 4130, the compression of the compliant portion 5116 is reacted by a force that encourages improved thermal engagement with the heating element 5240.

The force required for compression of the compliant portion 5116 when the water reservoir 5110 is connected with the humidifier 5000 is preferably in the same direction as the normal to a surface of the conductive portion. The direction may be also preferably in the same direction as the direction of thermal engagement. This force is reacted by the water reservoir dock 4130 at its contacting points and/or surfaces, thereby pushing the base 5112 of the water reservoir 5110 and the heating element 5240 together.

The magnitude of compression force may be between about 5 N and about 15 N when measured at the heating element 5240 when the water reservoir 5110 is placed in the water reservoir dock 4130. However, it should be understood that different configurations of the water reservoir 5110 may require different magnitudes of compression force. The magnitude of this force may be altered by modifying the design of any or all of the compliant portion 5116, the lid 5114, the base 5112, or the reservoir dock 4130. For instance, if the compliant portion 5116 was constructed of a material with higher Young's modulus, it would correspondingly increase the magnitude of the force. It should be noted that FIG. 20 only shows forces and pressures in the vertical direction.

In some cases, the amount of compression of the compliant portion 5116 in the reservoir 5110 may be used to vary a level of thermal engagement between the conductive portion and the heating element 5240.

5.5.2.13 Conductive Portion 5120

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.13.1 Thermal Contact/Engagement

According to one aspect of this technology, the water reservoir 5110 and the heater plate 5120 of the humidifier are in thermal contact, or thermal engagement, as described above. A degree of thermal contact, for example measured in thermal conductivity or thermal contact resistance, between two components may vary according to a number of parameters.

In the prior art, additional components have been used to improve thermal contact between a water reservoir and a heater plate by increasing the contact pressure therebetween. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

5.5.2.13.1.1 Use of Pressurised Gas for Improved Thermal Contact

According to another aspect, when the water reservoir 5110 is connected with the humidifier 5000, the flow of breathable gas received from the PAP device may pressurise a chamber such as the interior of the reservoir 5110. The pressurisation of the chamber may be used to increase a level of thermal engagement (i.e. thermal contact) between the reservoir 5110 and the heater plate 5120. The reservoir 5110 may be further configured so that by varying the level of pressure in the chamber may vary the level of thermal contact between the reservoir 5110 and the heater plate 5120.

In one form, the variable portion 5116 may be configured to be expandable in the direction of thermal contact, and the reservoir 5110 may be confined by the reservoir dock 5130 in the same direction. In this form, the internal pressure pushes the base 5112 of the water reservoir 5110 against the heater plate 5120 to improve the level of thermal engagement between the heater plate 5120 and the base 5112.

FIG. 32 illustrates this effect by indicating the distributed forces or pressures that are applied to the lid 5114 and the base 5112 by the arrows shown. FIG. 32 shows forces and pressures in the vertical direction only, as in this form the thermal engagement occurs in the vertical direction. The presence of above-atmospheric pressure within the water reservoir 5110 results in forces in the direction of thermal engagement, and is reacted by the water reservoir dock 5130 at its contacting surfaces, thereby pushing the base 5112 of the water reservoir 5110 and the heater plate 5120 towards each other in the direction of thermal engagement. The magnitude of this force may be between about 5 N and about 15 N when measured at the heater plate 5120 at 20 cm $H_2O$ of pressure.

It should be understood that different configurations of the water reservoir 5110 may require different magnitudes of force, which may be achieved by varying the surface area that the pressure acts on, or the effective pressure that acts on the surface. Such changes may be achieved, for example, by a pressure regulating valve.

In another arrangement, substantially the same effects as those described above may be achieved with a non-opening variable portion of a water reservoir 5110. The water reservoir 5110 and the reservoir dock 5130 may be arranged so that elasticity or flexibility is provided by an elastomeric material or a joint that allows freedom of movement (e.g. a sliding connection, or a concertina section of pliable plastic or a flexible portion in the water reservoir) in the direction of the heat transfer. In this configuration the lid 5114 and the base 5112 may be unconstrained relative to each other in the direction of thermal contact. The reservoir 5110 may then be constrained in the direction of the heat transfer in another manner (e.g. by a water reservoir dock or a similar housing) to create a force that reacts to balance the pressure created in the interior of the reservoir 5110 by the pressurized flow of breathable air, wherein some of the reaction force may occur at the heater plate 5120 to improve thermal contact. In such arrangements, another opening to re-fill the water reservoir 5110 may be introduced on the reservoir 5110, such as on the lid 5114, and it may comprise a separate seal.

FIG. 45 shows an example of such an arrangement, including a base 5174, a top 5176, a variable portion 5178 and a re-filling cap 5180. The base, the top and the variable portion may be affixed together in another arrangement, wherein re-filling of the reservoir would be accommodated by the re-filling cap, 5180. The re-filling cap 5180 may be placed such that when the humidifier reservoir 5110 is engaged with the reservoir dock 5130 the re-filling cap 5180 is not accessible. Such an arrangement may preserve the advantage described above, namely that the reservoir 5110 is not able to be re-filled while it is engaged with the reservoir dock 5130. Furthermore, the variable portion 5178 may be replaced by any mechanism known in the art that is able to accommodate a change in vertical length within a reservoir.

In a yet another alternate arrangement, the flow of breathable air may be used to improve the level of thermal contact between the humidifier reservoir 5110 and the heater plate 5120 by pressurisation or inflation of a secondary component. The secondary component may be a chamber, body or surface that acts on the humidifier reservoir 5110, which in turn pushes the water reservoir 5110 and the heater plate 5120 together in the direction of thermal engagement. Similarly, the secondary component may act upon the heater plate 5120 to push the heater plate 5120 and water reservoir 5110 together in the direction of thermal engagement.

The secondary component may be arranged externally to the reservoir 5110 and/or the heater plate 5120. Furthermore, the secondary component may be configured to vary the area in contact with the reservoir 5110 and/or the heater plate 5120, to further profile the change to thermal contact as pressure of the flow of breathable gas changes.

In an alternate arrangement, the water reservoir dock 5130 may include a retaining mechanism (for example, a lid that closes around the water reservoir 5110) to hold the water reservoir 5110 in its intended position. In such an arrangement, a reservoir dock lid may be configured to compress and/or confine the variable portion 5116 in order to improve the level of thermal contact.

The level of thermal contact may also be further improved using a spring loaded or sprung heater plate as is known in the prior art. The heater plate may be constructed with a convex or domed shape towards the humidifier reservoir 5110 so that when the humidifier 5110 is engaged with the reservoir dock 5130 the convex heater plate is flattened, which generates a clamping force pushing the heater plate 5120 to the water reservoir 5110. Similarly, the conductor plate 5152 of the water reservoir 5110 may be domed or convex shaped and be configured to be flattened towards to the heater plate when the water reservoir 5110 is engaged in the dock cavity 5160 of the humidifier 5000.

Any one of the above means of improving thermal contact may be used independently of each other, or in any combination thereof, including in combination with any prior art means of achieving or improving thermal engagement between the humidifier reservoir and the heater plate.

5.5.2.14 Humidifier Transducer(s) 5210

The humidifier 5000 may comprise one or more humidifier transducers (sensors) 5210 instead of, or in addition to, transducers 4270 described above. Humidifier transducers 5210 may include one or more of an air pressure sensor, an air flow sensor, a temperature sensor or a humidity sensor as shown in FIG. 5c. A humidifier transducer 5210 may produce one or more output signals which may be communicated to a controller such as the central controller 4230 or the humidifier controller 5250. In some forms, a humidifier transducer may be located externally to the humidifier 5000 (such as in the air circuit 4170) while communicating the output signal to the controller.

5.5.2.14.1 Pressure Transducer 5212

One or more pressure transducers 5212 may be provided to the humidifier 5000 in addition to, or instead of, a pressure transducer 4272 provided in the RPT device 4000.

5.5.2.14.2 Flow Transducer 5214

One or more flow transducers 5214 may be provided to the humidifier 5000 in addition to, or instead of, a flow transducer 4274 provided in the RPT device 4000.

5.5.2.14.3 Temperature Transducer 5216

The humidifier 5000 may comprise one or more temperature transducers 5216. The one or more temperature transducers 5216 may be configured to measure one or more temperatures such as of the heating element 5240 or of the flow of air downstream of the water reservoir outlet 5122. In some forms, the humidifier 5000 may further comprise a temperature sensor 5216 to detect the temperature of the ambient air.

5.5.2.14.4 Humidity Transducer 5218

In one form, the humidifier 5000 may comprise one or more humidity sensors 5218 to detect a humidity of a gas, such as the ambient air. The humidity sensor 5218 may be placed towards an outlet of the humidifier 5000 in some forms to measure a humidity of the gas delivered from the humidifier 5000. The humidity sensor may be an absolute humidity sensor or a relative humidity sensor.

5.5.2.15 Heating Element 5240

A heating element 5240 may be provided to the humidifier 5000 in some cases to provide a heat input to one or more of the volume of water in the water reservoir 5110 or to the flow of air. The heating element 5240 may comprise a heat generating component 5242 (see FIG. 17b) such as an electrically resistive heating track. One suitable example of a heating element 5240 is a layered heating element such as one described in the PCT Patent Application Publication Number WO 2012/171072, the entire document of which is incorporated herewithin by reference.

In some forms, the heating element 5240 may be provided in the chassis 4016 where heat may be provided to the water reservoir 5110 primarily by conduction, for example through a HE cover plate 5241 (see FIG. 17b) which may be composed of a conductive material such as a metal (e.g. stainless steel or aluminium).)

The heating element 5240 may be supported by a HE seal 5243 as shown in FIG. 17b, configured to prevent or discourage ingress of any water from the water reservoir 5110 or the dock 4130 into the heating element 5240. In one form, the HE seal 5243 (shown in greater detail in FIG. 17g-17h) may seal around the periphery of the heating element 5240, and elevate the heating element 5240 from the base of the RPT device 4000. The HE seal 5243 may comprise one or more resilient portions such as the HE cones 5245 as shown in FIGS. 17d and 17h, configured to provide a compressive force to help engage the heating element 5240 with the conductive portion 5120 of the water reservoir 5110. In one form, the HE seal 5243 and the heating element 5240 may be configured so that when the water reservoir 5110 is inserted into and engaged with the dock 4130, the HE cones 5245 are compressed axially to provide an upward force, thereby pushing the heating element 5240 toward the conductive portion 5120 of the water reservoir 5110 and improving the thermal contact therebetween.

The HE seal 5243 may further comprise one or more HE cable ports 5246 to allow a cable (e.g. for electrical power) to travel therethrough, for example from another portion of the chassis 4016 such as outside of the dock 4130 and near the pneumatic block 4020. The one or more HE cable ports 5246 may sealingly engage around a periphery of the cable travelling therethrough to prevent ingress of water into the heating element 5240. In one form, the HE seal 5243 may be constructed from a resilient material such as silicone, and comprise integrally formed HE cones 5245 and HE cable ports 5246. The HE cable port 5246 may comprise a cavity for the cable to travel therethrough, and may be configured to engage with another cavity for location and/or retention, such as by being shaped as a protrusion to be inserted into a cavity in the chassis 4016.

The humidifier 5000 may comprise a HE base cover 5244 as shown in FIG. 17*b* and in further detail in FIGS. 17*i* and 17*j*. The HE base cover 5244 may be removably coupled to the chassis 4016 (e.g. by screws) to allow access to the heating element 5240, and comprise one or more features configured to support and locate the HE seal 5243. In one form, the HE base cover 5244 may further comprise HE cone slots 52475246 configured to receive HE cones 5245 while allowing a compression thereof.

5.5.2.15.1 Humidifier Controller 5250

According to one arrangement of the present technology, a humidifier 5000 may comprise a humidifier controller 5250 as shown in FIG. 5*c*. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure or flow rate), for example of the flow of air, the water in the reservoir 5110 or the humidifier 5000. The humidifier controller 5250 may also be configured to execute or implement humidifier algorithms or deliver one or more output signals.

As shown in FIG. 5*c*, the humidifier controller may comprise one or more controllers, such as a central humidifier controller 5251, a heated air circuit controller 5254 configured to control the temperature of a heated air circuit or a heating element controller 5252 configured to control the temperature of a hot plate.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

CDMA: is an abbreviation for Code division multiple access.

GSM: is an abbreviation for Global System for Mobile.

LTE: is an abbreviation for Long Term Evolution.

USB: is an abbreviation for Universal Serial Bus.

5.6.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.7 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods, materials (or both) which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified. Additionally, or alternatively, aspects thereof may be conducted concurrently or even synchronously.

It is therefore to be understood that numerous modifications may be made to the illustrative embodiments and that other arrangements may be devised without departing from the spirit and scope of the technology.

5.8 Reference Signs List

| Component | Reference |
|---|---|
| patient | 1000 |
| bed partner | 1100 |
| patient interface | 3000 |
| seal-forming structure | 3100 |
| plenum chamber | 3200 |
| structure | 3300 |
| connection port | 3600 |
| rpt device | 4000 |
| rpt device inlet | 4002 |
| rpt device outlet | 4004 |
| outlet tube | 4006 |
| first portion | 4006a |
| second portion | 4006b |
| flange | 4006fl |
| outlet tube guide portion | 4006gu |
| outlet tube latch portion | 4006la |
| outlet end | 4006oe |
| intermediate tube | 4008 |
| external housing | 4010 |
| front panel cutout | 4010co |
| external housing light port | 4010lp |
| protrusion | 4010pr |
| front panel | 4012 |
| internal shoulder | 4012sh |
| side panel | 4014 |
| access cover | 4014ac |
| access cover anchoring portion | 4014an |
| recess | 4014ch |
| cover portion | 4014co |
| connection port | 4014cp |
| side panel frame | 4014f |
| inlet air filter cover | 4014fc |
| air filter housing | 4014h |
| access cover hinge portion | 4014hi |
| complementary recess | 4014re |
| wall | 4014w |
| chassis | 4016 |
| platform | 4016pl |
| pneumatic block | 4020 |
| acoustic foam | 4020af |
| blower sleeve | 4020bs |
| first chamber | 4020c1 |
| second chamber | 4020c2 |
| flow plate | 4020fp |
| flow tube | 4020ft |
| first PB housing | 4020h1 |
| second PB housing | 4020h2 |
| pb inlet | 4020in |
| pb inlet tube | 4020it |
| pb outlet rim | 4020or |
| pb outlet | 4020ou |
| sleeve pull tab | 4020pt |
| pb sensor coupler | 4020sc |
| flow sensor port | 4020sp |
| sleeve tab | 4020st |
| pb water shield | 4020ws |
| pb water trap | 4020wt |
| patient interface connector | 4107 |
| air filter | 4110 |
| inlet air filter | 4112 |
| outlet air filter | 4114 |
| muffler | 4120 |
| inlet muffler | 4122 |
| outlet muffler | 4124 |
| muffler body | 4124bo |
| muffler cap | 4124ca |
| muffler clip | 4124cl |
| muffler damper | 4124da |
| muffler expansion chamber | 4124ex |
| muffler foam | 4124fo |
| muffler hinge | 4124hi |
| muffler entry | 4124in |
| muffler lever | 4124le |
| muffler exit | 4124ou |
| muffler travel limiter | 4124tl |

-continued

| Component | Reference |
|---|---|
| dock | 4130 |
| corresponding dock guide portion | 4130gu |
| complementary recess | 4130re |
| dock outlet slot | 4130sl |
| dock outlet | 4132 |
| dock outlet pressure port | 4132pp |
| dock inlet | 4134 |
| pressure generator | 4140 |
| blower | 4142 |
| blower inlet | 4142in |
| blower outlet | 4142ou |
| motor | 4144 |
| tab | 4148 |
| back valve | 4160 |
| air circuit | 4170 |
| ac helical coil | 4170co |
| ac electrical connector | 4170ec |
| electrical lead | 4170le |
| ac outlet connector | 4170oc |
| ac overmould | 4170om |
| block | 4170pb |
| recess | 4170re |
| base seal | 4170se |
| ac tube portion | 4170tp |
| actuator | 4172 |
| retention feature | 4174 |
| AC tab | 4176 |
| internal rib | 4177 |
| travel stop | 4178 |
| oxygen delivery port | 4180 |
| user interface panel | 4190 |
| ui base | 4190ba |
| light well | 4190lw |
| ui seal | 4190se |
| pcba | 4202 |
| power supply | 4210 |
| input device | 4220 |
| first button | 4222 |
| second button | 4224 |
| dial | 4226 |
| dial aperture | 4226ap |
| dial cover | 4226co |
| dial seal | 4226se |
| encoder shaft | 4226sh |
| central controller | 4230 |
| clock | 4232 |
| therapy device controller | 4240 |
| protection circuit | 4250 |
| memory | 4260 |
| transducer | 4270 |
| pressure transducer | 4272 |
| flow transducer | 4274 |
| motor speed transducer | 4276 |
| ambient light sensor | 4278 |
| data communication interface | 4280 |
| antenna | 4280an |
| antenna ground plane | 4280gp |
| first side | 4280n1 |
| second side | 4280n2 |
| remote external communication network | 4282 |
| local external communication network | 4284 |
| remote external device | 4286 |
| local external device | 4288 |
| output device | 4290 |
| display driver | 4292 |
| display | 4294 |
| display cover | 4294co |
| visual interface | 4295 |
| report sub-menu | 4295a1 |
| report sub-menu | 4295a2 |
| report sub-menu | 4295a3 |
| report sub-menu | 4295a4 |
| report sub-menu | 4295a5 |
| report sub-menu | 4295a6 |
| report sub-menu | 4295a7 |
| report sub-menu | 4295a8 |
| report sub-menu | 4295b1 |

-continued

| Component | Reference |
|---|---|
| report sub-menu | 4295b2 |
| report sub-menu | 4295b3 |
| report sub-menu | 4295b4 |
| first clinical menu screen | 4295c1 |
| first menu screen | 4295m1 |
| first clinical menu screen | 4295m2 |
| selectable sub-menu | 4295o1 |
| selectable sub-menu | 4295o2 |
| report sub-menu | 4295r1 |
| report sub-menu | 4295r2 |
| report sub-menu | 4295r3 |
| report sub-menu | 4295r4 |
| report menu | 4295re |
| selectable sub-menu | 4295s1 |
| selectable sub-menu | 4295s2 |
| selectable sub-menu | 4295s3 |
| selectable menu | 4295se |
| window portion | 4295w |
| control module | 4330 |
| humidifier | 5000 |
| outlet assembly | 5004 |
| swivelling disc | 5050 |
| swivel disc seal | 5051 |
| electrical connector receiver | 5052 |
| notch | 5054 |
| outlet connection region | 5056 |
| female electrical connector | 5058 |
| receiver contact element | 5058ce |
| disc stop surface | 5060 |
| disc stop surface | 5062 |
| housing stop surface | 5064 |
| housing stop surface | 5066 |
| cable | 5070 |
| cable housing | 5080 |
| inner wall | 5082 |
| outer wall | 5084 |
| void | 5086 |
| annular section | 5088 |
| retainer | 5090 |
| opening | 5092 |
| housing tab | 5094 |
| water reservoir | 5110 |
| water reservoir base | 5112 |
| water reservoir lid | 5114 |
| compliant portion | 5116 |
| water reservoir inlet | 5118 |
| conductive portion | 5120 |
| water reservoir outlet | 5122 |
| plate | 5123 |
| reservoir inlet tube | 5124 |
| inlet cap | 5125 |
| reservoir outlet tube | 5126 |
| contact element | 5146 |
| base conductor plate | 5152 |
| handle recess | 5154 |
| handle recess | 5156 |
| hinge | 5158 |
| complementary hinge recess portion | 5159 |
| dock cavity | 5160 |
| humidifier outlet | 5172 |
| latch | 5186 |
| intermediate portion | 5202 |
| humidifier transducer | 5210 |
| pressure transducer | 5212 |
| flow transducer | 5214 |
| temperature transducer | 5216 |
| humidity transducer | 5218 |
| heating element | 5240 |
| he cover plate | 5241 |
| heat generating component | 5242 |
| he seal | 5243 |
| he base cover | 5244 |
| he cone | 5245 |
| he cable port | 5246 |
| he cone slot | 5247 |
| humidifier controller | 5250 |
| central humidifier controller | 5251 |

-continued

| Component | Reference |
|---|---|
| heating element controller | 5252 |
| air circuit controller | 5254 |
| humidifier end cap | 5300 |
| magnet | 5340 |
| endcap magnet holder | 5345 |

The invention claimed is:

1. A respiratory pressure therapy (RPT) device for pressurising breathable air to treat a respiratory disorder in a patient, the RPT device comprising:
a water reservoir configured to hold a volume of water to be used for humidification of the breathable air;
a pressure generator configured to pressurise breathable air;
a chassis supporting the pressure generator and the chassis comprising:
an RPT device outlet configured to be connected to an air circuit to direct breathable air pressurised by the pressure generator to the patient, the RPT device outlet being positioned on a first side of the chassis, and the RPT device outlet comprising an outlet tube that is removably coupled to the chassis;
a visual display configured to visually display characters, symbols, and/or images, the visual display being positioned on a second side of the chassis that has a different orientation from the first side; and
a dock configured to receive the water reservoir; and
an external housing supported on the chassis, the pressure generator being enclosed by the external housing, and the external housing forming an opening such that the water reservoir is slidable into and out of the dock through the opening.

2. The RPT device of claim 1, wherein the chassis comprises an input device configured to receive input to control operation of the RPT device.

3. The RPT device of claim 2, wherein the input device is positioned on the second side of the chassis.

4. The RPT device of claim 2, wherein the input device is positioned on a third side of the chassis that has a different orientation from the first side and the second side.

5. The RPT device of claim 2, wherein the input device is a button, a switch, a dial, or a touchscreen.

6. The RPT device of claim 5, wherein the input device is the touchscreen and the visual display includes the touchscreen.

7. The RPT device of claim 1, wherein the visual display comprises a Liquid Crystal Display (LCD) screen or a Light Emitting Diode (LED) display.

8. The RPT device of claim 1, wherein the first side and the second side are positioned opposite each other relative to the chassis.

9. The RPT device of claim 1, wherein the first side and the second side are positioned opposite each other such that in use the visual display faces towards the patient and the RPT device outlet faces away from the patient.

10. The RPT device of claim 1, wherein the chassis comprises an RPT device inlet configured to receive breathable air from externally of the RPT device to be pressurised by the pressure generator.

11. The RPT device of claim 1, comprising a dock inlet positioned on the dock and configured to receive breathable air pressurised by the pressure generator from the water reservoir.

12. The RPT device of claim 11, wherein the dock inlet is in pneumatic communication with the RPT device outlet through the chassis.

13. The RPT device of claim 11, comprising a dock outlet positioned on the dock and configured to direct breathable air pressurised by the pressure generator into the water reservoir.

14. The RPT device of claim 13, wherein the water reservoir comprises a water reservoir inlet and a water reservoir outlet.

15. The RPT device of claim 14, wherein the dock outlet is configured to direct breathable air pressurised by the pressure generator into the water reservoir via the water reservoir inlet when the water reservoir is received in the dock, and
wherein the dock inlet is configured to receive breathable air pressurised by the pressure generator from the water reservoir via the water reservoir outlet when the water reservoir is received in the dock.

16. The RPT device of claim 14, further comprising a first face seal and a second face seal, the first face seal being configured to seal between the dock outlet and the water reservoir inlet, and the second face seal being configured to seal between the water reservoir outlet and the dock inlet when the water reservoir is received in the dock.

17. The RPT device of claim 16, wherein the first face seal and the second face seal are positioned to seal between the dock outlet and the water reservoir inlet and between the water reservoir outlet and the dock inlet, respectively, when the water reservoir is received in the dock along a linear path.

18. The RPT device of claim 1, wherein the dock and the water reservoir are shaped and dimensioned such that a portion of the water reservoir is positioned outside of the dock when the water reservoir is received in the dock.

19. The RPT device of claim 1, wherein the water reservoir comprises a water reservoir base and a water reservoir lid connected to the water reservoir base with a hinge that allows the water reservoir lid to rotate relative to the water reservoir base between an open position and a closed position.

20. The RPT device of claim 19, wherein the water reservoir comprises a compliant portion, the compliant portion being constructed from a resilient material and configured to seal between the water reservoir base and the water reservoir lid when the water reservoir lid is in a closed position on the water reservoir base.

21. The RPT device of claim 19, wherein the water reservoir includes a friction grip configured to be positioned outside of the dock when the water reservoir is received in the dock.

22. The RPT device of claim 19, wherein the water reservoir lid includes one of a protrusion and a recess and the dock includes the other one of the protrusion and the recess, the protrusion and the recess being configured to releasably engage one another when the water reservoir is received in the dock to secure the water reservoir in the dock.

23. The RPT device of claim 1, further comprising a heating element supported on the chassis and configured to generate and conduct heat to the water reservoir when the water reservoir is received in the dock.

24. The RPT device of claim 1, wherein the RPT device outlet is configured to be connected to the air circuit such that the water reservoir is removable from the dock while the air circuit remains attached to the RPT device outlet.

25. The RPT device of claim 1, wherein the water reservoir is configured such that the water reservoir must be removed from the dock to be refilled.

26. The RPT device of claim 1, wherein the chassis comprises a slot and the outlet tube comprises a latch portion configured to releasably engage the slot and removably couple the outlet tube to the chassis.

27. The RPT device of claim 1, wherein the outlet tube comprises a face seal configured to seal against the water reservoir at a water reservoir outlet when the water reservoir is inserted into the dock.

28. The RPT device of claim 1, comprising:
a dock inlet positioned on the dock and configured to receive breathable air pressurised by the pressure generator from the water reservoir;
a dock outlet positioned on the dock and configured to direct breathable air pressurised by the pressure generator into the water reservoir; and
a heating element supported on the chassis and configured to generate and conduct heat to the water reservoir when the water reservoir is received in the dock,
wherein:
the chassis comprises an input device configured to receive input to control operation of the RPT device,
the input device is a button, a switch, a dial, or a touchscreen,
the visual display comprises a Liquid Crystal Display (LCD) screen or a Light Emitting Diode (LED) display,
the first side and the second side are positioned opposite each other relative to the chassis,
the chassis comprises an RPT device inlet configured to receive breathable air from externally of the RPT device to be pressurised by the pressure generator,
the dock inlet is in pneumatic communication with the RPT device outlet through the chassis,
the water reservoir comprises a water reservoir inlet and a water reservoir outlet,
the dock outlet is configured to direct breathable air pressurised by the pressure generator into the water reservoir via the water reservoir inlet when the water reservoir is received in the dock,
the dock inlet is configured to receive breathable air pressurised by the pressure generator from the water reservoir via the water reservoir outlet when the water reservoir is received in the dock,
the dock and the water reservoir are shaped and dimensioned such that a portion of the water reservoir is positioned outside of the dock when the water reservoir is received in the dock,
the water reservoir comprises a water reservoir base and a water reservoir lid connected to the water reservoir base with a hinge that allows the water reservoir lid to rotate relative to the water reservoir base between an open position and a closed position, and
the water reservoir comprises a compliant portion, the compliant portion being constructed from a resilient material and configured to seal between the water reservoir base and the water reservoir lid when the water reservoir lid is in a closed position on the water reservoir base.

29. A respiratory pressure therapy (RPT) device for pressurising breathable air to treat a respiratory disorder in a patient, the RPT device comprising:
a pressure generator configured to pressurise breathable air;
a chassis supporting the pressure generator and the chassis comprising:
an RPT device outlet configured to be connected to an air circuit to direct breathable air pressurised by the pressure generator to the patient, the RPT device outlet being positioned on a first side of the chassis, and the RPT device outlet comprising an outlet tube that is removably coupled to the chassis; and
a dock configured to receive a water reservoir; and
an external housing supported on the chassis, the pressure generator being enclosed by the external housing, and the external housing forming an opening such that the water reservoir is slidable into and out of the dock through the opening.

30. The RPT device of claim 29, comprising:
a water reservoir configured to hold a volume of water to be used for humidification of the breathable air;
a visual display positioned on a second side of the chassis that has a different orientation from the first side;
a dock inlet positioned on the dock and configured to receive breathable air pressurised by the pressure generator from the water reservoir;
a dock outlet positioned on the dock and configured to direct breathable air pressurised by the pressure generator into the water reservoir; and
a heating element supported on the chassis and configured to generate and conduct heat to the water reservoir when the water reservoir is received in the dock,
wherein:
the chassis comprises an input device configured to receive input to control operation of the RPT device,
the input device is a button, a switch, a dial, or a touchscreen,
the visual display comprises a Liquid Crystal Display (LCD) screen or a Light Emitting Diode (LED) display,
the first side and the second side are positioned opposite each other relative to the chassis,
the chassis comprises an RPT device inlet configured to receive breathable air from externally of the RPT device to be pressurised by the pressure generator,
the dock inlet is in pneumatic communication with the RPT device outlet through the chassis,
the water reservoir comprises a water reservoir inlet and a water reservoir outlet, the dock outlet is configured to direct breathable air pressurised by the pressure generator into the water reservoir via the water reservoir inlet when the water reservoir is received in the dock,
the dock inlet is configured to receive breathable air pressurised by the pressure generator from the water reservoir via the water reservoir outlet when the water reservoir is received in the dock,
the dock and the water reservoir are shaped and dimensioned such that a portion of the water reservoir is positioned outside of the dock when the water reservoir is received in the dock,
the water reservoir comprises a water reservoir base and a water reservoir lid connected to the water reservoir base with a hinge that allows the water reservoir lid to rotate relative to the water reservoir base between an open position and a closed position, and
the water reservoir comprises a compliant portion, the compliant portion being constructed from a resilient material and configured to seal between the water reservoir base and the water reservoir lid when the water reservoir lid is in a closed position on the water reservoir base.

\* \* \* \* \*